(12) United States Patent
Wang et al.

(10) Patent No.: US 11,873,311 B2
(45) Date of Patent: Jan. 16, 2024

(54) HETEROCYCLIC COMPOUND, ORGANIC ELECTROLUMINESCENT DEVICE, AND ELECTRONIC DEVICE

(71) Applicant: Shaanxi Lighte Optoelectronics Material Co., Ltd., Xi'an (CN)

(72) Inventors: Jinping Wang, Xi'an (CN); Zhen Xue, Xi'an (CN); Zhiwei Chen, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 115 days.

(21) Appl. No.: 17/788,850

(22) PCT Filed: Dec. 29, 2020

(86) PCT No.: PCT/CN2020/140903
§ 371 (c)(1),
(2) Date: Jun. 24, 2022

(87) PCT Pub. No.: WO2021/136277
PCT Pub. Date: Jul. 8, 2021

(65) Prior Publication Data
US 2023/0312604 A1 Oct. 5, 2023

(30) Foreign Application Priority Data

Dec. 30, 2019 (CN) .......................... 201911404324.0
Dec. 21, 2020 (CN) .......................... 202011519965.3

(51) Int. Cl.
*C07D 251/24* (2006.01)
*C07D 519/00* (2006.01)
(Continued)

(52) U.S. Cl.
CPC ......... *C07D 519/00* (2013.01); *C07D 471/04* (2013.01); *H10K 50/11* (2023.02);
(Continued)

(58) Field of Classification Search
CPC .. C07D 251/24; C07D 519/00; H10K 85/654; H10K 85/6572; H10K 85/6574; H10K 85/6576
See application file for complete search history.

(56) References Cited

U.S. PATENT DOCUMENTS

2014/0332777 A1 11/2014 Cho
2019/0252623 A1 8/2019 Layek

FOREIGN PATENT DOCUMENTS

CN 103833738 A 6/2014
CN 105254555 A 1/2016
(Continued)

OTHER PUBLICATIONS

International Search Report from corresponding International Application No. PCT/CN2020/140903, dated Mar. 25, 2021; 5 pages with translation.
(Continued)

*Primary Examiner* — Vu A Nguyen
(74) *Attorney, Agent, or Firm* — TUCKER ELLIS LLP

(57) ABSTRACT

A heterocyclic compound as shown in Formula 1, an organic electroluminescent device and an electronic device, belong to the technical field of organic electroluminescence. The heterocyclic compound can improve the performance of an organic electroluminescent device.

(Continued)

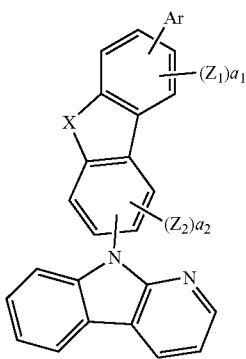

12 Claims, 1 Drawing Sheet

(51) Int. Cl.
*H01L 51/00* (2006.01)
*H01L 51/50* (2006.01)
*C07D 471/04* (2006.01)
*H10K 50/11* (2023.01)
*H10K 85/60* (2023.01)

(52) U.S. Cl.
CPC ......... *H10K 85/615* (2023.02); *H10K 85/622* (2023.02); *H10K 85/652* (2023.02); *H10K 85/654* (2023.02); *H10K 85/6572* (2023.02); *H10K 85/6574* (2023.02); *H10K 85/6576* (2023.02); *C07B 2200/05* (2013.01)

(56) References Cited

FOREIGN PATENT DOCUMENTS

| | | | |
|---|---|---|---|
| CN | 104693105 A | 6/2016 | |
| JP | 2006131783 A | 5/2006 | |
| KR | 1020130067177 A | 6/2013 | |
| KR | 1020190068103 A | 6/2019 | |
| WO | WO-2020138944 A1 * | 7/2020 | ........... C07D 403/04 |

OTHER PUBLICATIONS

Varathan, E., et al: "the role of sulfur oxidation in controlling the electronic properties of sulfur-containing host molecules for phosphorescent organic light-emitting diodes"; vol. 19; dated Apr. 7, 2017; 33 pages.

Ju Sik Kang et al.: "High-performance bipolar host materials for blue TADF devices with excellent external quantum efficiencies"; Journal of Materials Chemistry C.; dated Jan. 16, 2016; 18 pages.

* cited by examiner

HETEROCYCLIC COMPOUND, ORGANIC ELECTROLUMINESCENT DEVICE, AND ELECTRONIC DEVICE

CROSS REFERENCE TO RELATED APPLICATIONS

The application claims the priority of Chinese patent application No. CN201911404324.0 filed on Dec. 30, 2019 and the priority of Chinese patent application No. CN202011519965.3 filed on Dec. 21, 2020, and the contents of the Chinese patent applications are hereby incorporated by reference in their entirety as a part of the application.

TECHNICAL FIELD

The application relates to the technical field of organic electroluminescence, in particular to a heterocyclic compound, an organic electroluminescence device and an electronic device.

BACKGROUND

Organic electroluminescent devices, such as organic light-emitting diodes (OLEDs), generally include a cathode and an anode which are disposed oppositely, and a functional layer disposed between the cathode and the anode. The functional layer is composed of multiple organic or inorganic film layers and generally includes an organic light-emitting layer, a hole transporting layer located between the organic light-emitting layer and the anode and an electron transporting layer located between the organic light-emitting layer and the cathode. When voltage is applied to the cathode and the anode, an electric field is generated between the two electrode, electrons on the cathode side move towards an electroluminescent layer and holes on the anode side also move towards the electroluminescent layer under the action of the electric field, the electrons and the holes are combined in the electroluminescent layer to form excitons, the excitons are in an excited state and release energy outwards, and then the electroluminescent layer emits light outwards.

Materials capable of preparing a light-emitting layer in an organic electroluminescent device have been applied in the prior art. However, it is still necessary to continue to develop novel materials so as to further improve the performance of the organic electroluminescent device.

The information applied by the background part is only used for enhancing the understanding of the background of the discloser, so the information can include information which does not constitute the prior art known to those of ordinary skill in the art.

SUMMARY

The discloser aims to provide a heterocyclic compound, an organic electroluminescent device and an electronic device so as to improve the performance of the organic electroluminescent device.

In order to realize the above discloser purpose, the discloser adopts the following technical solution.

According to a first aspect of the discloser, a heterocyclic compound is provided, and the heterocyclic compound has a structure shown in Formula 1-1:

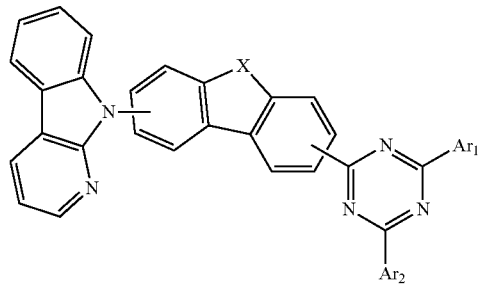

Formula 1-1 where X is selected from $C(R_1R_2)$, $N(R_3)$, O, S or $Si(R_1R_2)$; and $R_1$, $R_2$ and $R_3$ are each independently selected from an alkyl with 1 to 4 carbon atoms, or an aryl with 6 to 12 carbon atoms; and $Ar_1$ and $Ar_2$ are the same or different, and are each independently selected from a substituted or unsubstituted aryl with 6 to 18 carbon atoms, or a substituted or unsubstituted heteroaryl with 6 to 15 carbon atoms; and the substituents in $Ar_1$ and $Ar_2$ are each independently selected from fluorine, deuterium, cyano, phenyl, an alkyl with 1 to 4 carbon atoms, cyclopentyl, or cyclohexyl.

According to a second aspect of the discloser, a heterocyclic compound is provided, and the heterocyclic compound has a structure shown in Formula 1:

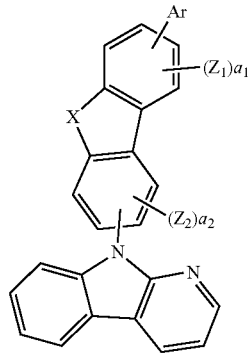

Formula 1 where X is selected from $C(R_1R_2)$, $N(R_3)$, O, S, or $Si(R_1R_2)$;

$R_1$, $R_2$ and $R_3$ are each independently selected from an alkyl with 1 to 4 carbon atoms, or an aryl with 6 to 12 carbon atoms; and $R_1$ and $R_2$ may also be connected to form a ring together with the atom to which they are jointly connected;

$a_1$ and $a_2$ are each independently selected from 1, 2, or 3;

$Z_1$ and $Z_2$ are each independently selected from hydrogen, deuterium, a halogen group, cyano, or an alkyl with 1 to 4 carbon atoms; and any two $Z_1$ are the same or different, and any two $Z_2$ are the same or different;

Ar is selected from a substituted or unsubstituted aryl with 12 to 60 carbon atoms, or a substituted or unsubstituted heteroaryl with 12 to 30 carbon atoms; and when there are substituents in Ar, the substituents in Ar are each independently selected from deuterium, a halogen group, cyano, $Si(R_4)_3$, alkyl, cycloalkyl, alkoxy, alkylthio, aryloxy, or arylthio, where $R_4$ is selected from alkyl or phenyl, and any two $R_4$ are the same or different.

According to a third aspect of the discloser, provided is an organic electroluminescent device, including an anode and a cathode which are oppositely arranged, and a functional layer arranged between the anode and the cathode, and the functional layer includes the heterocyclic compounds.

According to a fourth aspect of the discloser, provided is an electronic device, including the above organic electroluminescent device.

A molecular structure of the heterocyclic compound of Formula 1 provided by the discloser is integrally of a planar structure, so that electron migration is facilitated, the electron transport rate is increased, and the luminous efficiency is high, and meanwhile, the molecule contains a plurality of electron-donating atom nitrogen, and the structure can form large conjugation, so that the electron cloud density is large, and the efficiency is high. In one preferred embodiment, the structure of the heterocyclic compound is shown as Formula 1-1, in this structure, pyrido[2,3-b]indole in the heterocyclic compound is bound to a triazine group which is also electron-deficient, so that the electron injection and transport capability of the material can be effectively improved, the balance degree of hole and electron injection is enhanced, and this heterocyclic compound is particularly suitable for being used as a host material of a light-emitting layer to improve the luminous efficiency and the service life of the device.

BRIEF DESCRIPTION OF THE DRAWINGS

The above and other features and advantages of the present discloser will become more obvious by referring to the drawings to describe exemplary embodiments thereof in detail.

Figure 1:
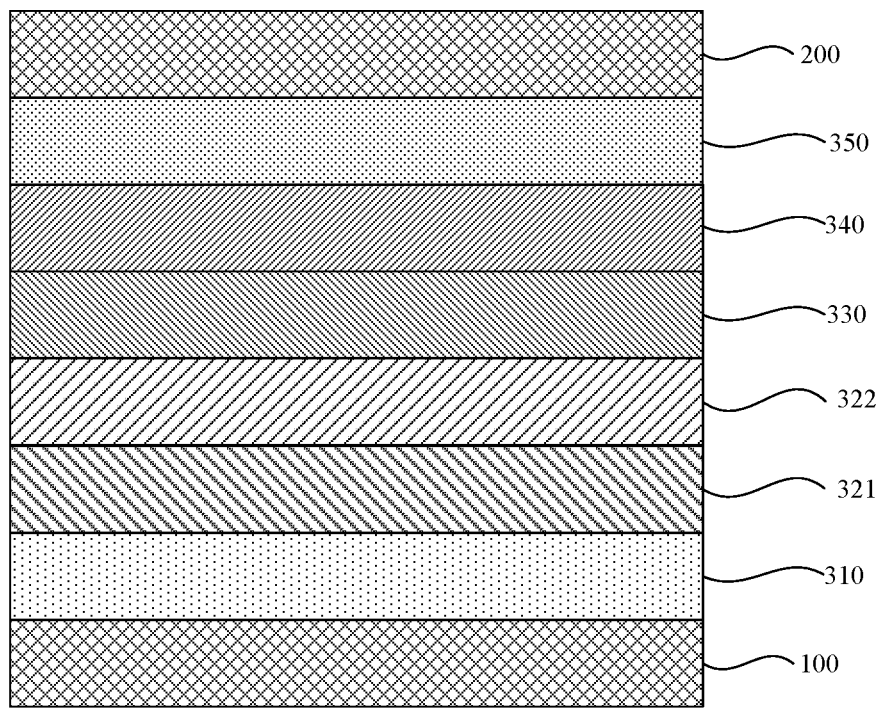
FIG. 1 is a structural schematic diagram of an organic electroluminescent device in one embodiment of the discloser.

The reference signs of main elements in the drawings are described as follows:

100, anode; 200, cathode; 310, hole injecting layer; 321, hole transporting layer; 322, electron blocking layer; 330, organic light-emitting layer; 340, electron transporting layer; 350, electron injecting layer; 400, electronic device.

DETAILED DESCRIPTION

Exemplary examples will now be described more comprehensively with reference to the drawings. However, the exemplary examples can be implemented in a variety of forms, and should not be understood as a limitation to the examples set forth herein; on the contrary, these examples are provided such that the present discloser will be more comprehensive and complete, and the concepts of the exemplary examples are comprehensively conveyed to those skilled in the art. The described features, structures, or characteristics may be incorporated in one or more examples in any suitable manner. In the following description, many specific details are provided to give a sufficient understanding of the examples of the present discloser.

In the drawings, for clearness, the thickness of regions and layers may be exaggerated. The same reference signs in the drawings represent the same or similar structure, so that detailed description thereof will be omitted.

The disclosure provides a heterocyclic compound, having a structure as shown in Formula 1:

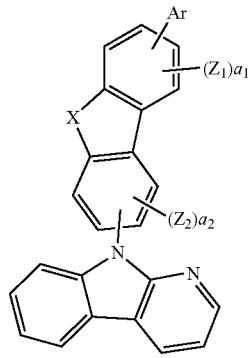

Formula 1

X is selected from $C(R_1R_2)$, $N(R_3)$, O, S, or $Si(R_1R_2)$;

$R_1$, $R_2$ and $R_3$ are each independently selected from an alkyl with 1 to 4 carbon atoms, or an aryl with 6 to 12 carbon atoms; and $R_1$ and $R_2$ may also be connected to form a ring together with the atom to which they are jointly connected;

$a_1$ and $a_2$ are each independently selected from 1, 2, or 3;

$Z_1$ and $Z_2$ are each independently selected from hydrogen, deuterium, a halogen group, cyano, or an alkyl with 1 to 4 carbon atoms; and any two $Z_1$ are the same or different, and any two $Z_2$ are the same or different;

Ar is selected from a substituted or unsubstituted aryl with 12 to 60 carbon atoms, or a substituted and unsubstituted heteroaryl with 12 to 30 carbon atoms; when there are substituents in Ar, the substituents in Ar are each independently selected from deuterium, a halogen group, cyano, $Si(R_4)_3$, alkyl, cycloalkyl, alkoxy, alkylthio, aryloxy, or arylthio, where $R_4$ is selected from alkyl or phenyl, and any two $R_4$ are the same or different.

In the discloser, the number of carbon atoms in Ar refers to the number of all carbon atoms. For example, if Ar is selected from a substituted aryl with 10 carbon atoms, the number of all carbon atoms of the aryl and substituents on the aryl is 10. For example, if Ar is 9,9-dimethylfluorenyl, Ar is a substituted fluorenyl with 15 carbon atoms, the substituents in Ar are two methyl, and the number of ring-forming carbon atoms in Ar is 13.

In the present discloser, "$R_1$ and $R_2$ may also be connected to form a ring together with the atom to which they are jointly connected" includes the following two cases: a case in which $R_1$ and $R_2$ are connected to form a ring together with the atom to which they are jointly connected; and a case in which $R_1$ and $R_2$ are each independently present and are not connected to each other and do not form a ring.

In the present discloser, "aryl" refers to an optional functional group or substituent derived from an aromatic hydrocarbon ring. The aryl may be a monocyclic aryl or a polycyclic aryl, in other words, the aryl can be a monocyclic aryl, a condensed ring aryl (i.e., fused aryl), two or more monocyclic aryl conjugatedly connected through carbon-carbon bonds, a monocyclic aryl and a fused aryl which are conjugatedly connected through a carbon-carbon bond, and two or more fused aryl conjugatedly connected through carbon-carbon bonds. In other words, two or more aromatic groups conjugatedly connected by carbon-carbon bonds may also be regarded as the aryl of the present discloser. The aryl does not contain heteroatoms such as B, N, O, S or P. For example, in the present discloser, biphenyl, terphenyl, etc. are aryl groups. Examples of the aryl groups may include phenyl, naphthyl, fluorenyl, anthryl, phenanthryl, biphenyl, terphenyl, quaterphenyl, quinquephenyl, benzo[9,10]phenanthryl, pyrenyl, benzofluoranthenyl, chrysene, and the like, but are not limited thereto. Among them, naphthyl, fluorenyl, anthryl, phenanthryl and the like belong to the condensed ring aryl, and phenyl, biphenyl, terphenyl and other monocyclic aryl connected through a carbon-carbon single bond do not belong to the condensed ring aryl.

In the discloser, the substituted aryl means that one or more hydrogen atoms in the aryl are substituted by other groups. For example, at least one hydrogen atom is substituted by a deuterium atom, F, Cl, I, CN, branched alkyl, linear alkyl, cycloalkyl, alkoxy, alkylthio or other groups. It can be understood that the number of carbon atoms in the substituted aryl is the total number of carbon atoms in the aryl and substituents on the aryl. For example, substituted aryl having 18 carbon atoms means that the total number of carbon atoms in the aryl and the substituents on the aryl is 18. For example, 9,9-dimethylfluorenyl is fluorenyl which has 15 carbon atoms and is substituted by methyl.

In the present discloser, "heteroaryl" may be a heteroaryl group including at least one of B, O, N, P, Se, Si, and S as a heteroatom. The heteroaryl group may be a monocyclic heteroaryl or a polycyclic heteroaryl. In other words, the heteroaryl group may be a single aromatic ring system or multiple aromatic ring systems conjugatedly connected through carbon-carbon bonds, and any aromatic ring system is an aromatic monocyclic ring or an aromatic fused ring. Exemplarily, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, N-phenylcarbazolyl, N-pyridylcarbazolyl, N-methylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, phenyl-substituted dibenzofuranyl, dibenzofuranyl-substituted phenyl, 4,6-diaryl-1,3,5-triazin-2-yl and the like, but is not limited thereto. Among them, thienyl, furyl, phenanthrolinyl and the like are heteroaryl groups of the single aromatic ring system, and the N-phenylcarbazolyl, N-pyridylcarbazolyl, phenyl-substituted dibenzofuranyl, dibenzofuranyl-substituted phenyl and the like are heteroaryl groups of the multiple aromatic ring systems conjugatedly connected through carbon-carbon bonds.

In the discloser, the adopted description modes "each . . . independently", " . . . respectively and independently" and " . . . independently selected from" can be interchanged, and should be understood in a broad sense, which means that in different groups, specific options expressed between the same symbols do not influence each other, or in a same group, specific options expressed between the same symbols do not influence each other.

For example, in the description of "

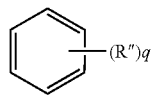

Formula Q-1

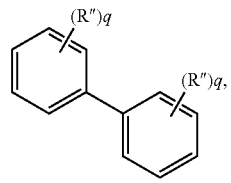

Formula Q-2 where each q is independently 0, 1, 2 or 3, and each R" is independently selected from hydrogen, fluorine, or chlorine", means that: Formula Q-1 represents that q substituents R" exist on a benzene ring, each R" may be the same or different, and options of each R" do not influence each other; Formula Q-2 represents that each benzene ring of biphenyl has q substituents R", the number q of the substituents R" on the two benzene rings may be the same or different, each R" may be the same or different, and options of each R" do not influence each other.

A non-localized connecting bond in the discloser is a single bond "-$\xi$-" extending from a ring system, which indicates that one end of the connecting bond can be connected with any position in the ring system through which the bond penetrates, and the other end of the connecting bond is connected with the remaining part of the compound molecule.

For example, as shown in the following Formula (f), naphthyl represented by Formula (f) is connected to other positions of a molecule through two non-localized connecting bonds penetrating the dicyclic ring, and its meaning includes any one possible connecting mode represented by Formula (f-1) to Formula (f-10).

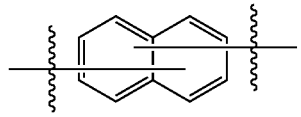

Formula (f)

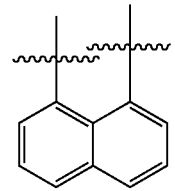

Formula (f-1)

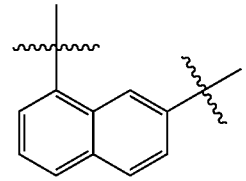

Formula (f-2)

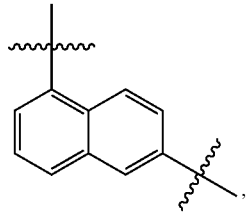

Formula (f-3)

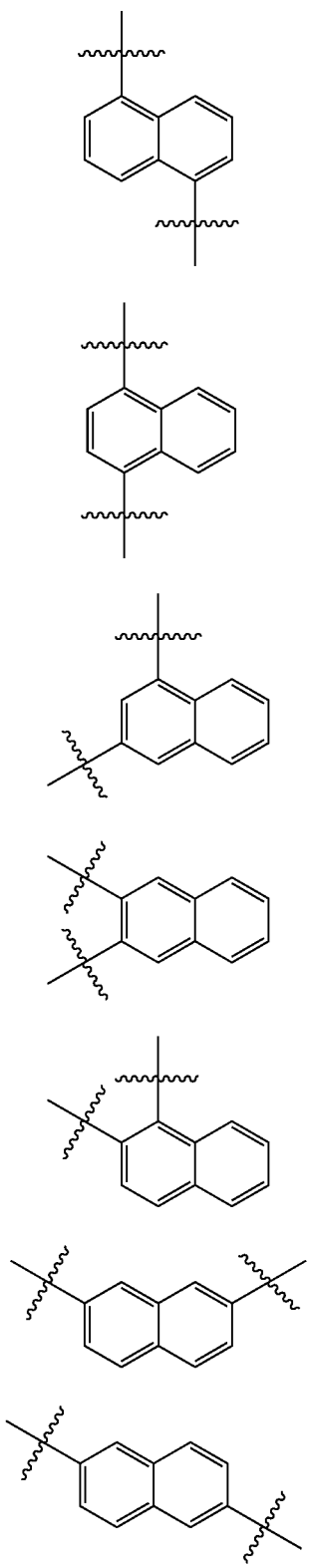

Formula (f-4)

Formula (f-5)

Formula (f-6)

Formula (f-7)

Formula (f-8)

Formula (f-9)

Formula (f-10)

For another example, as shown in the following Formula (X'), phenanthryl represented by the Formula (X') is connected to other position of a molecule through one non-localized connecting bond extending from the middle of the benzene ring on one side, and its meaning includes any possible connecting mode represented by Formula (X'-1) to (X'-4).

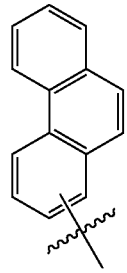

(X')

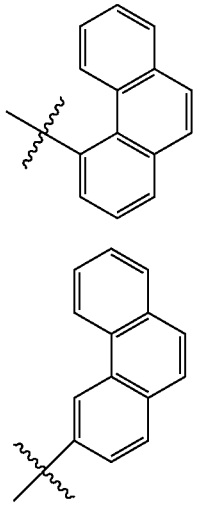

(X'-1)

(X'-2)

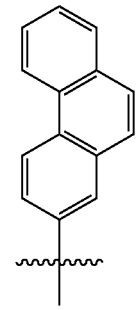

(X'-3)

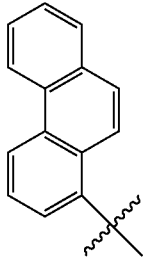

(X'-4)

A non-localized substituent in the discloser refers to a substituent connected through a single bond extending from the center of a ring system, which means that the substituent can be connected to any possible position of the ring system. For example, as shown in the following Formula (Y), the substituent R represented by Formula (Y) is connected with the quinoline ring through one non-localized connecting bond, and its meaning includes any possible connecting mode represented by Formula (Y-1) to (Y-7).

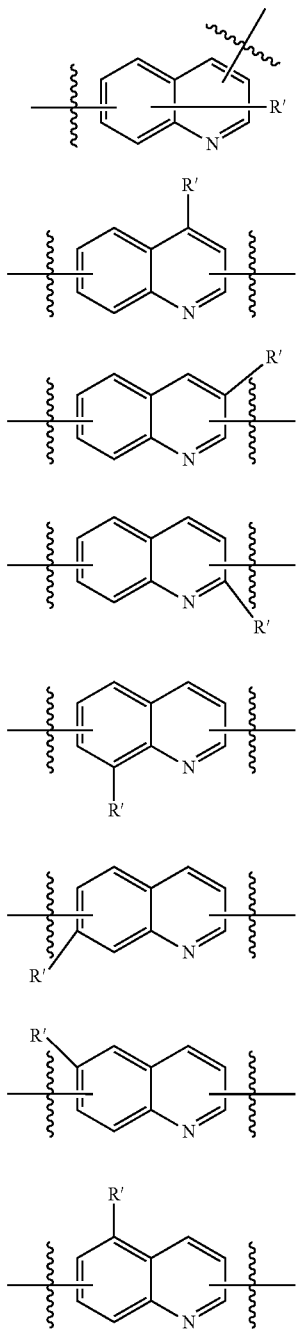

Formula (Y)

Formula (Y-1)

Formula (Y-2)

Formula (Y-3)

Formula (Y-4)

Formula (Y-5)

Formula (Y-6)

Formula (Y-7)

In the discloser, the number of carbon atoms of the alkyl as a substituent in Ar may be 1 to 10, and specifically include a linear alkyl with 1 to 10 carbon atoms and a branched alkyl with 3 to 10 carbon atoms. The number of carbon atoms may be, for example, 1, 2, 3, 4, 5, 6, 7, 8, 9, or 10. Specific examples of the alkyl include, but are not limited to, methyl, ethyl, n-propyl, isopropyl, n-butyl, isobutyl, tert-butyl, n-amyl, isoamyl, neopentyl, cyclopentyl, n-hexyl, heptyl, n-octyl, 2-ethylhexyl, nonyl, decyl, 3,7-dimethyloctyl and the like.

In the discloser, the number of carbon atoms of the alkoxy as a substituent in Ar may be 1 to 10, for example, may be 1, 2, 3, 4, 5, 6, 7, 8, 9 or 10, and specific examples of the alkoxy include, but are not limited to, methoxy, ethyoxy, n-propoxy and the like.

In the discloser, the number of carbon atoms of the alkylthio as a substituent in Ar may be 1 to 10, for example, 1, 2, 3, 4, 5, 6, 7, 8, 9 or 10, and specific examples of the alkylthio include, but are not limited to, methylthio, ethylthio, n-propylthio and the like.

In the discloser, the number of carbon atoms of the cycloalkyl as a substituent in Ar may be 3 to 10, and specific examples of the cycloalkyl include, but are not limited to, cyclopentyl, cyclohexyl, adamantyl and the like.

In the discloser, the halogen group may include fluorine, bromine, chlorine, iodine and the like.

In the discloser, optionally, substituents in Ar are each independently selected from deuterium, fluorine, chlorine, cyano, $Si(R)_3$, an alkyl with 1 to 3 carbon atoms, a cycloalkyl with 3 to 10 carbon atoms, an alkoxy with 1 to 3 carbon atoms, an alkylthio with 1 to 3 carbon atoms, an aryloxy with 6 to 12 carbon atoms, or an arylthio with 6 to 12 carbon atoms, where $R_4$ is selected from an alkyl with 1 to 3 carbon atoms or phenyl, and any two $R_4$ are the same or different. Wherein the specific examples of $Si(R_4)_3$ include, but are not limited to, triphenylsilyl, trimethylsilyl, dimethylphenylsilyl and the like.

Optionally, specific examples of substituents in Ar include, but are not limited to, deuterium, fluorine, cyano, trimethylsilyl, methyl, ethyl, isopropyl, tert-butyl, cyclopentyl, cyclohexyl, trimethylsilyl, and the like.

In the discloser, the specific examples of each of $R_1$ and $R_2$ include, but are not limited to, methyl, ethyl and n-propyl. Specific examples of $R_3$ include methyl, naphthyl and biphenyl.

Optionally,

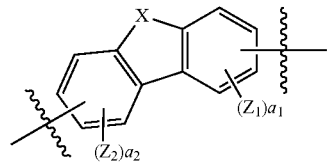

is selected from the following groups:

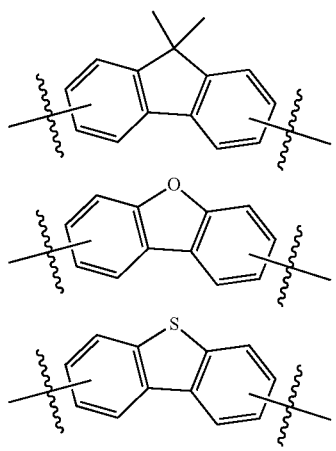

-continued
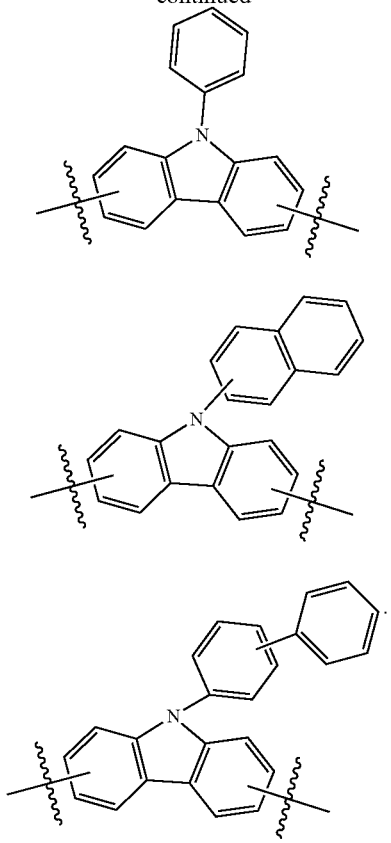
Optionally,
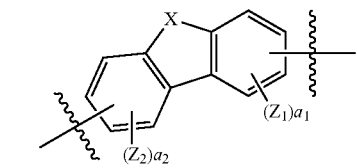
is an unsubstituted group Q, and the unsubstituted group Q is selected from the following groups:
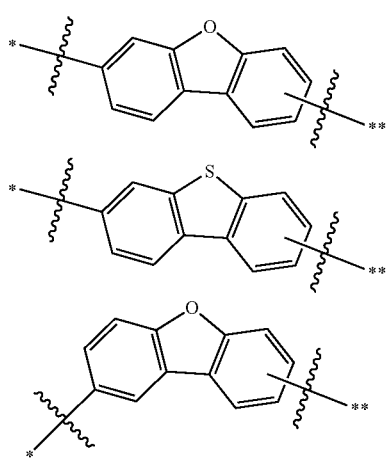
-continued
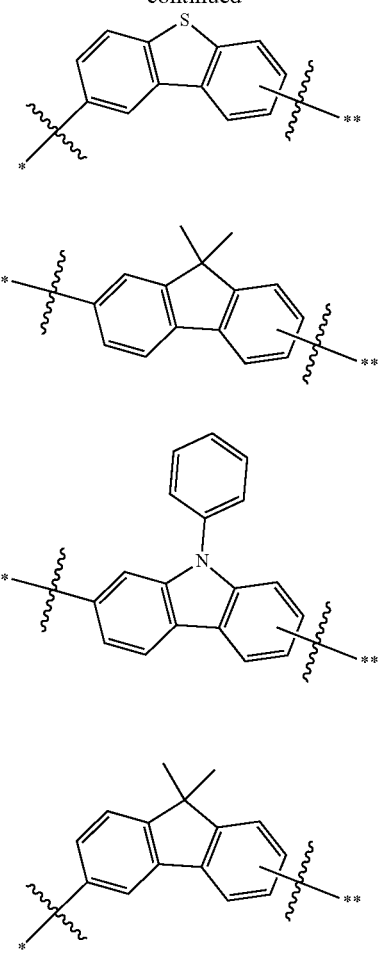
where * represents a connecting point of the unsubstituted group Q to
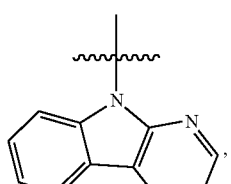
and ** represents a connecting point of the unsubstituted group Q to Ar.

In some embodiments, Ar is selected from groups represented by the following chemical formulas:

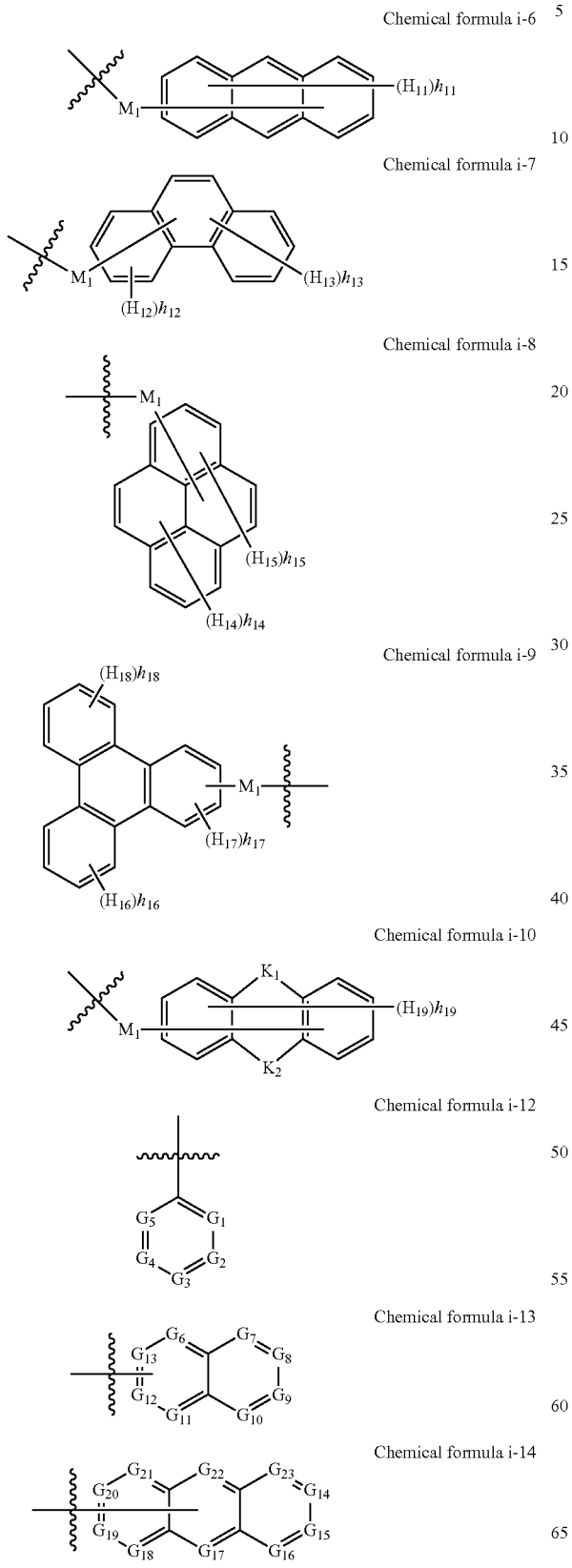

Chemical formula i-6

Chemical formula i-7

Chemical formula i-8

Chemical formula i-9

Chemical formula i-10

Chemical formula i-12

Chemical formula i-13

Chemical formula i-14

Chemical formula i-15

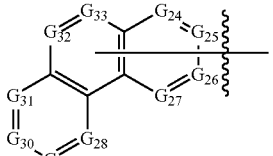

where $M_1$ is selected from a single bond or

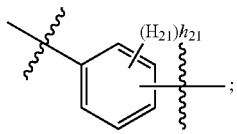

$G_1$ to $G_5$ are each independently selected from N or $C(F_1)$, and at least one of $G_1$ to $G_5$ is selected from N; and when two or more of $G_1$ to $G_5$ are selected from $C(F_1)$, any two $F_1$ are the same or different;

$G_6$ to $G_{13}$ are each independently selected from N or $C(F_2)$, and at least one of $G_6$ to $G_{13}$ is selected from N; and when two or more of $G_6$ to $G_{13}$ are selected from $C(F_2)$, any two $F_2$ are the same or different;

$G_{14}$ to $G_{23}$ are each independently selected from N or $C(F_3)$, and at least one of $G_{14}$ to $G_{23}$ is selected from N; and when two or more of $G_{14}$ to $G_{23}$ are selected from $C(F_3)$, any two $F_3$ are the same or different;

$G_{24}$ to $G_{33}$ are each independently selected from N or $C(F_4)$, and at least one of $G_{24}$ to $G_{33}$ is selected from N; and when two or more of $G_{24}$ to $G_{33}$ are selected from $C(F_4)$, any two $F_4$ are the same or different;

$H_{11}$ to $H_{19}$, $H_{21}$, and $F_1$ to $F_4$ are each independently selected from deuterium, fluorine, chlorine, bromine, cyano, a trialkylsilyl with 3 to 12 carbon atoms, an alkyl with 1 to 10 carbon atoms, a cycloalkyl with 3 to 10 carbon atoms, an alkoxy with 1 to 10 carbon atoms, an alkylthio with 1 to 10 carbon atoms, an aryloxy with 6 to 18 carbon atoms, or an arylthio with 6 to 18 carbon atoms; any one of $H_{11}$ to $H_{20}$ and $H_{22}$ may also be independently selected from an aryl with 6 to 18 carbon atoms; any one of $F_1$ to $F_4$ may also be independently selected from hydrogen or an aryl with 6 to 18 carbon atoms;

$h_k$ is the number of substituents $H_k$, and k is any integer of 11 to 19 and 21; when k is 17, $h_k$ is selected from 0, 1, 2, or 3; when k is selected from 12, 15, 16, 18, or 21, $h_k$ is selected from 0, 1, 2, 3, or 4; when k is 14, $h_k$ is selected from 0, 1, 2, 3, 4, or 5; when k is 13, $h_k$ is selected from 0, 1, 2, 3, 4, 5, or 6; when k is 19, $h_k$ is selected from 0, 1, 2, 3, 4, 5, 6, or 7; when k is 11, $h_k$ is selected from 0, 1, 2, 3, 4, 5, 6, 7, 8, or 9; and when $h_k$ is greater than 1, any two $H_k$ are the same or different;

$K_1$ is selected from $N(H_{28})$, $C(H_{23}H_{24})$, or $Si(H_{23}H_{24})$; wherein $H_{28}$, $H_{23}$ and $H_{24}$ are each independently selected from an aryl with 6 to 18 carbon atoms, a heteroaryl with 3 to 18 carbon atoms, an alkyl with 1 to 10 carbon atoms, or a cycloalkyl with 3 to 10 carbon atoms, or $H_{23}$ and $H_{24}$ are connected with each other to form a ring together with the atom to which they are jointly connected; and K₂ is selected from a single bond, C(H₂₆H₂₇), or Si(H₂₆H₂₇); wherein H₂₆ and H₂₇ are each independently selected from an aryl with 6 to 18 carbon atoms, a heteroaryl with 3 to 18 carbon atoms, an alkyl with 1 to 10 carbon atoms, or a cycloalkyl with 3 to 10 carbon atoms, or H₂₆ and H₂₇ are connected with each other to form a ring together with the atom to which they are jointly connected.

Optionally, Ar is selected from the following groups:

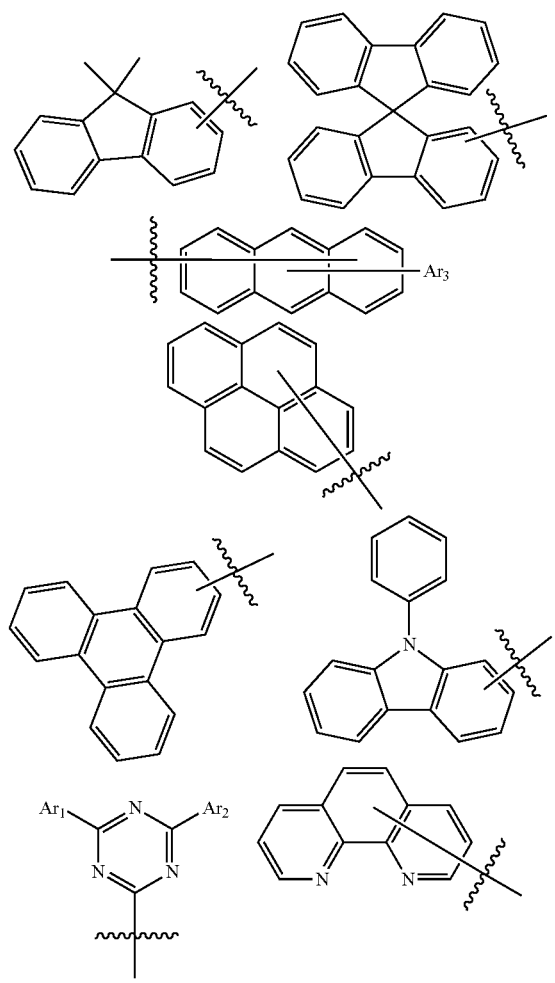

wherein Ar₁ and Ar₂ are the same or different, and are each independently selected from a substituted or unsubstituted aryl with 6 to 18 carbon atoms, or a substituted or unsubstituted heteroaryl with 6 to 15 carbon atoms; Ar₃ is selected from a substituted or unsubstituted aryl with 6 to 15 carbon atoms; and substituents in Ar₁, Ar₂ and Ar₃ are each independently selected from fluorine, deuterium, cyano, an alkyl with 1 to 4 carbon atoms, phenyl, cyclopentyl, or cyclohexyl.

Optionally, Ar₁ and Ar₂ are the same or different, and are each independently selected from a substituted or unsubstituted phenyl, a substituted or unsubstituted naphthyl, a substituted or unsubstituted biphenyl, a substituted or unsubstituted fluorenyl, a substituted or unsubstituted dibenzofuryl, a substituted or unsubstituted dibenzothienyl, or a substituted or unsubstituted pyridyl.

Optionally, Ar₃ is selected from a substituted or unsubstituted phenyl, a substituted or unsubstituted naphthyl, or a substituted and unsubstituted biphenyl. Further optionally, Ar₃ is selected from phenyl, naphthyl, or biphenyl.

Optionally, Ar₁ and Ar₂ are the same or different, and are each independently selected from a substituted or unsubstituted group W, and the unsubstituted group W is selected from the following groups:

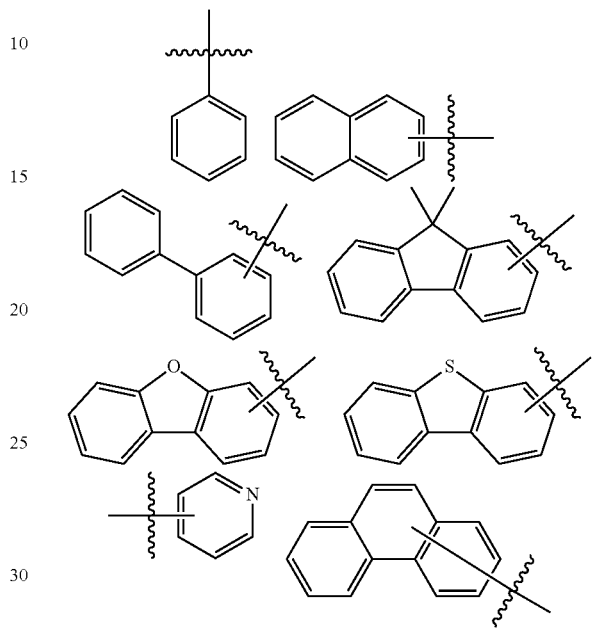

wherein the substituted group W has one or two or more substituents, and the substituents are each independently selected from deuterium, fluorine, cyano, methyl, tert-butyl, phenyl, cyclopentyl, or cyclohexyl.

Further optionally, Ar₁ and Ar₂ are each independently selected from the following groups:

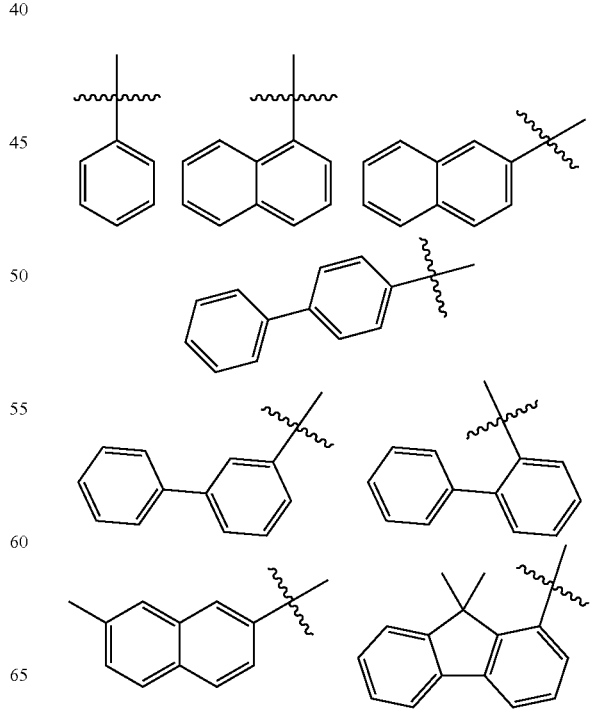

-continued
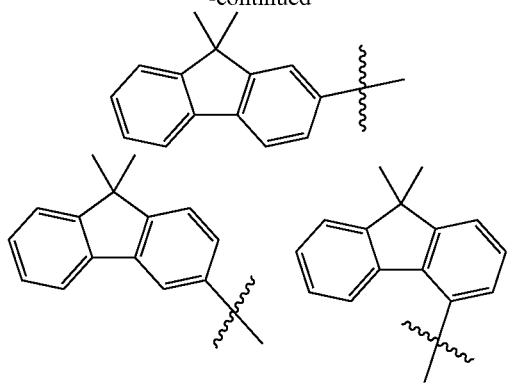
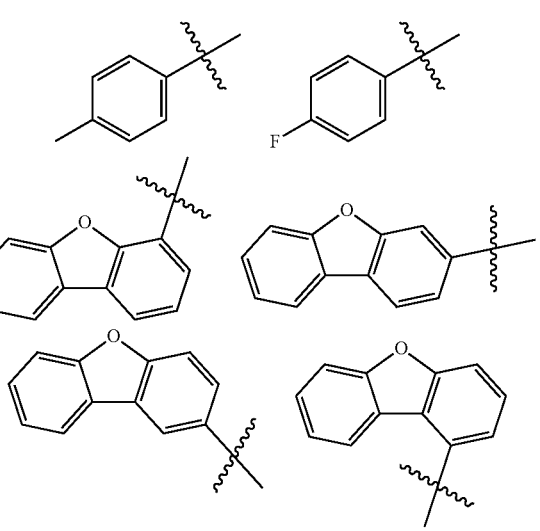
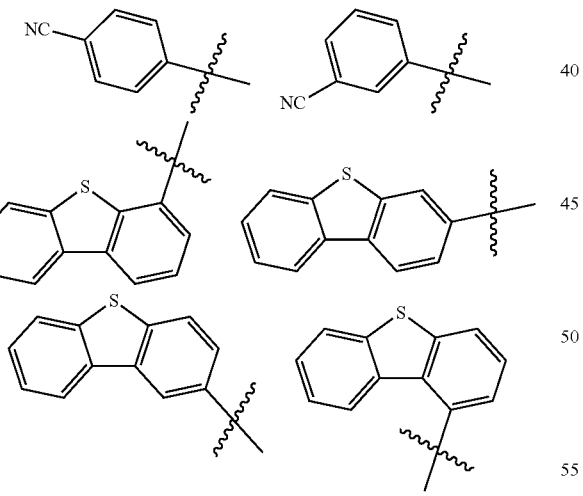
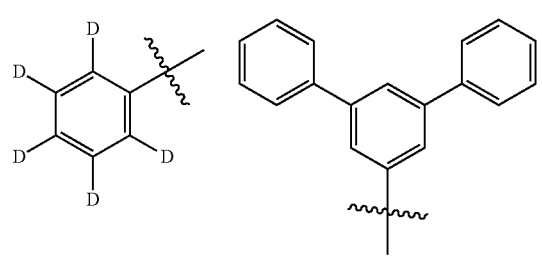
-continued
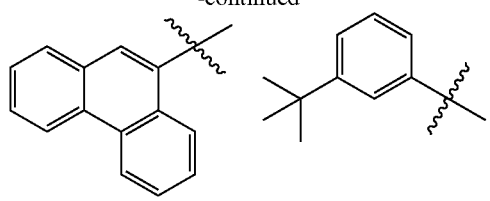
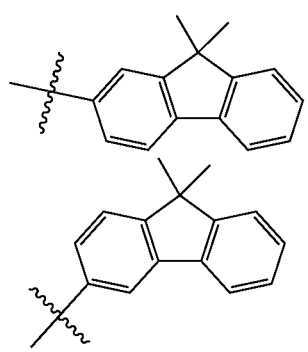
Optionally, Ar is selected from the following groups:
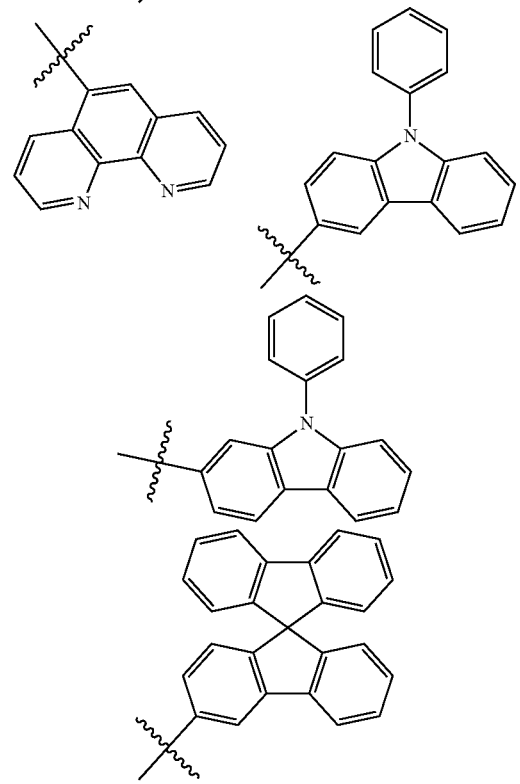

-continued

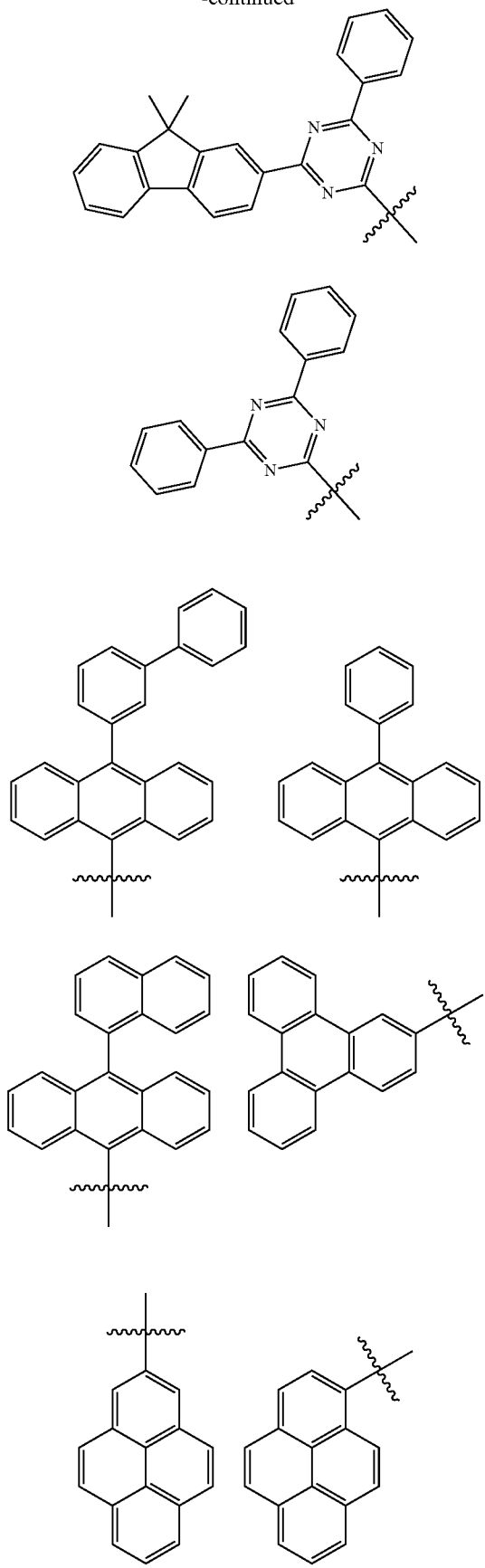

-continued

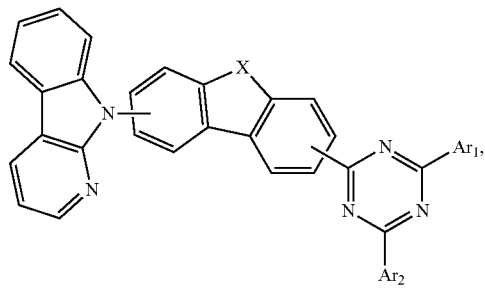

In one preferred embodiment, the heterocyclic compound has a structure as shown in Formula 1-1:

Formula 1-1

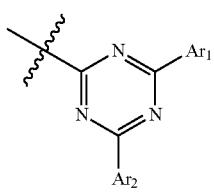

wherein X is selected from $C(R_1R_2)$, $N(R_3)$, O, S, or $Si(R_1R_2)$; $R_1$ to $R_3$ are each independently selected from an alkyl with 1 to 4 carbon atoms or an aryl with 6 to 12 carbon atoms; and the definitions of $Ar_1$ and $Ar_2$ are as described above. In this embodiment, pyrido[2,3-b]indole in the heterocyclic compound is bound to a triazine group which is also electron-deficient, so that the electron injection and transport capability of the material can be effectively improved, the balance degree of hole and electron injection is enhanced, and the heterocyclic compound is particularly suitable for being used as a host material of an organic light-emitting layer to improve the luminous efficiency and the service life of the device.

Optionally, the total number of carbon atoms of $Ar_1$ and $Ar_2$ is 12 to 30.

Optionally, the total number of carbon atoms of the structure

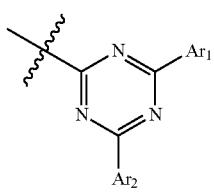

is 15 to 28.

Optionally, the structures of the heterocyclic compound are as follows:

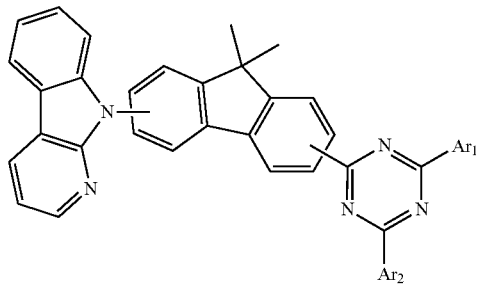

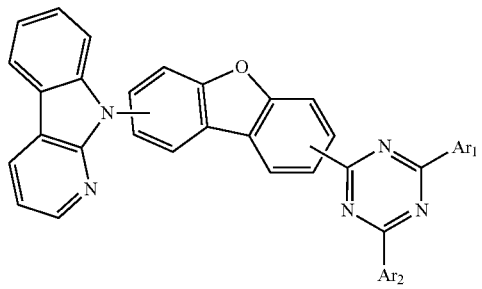

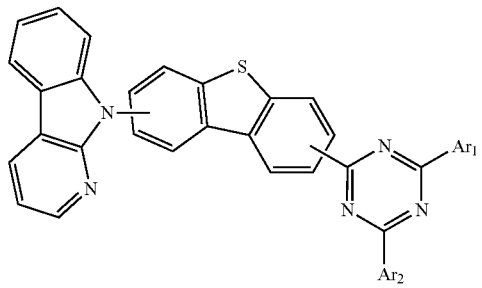

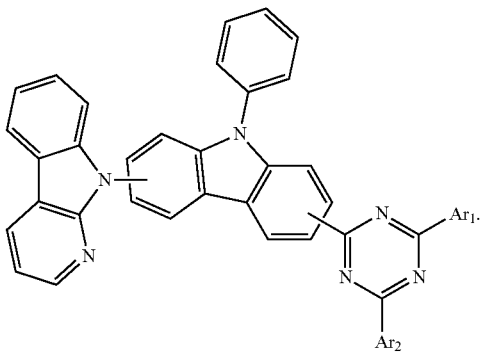

Optionally,

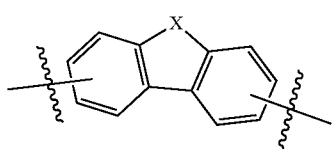

is selected from the following groups:

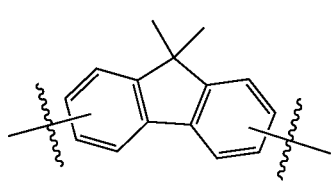

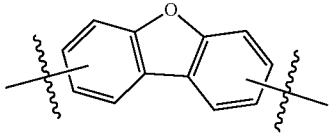

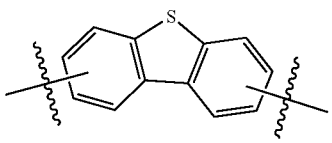

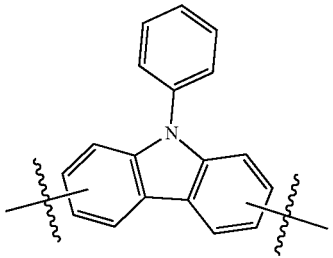

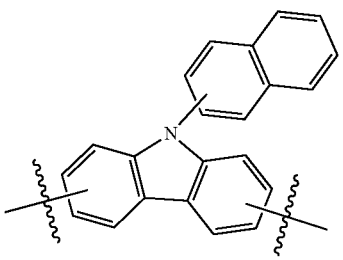

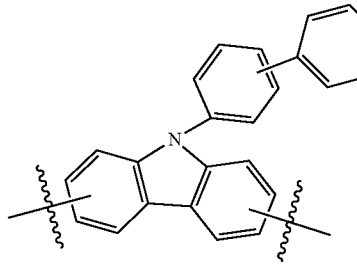

In another embodiment, Ar is selected from a substituted or unsubstituted fused aryl having 13 to 40 ring-forming carbon atoms. The number of ring-forming carbon atoms refers to the number of carbon atoms forming the fused aromatic ring structure. For example, the number of ring-forming carbon atoms of anthryl is 14, the number of ring-forming carbon atoms of fluorenyl is 13, and the number of ring-forming carbon atoms of spirobifluorenyl is 25; in addition, the number of ring-forming carbon atoms of 9,9-diphenylfluorene is 13, and the total number of carbon atoms of 9,9-diphenylfluorene is 25.

Optionally, the substituents in Ar are each independently selected from fluorine, deuterium, cyano, an alkyl with 1 to 4 carbon atoms (such as methyl and tert-butyl), phenyl, cyclopentyl, or cyclohexyl.

Optionally, the total number of carbon atoms of Ar is 15 to 40.

Optionally, the fused aryl is selected from anthryl, phenanthryl, pyrenyl, triphenylene, fluorenyl, or spirobifluorenyl.

Optionally, Ar is selected from the following groups:
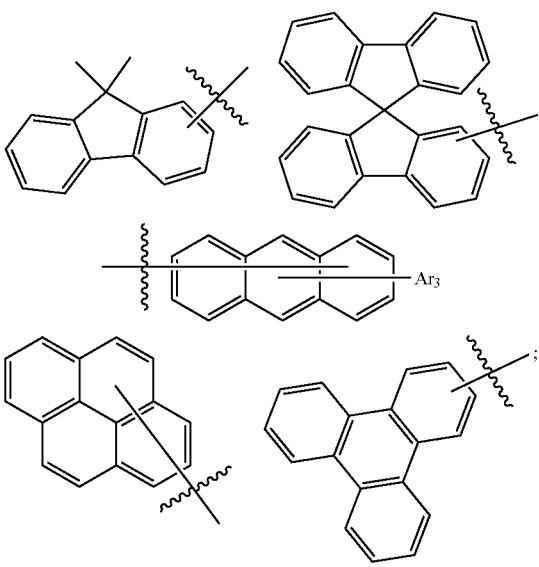
and
the definition of Ar₃ is as described above.
Optionally, the heterocyclic compound is selected from the following compounds:
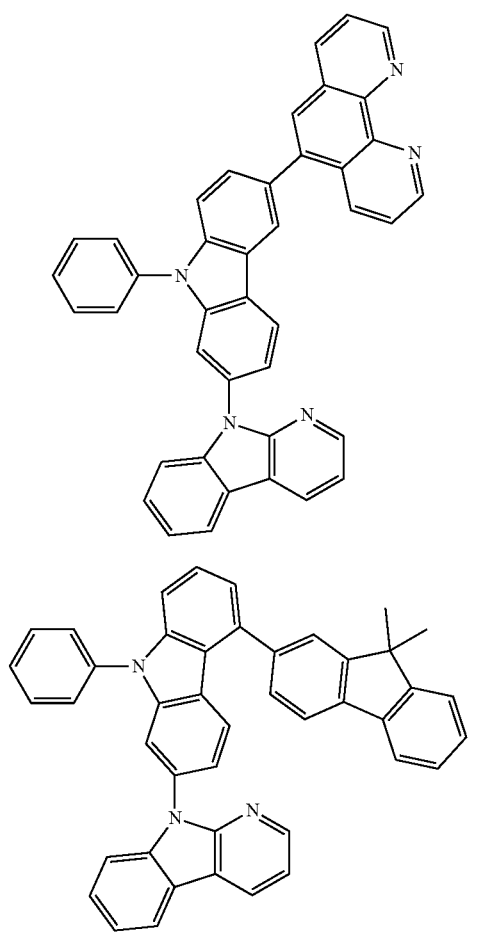
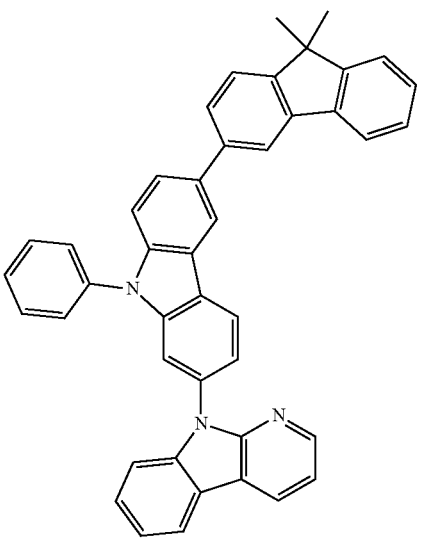
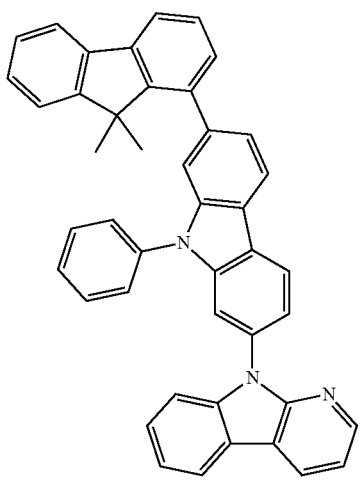
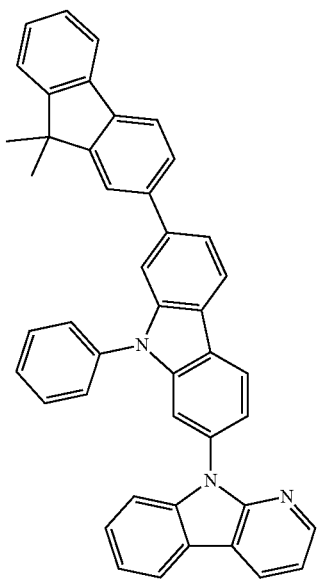

6
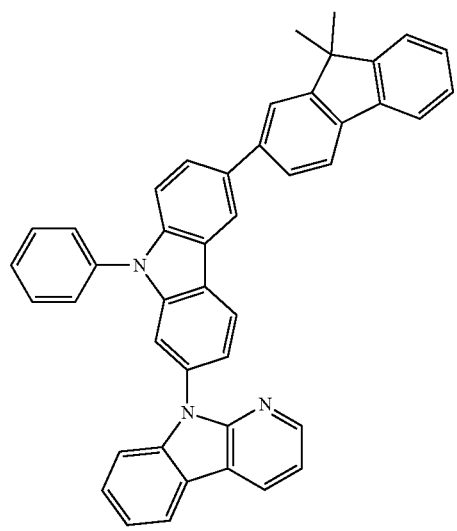
7
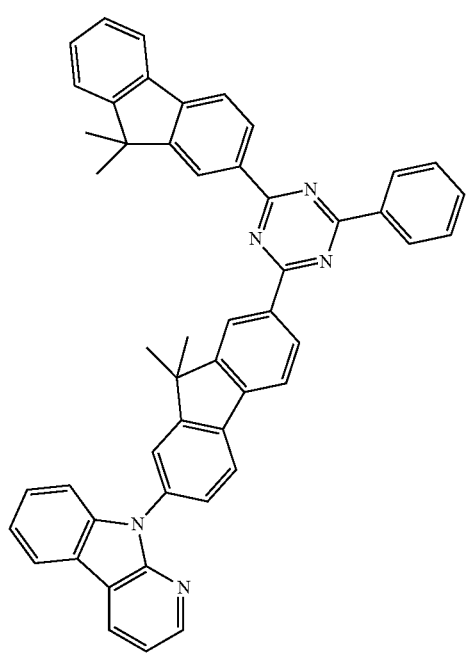
8
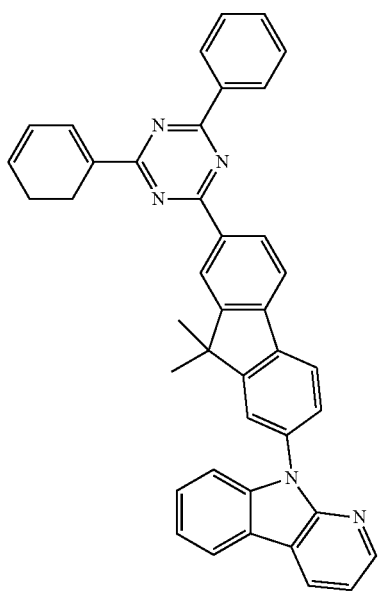
10
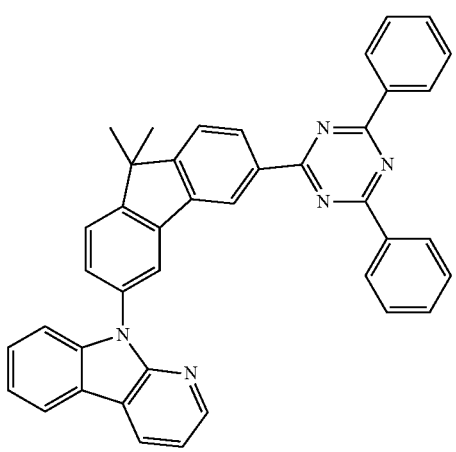
11
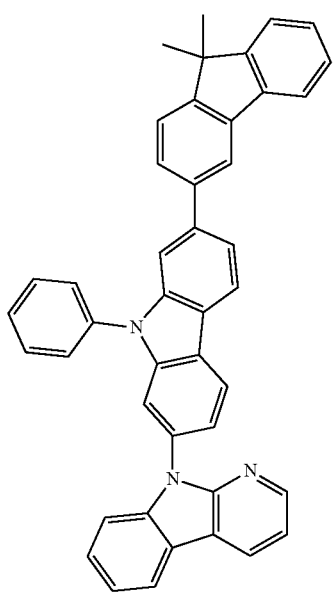

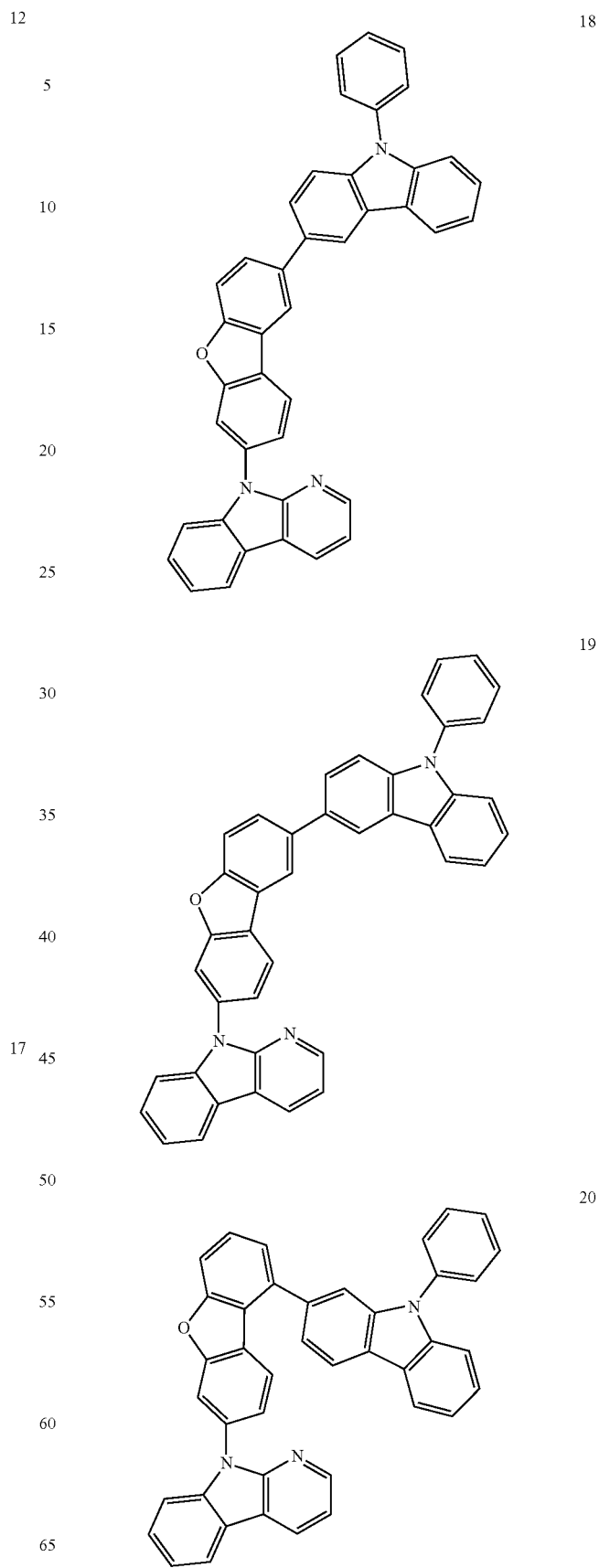

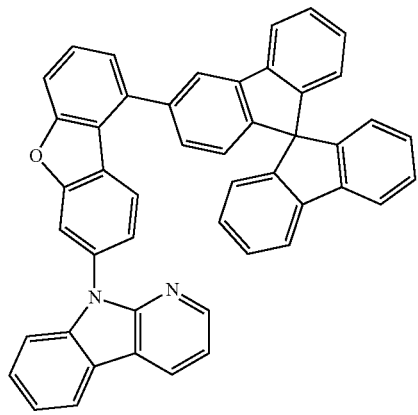
21
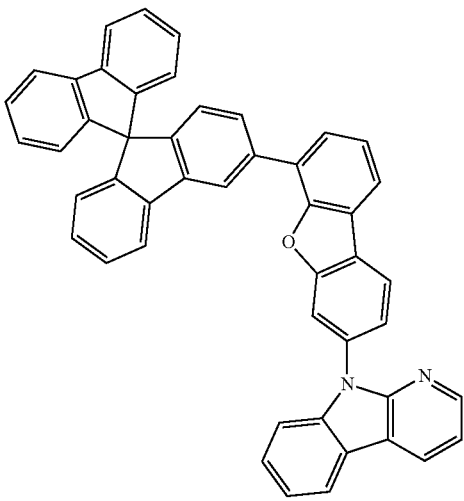
24
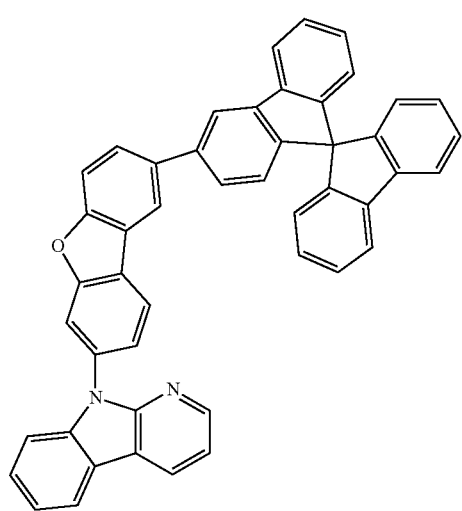
22
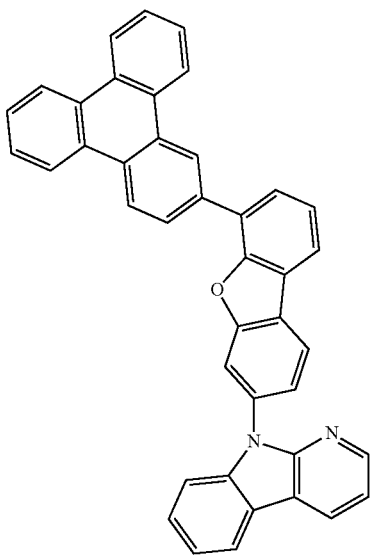
25
23

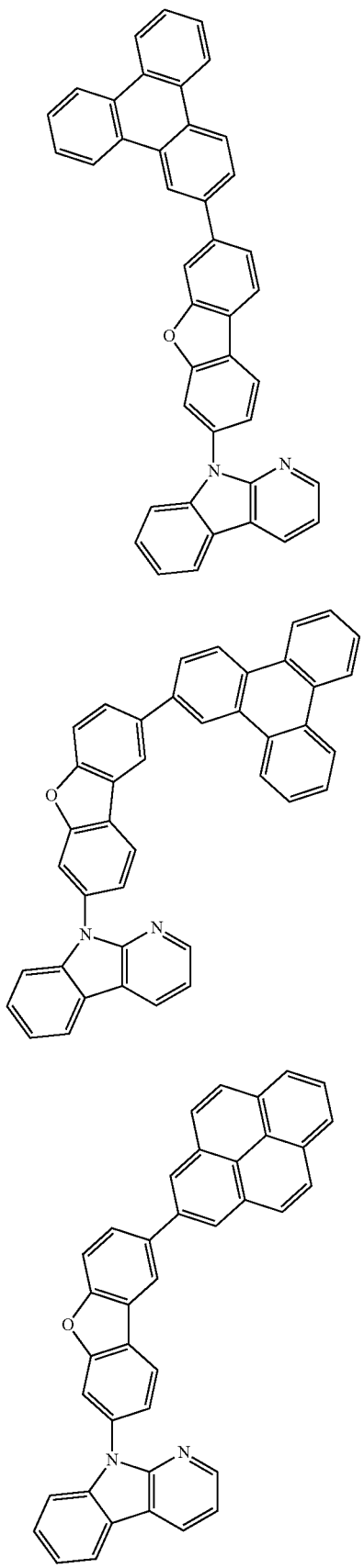
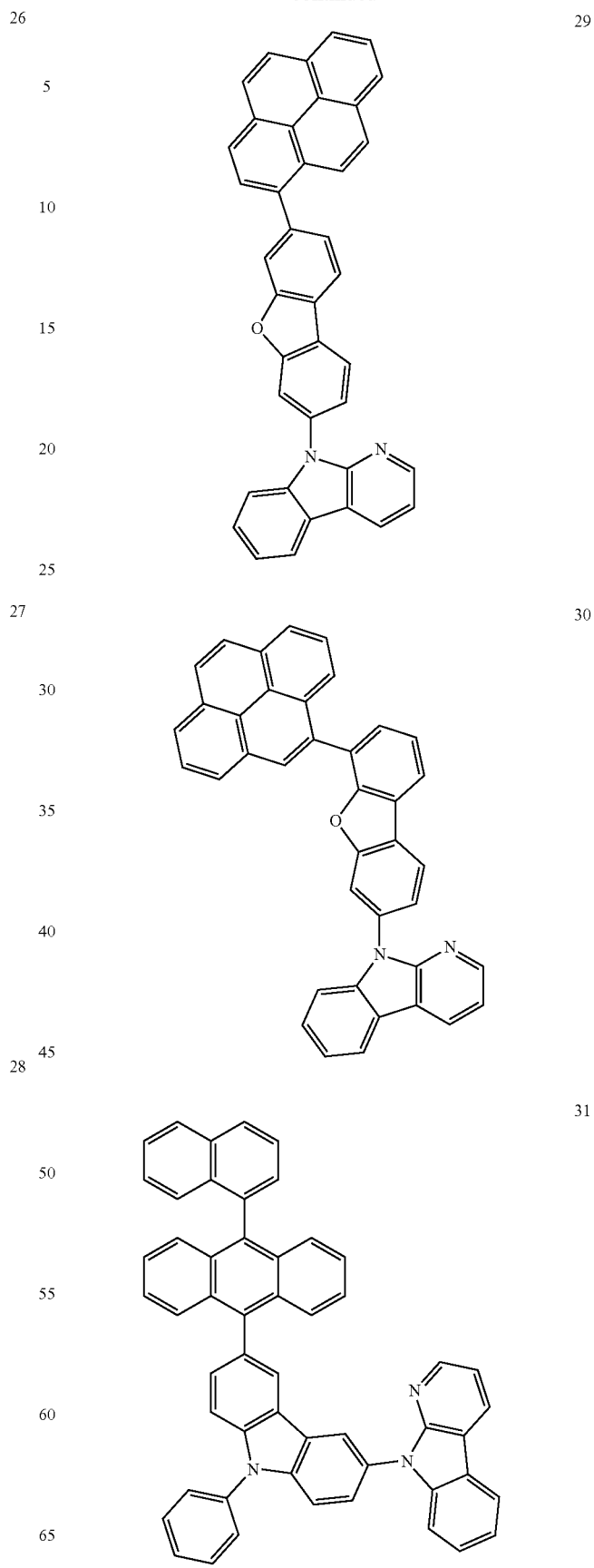

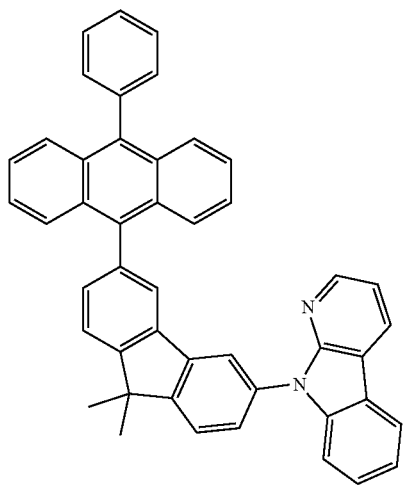
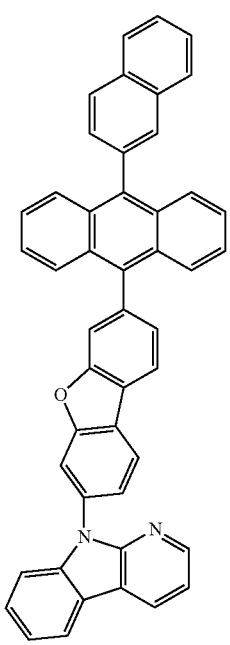
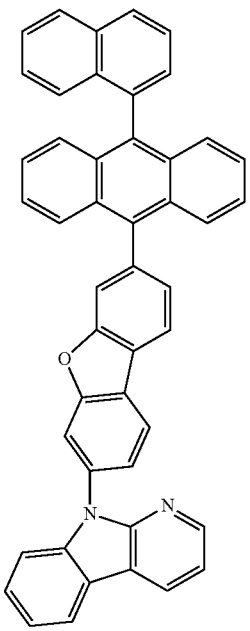

37
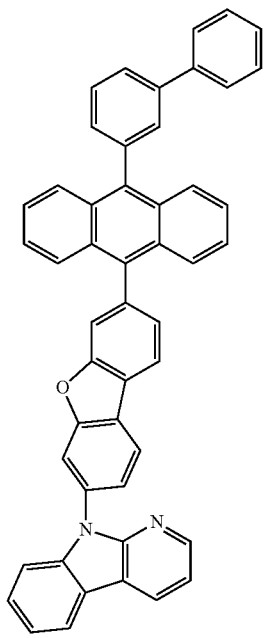
38
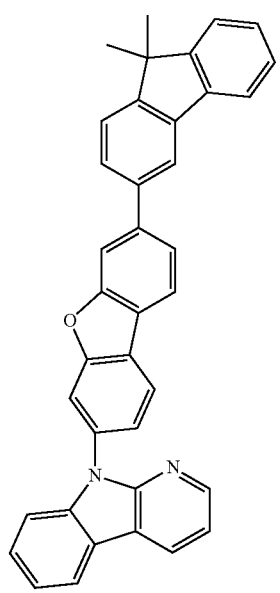
39
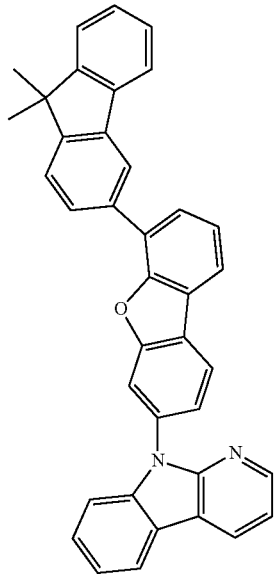
40
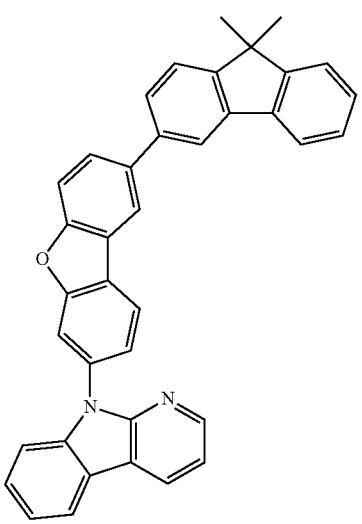
41
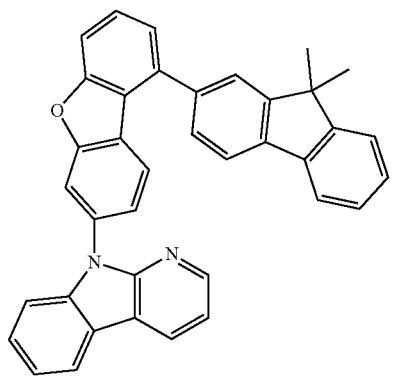

46
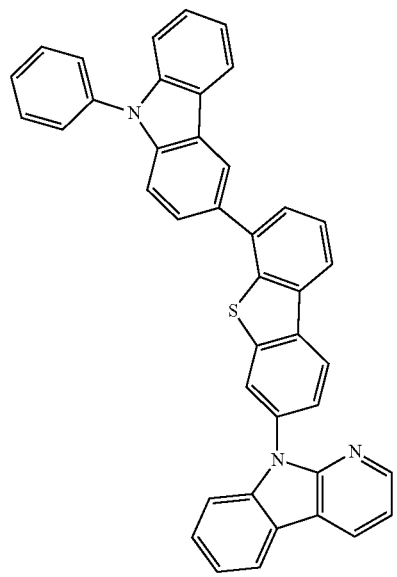
47
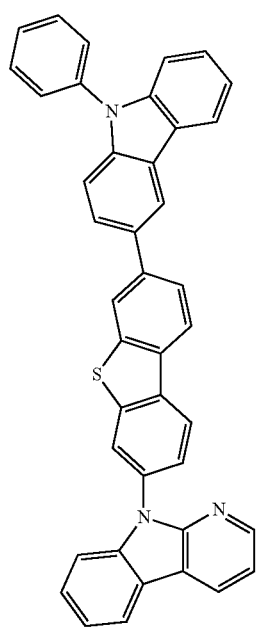
48
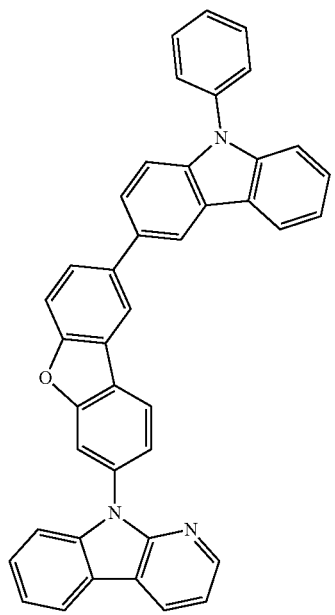
49
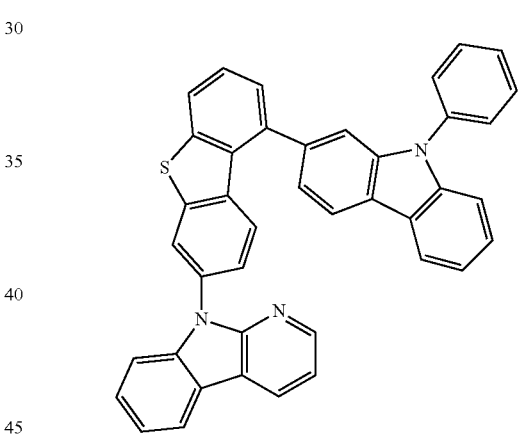
50
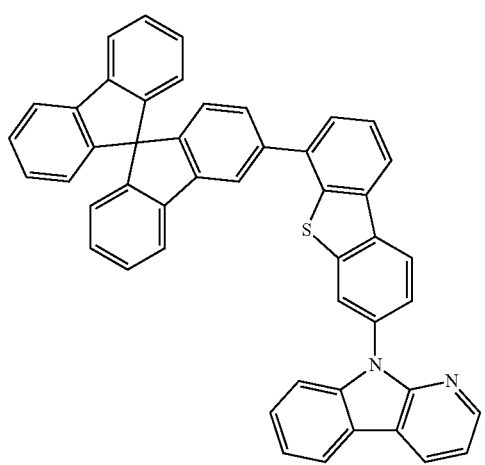

51
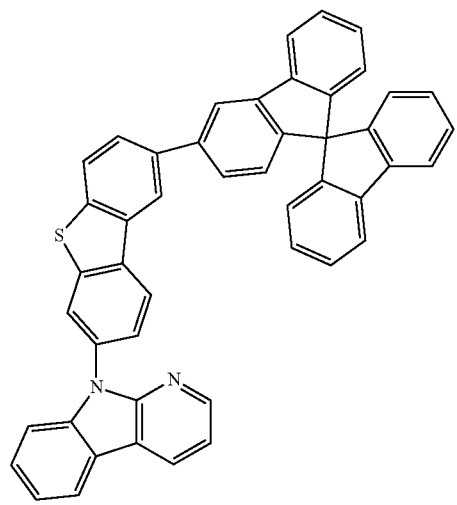
52
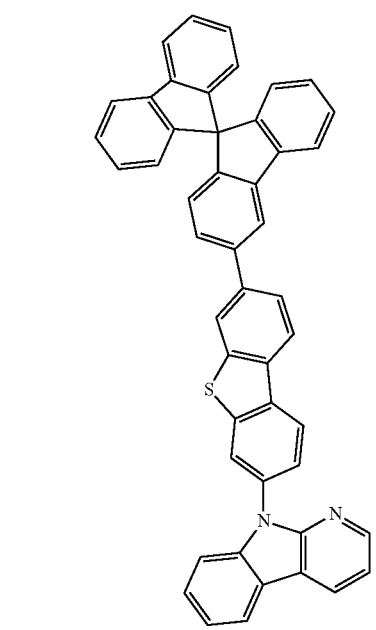
53
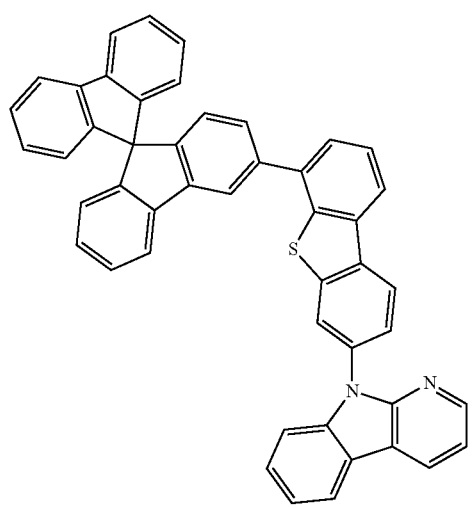
54
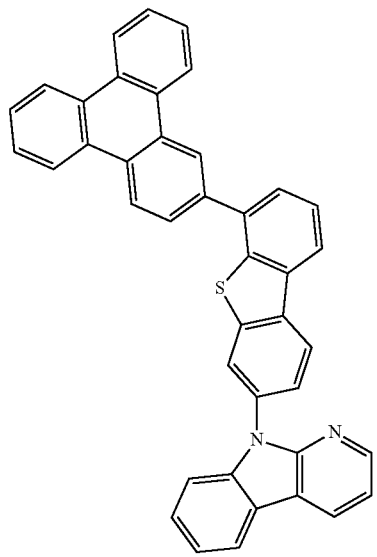
55
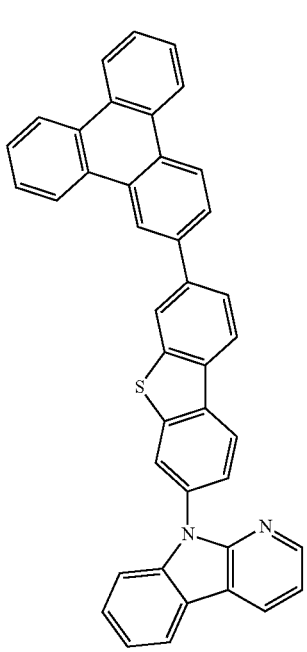
56
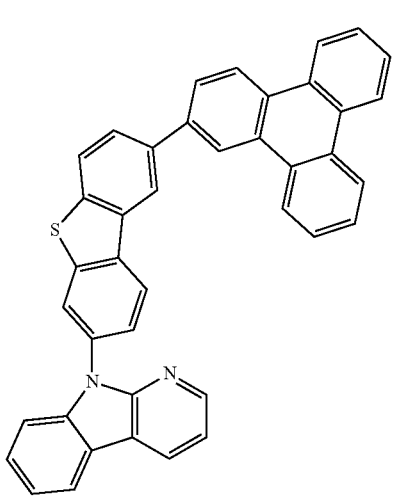

57
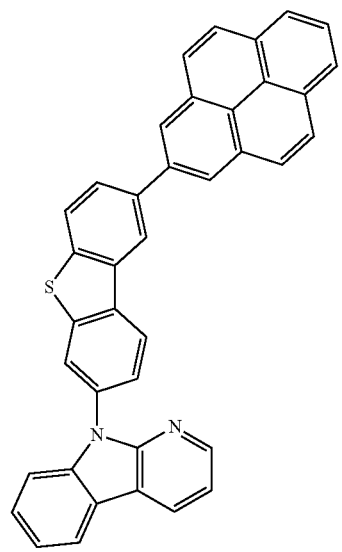
58
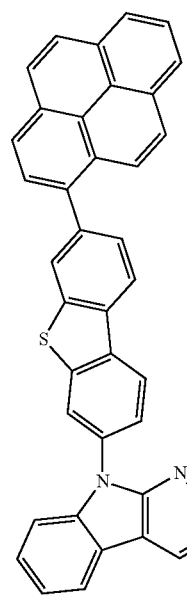
59
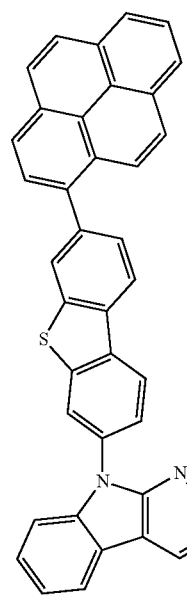
60
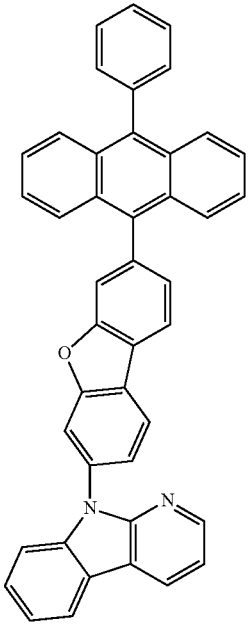
61
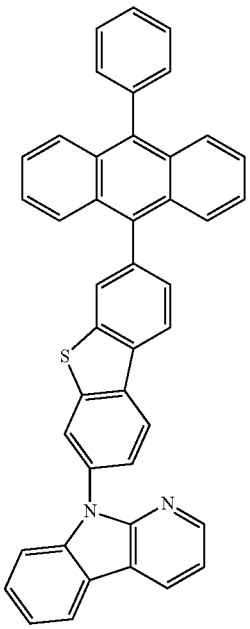

62
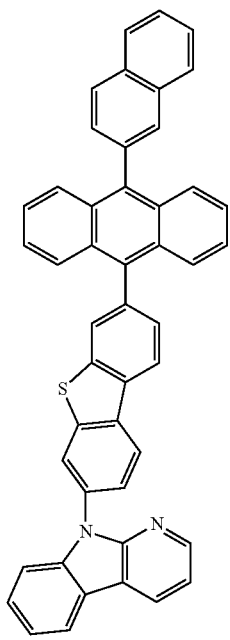
63
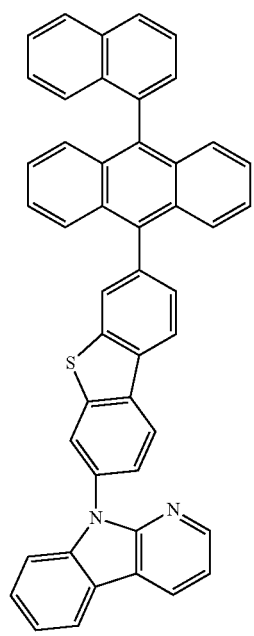
64
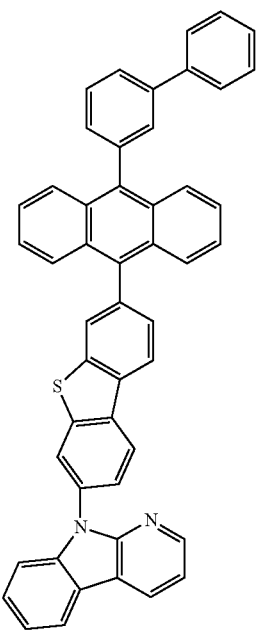
65
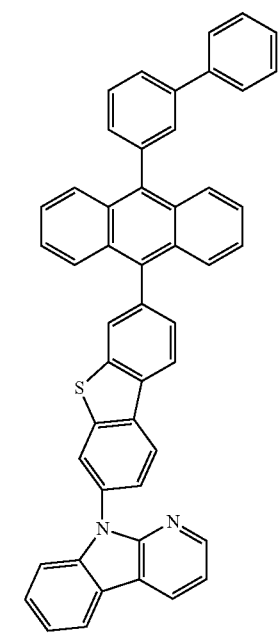

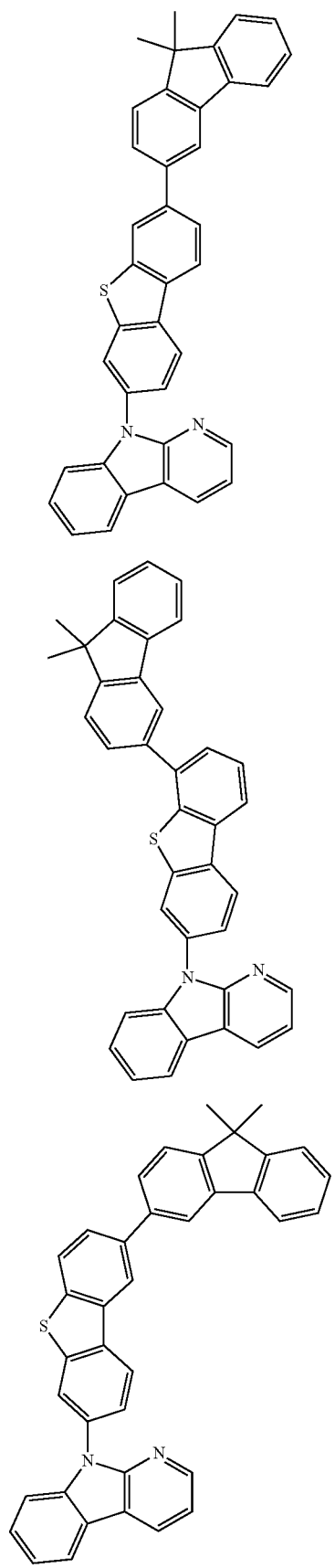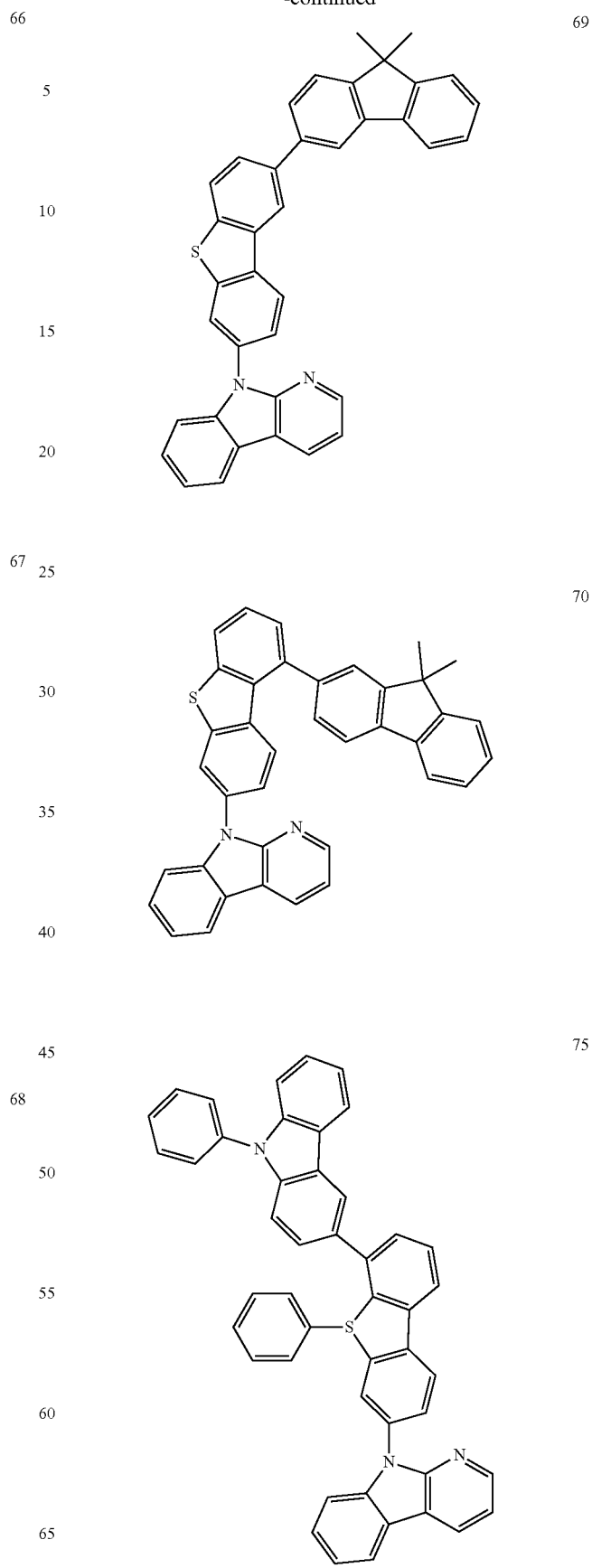

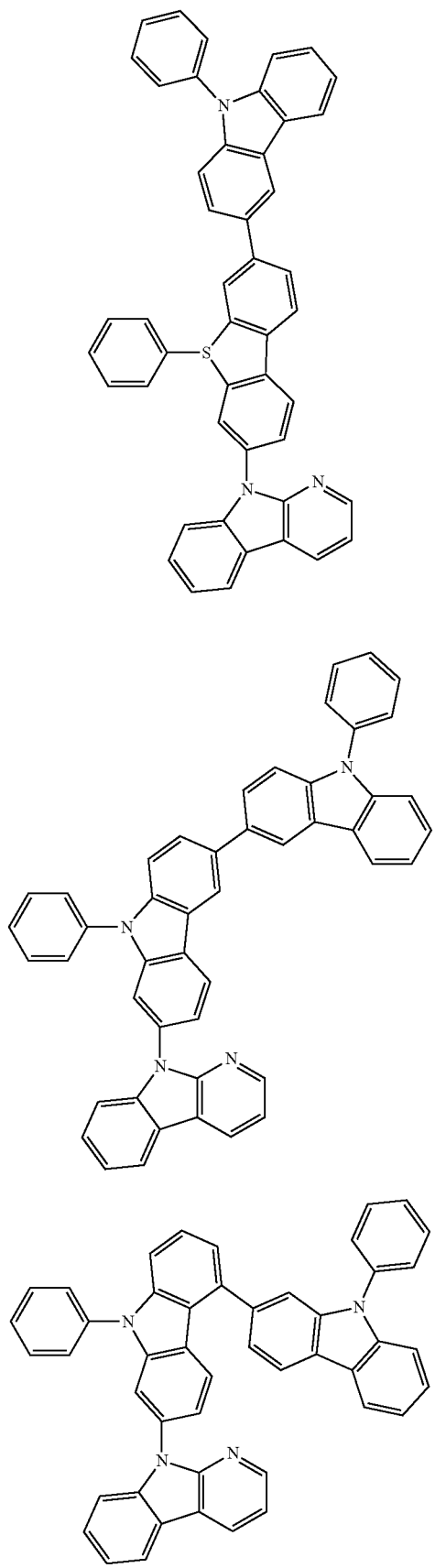
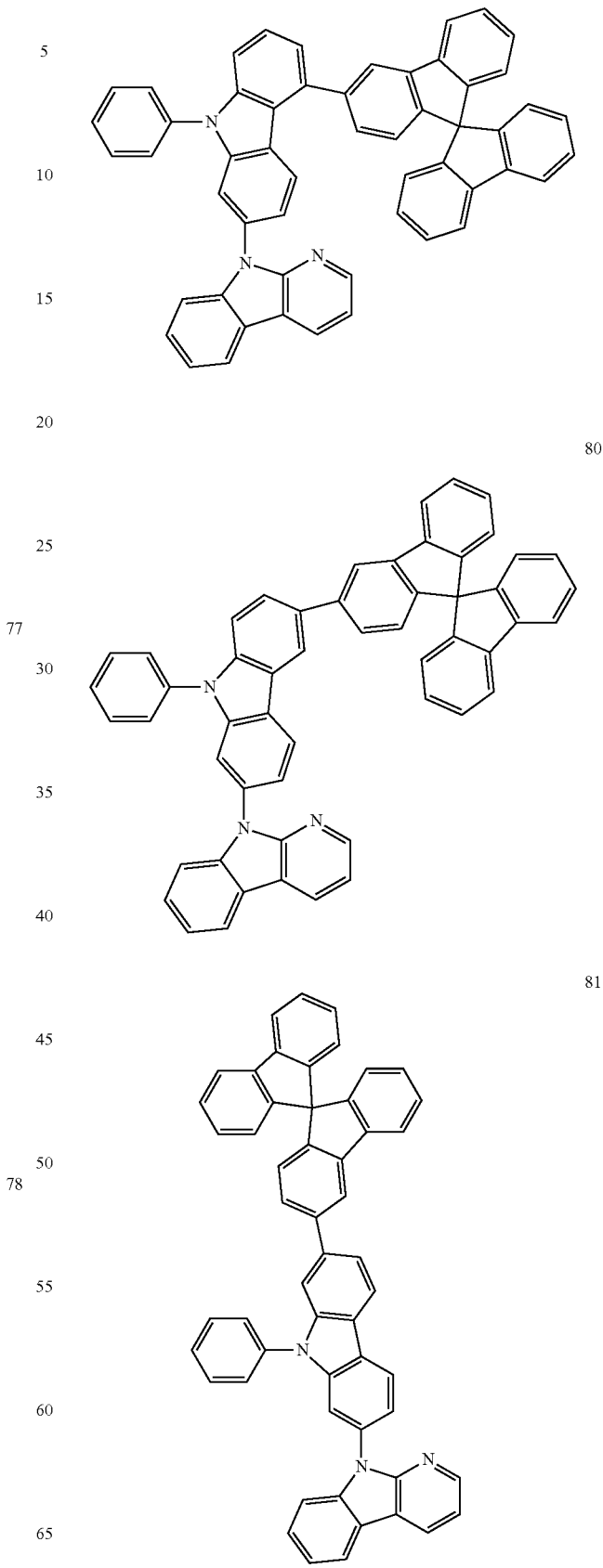

82
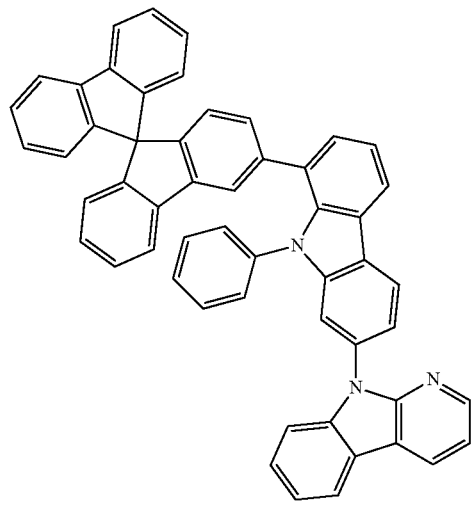
83
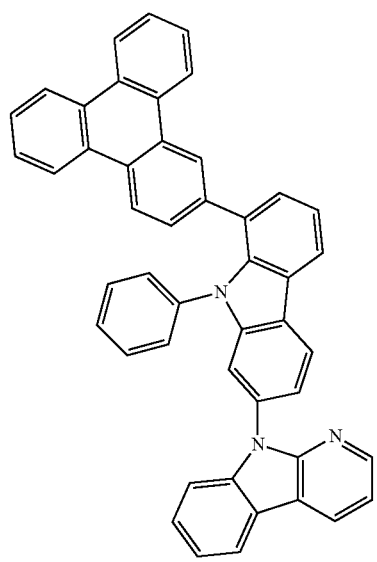
84
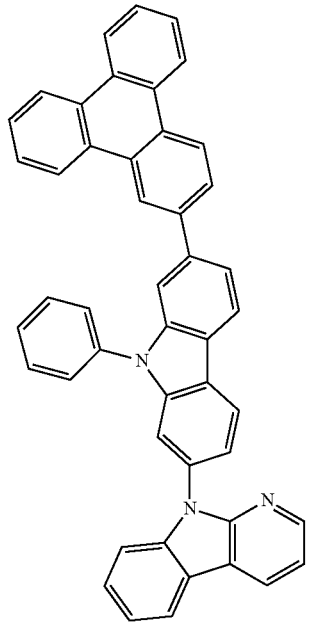
85
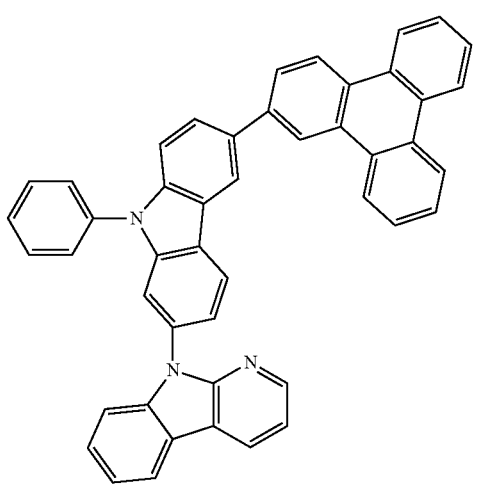
86
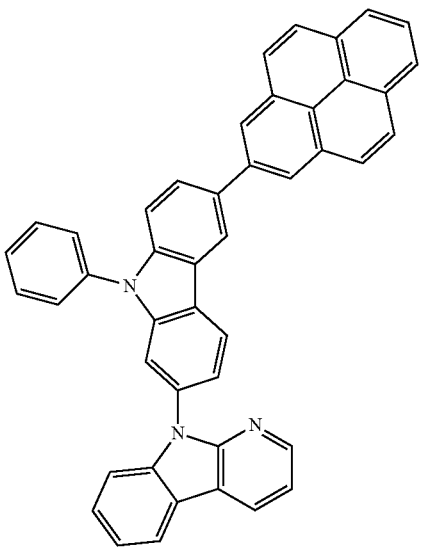

87
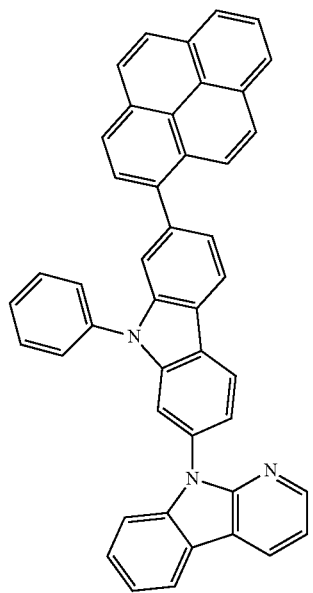
88
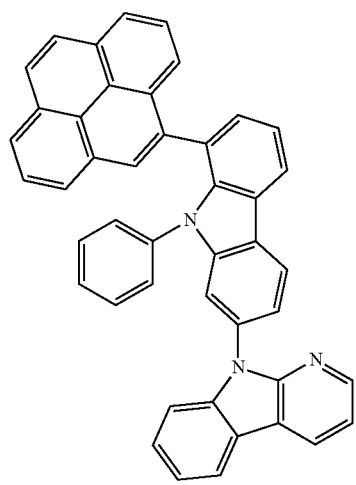
92
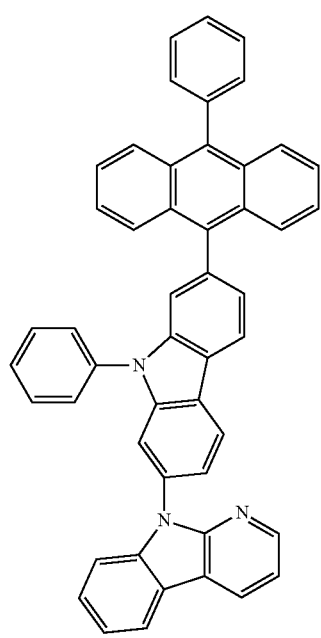
93
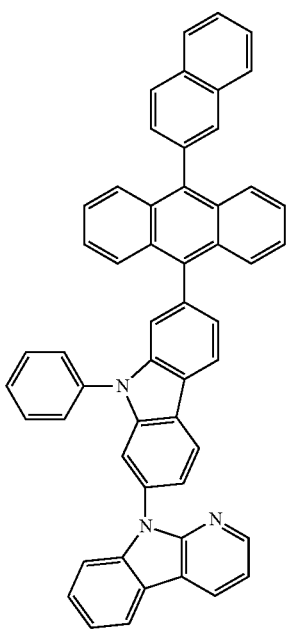

94
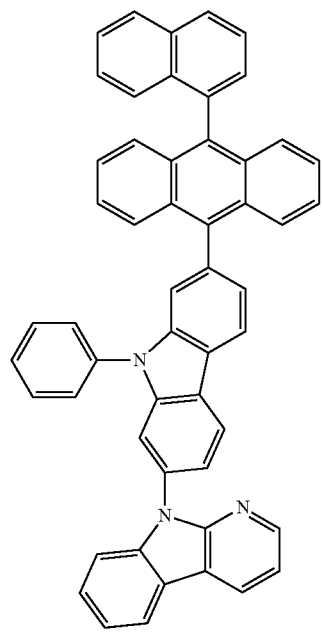
96
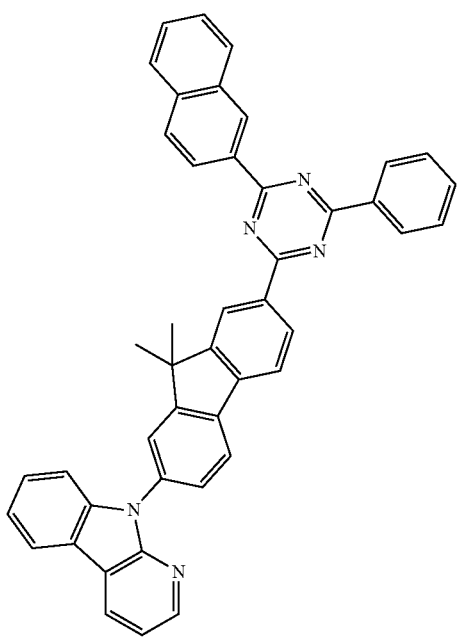
95
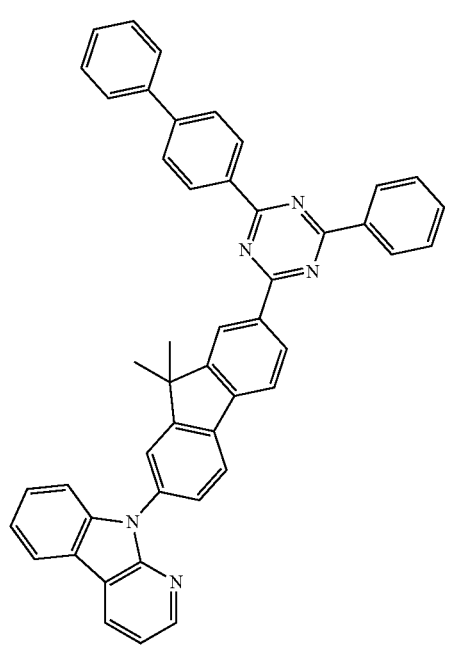
97
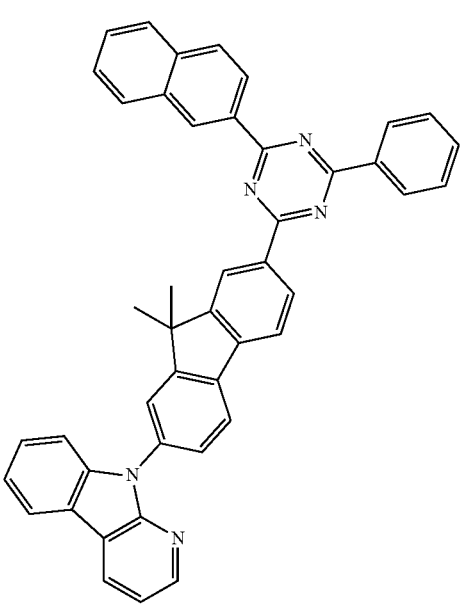

98
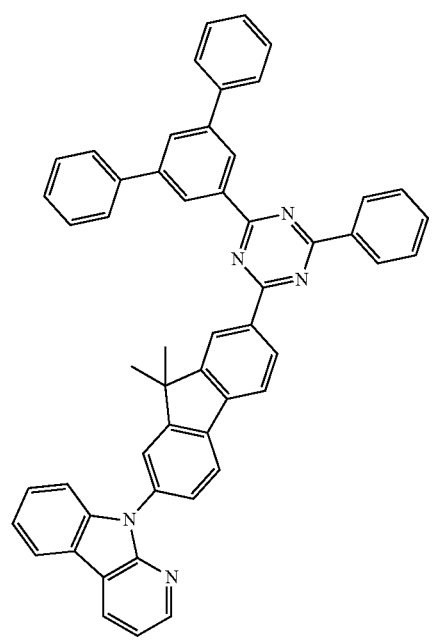
99
100
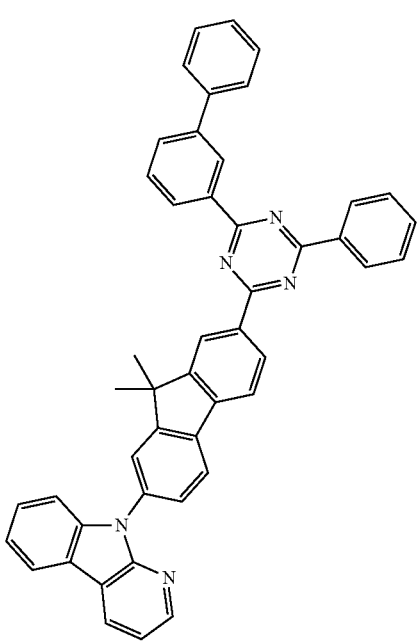
101

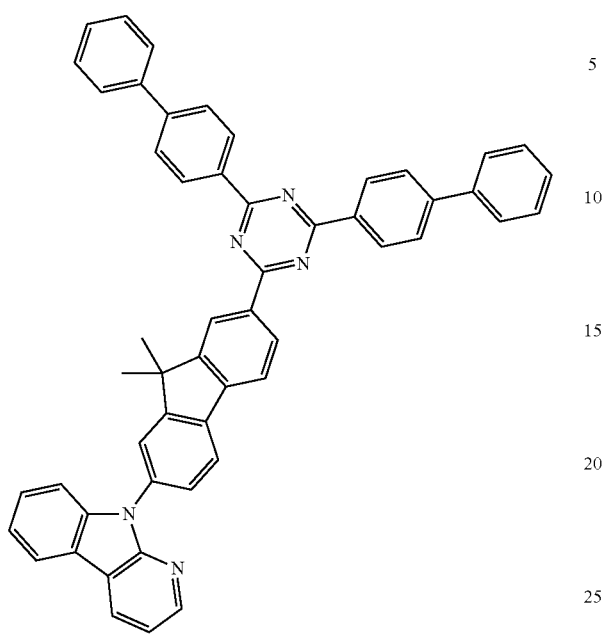
102
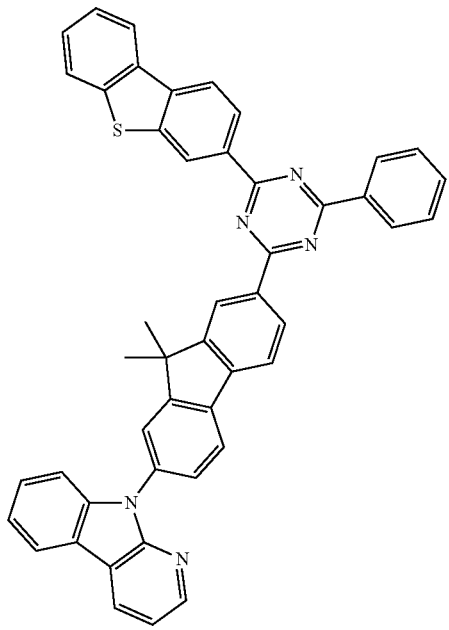
104
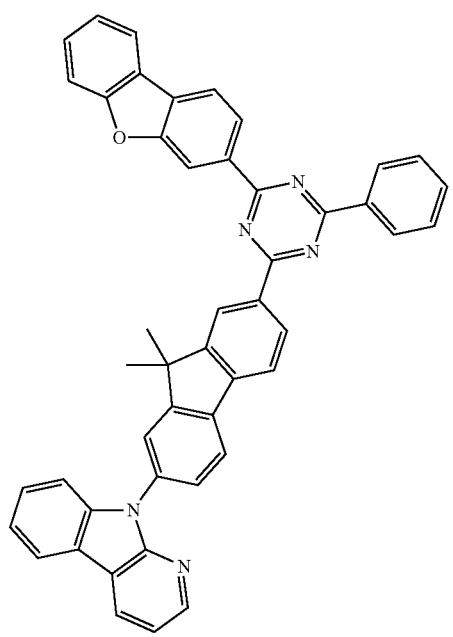
103
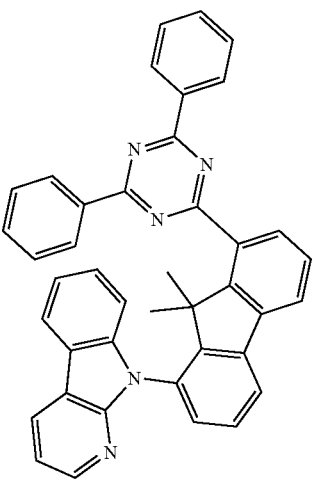
105

106
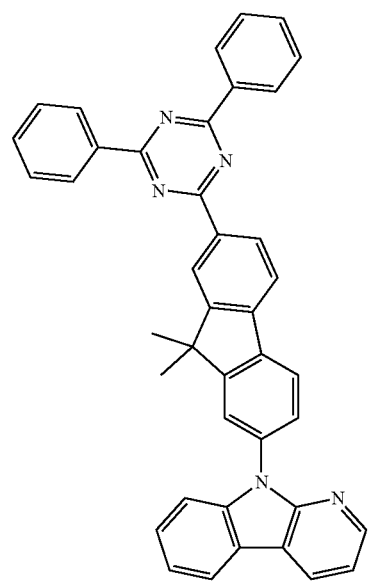
107
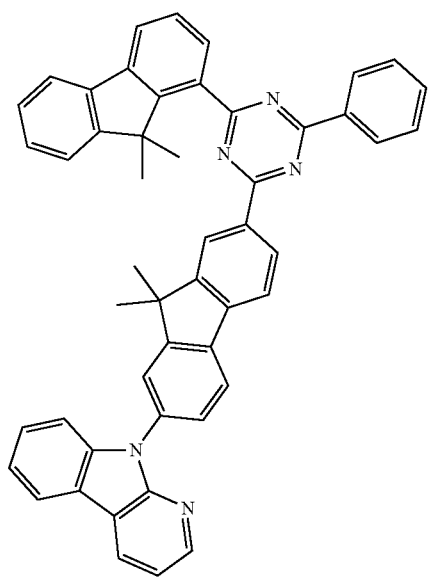
108
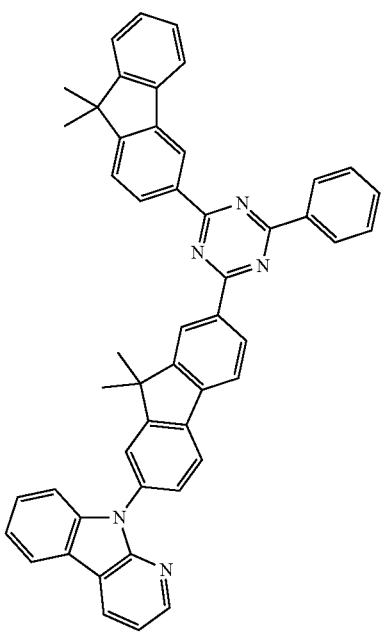
109
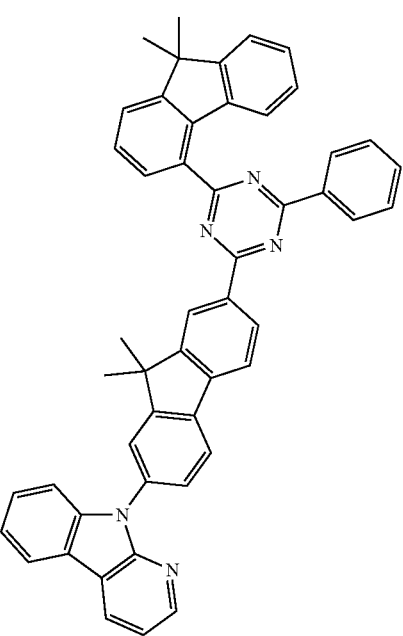

110
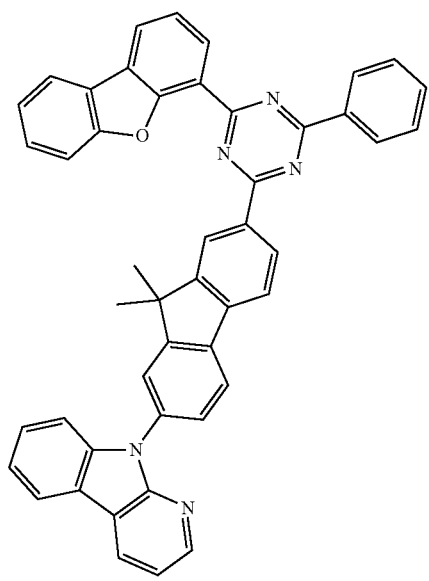
111
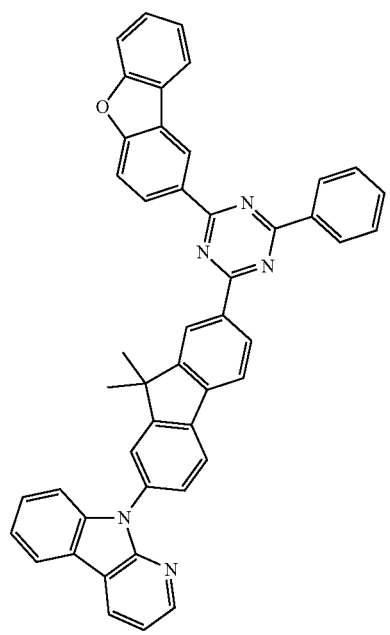
112
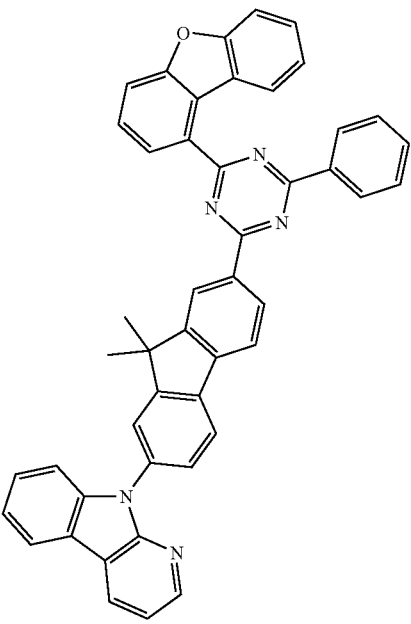
113
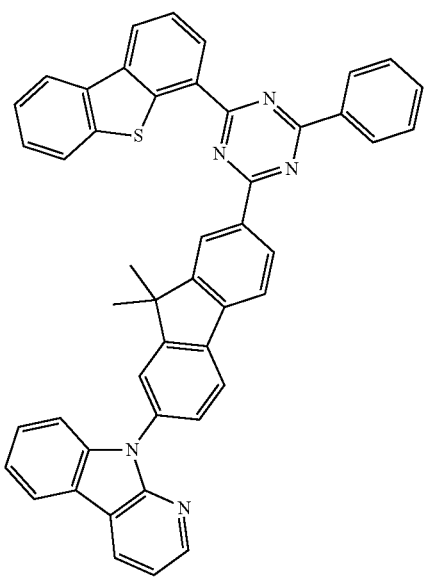

114
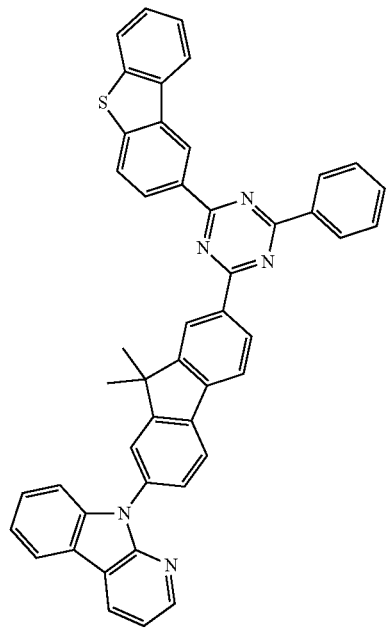
115
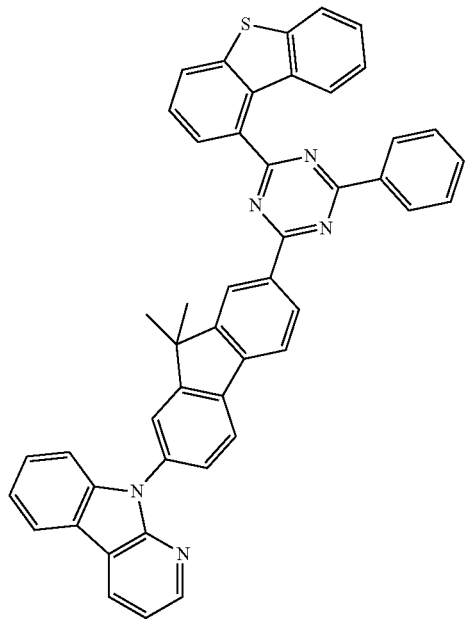
116
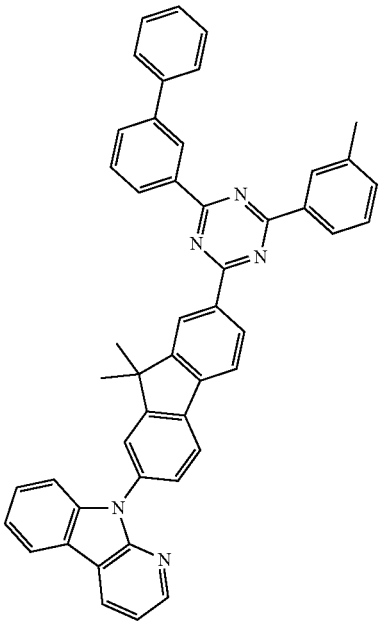
117
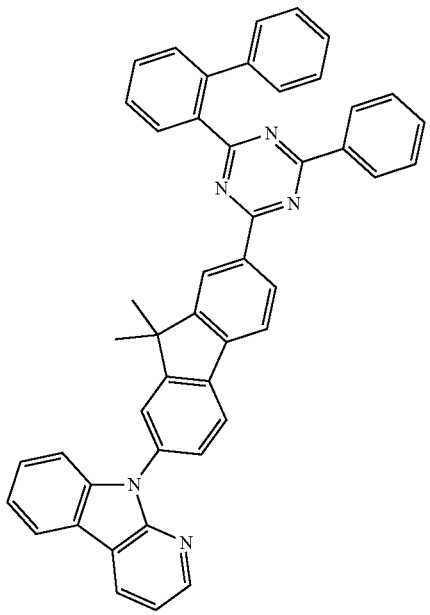

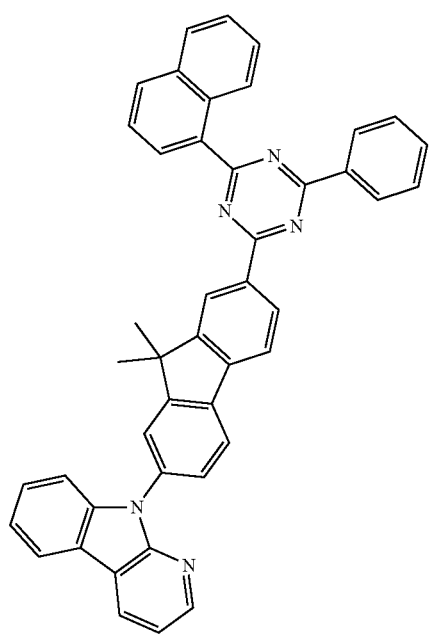
118
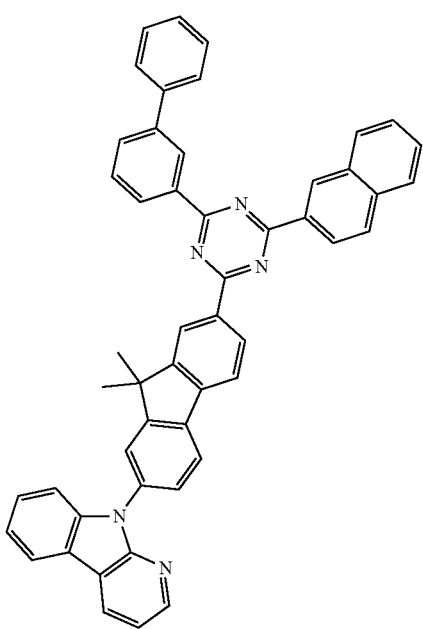
120
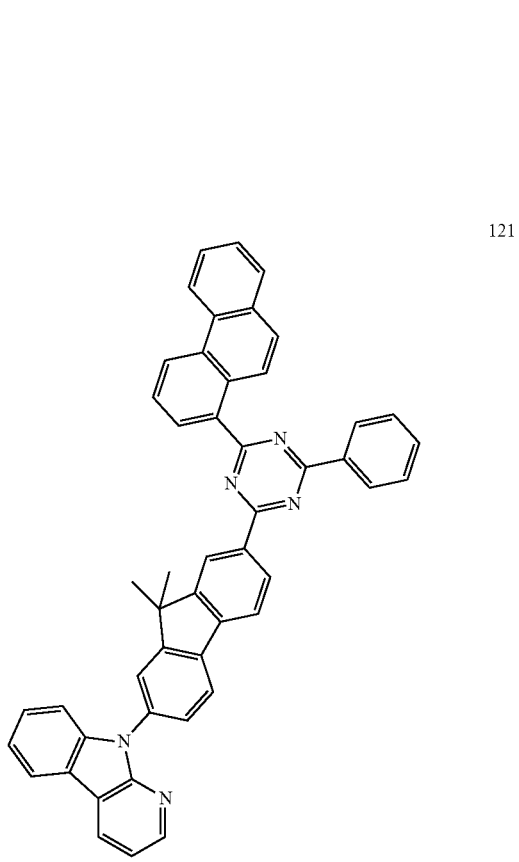
121
119

122
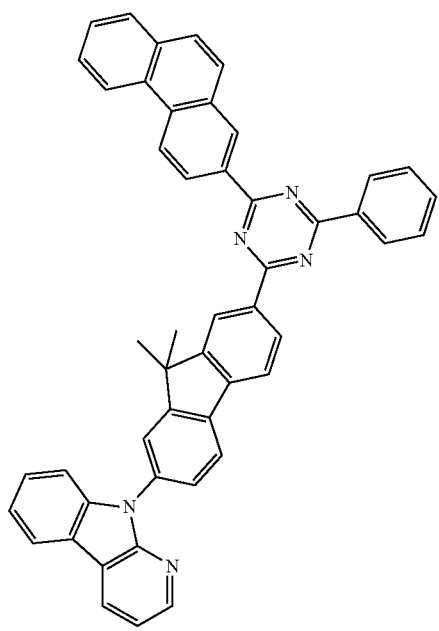
123
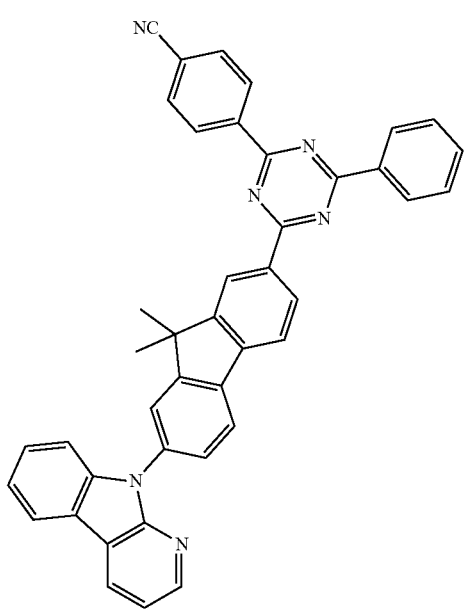
124
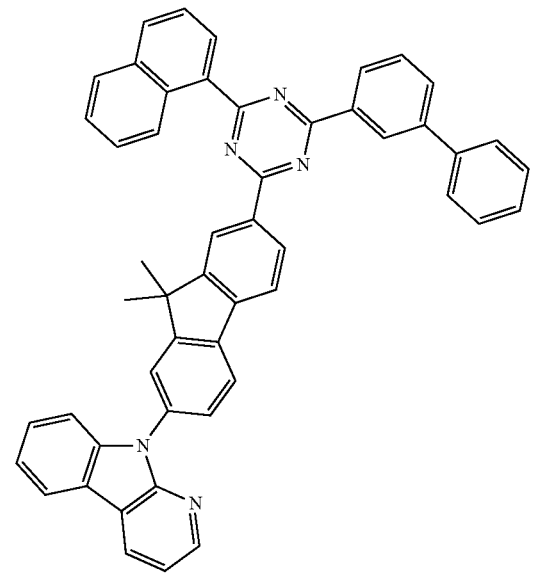
125
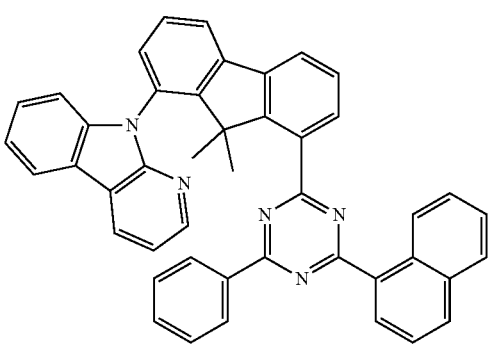
126
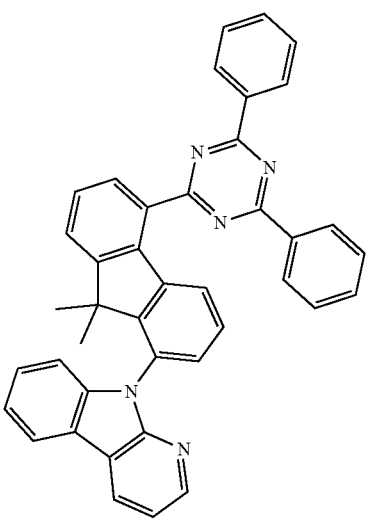

127
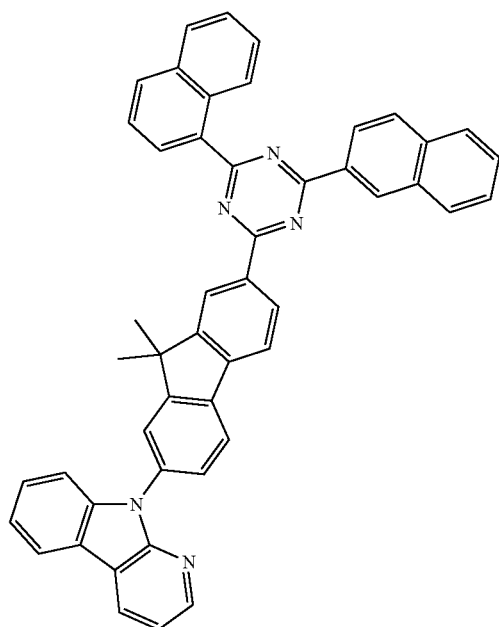
129
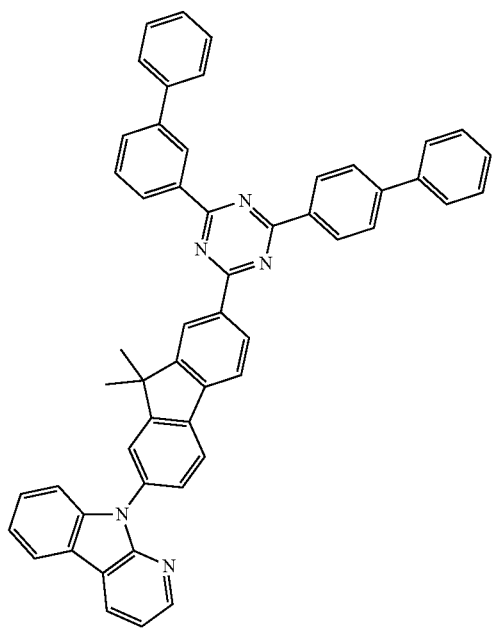
128
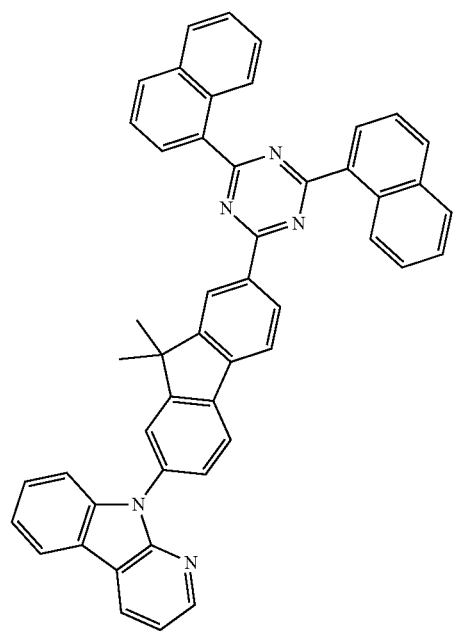
130
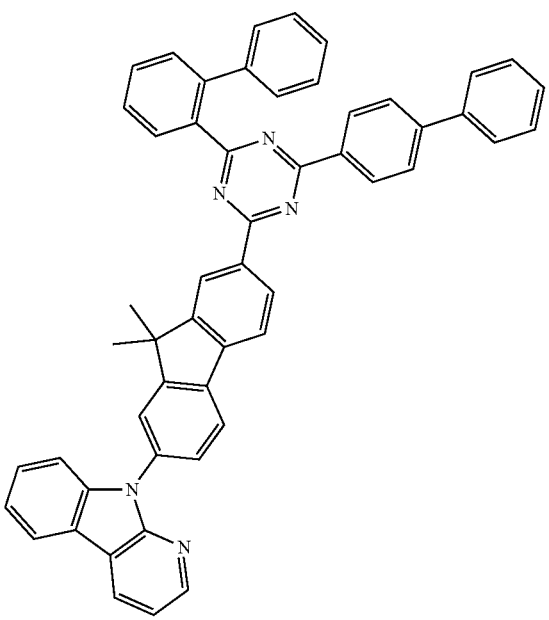

71
-continued
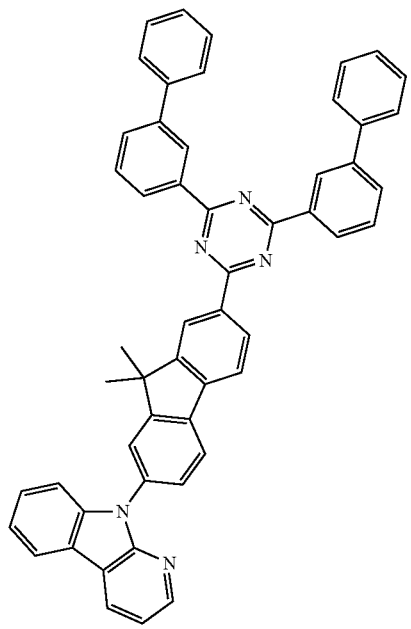
131
72
-continued
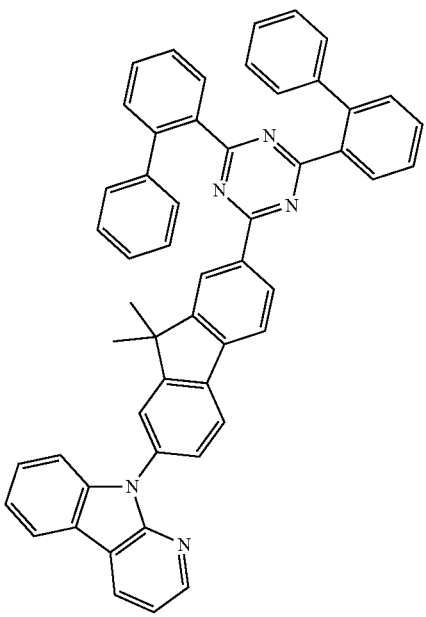
133
132
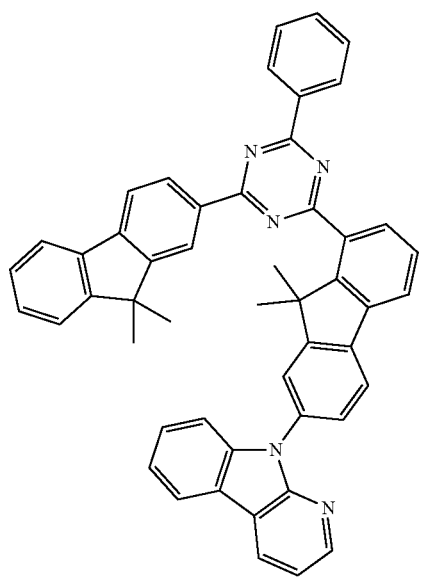
134

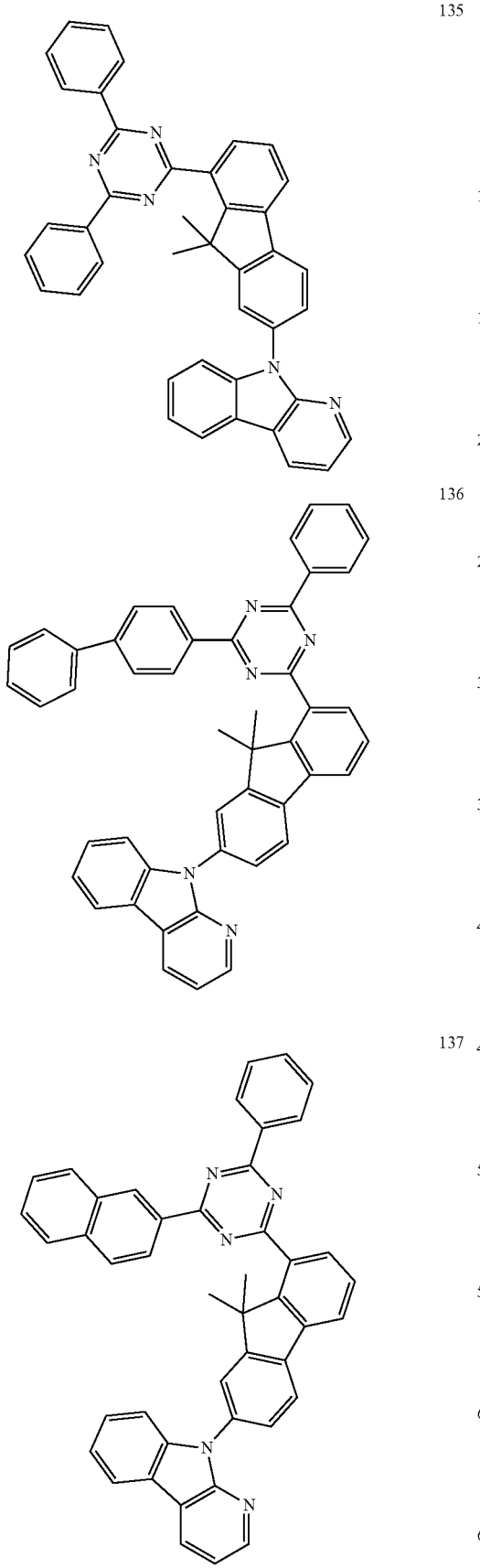

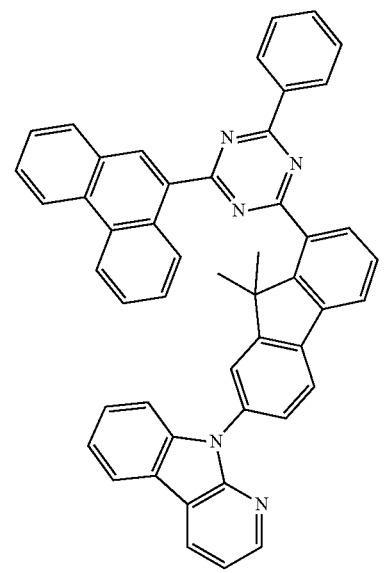
140
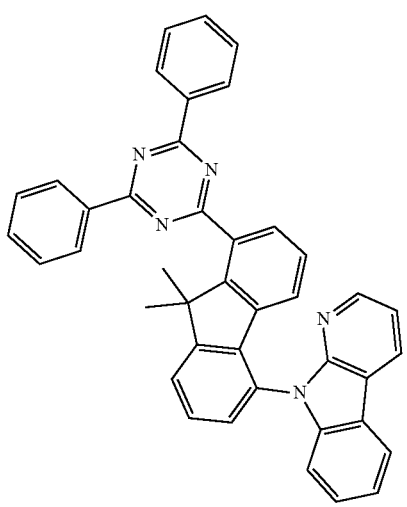
141
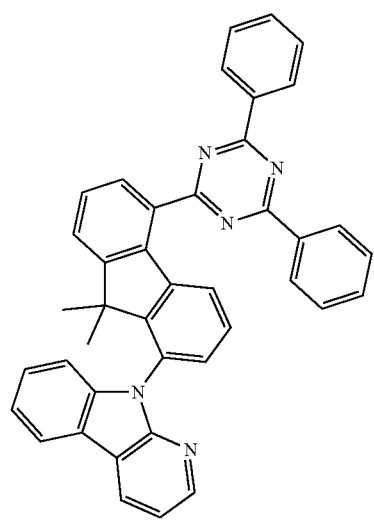
142
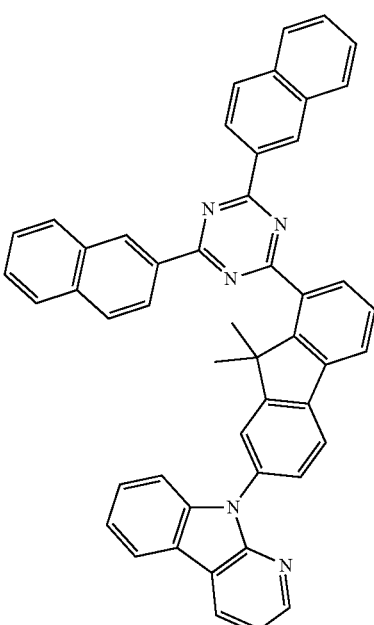
143
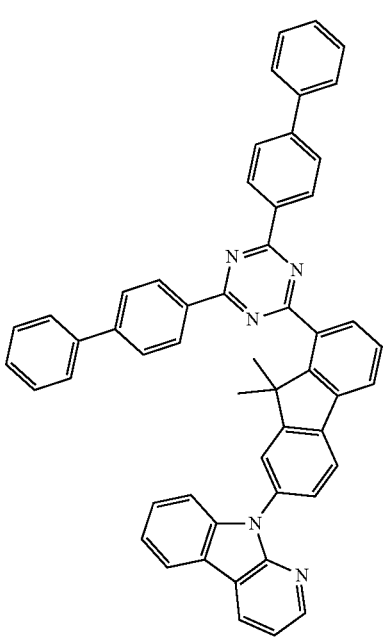
144

145
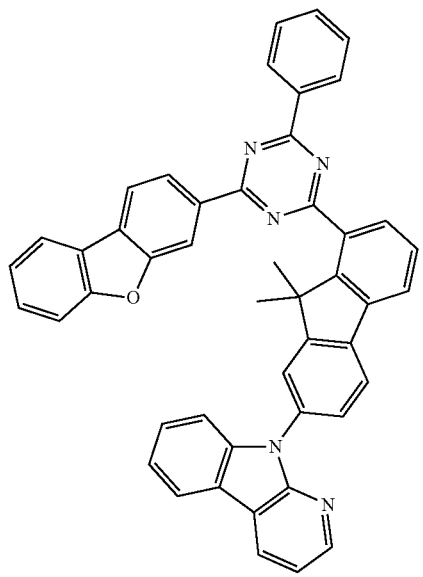
146
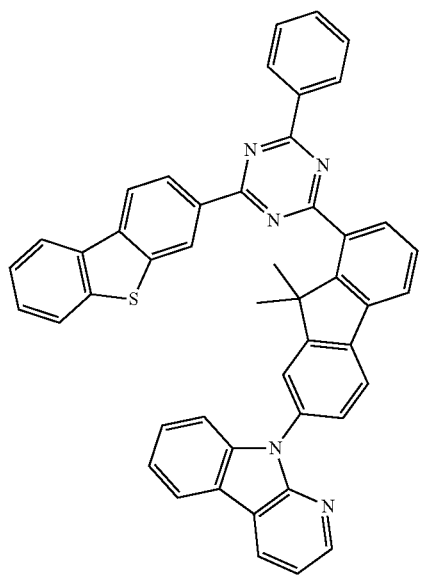
147
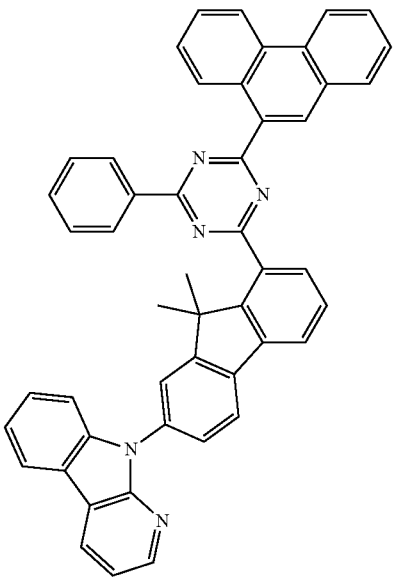
148
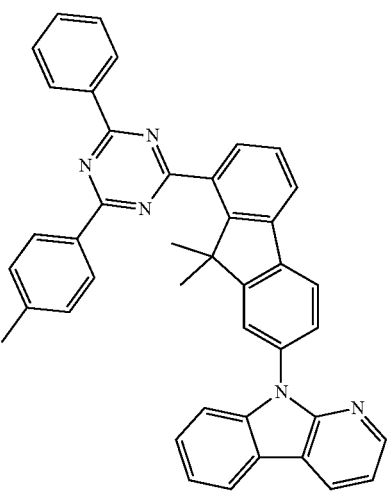
149
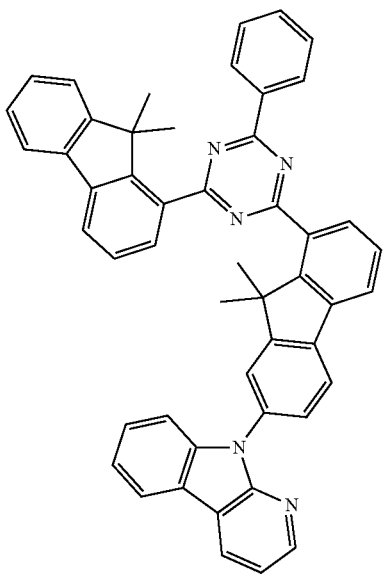

150
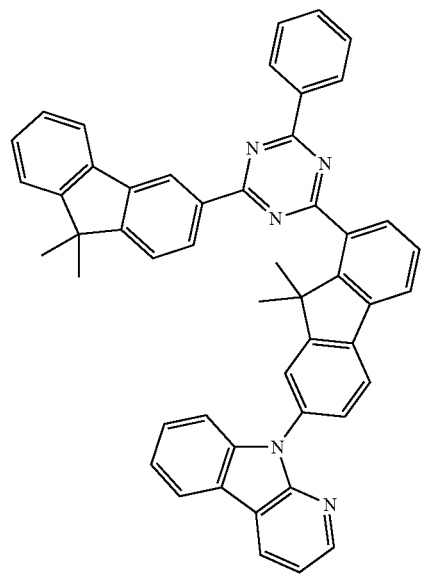
152
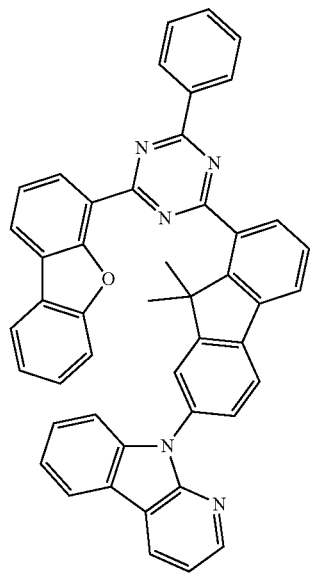
151
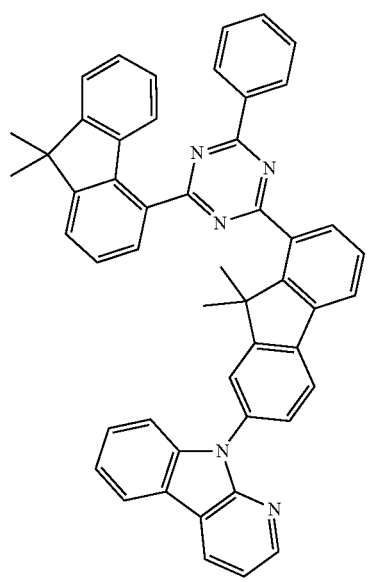
153
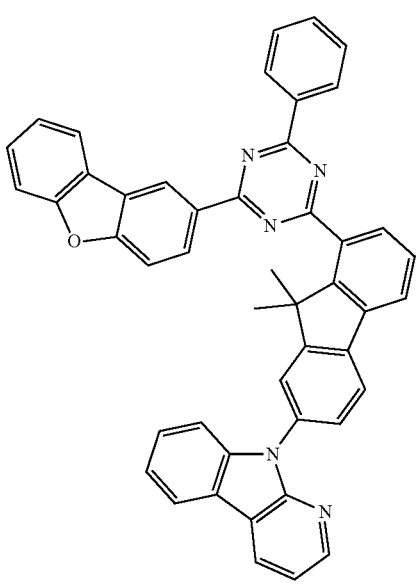

154
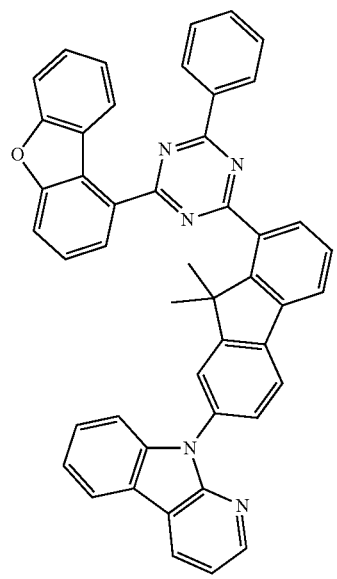
155
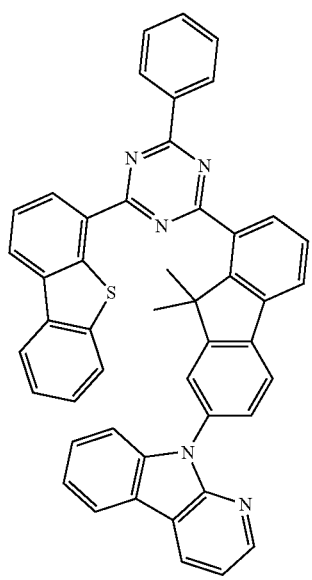
156
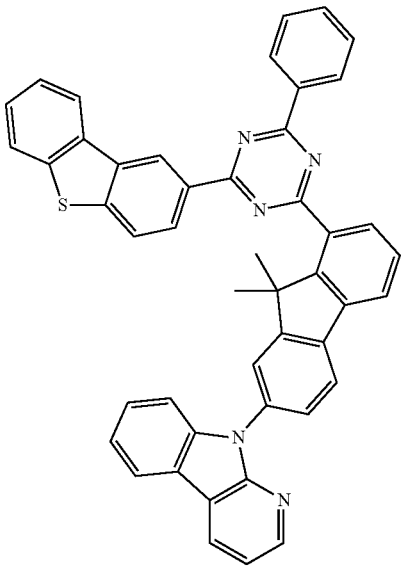
157
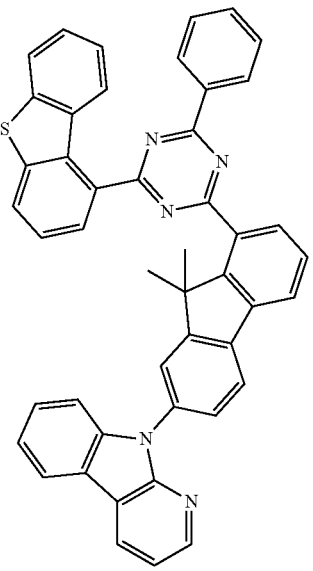

158
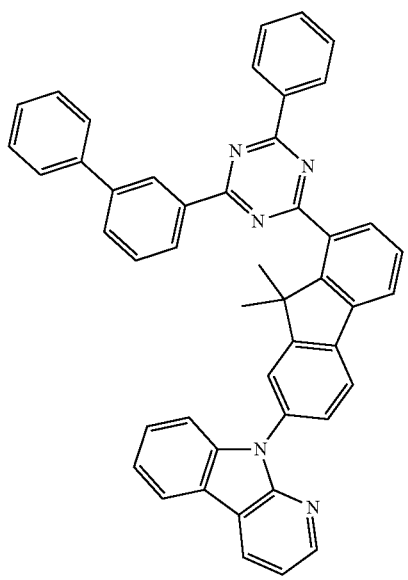
159
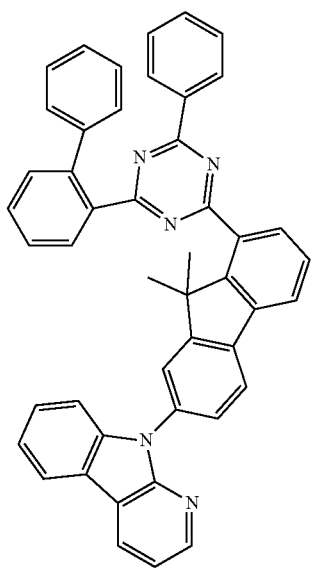
160
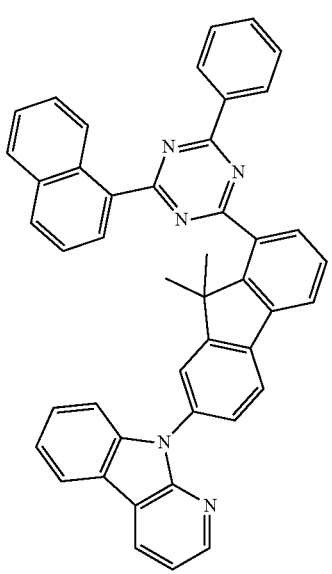
161
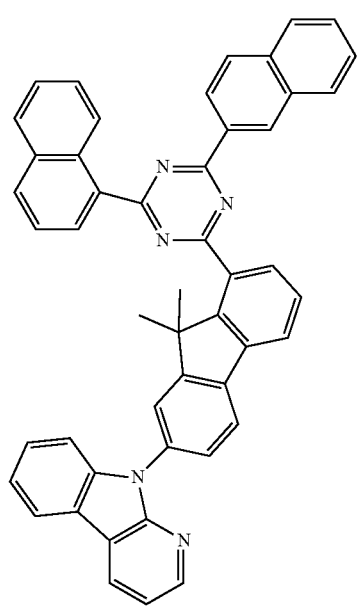

162
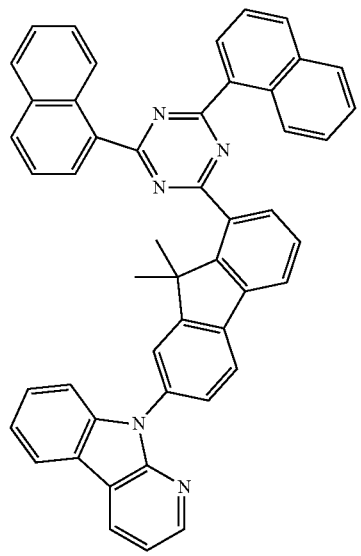
163
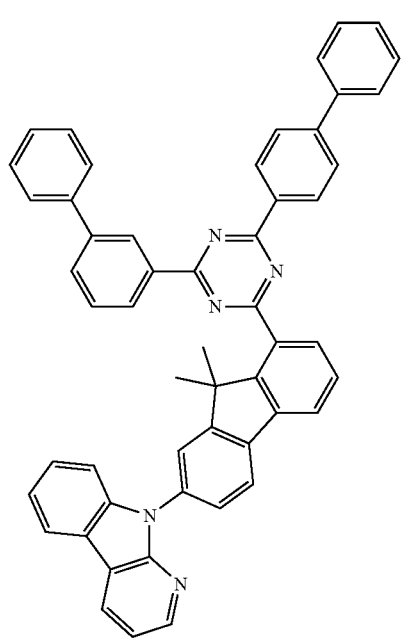
164
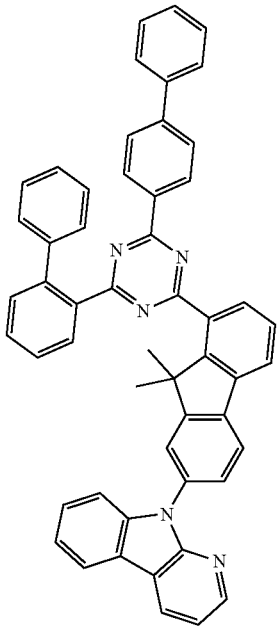
165
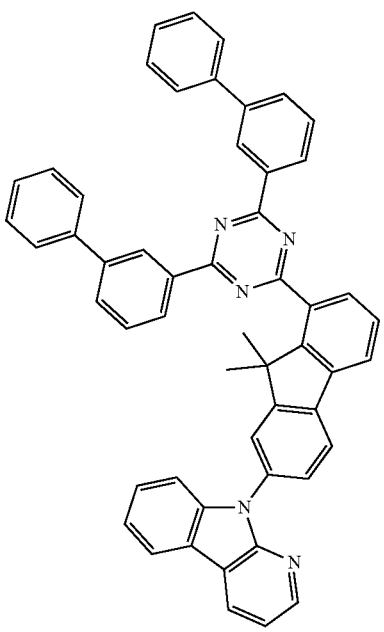

166
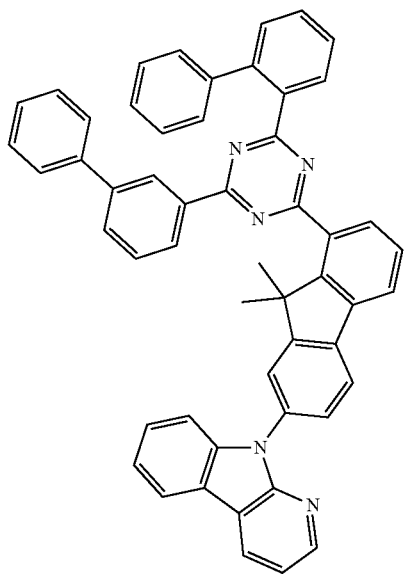
167
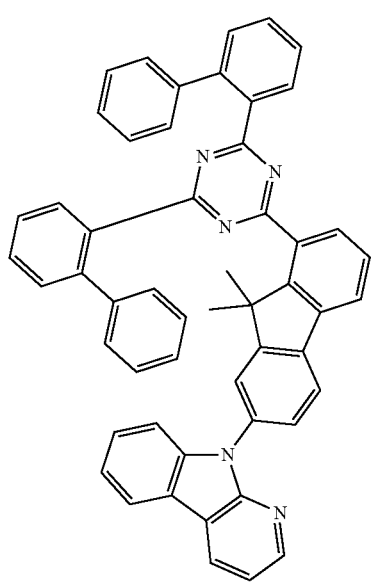
168
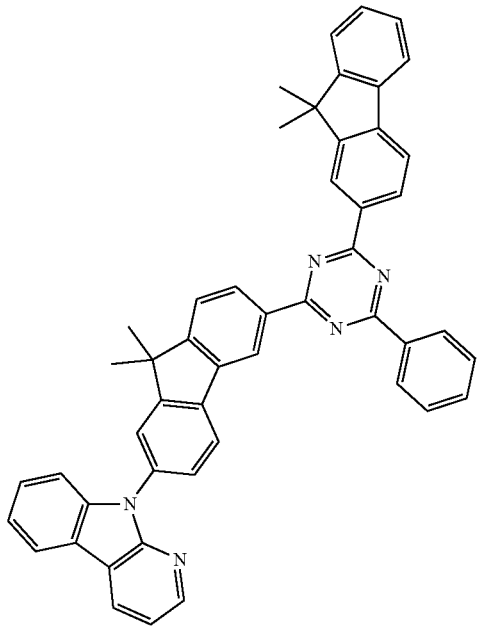
169
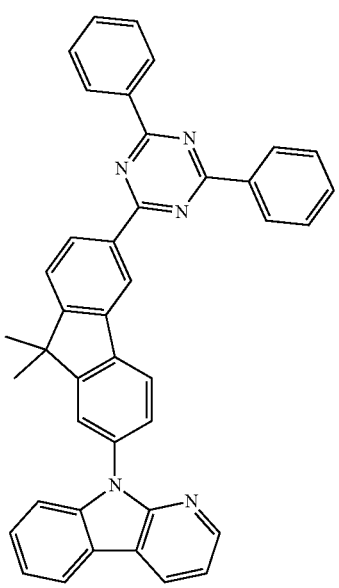

170
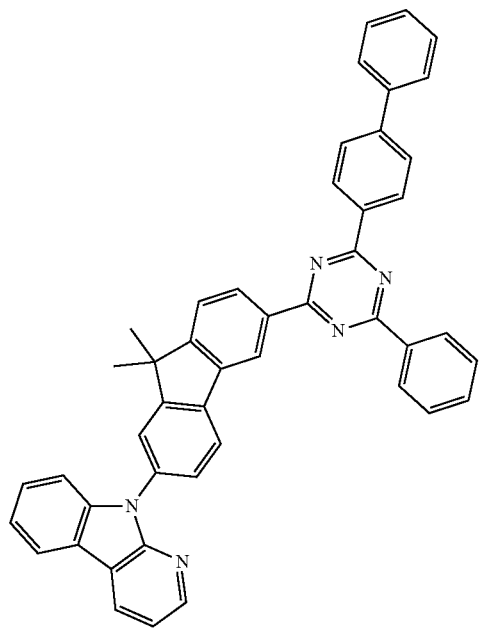
172
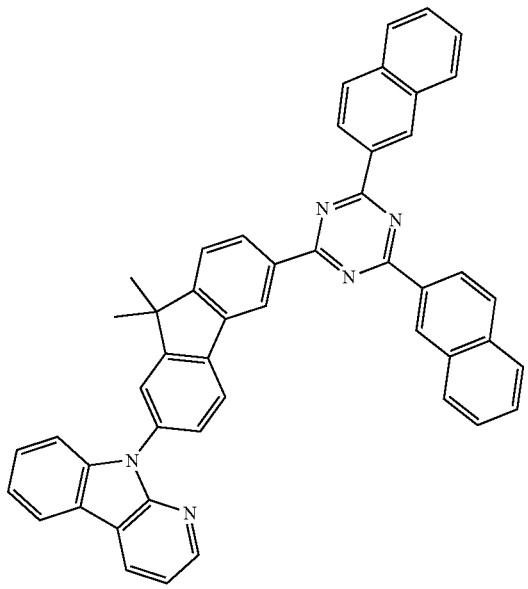
171
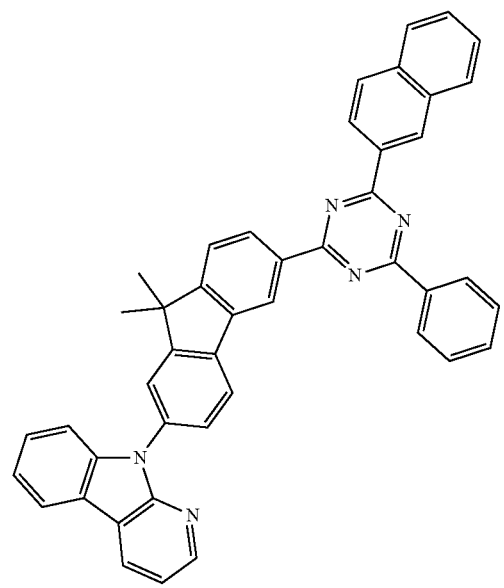
173
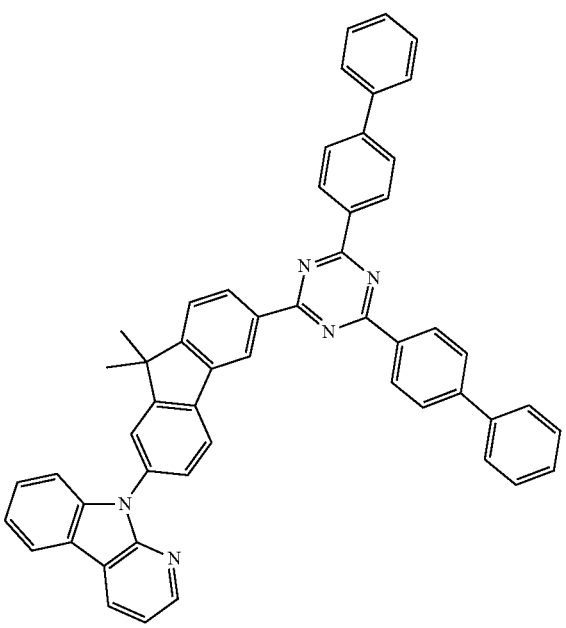

174
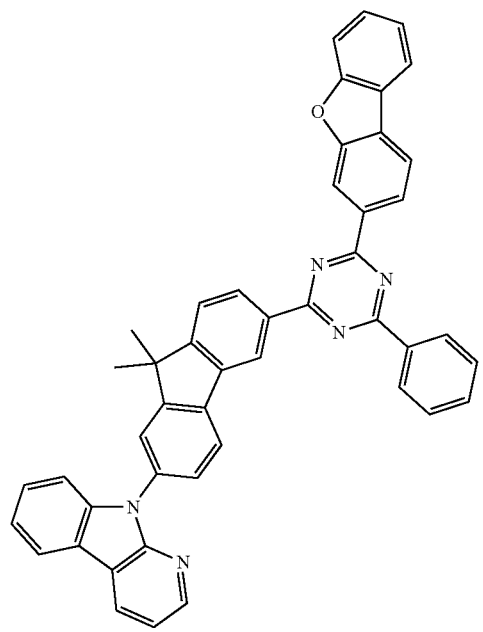
175
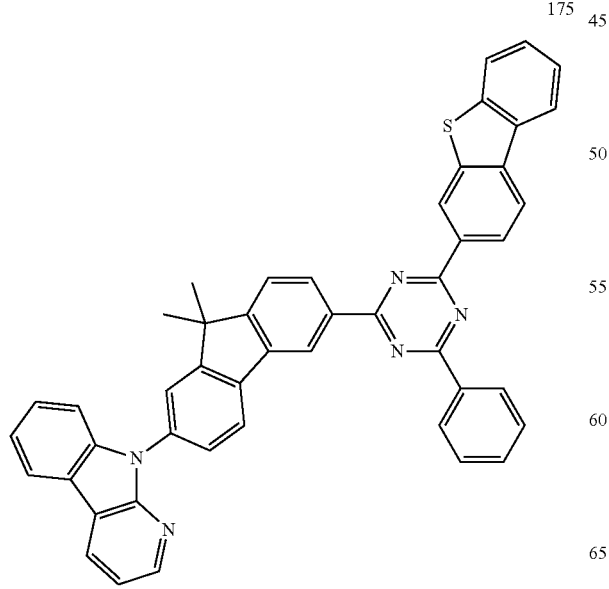
176
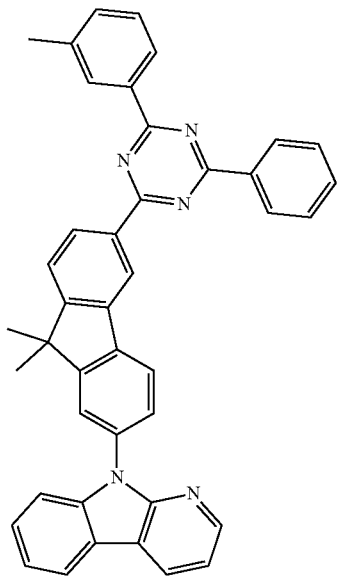
177
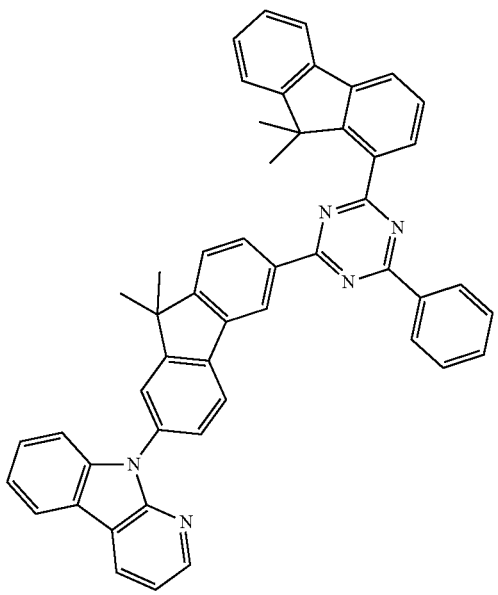

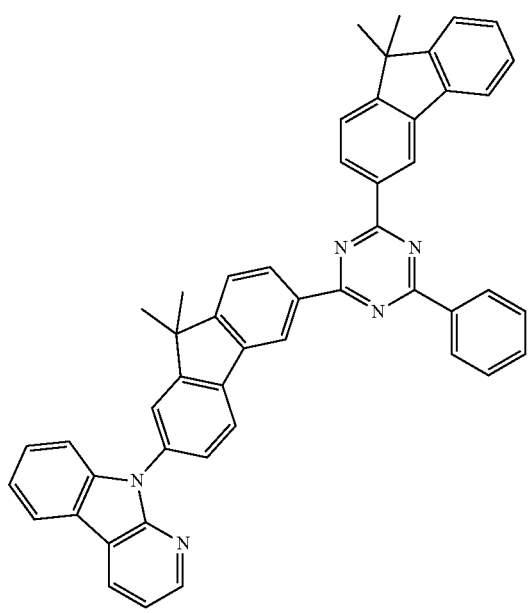
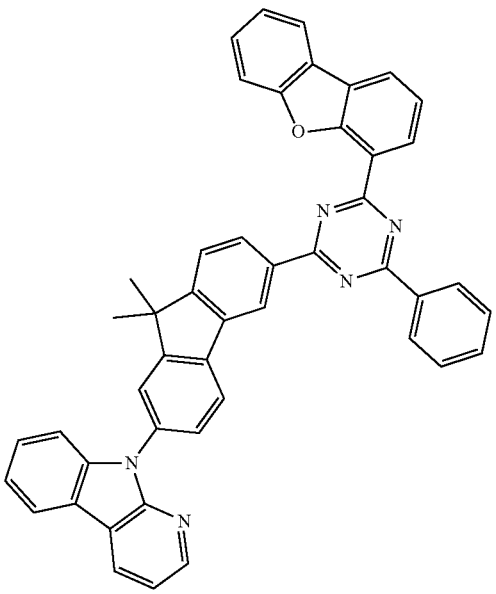
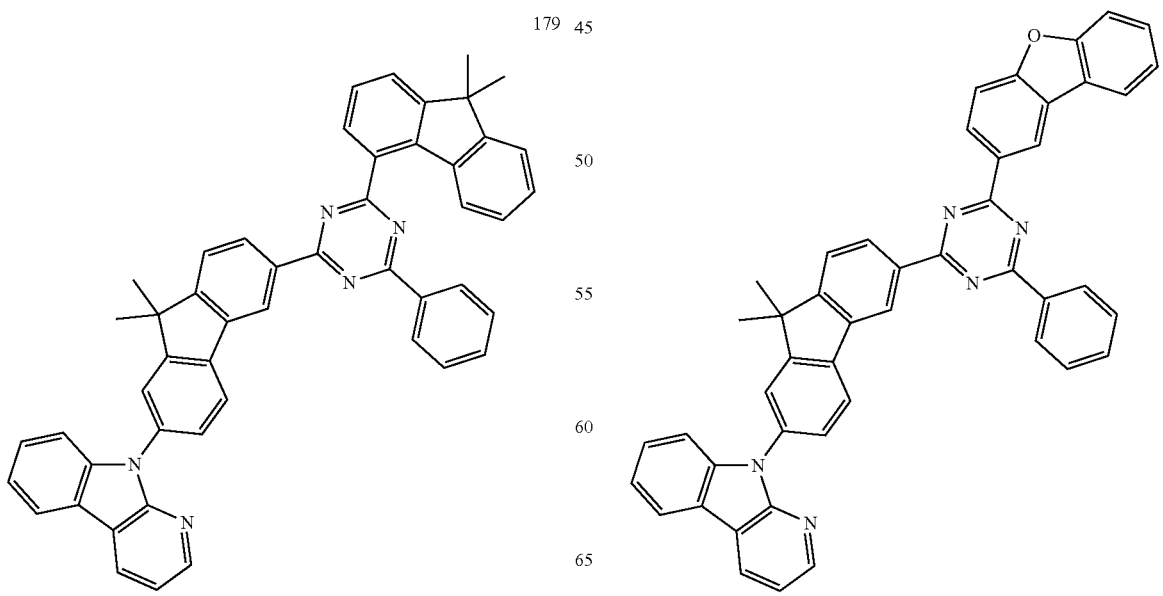

182
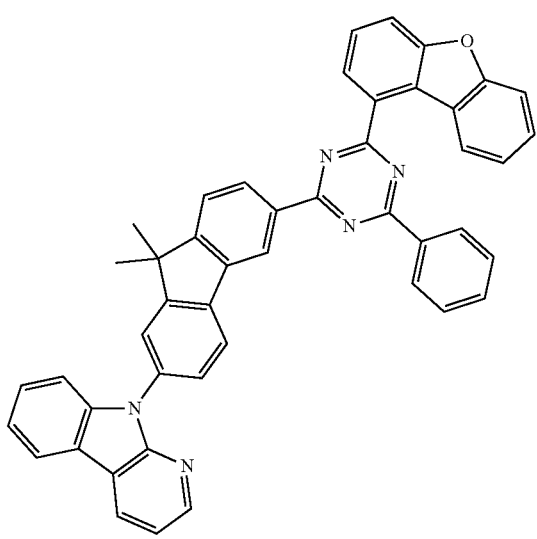
184
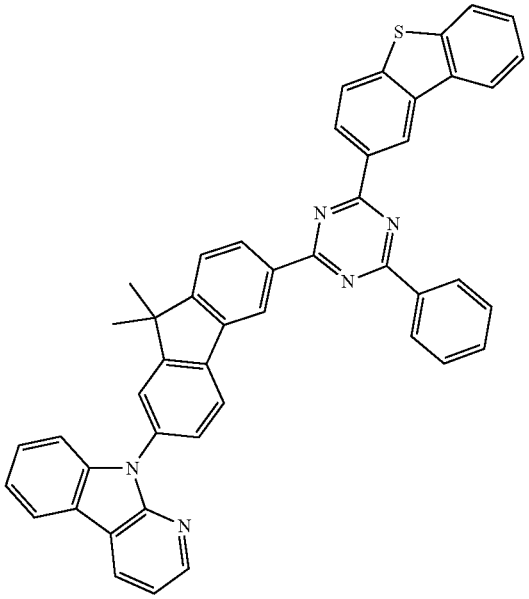
183
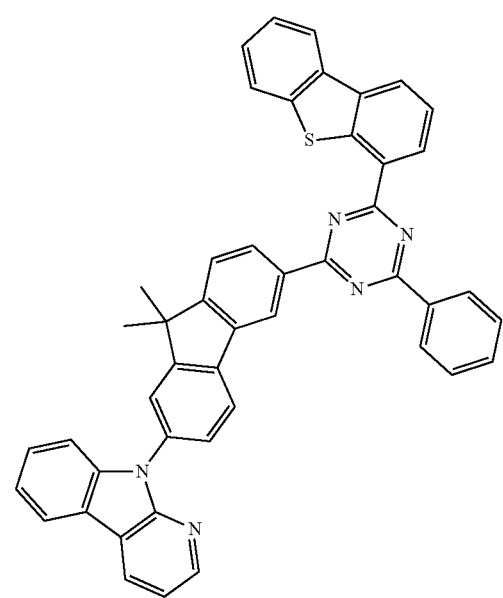
185
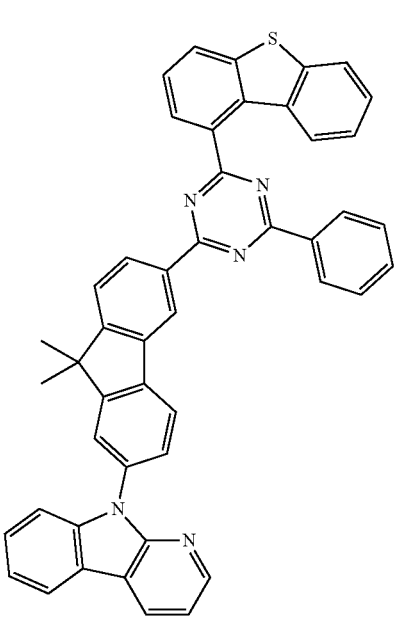

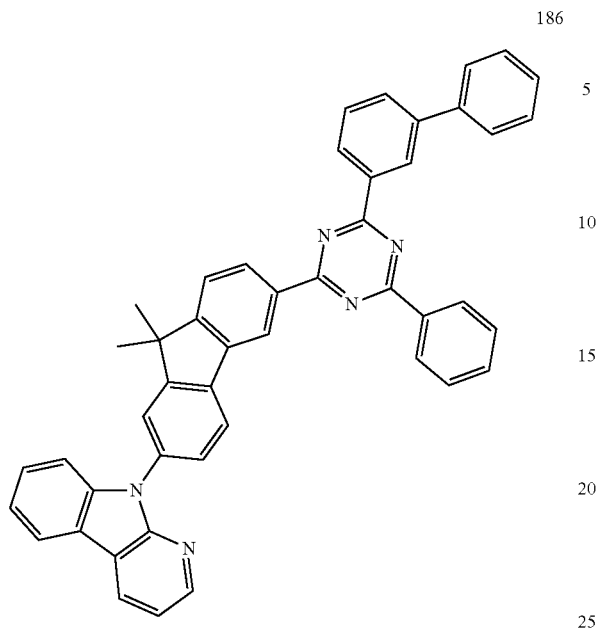
186
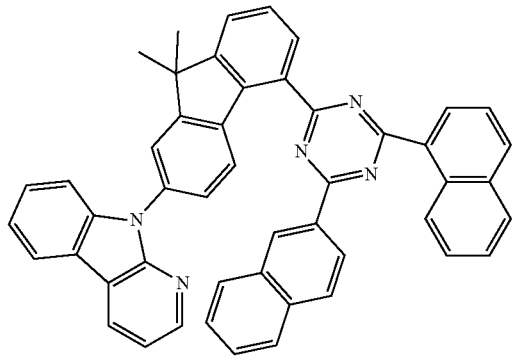
189
187
188
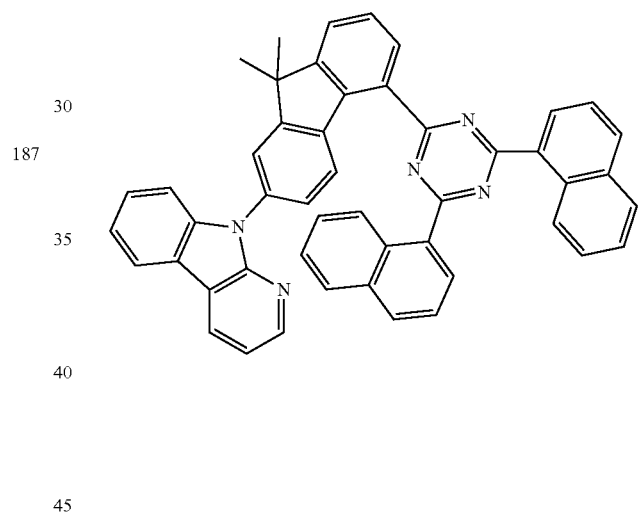
190
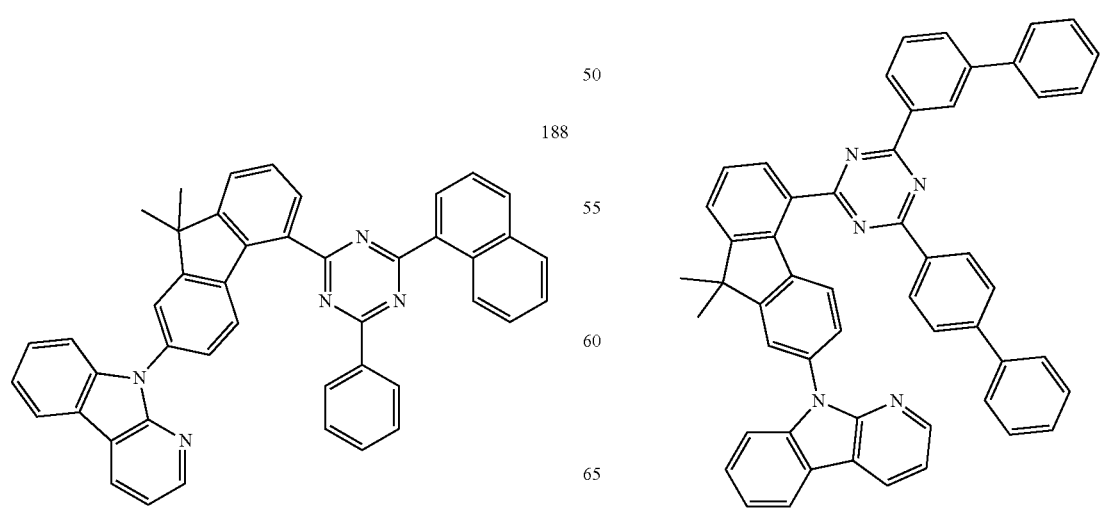
191

192
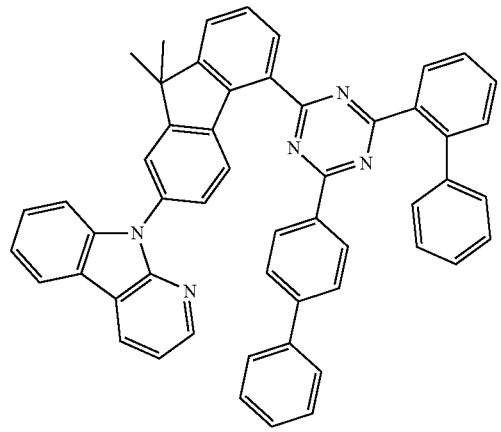
193
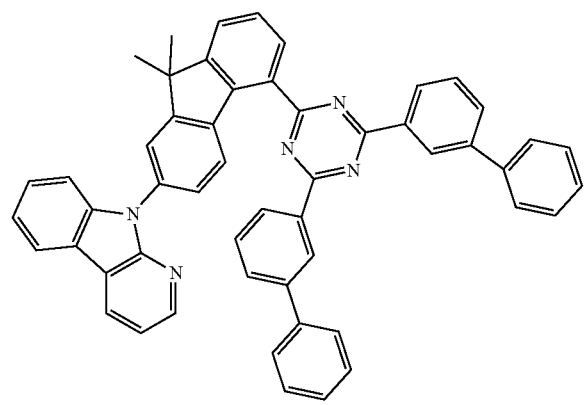
194
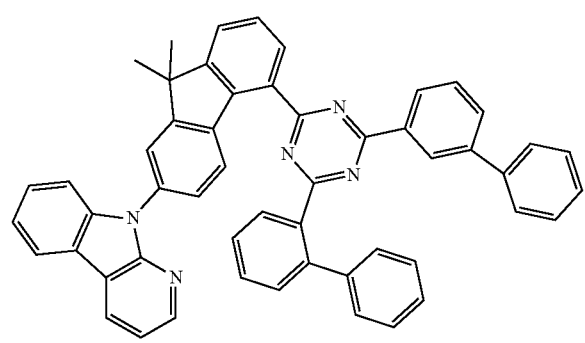
195
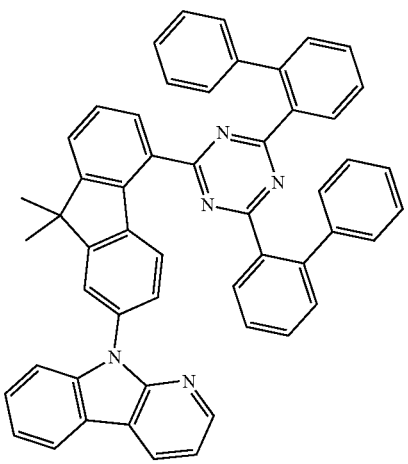
196
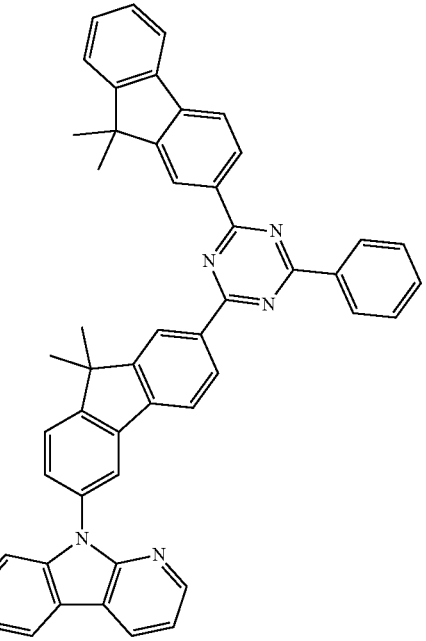
197
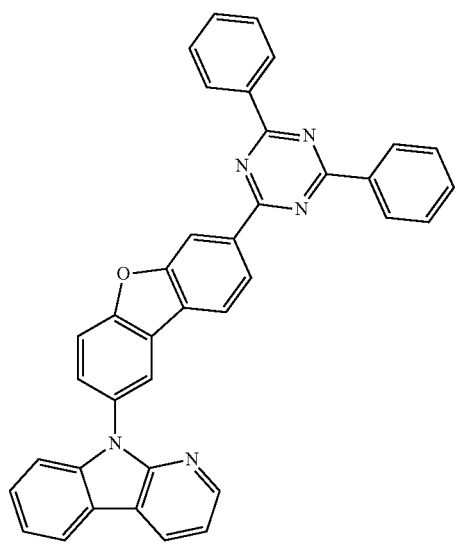

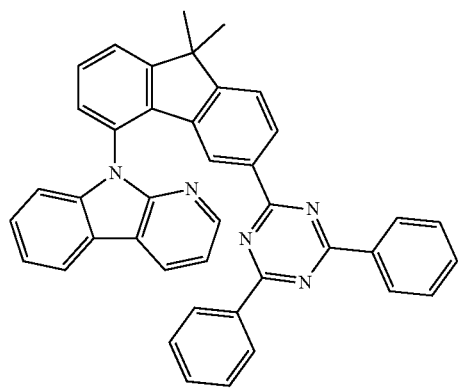
198
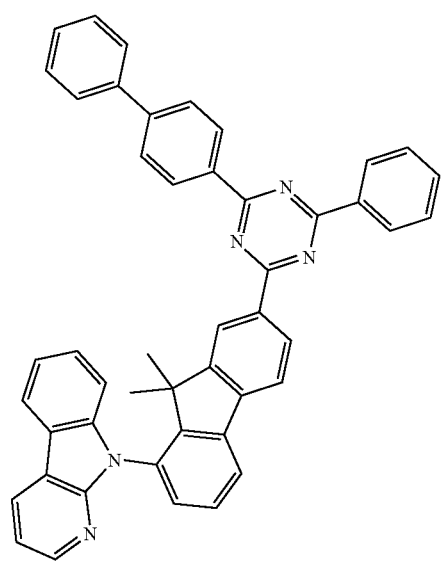
199
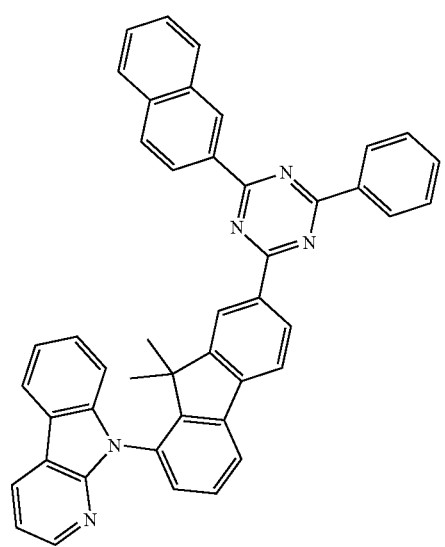
200
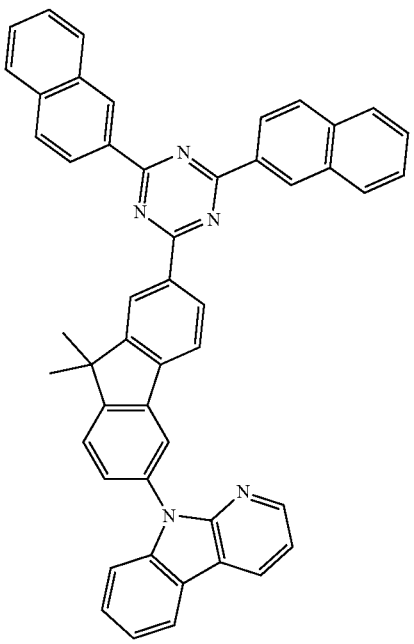
201
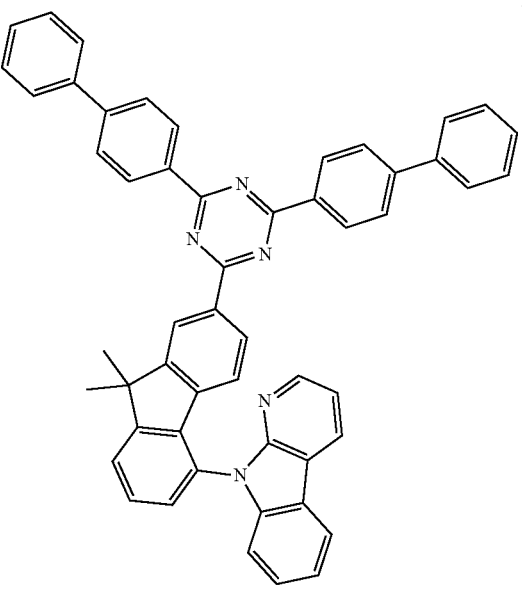
202

103
-continued
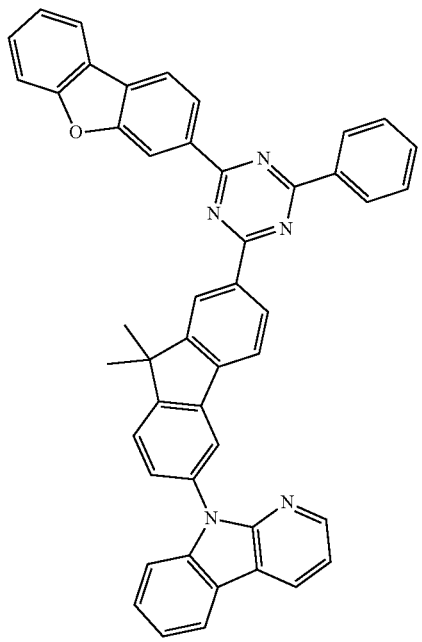
203
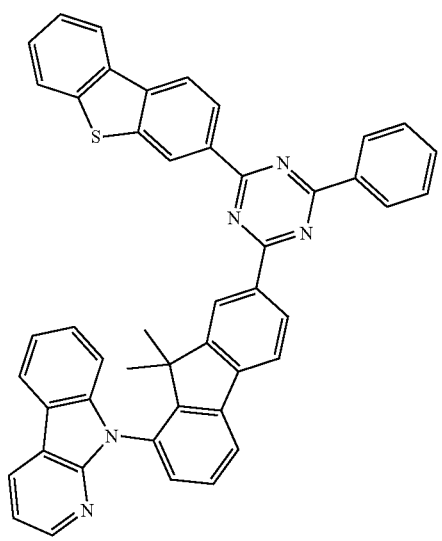
204
104
-continued
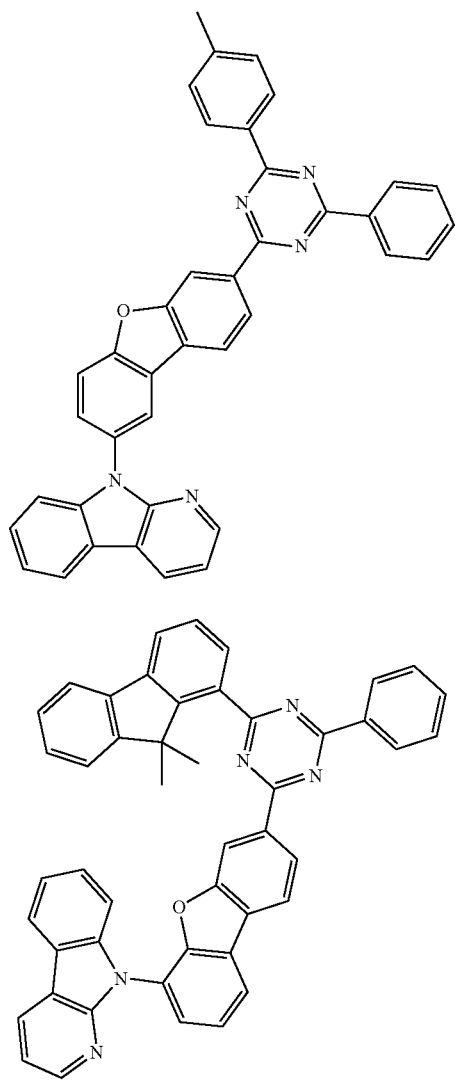
205
206
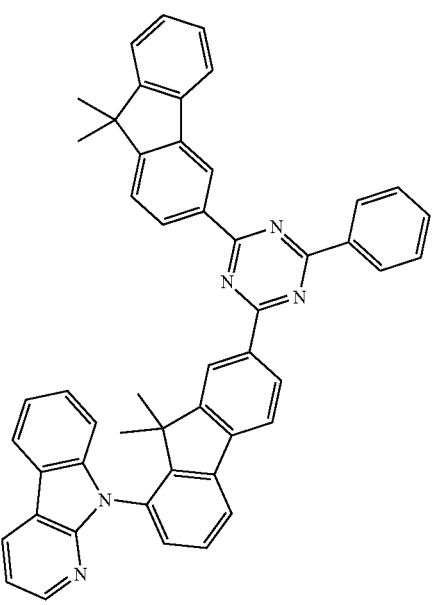
207

208
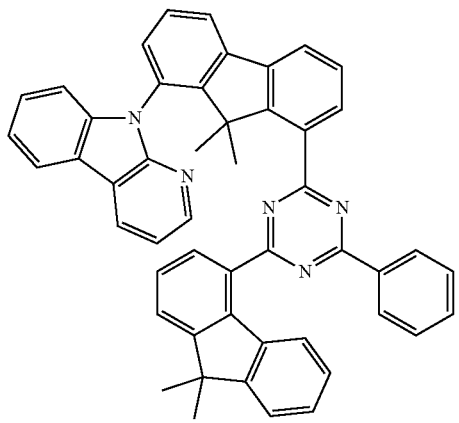
209
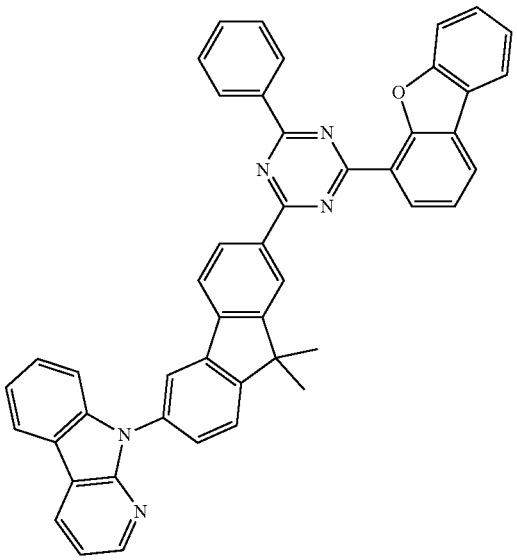
210
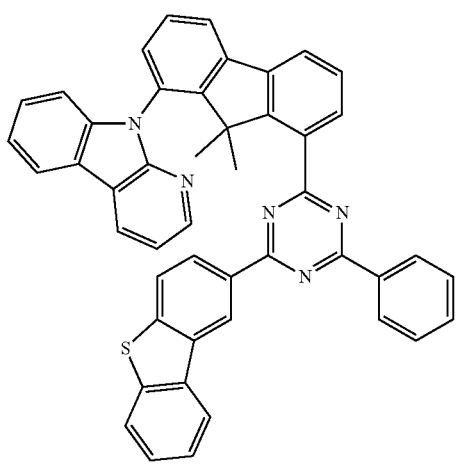
211
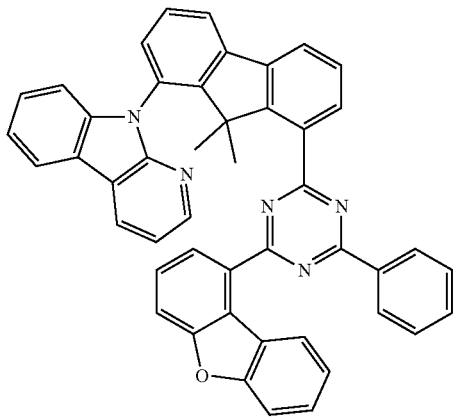
212
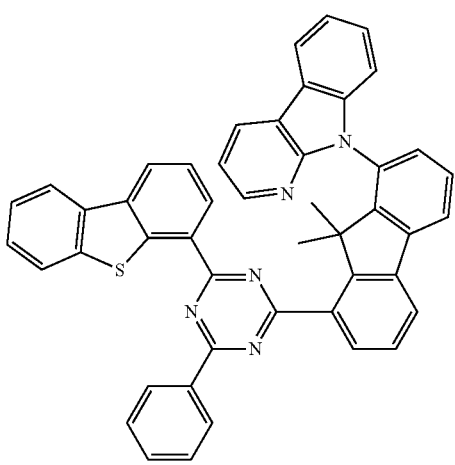
213
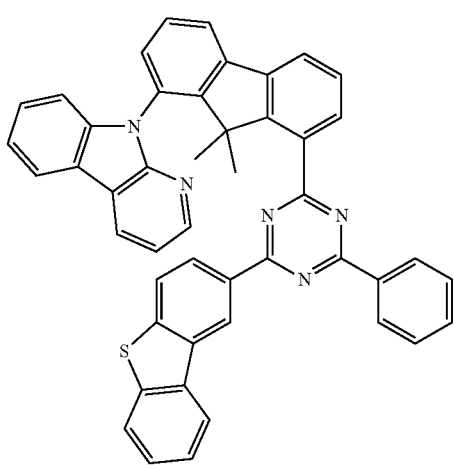

107
-continued
214
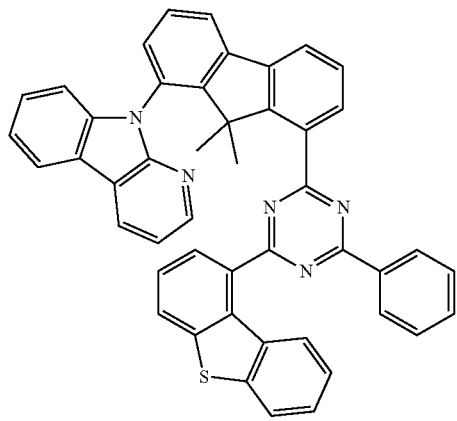
215
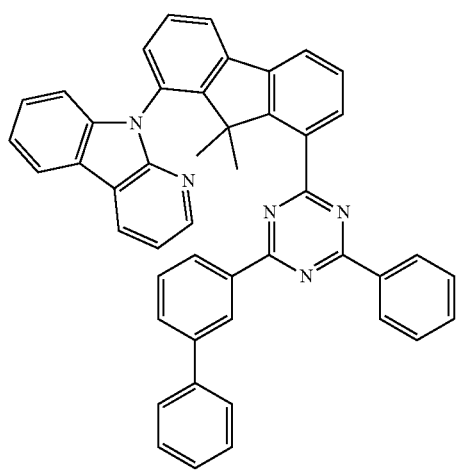
216
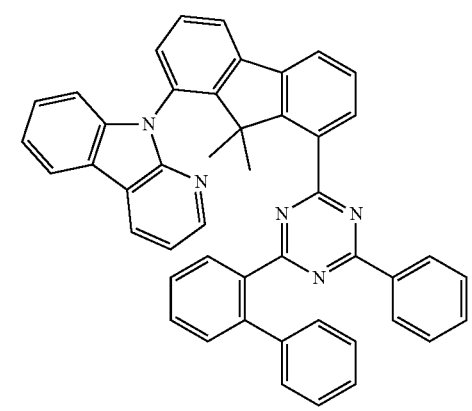
108
-continued
217
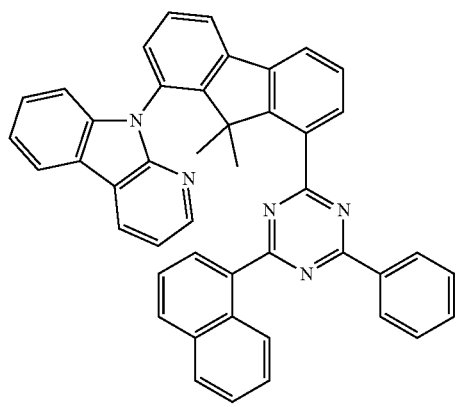
218
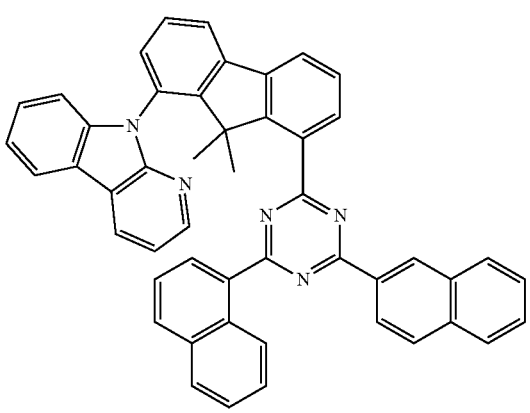
219
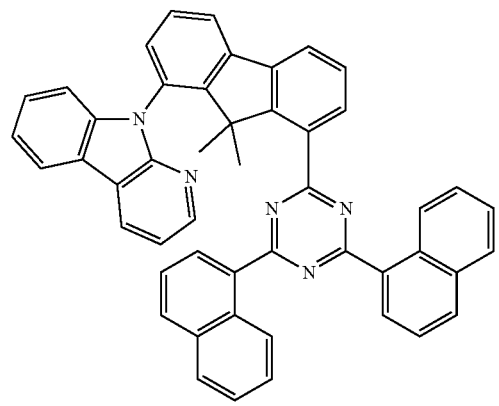

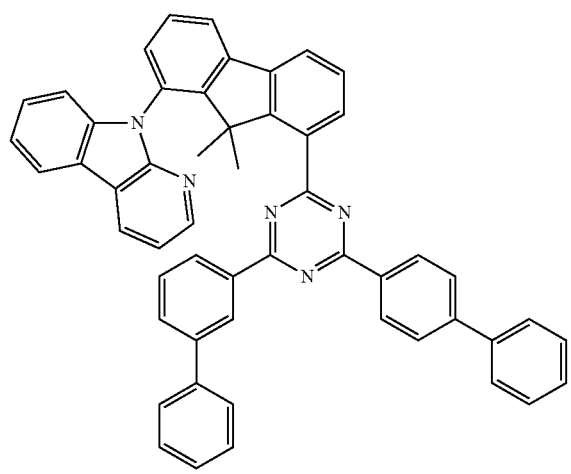
220
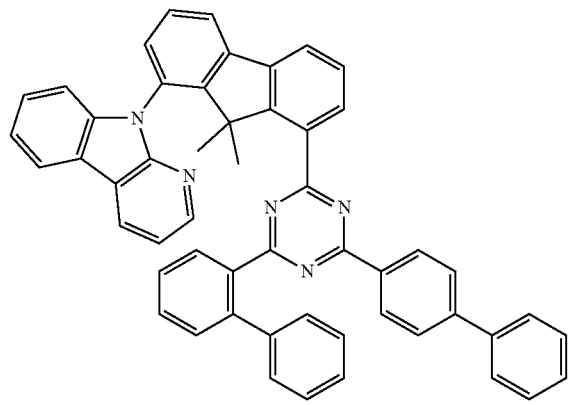
221
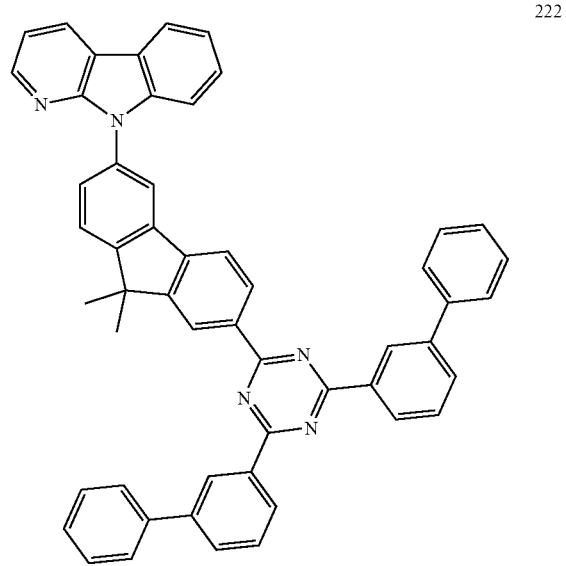
222
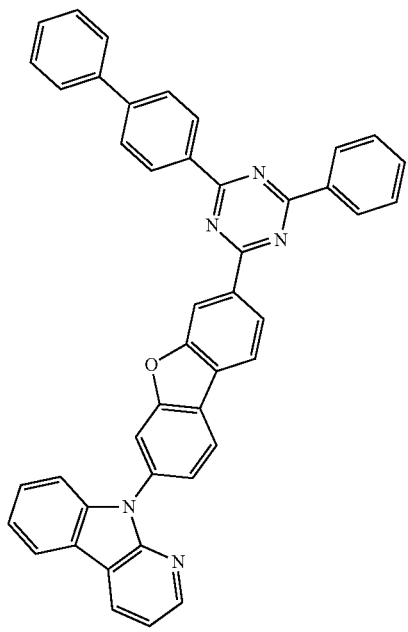
223
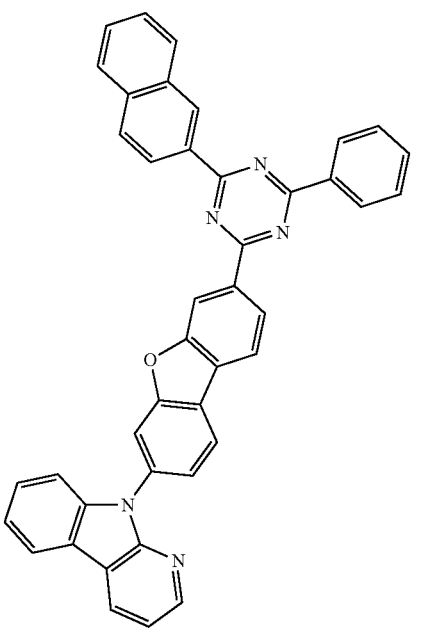
224

111
-continued
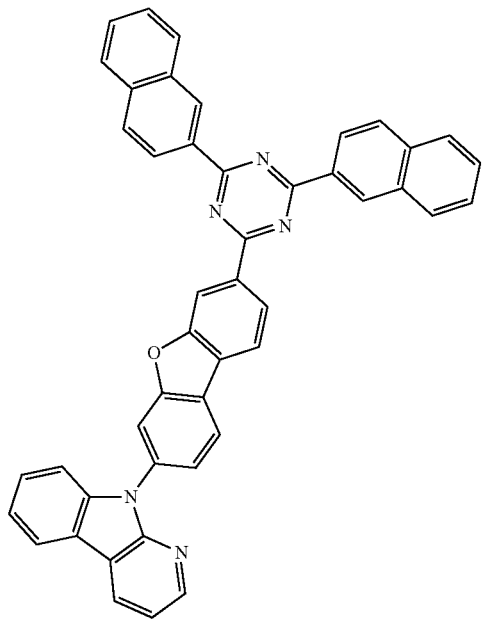
225
112
-continued
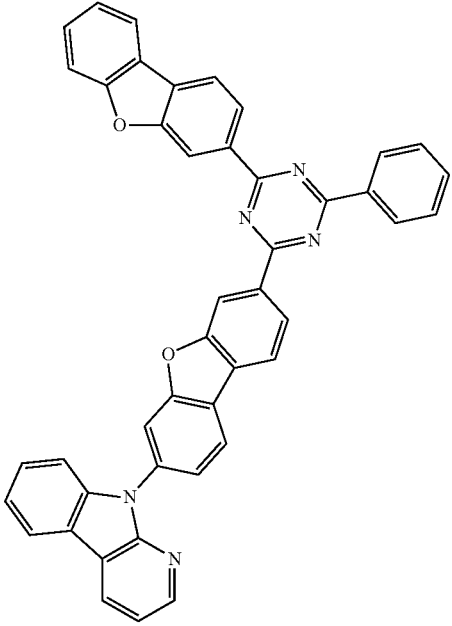
227
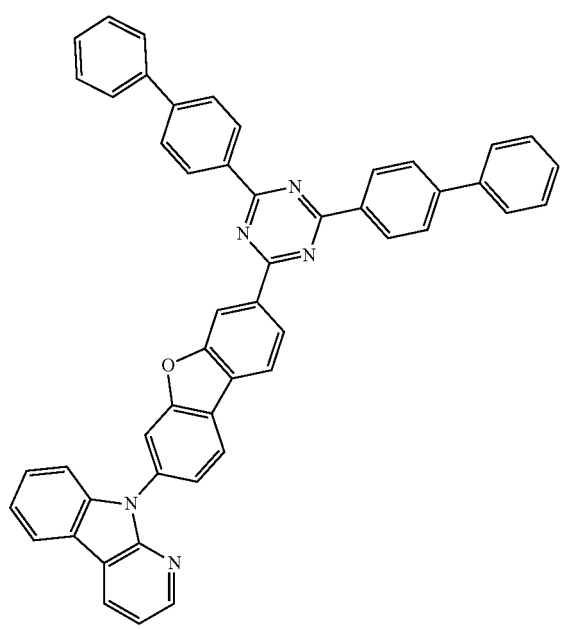
226
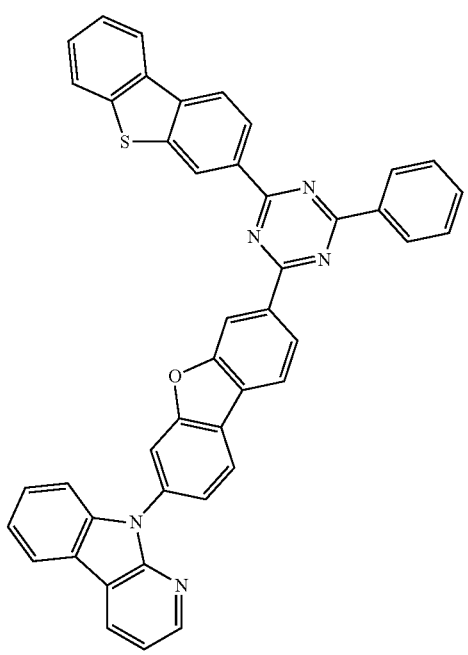
228

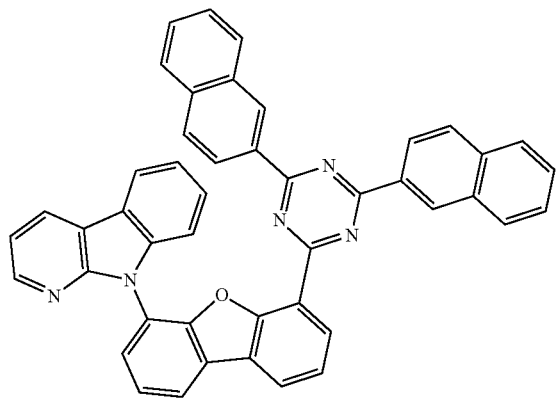
229
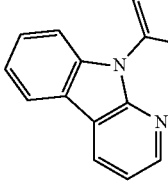
230
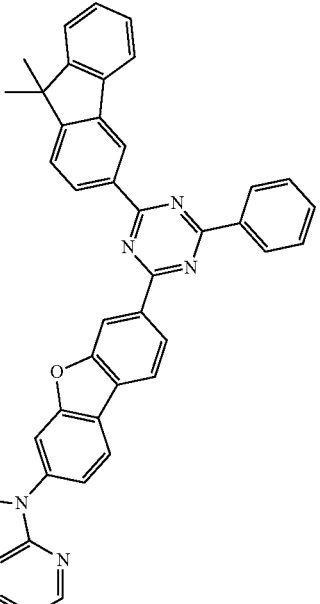
232
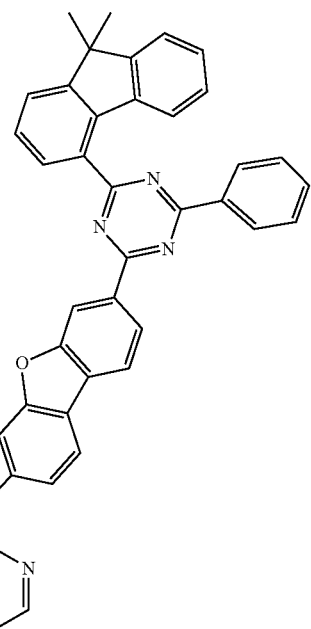
233
231

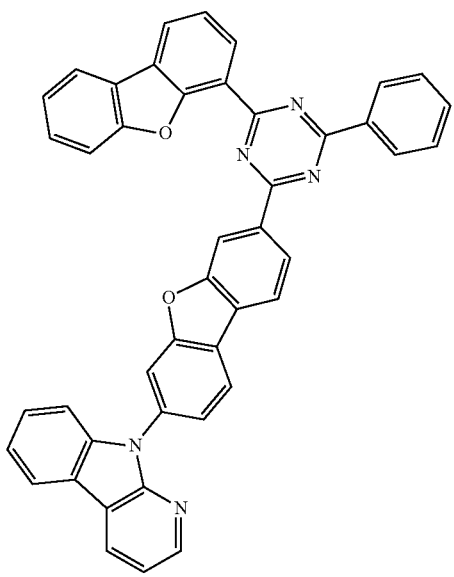
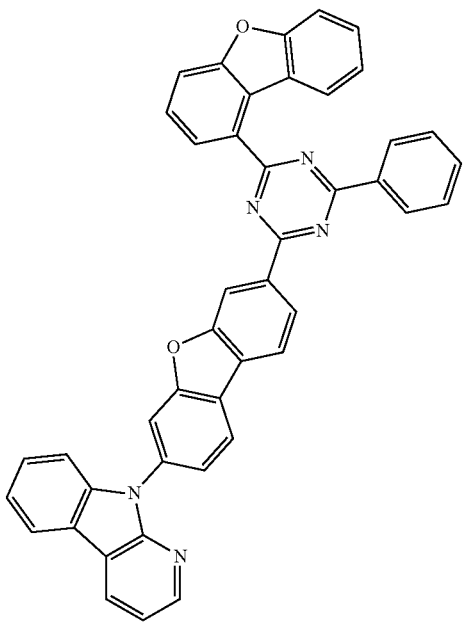

238
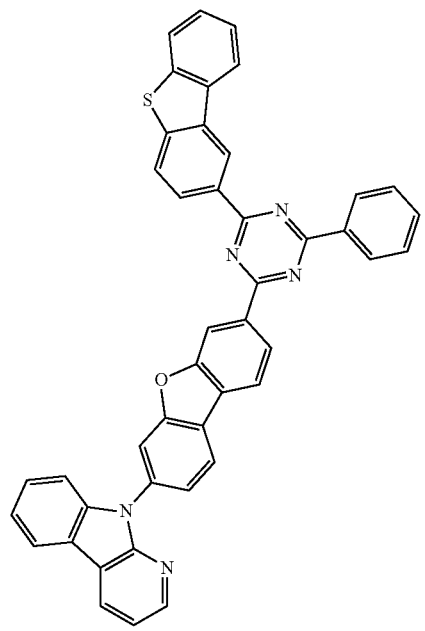
239
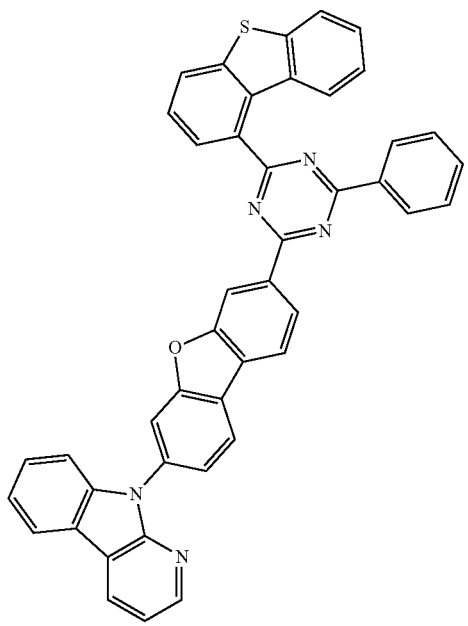
240
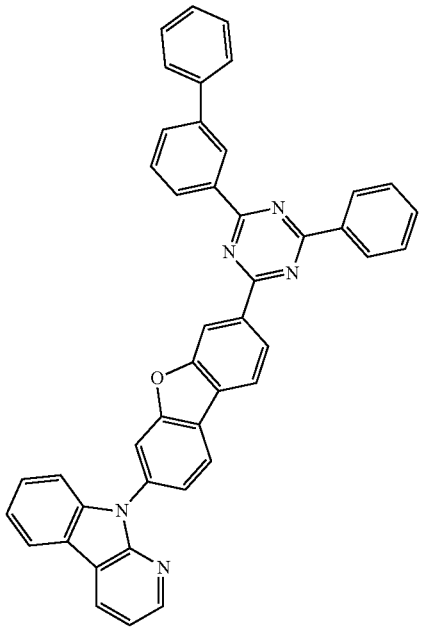
241
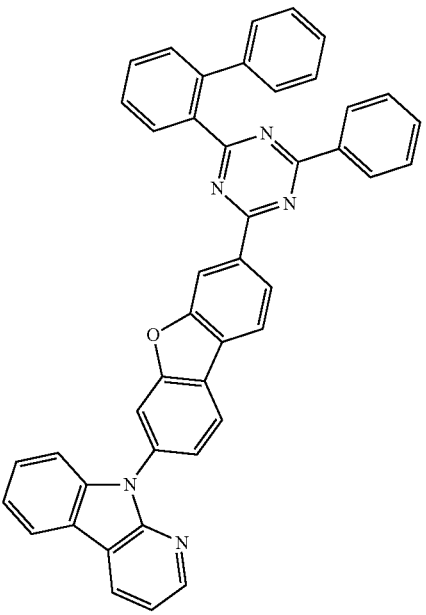

242
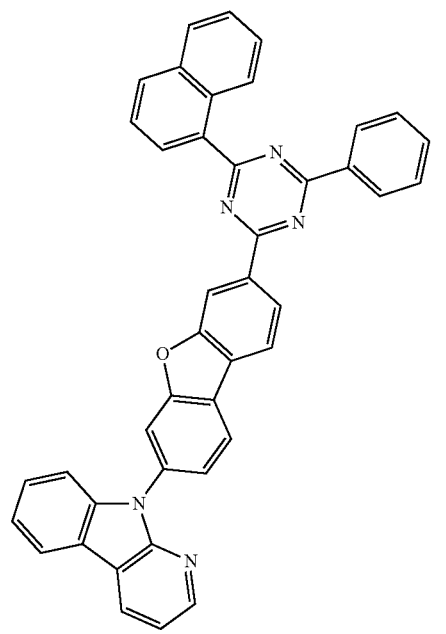
243
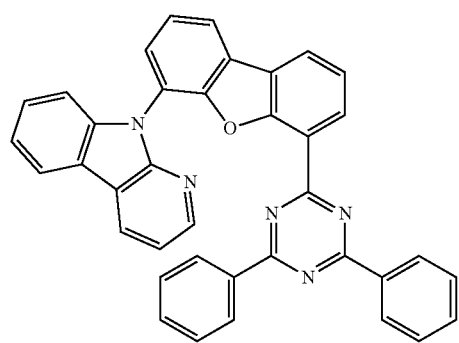
244
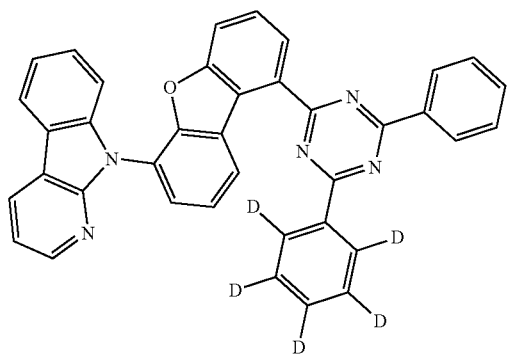
245
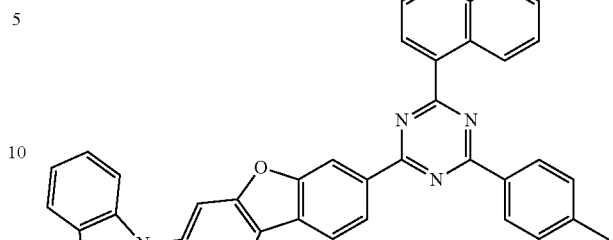
246
247
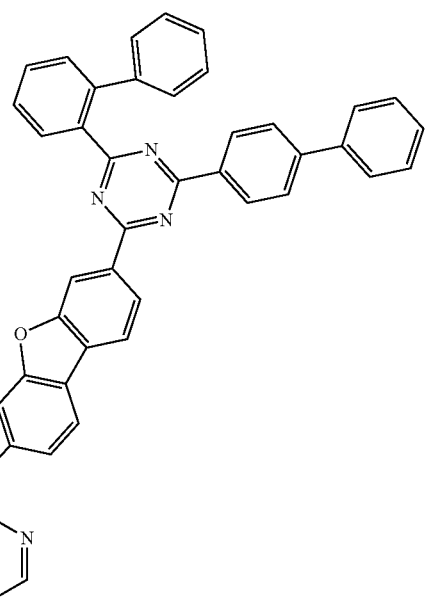

248
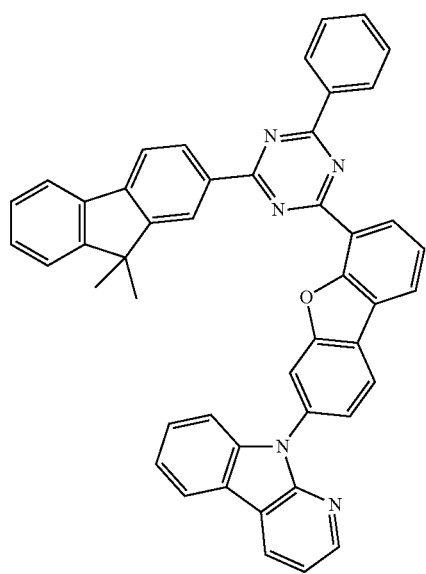
249
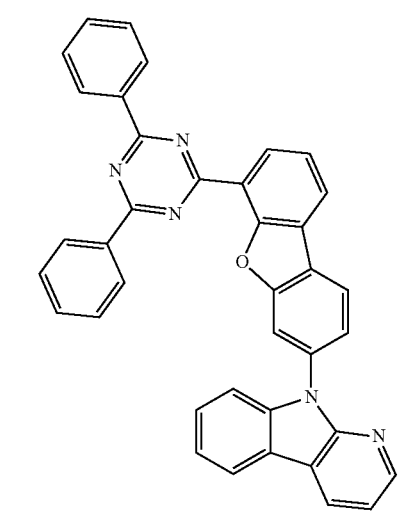
250
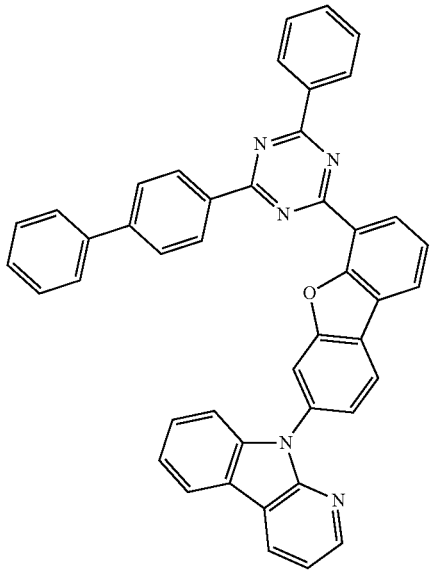
251
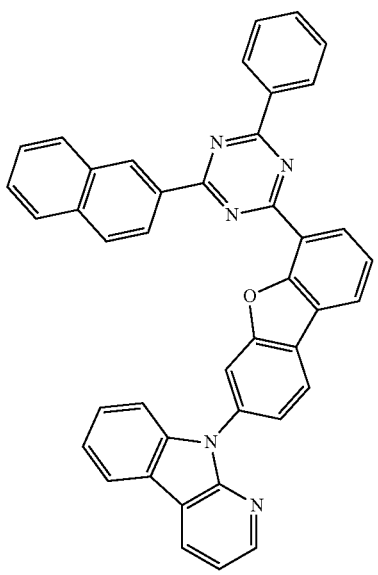
252
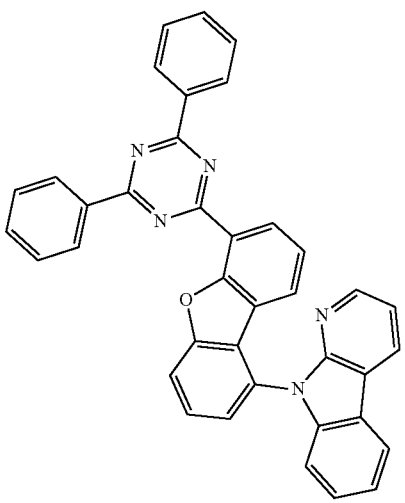
253
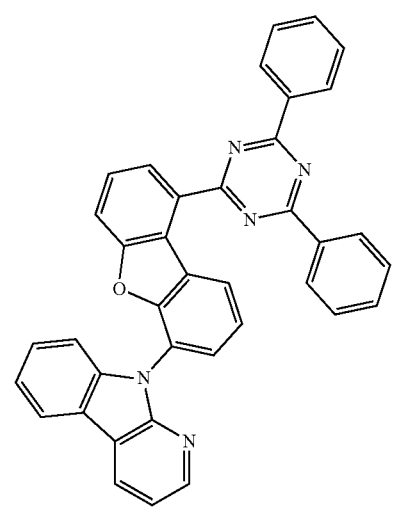

123
-continued
254
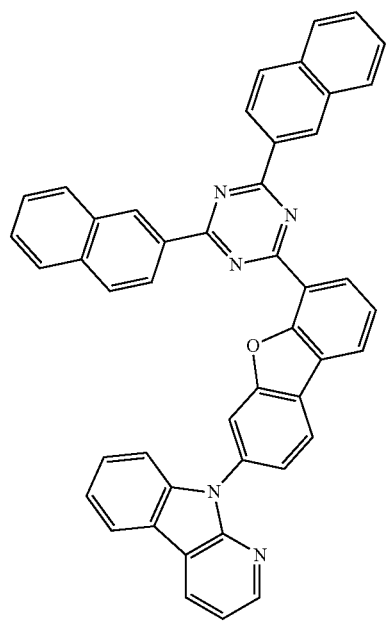
255
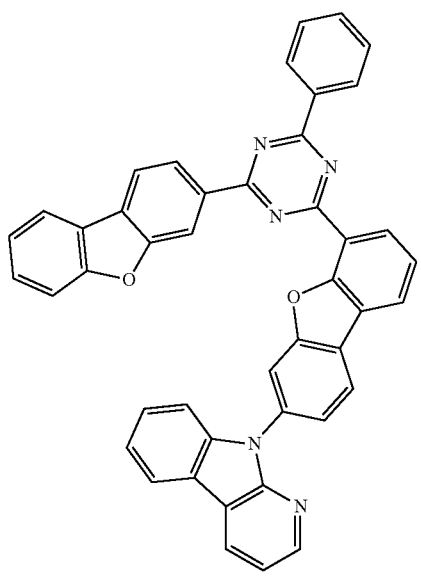
124
-continued
256
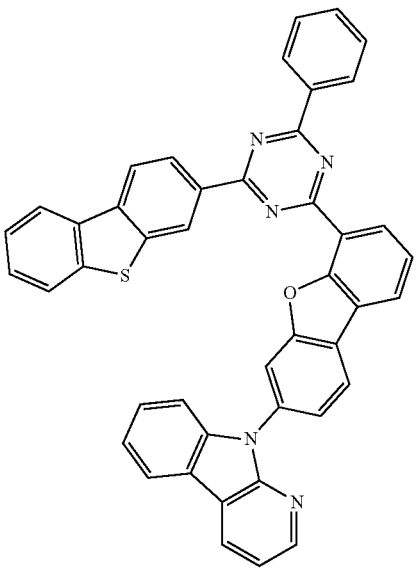
257

-continued
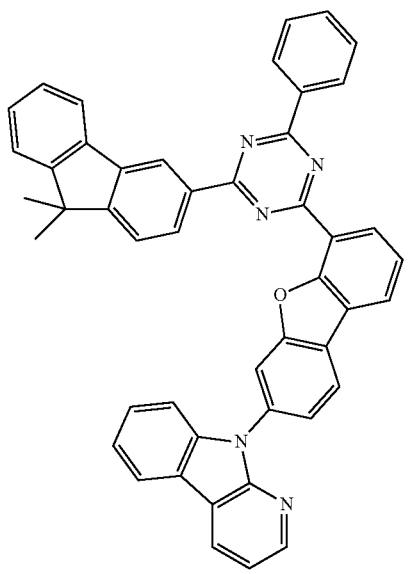
258
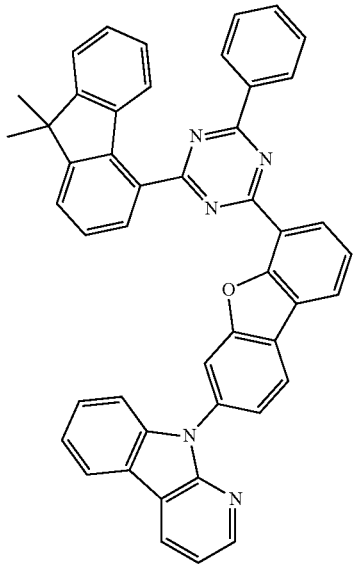
259
-continued
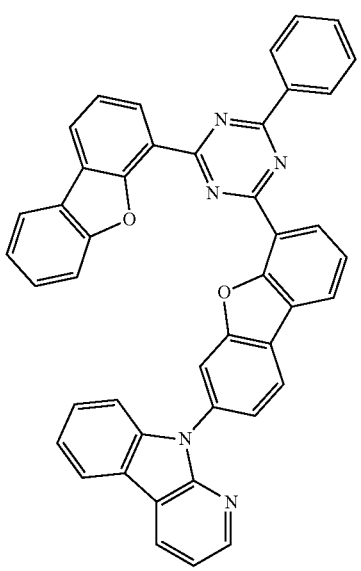
260
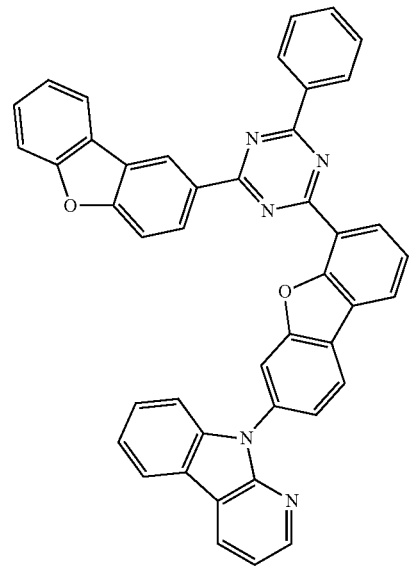
261

127
-continued
262
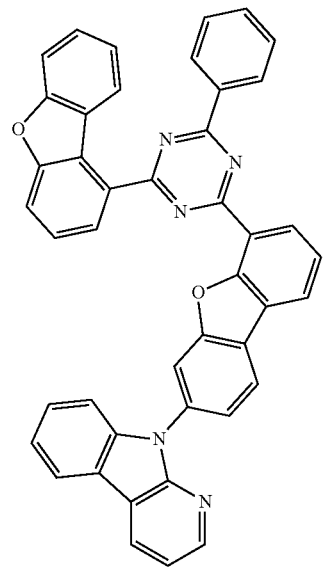
263
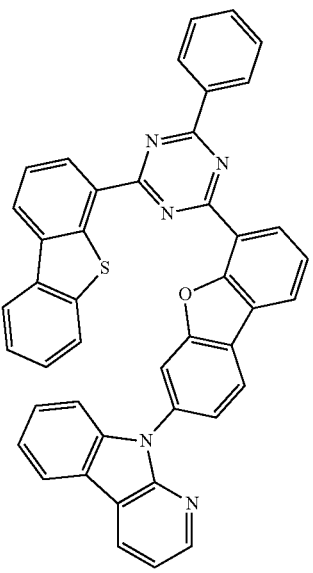
264
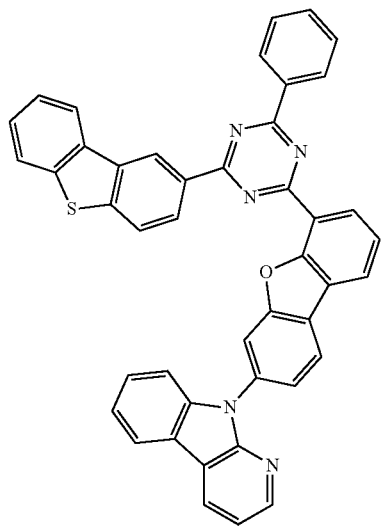
128
-continued
265
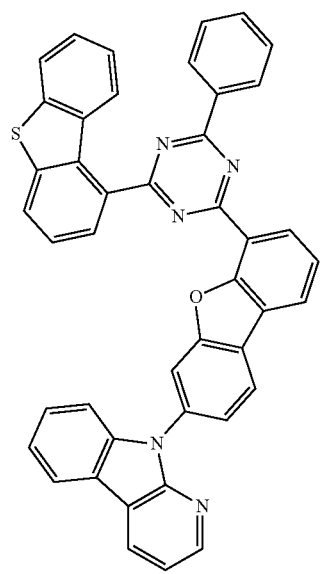
266
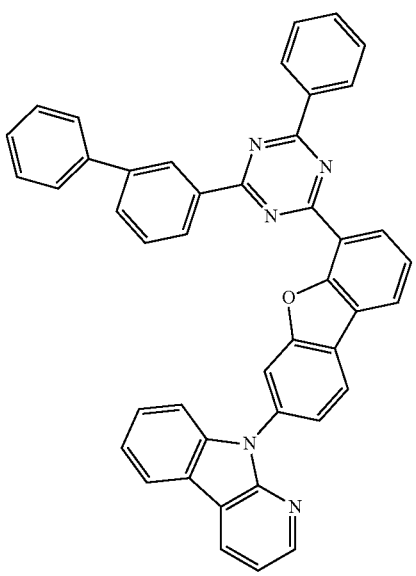

267
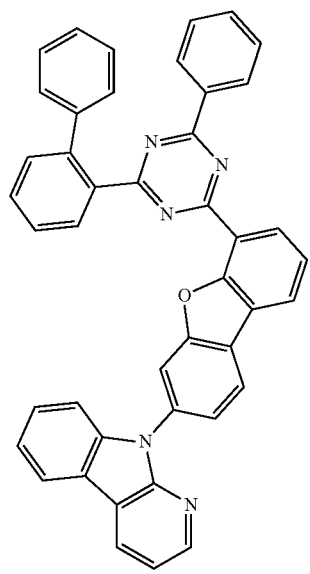
268
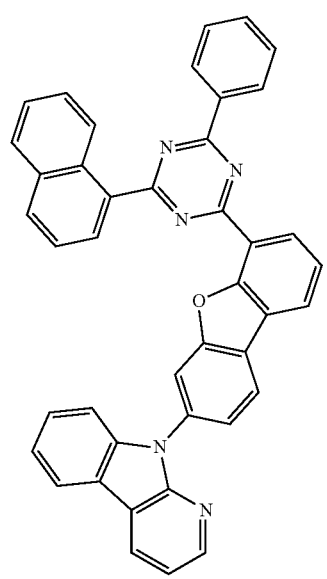
269
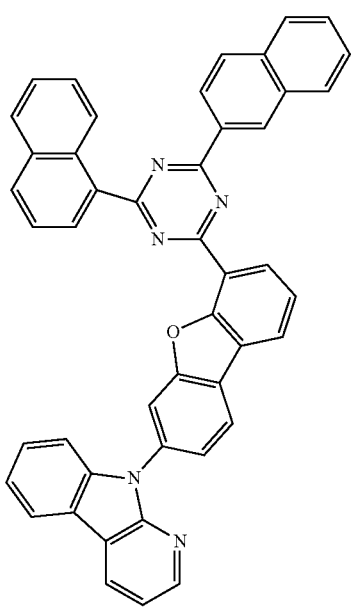
270
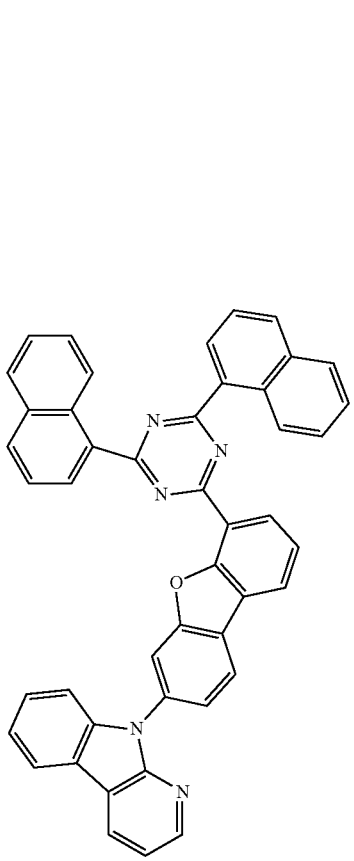

-continued
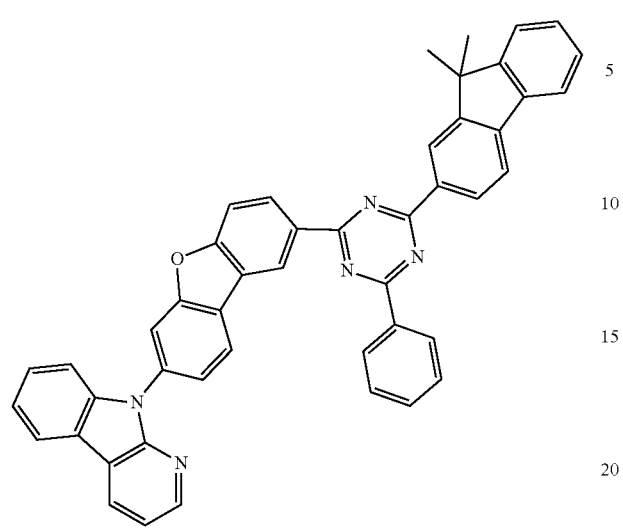
271
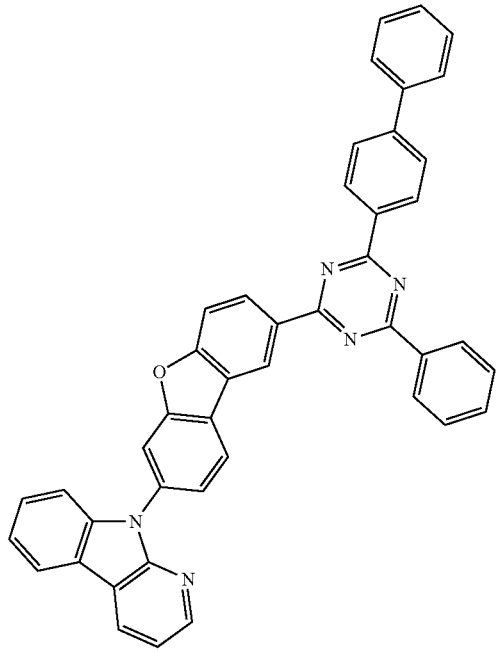
273
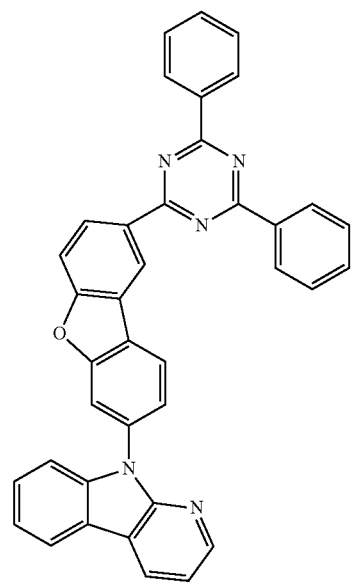
272
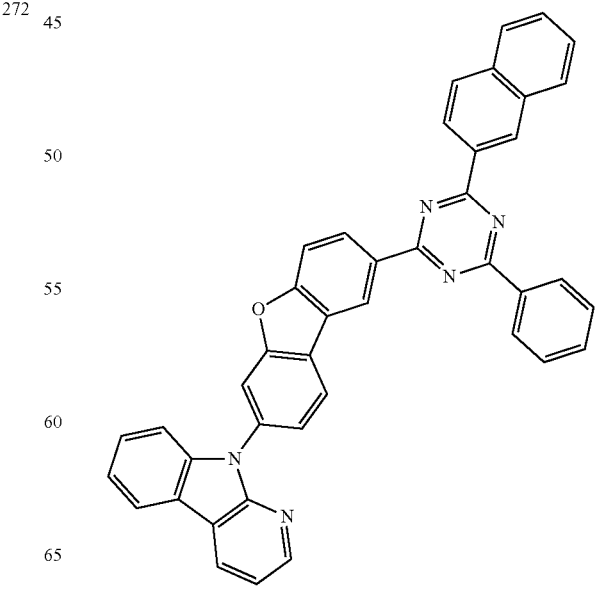
274

275
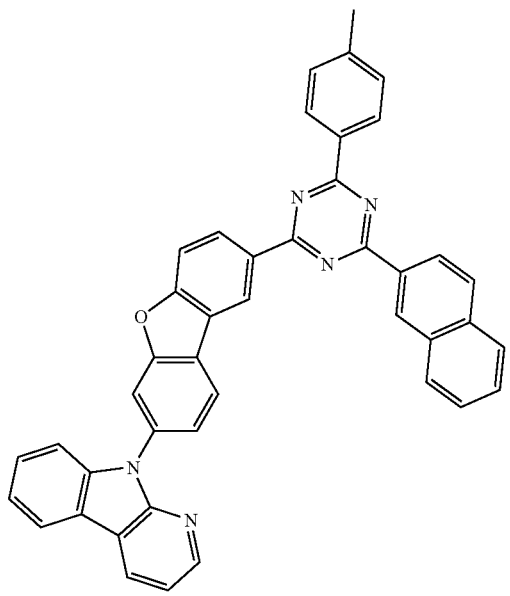
276
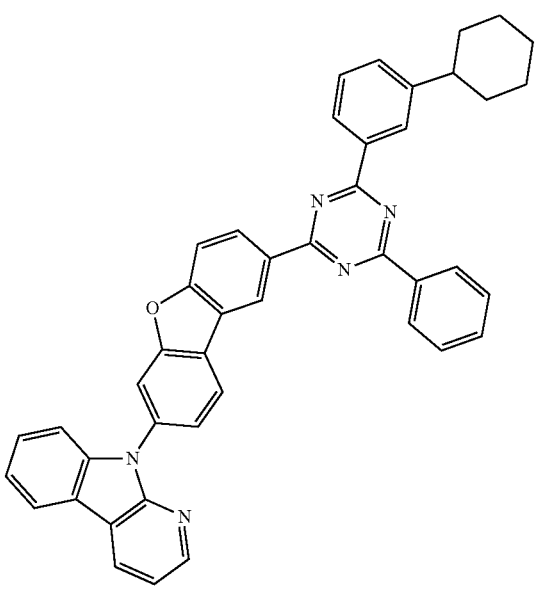
277
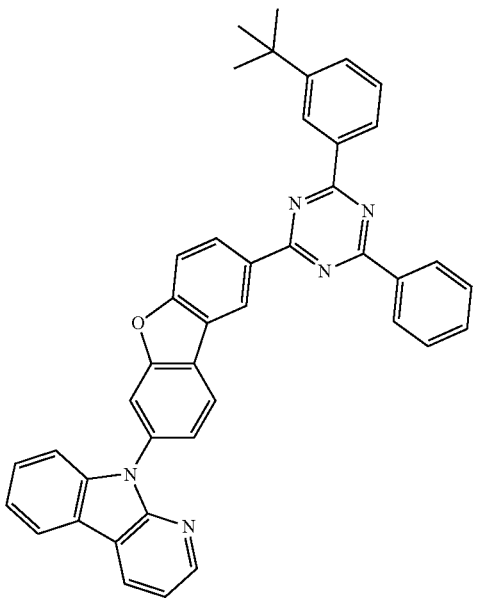
278
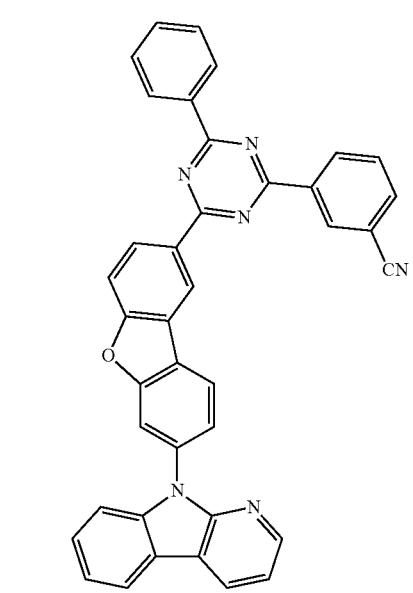

135
-continued
279
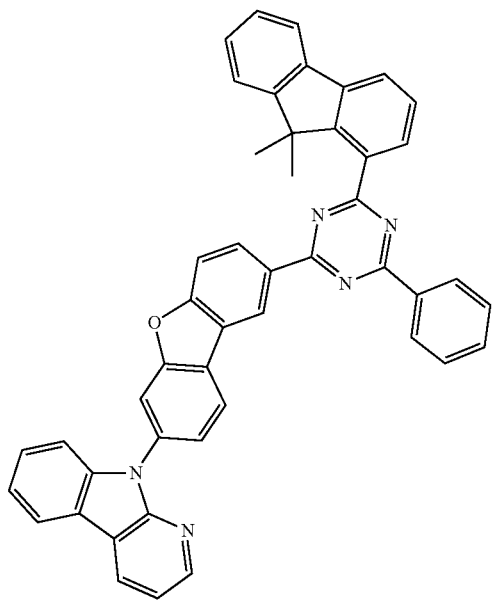
280
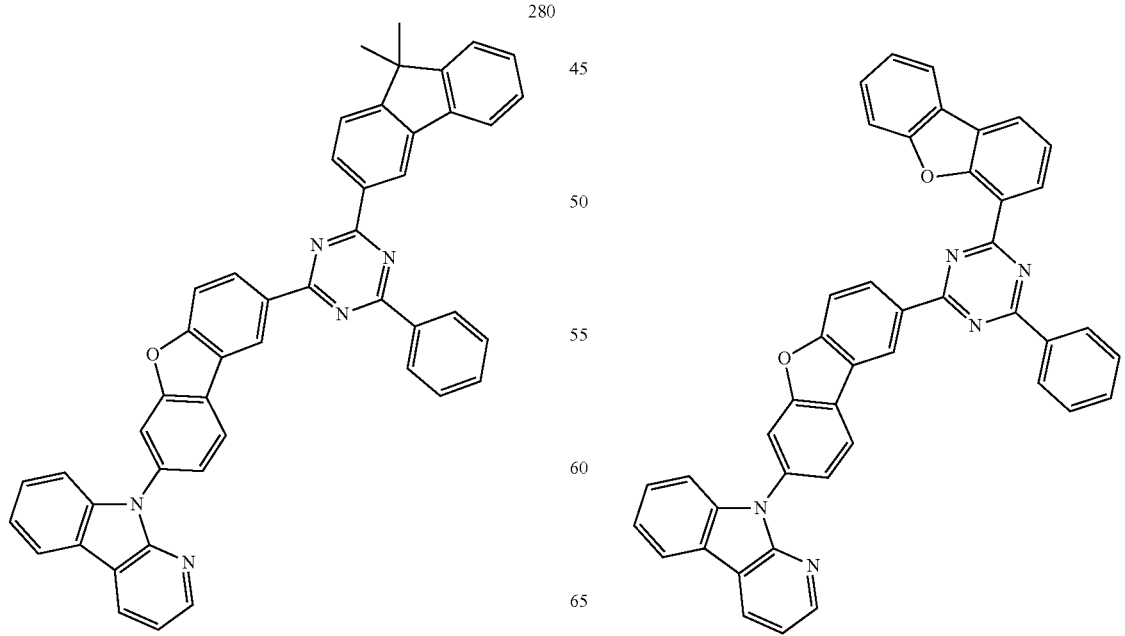
136
-continued
281
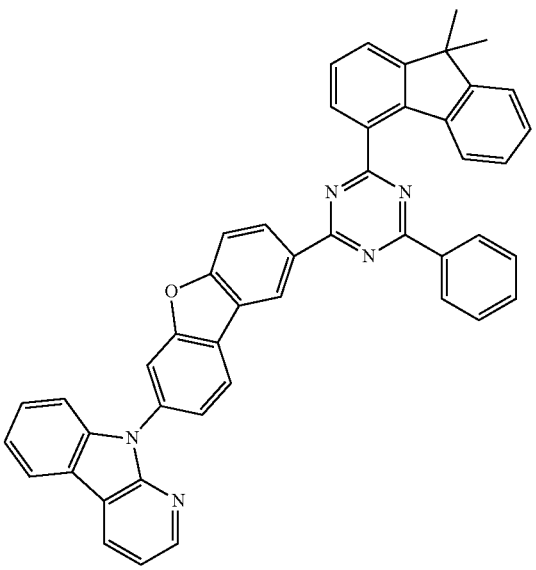
282

283
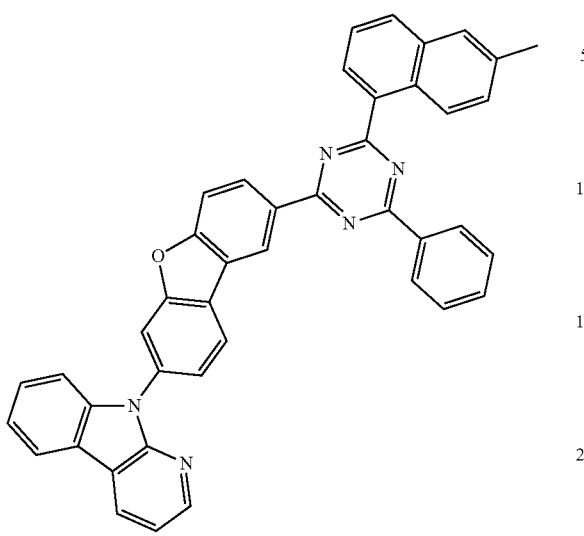
285
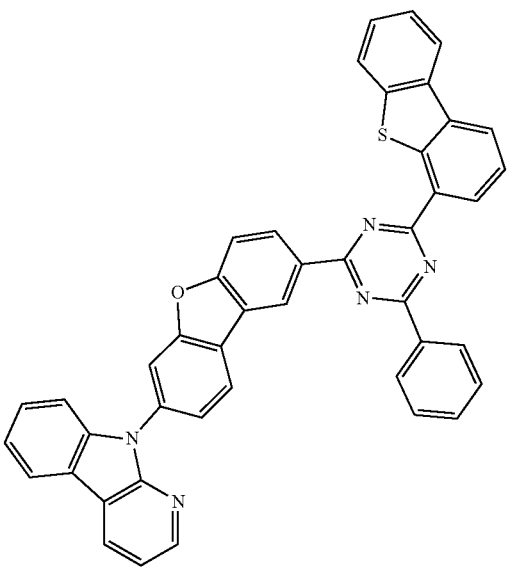
284
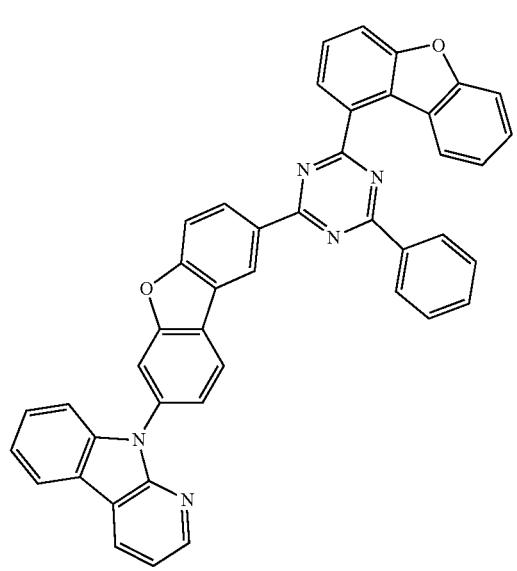
286
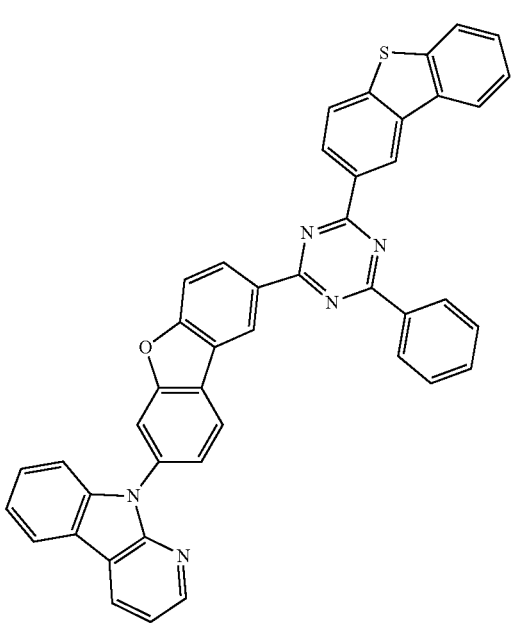

287
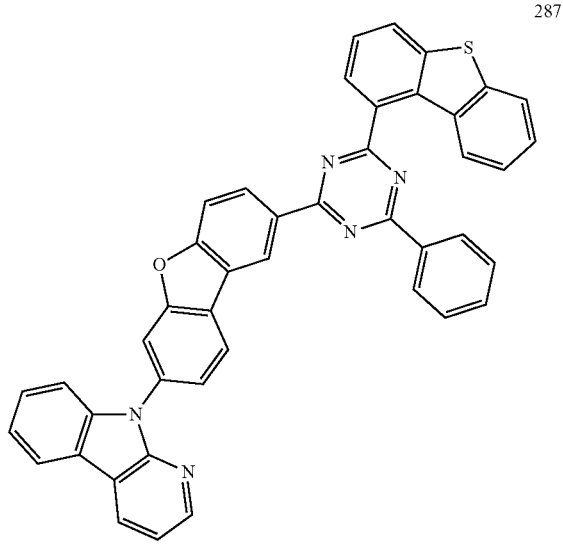
288
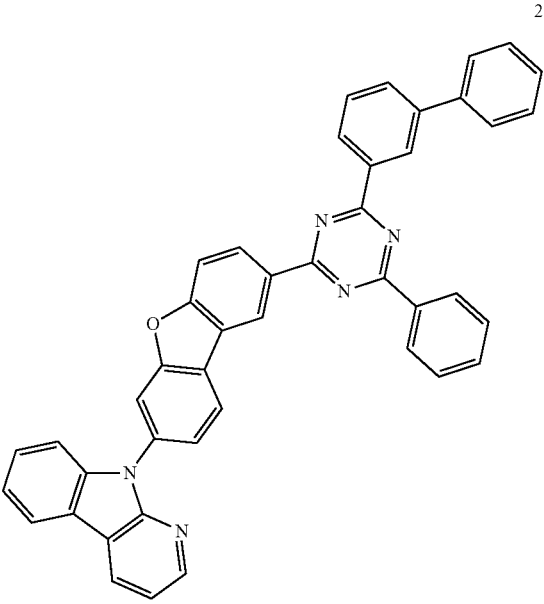
289
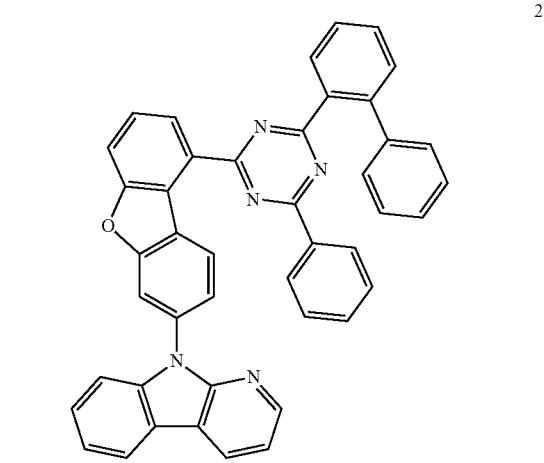
290
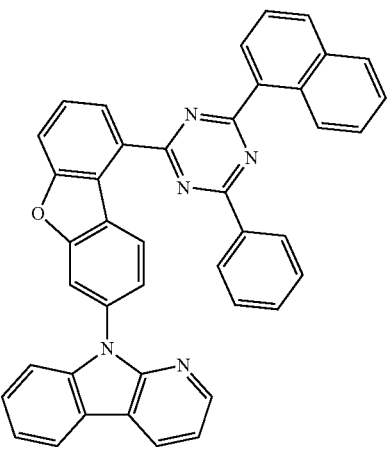
291
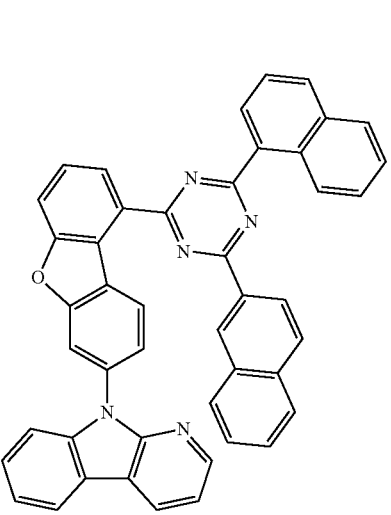
292
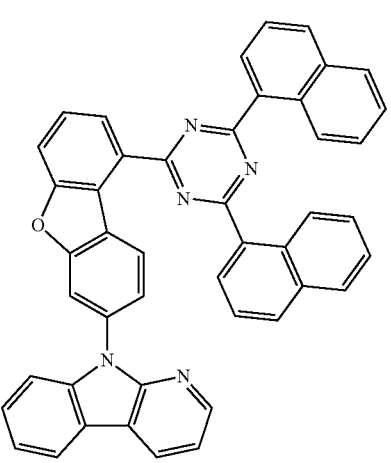

293
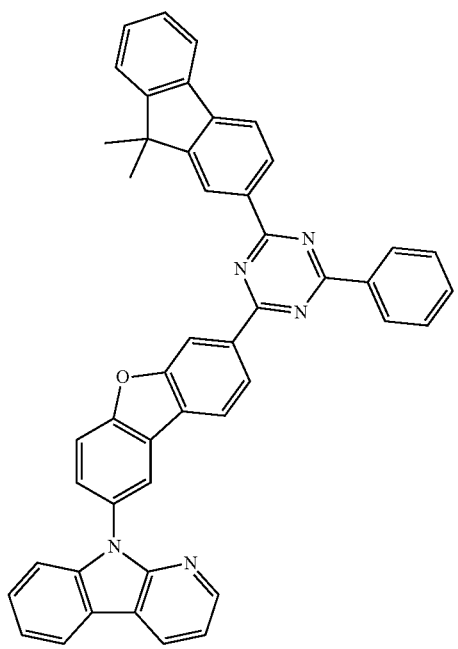
294
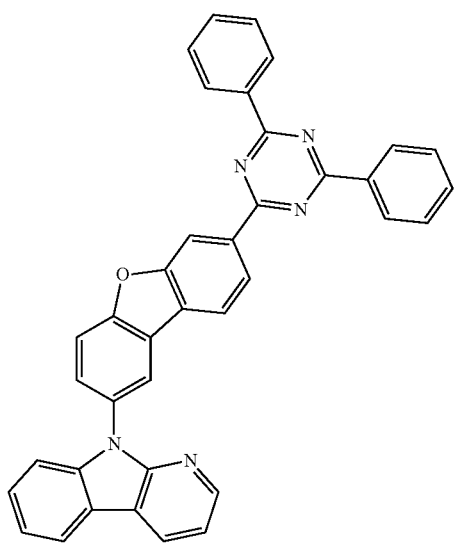
295
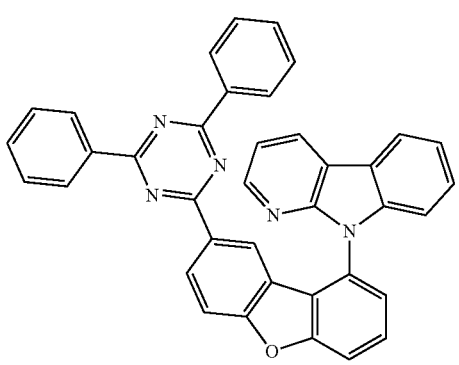
296
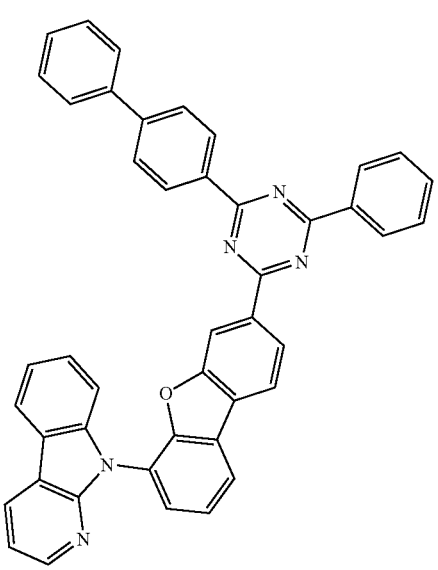
297
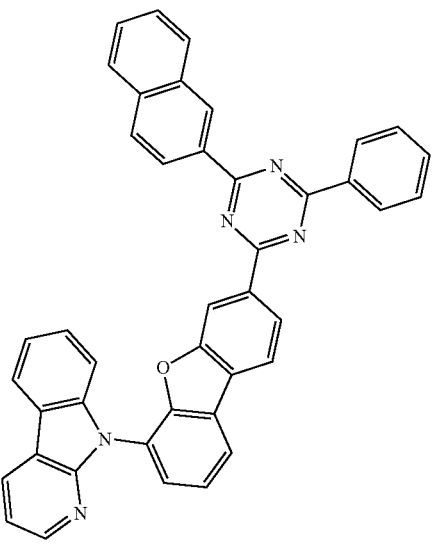

298
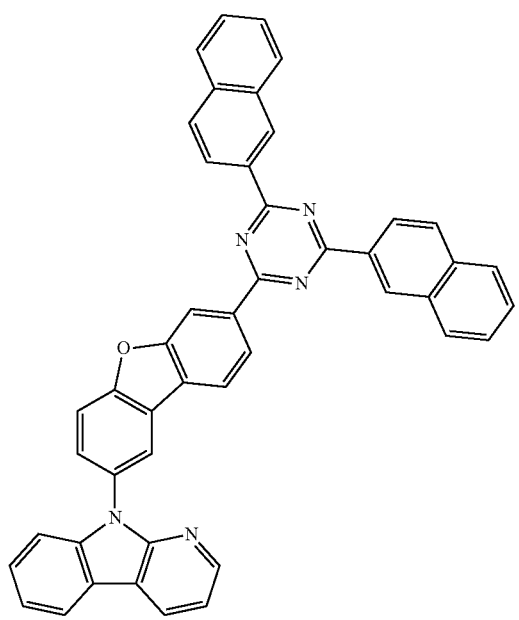
299
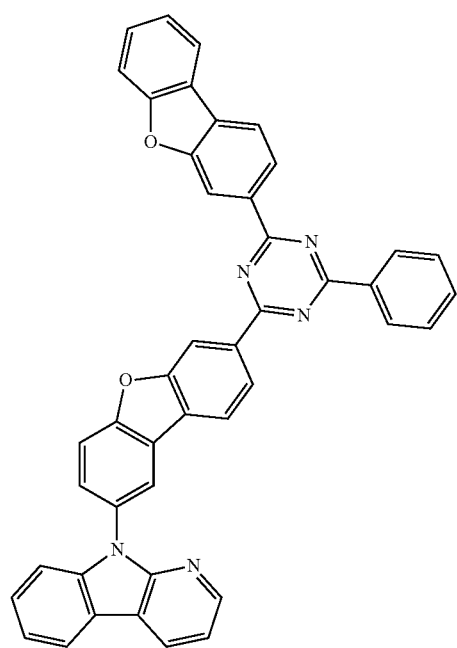
300
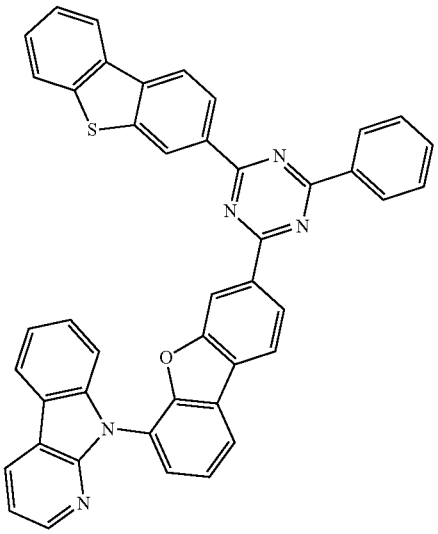
301
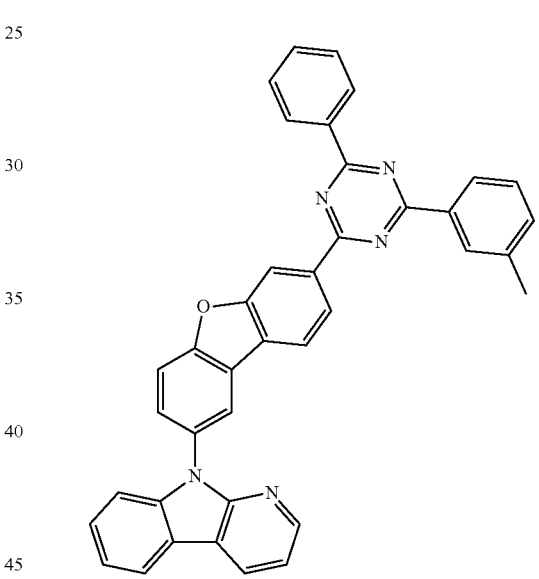
302
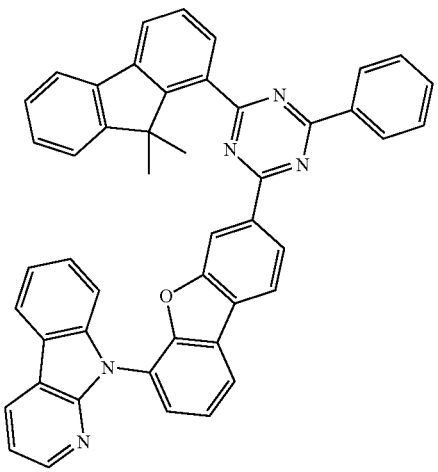

145
-continued
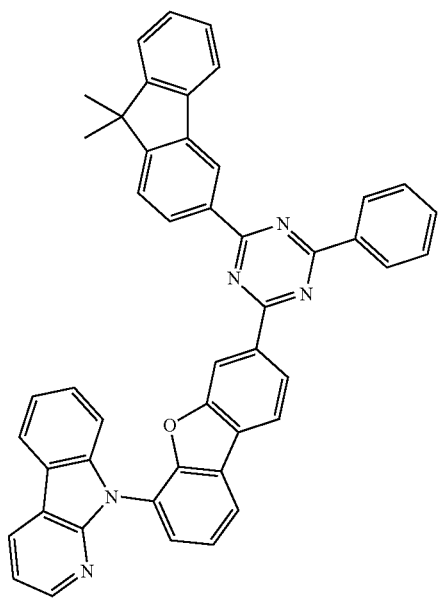
303
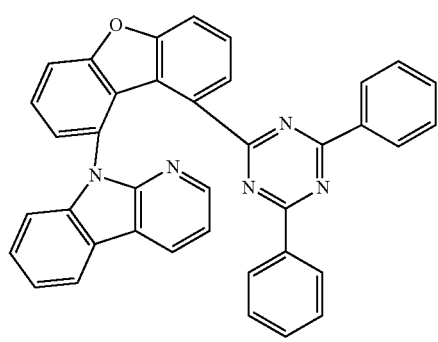
304
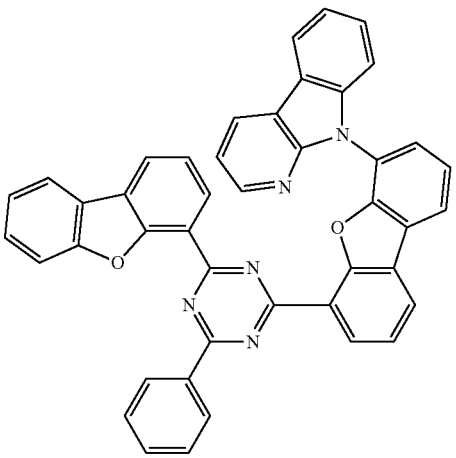
305
146
-continued
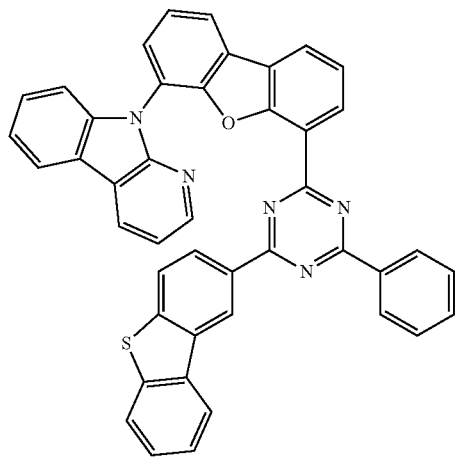
306
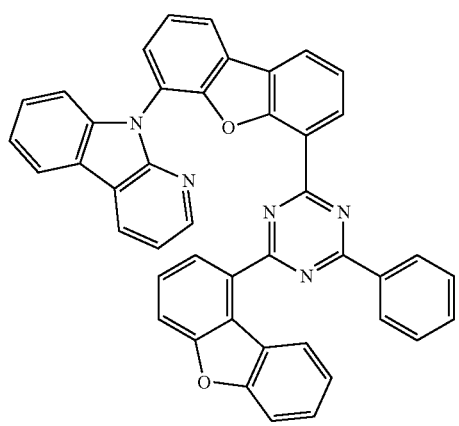
307
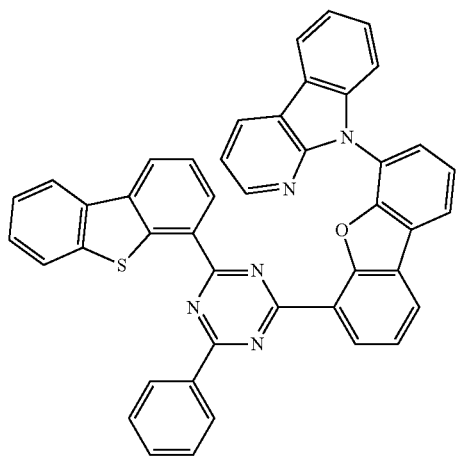
308

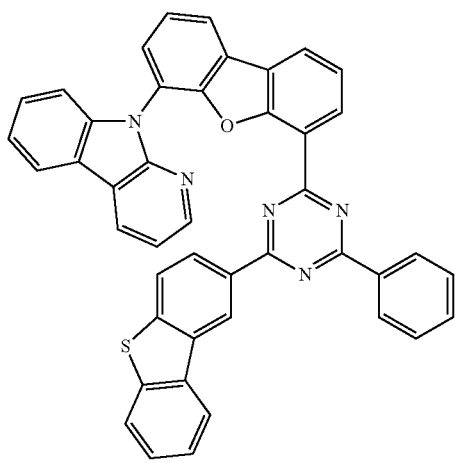
309
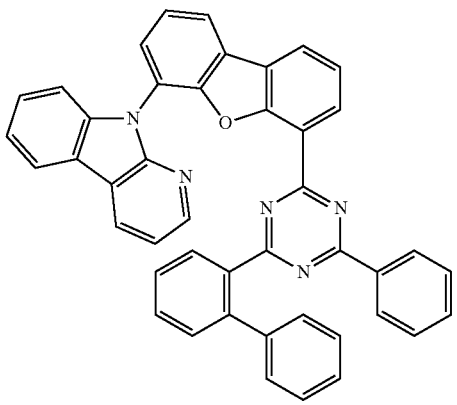
312
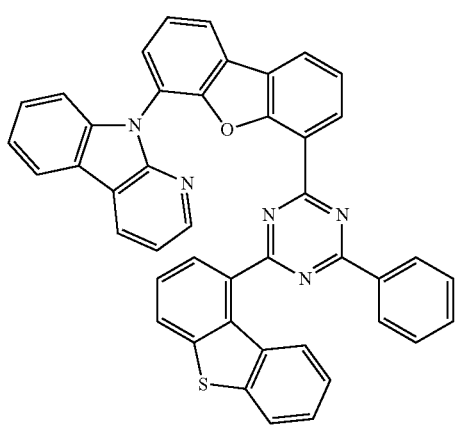
310
313
311
314

315
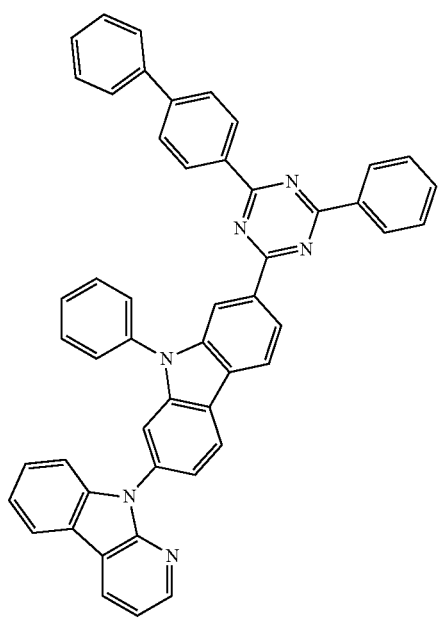
317
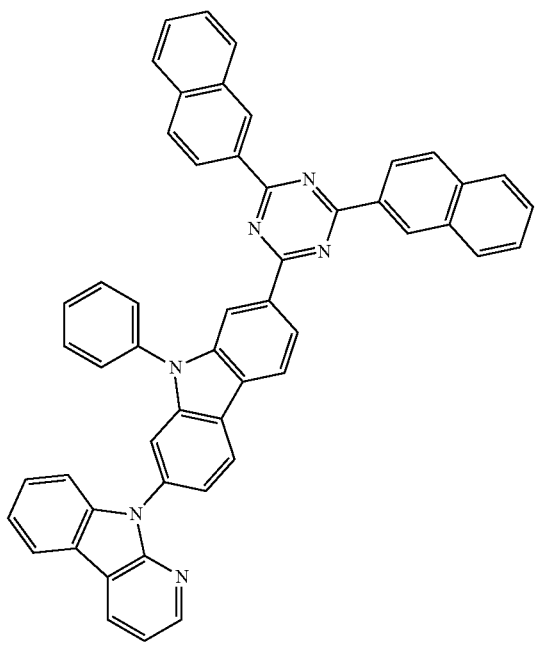
316
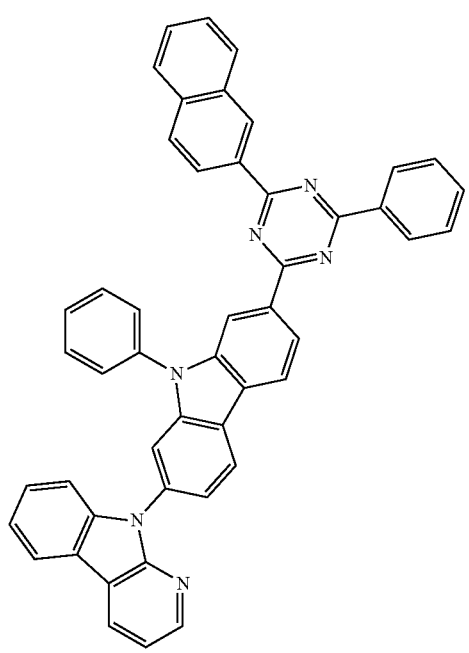
318
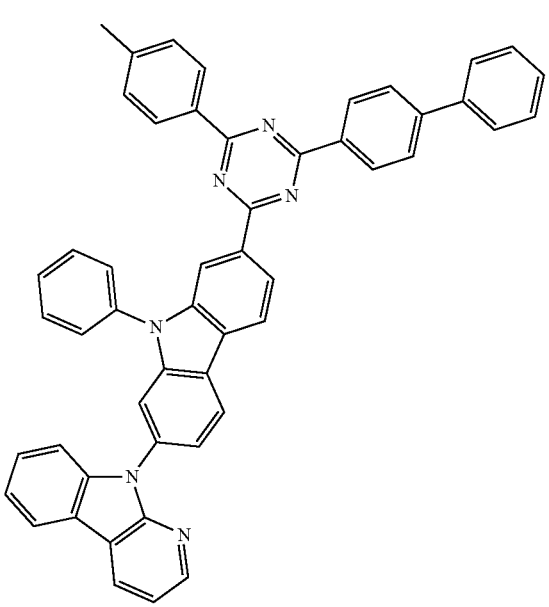

319
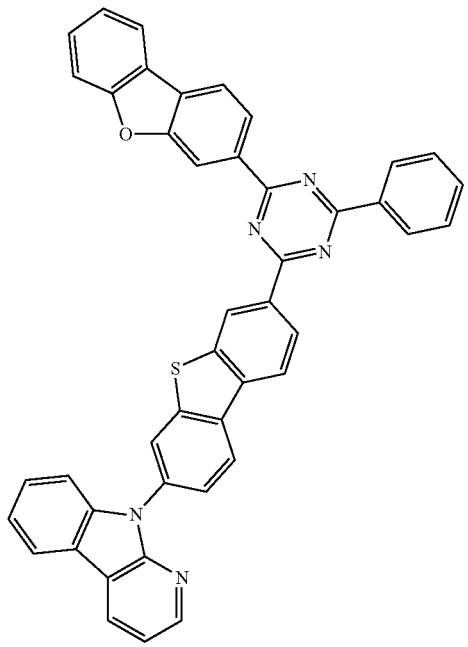
320
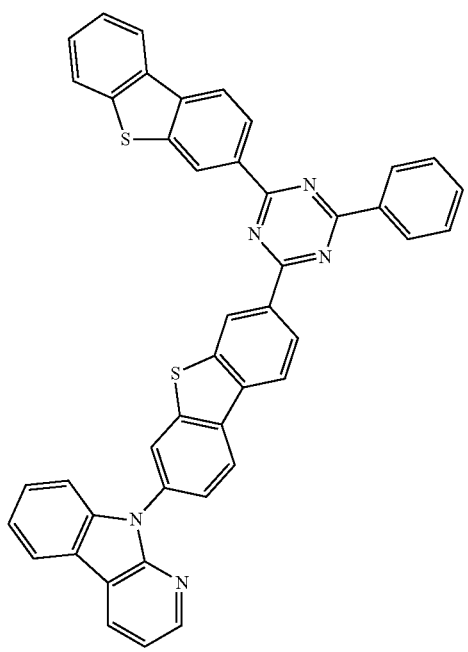
321
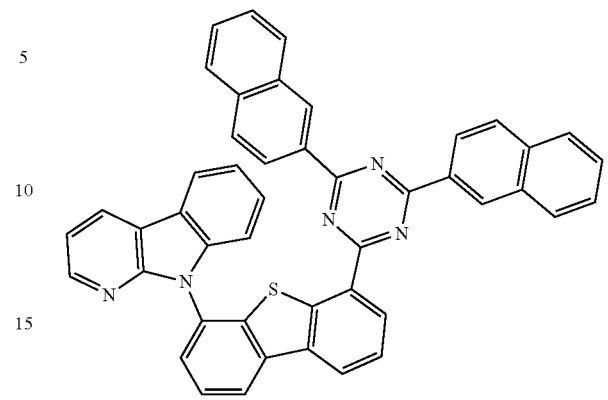
322
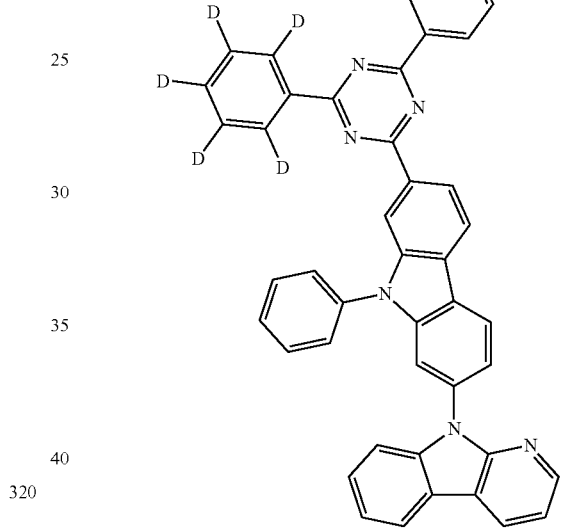
323
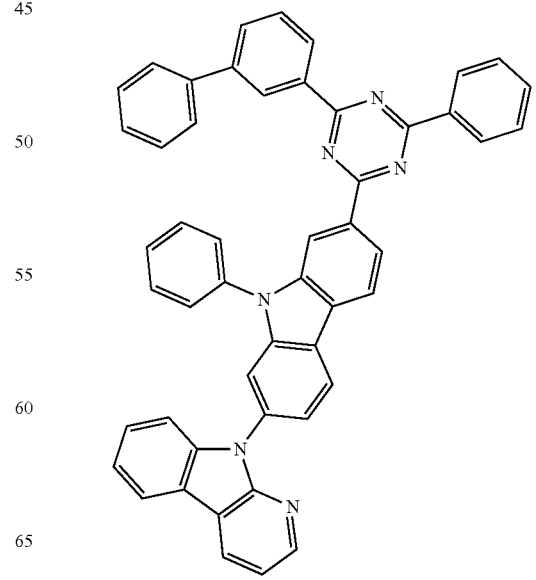

153
-continued
324
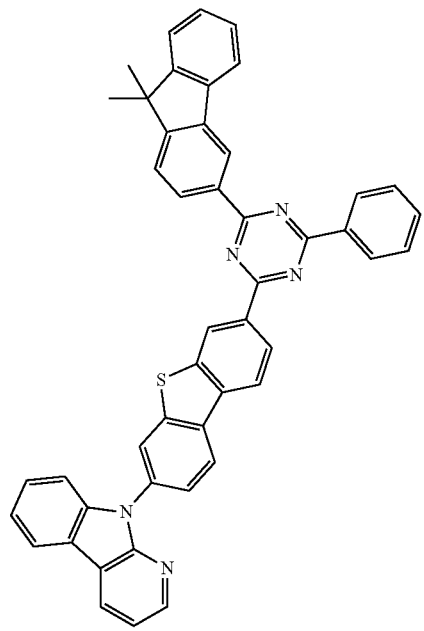
154
-continued
326
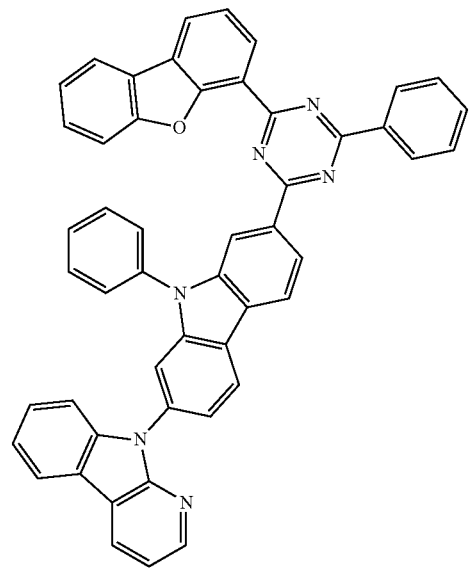
325
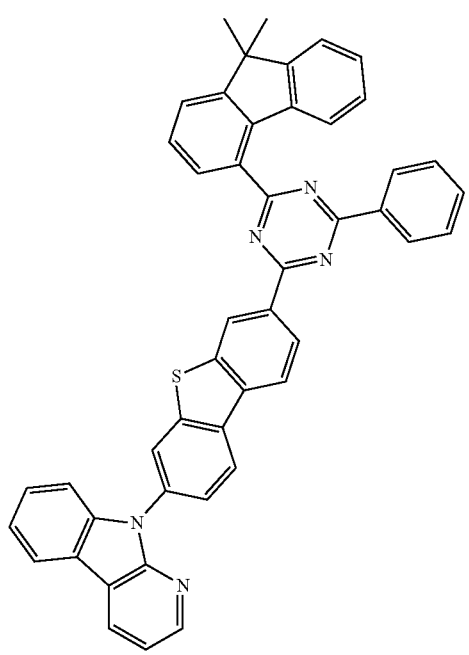
327
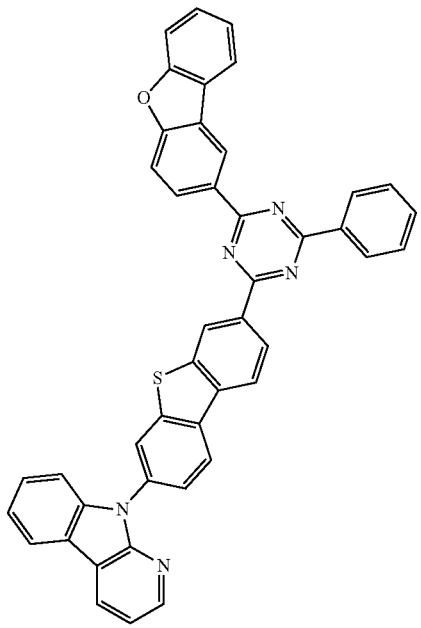

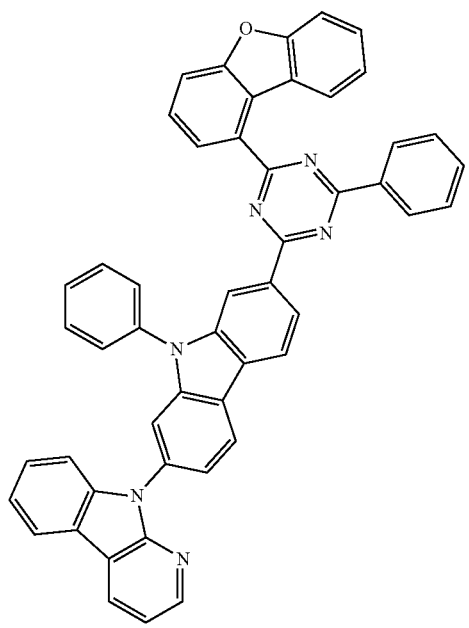
328
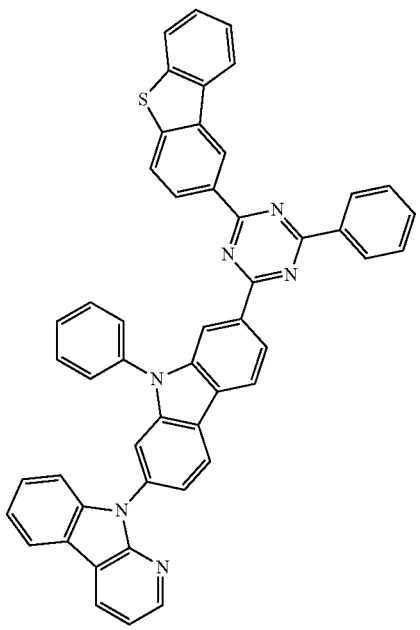
330
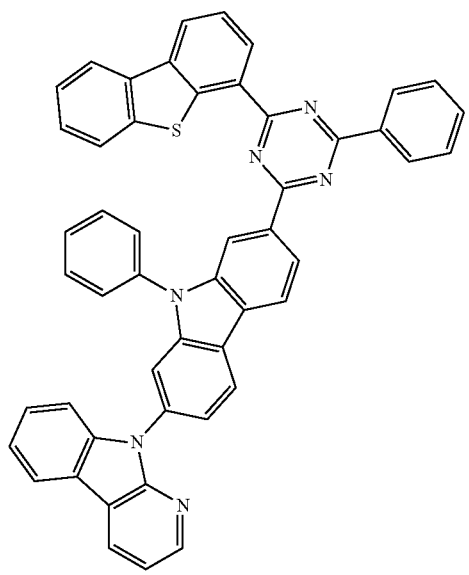
329
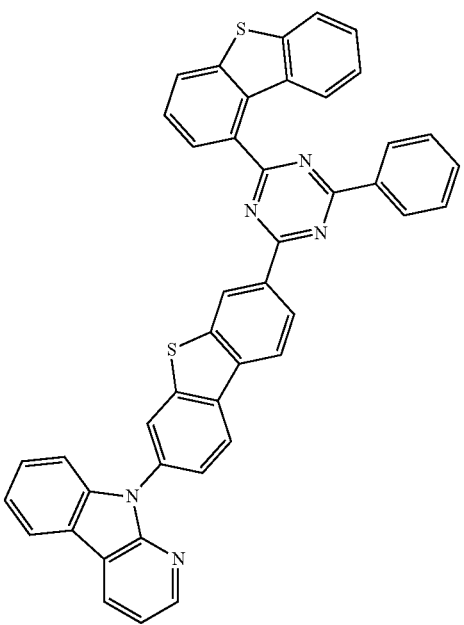
331

332
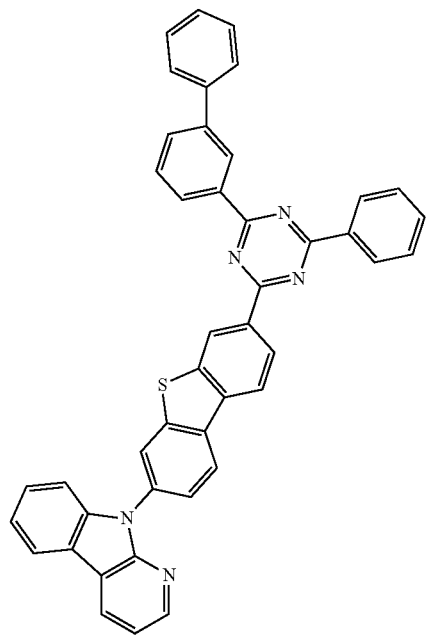
334
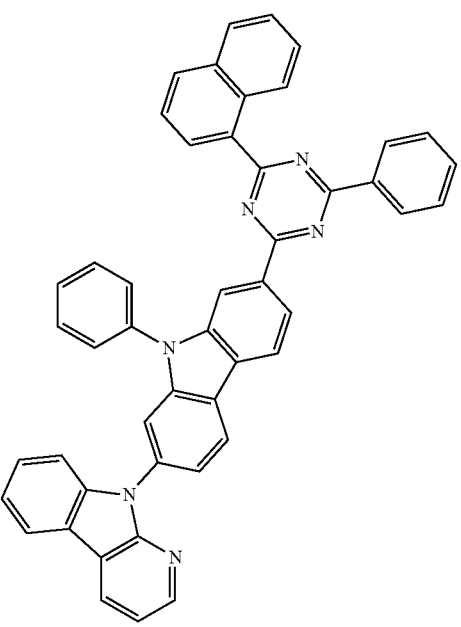
333
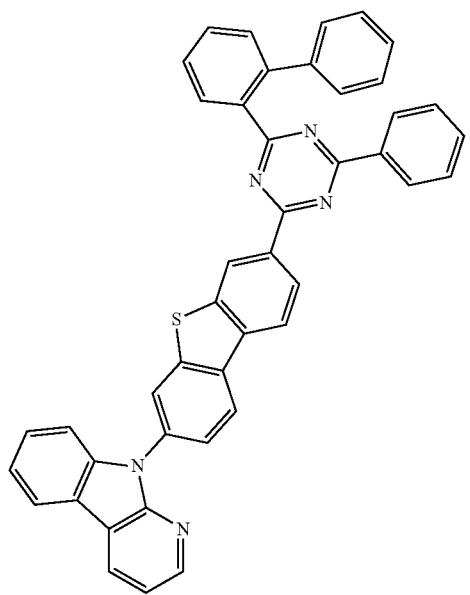
335
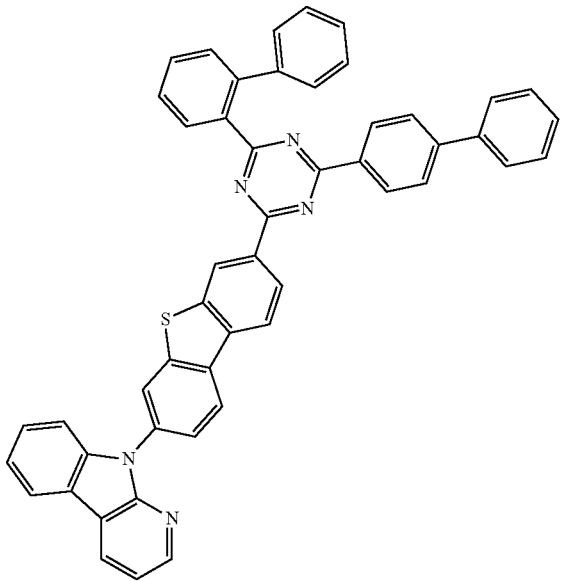

336
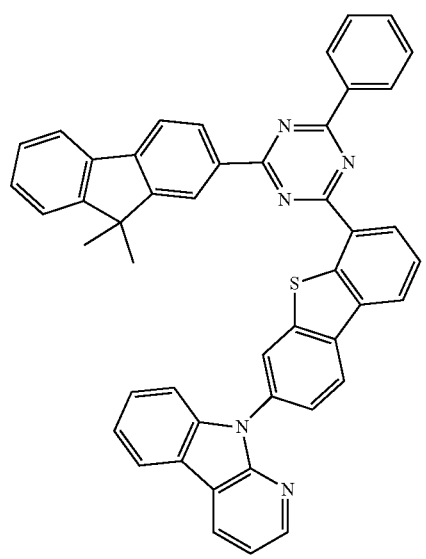
337
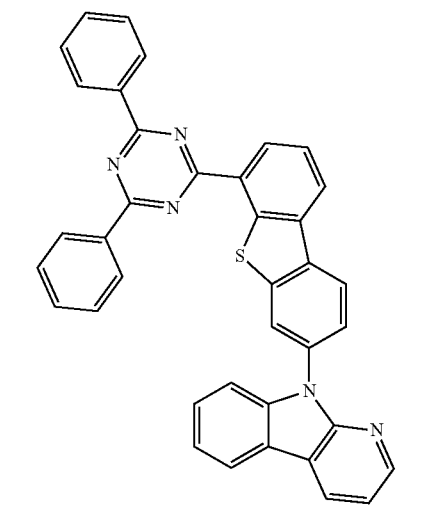
338
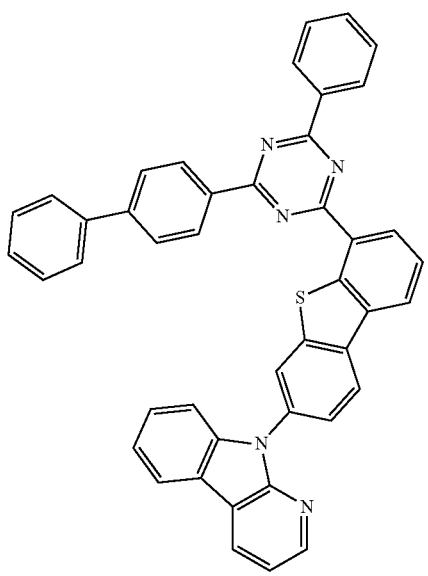
339
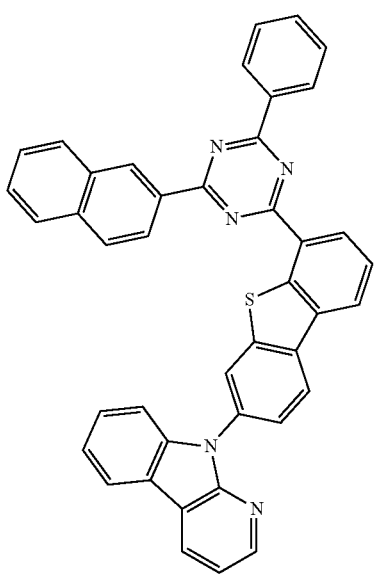
340
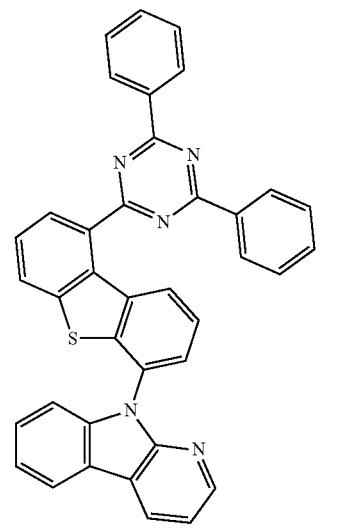
341

342
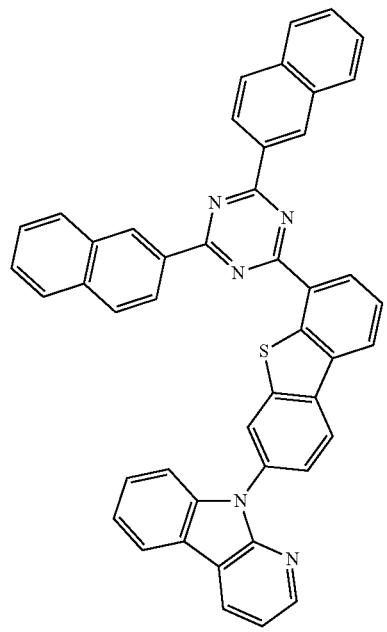
343
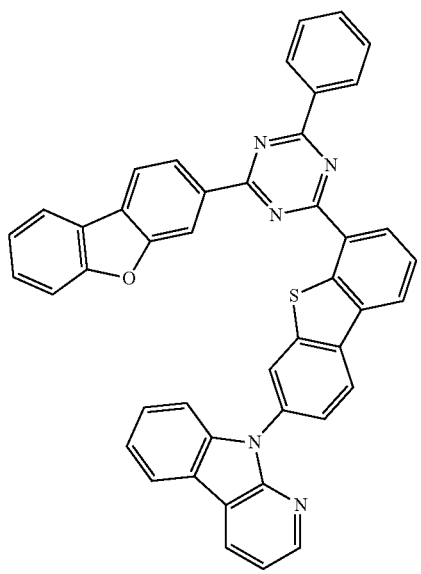
344
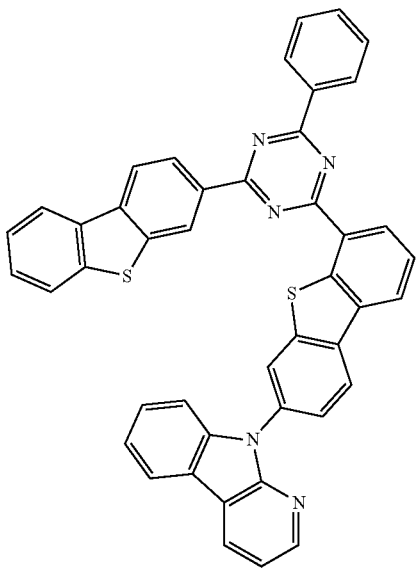
345
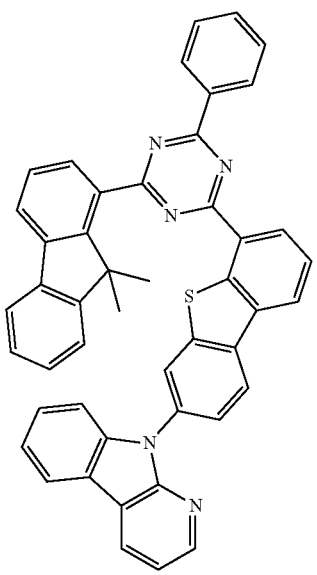

-continued
346
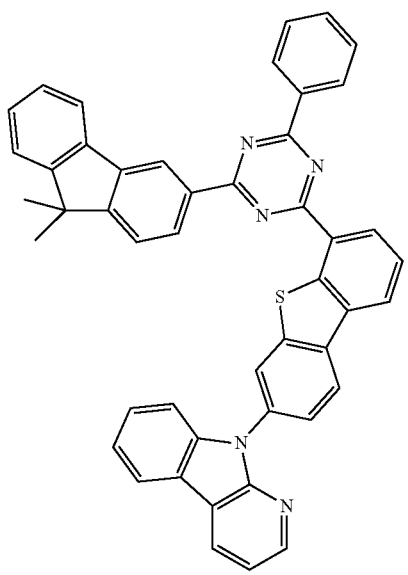
347
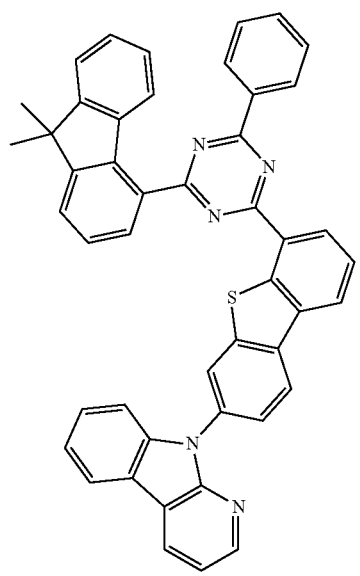
-continued
348
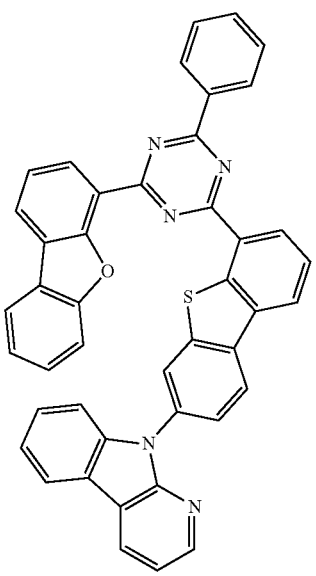
349

350
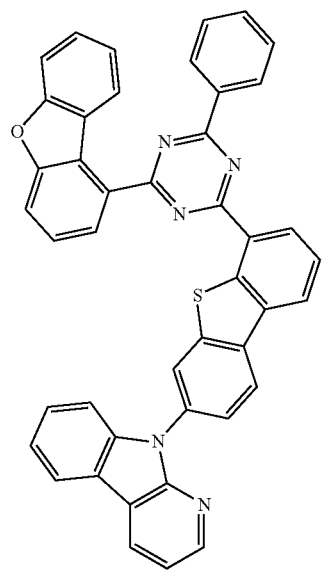
351
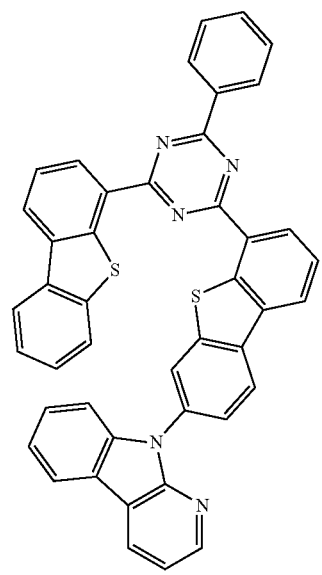
352
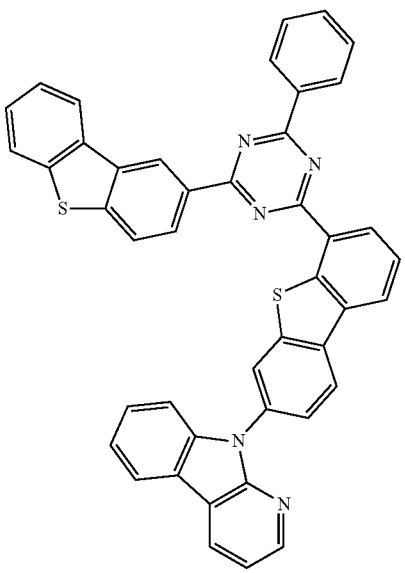
353
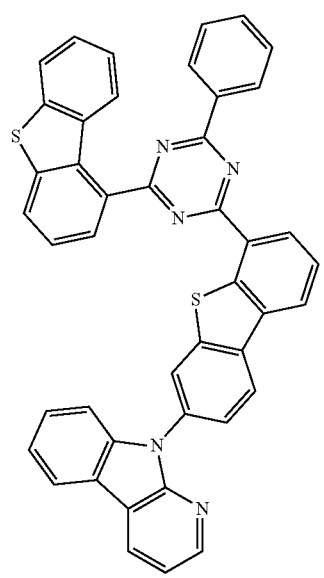

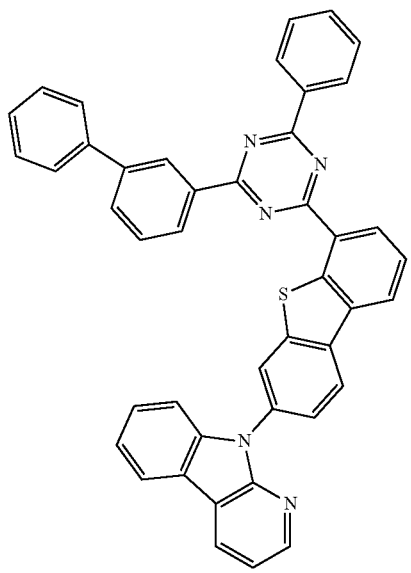
354
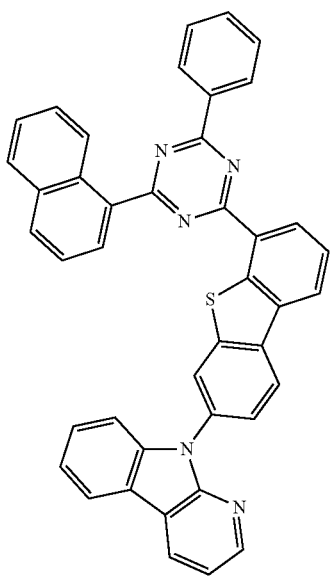
356
355
357
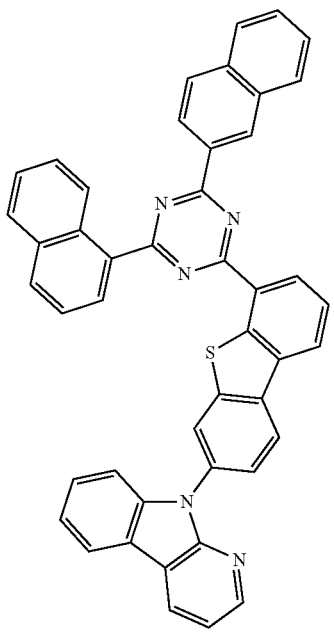

358
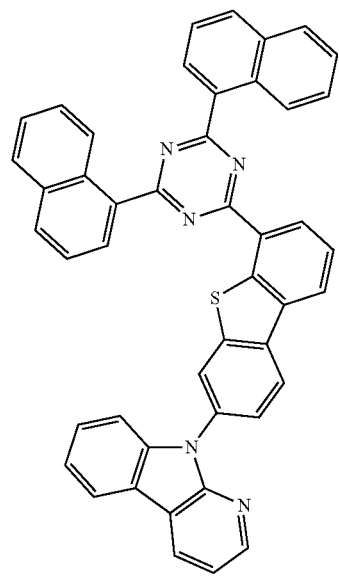
359
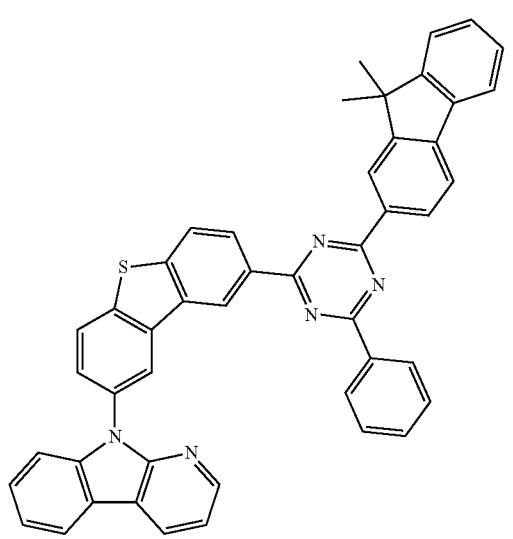
360
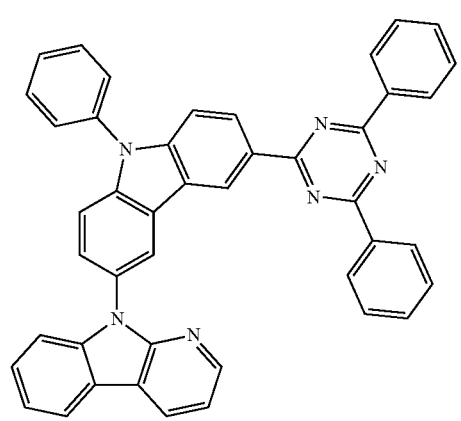
361
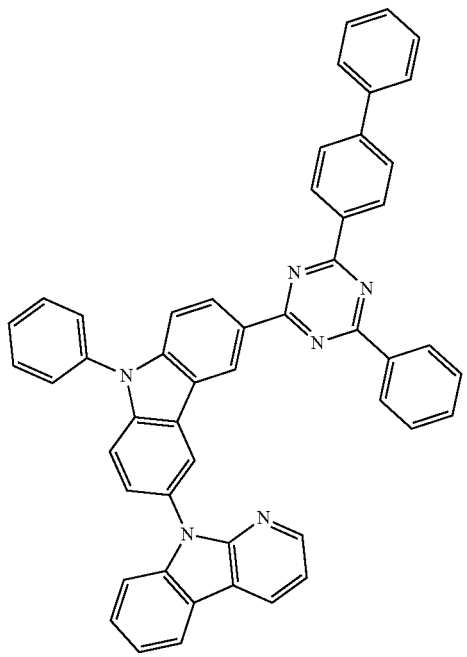
362
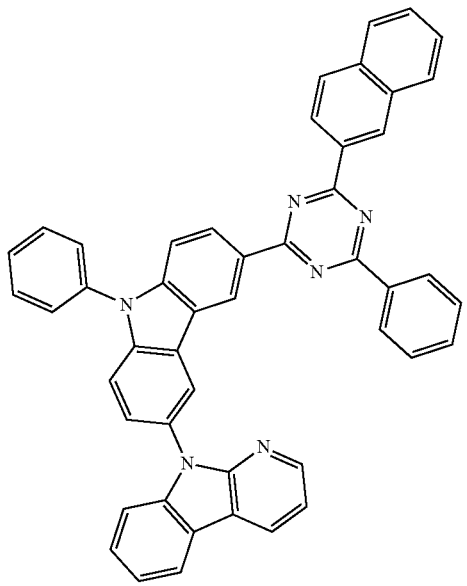

363
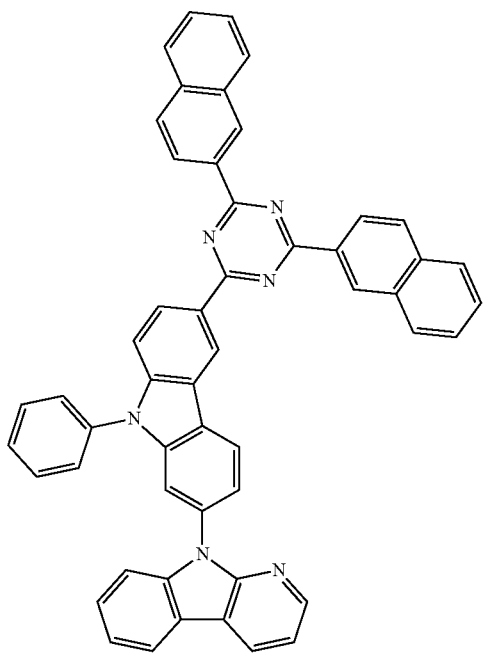
365
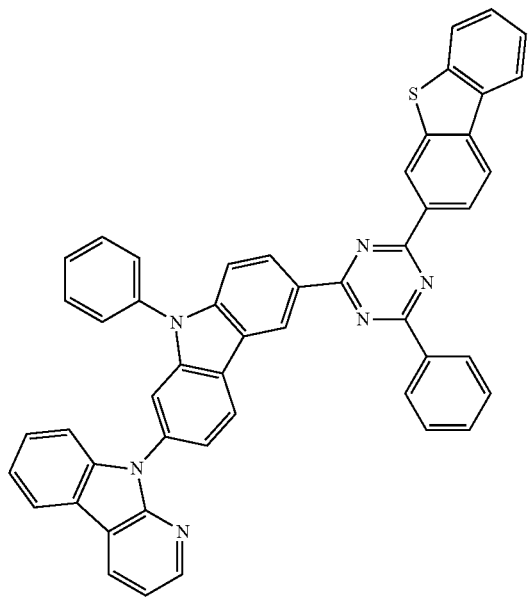
364
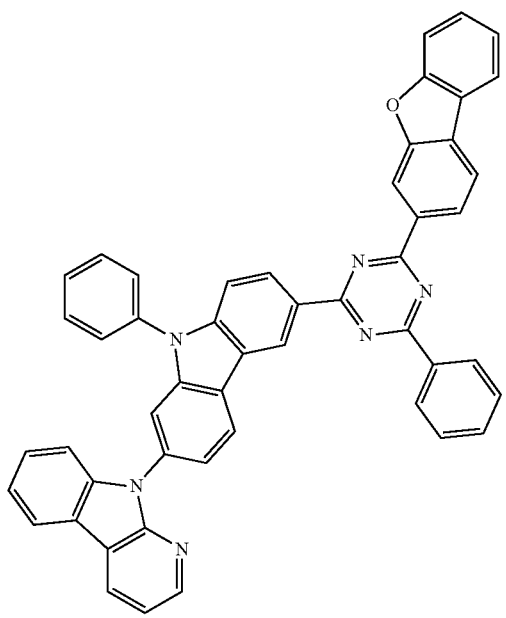
366
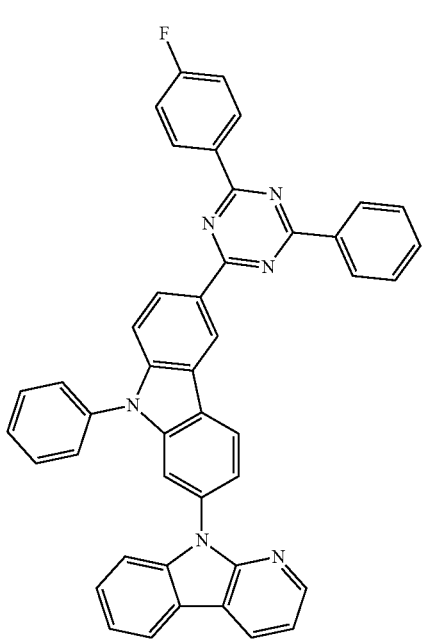

-continued
367
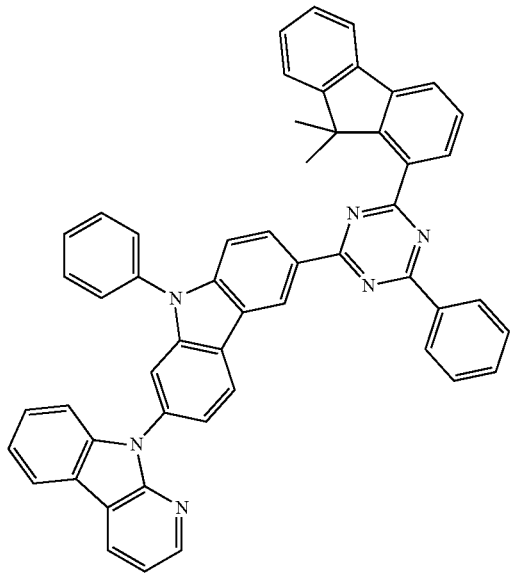
368
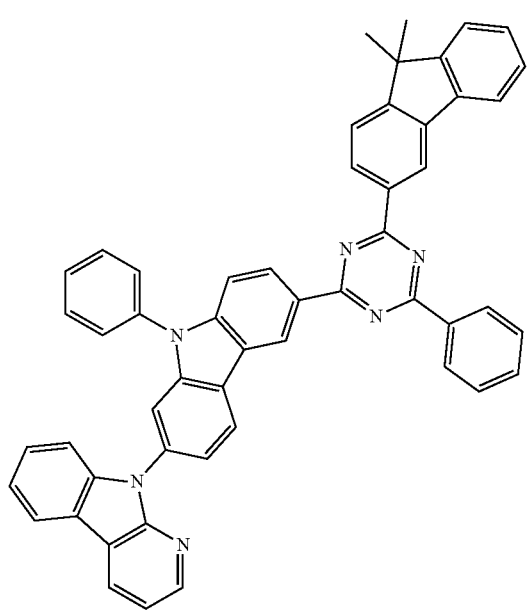
-continued
369
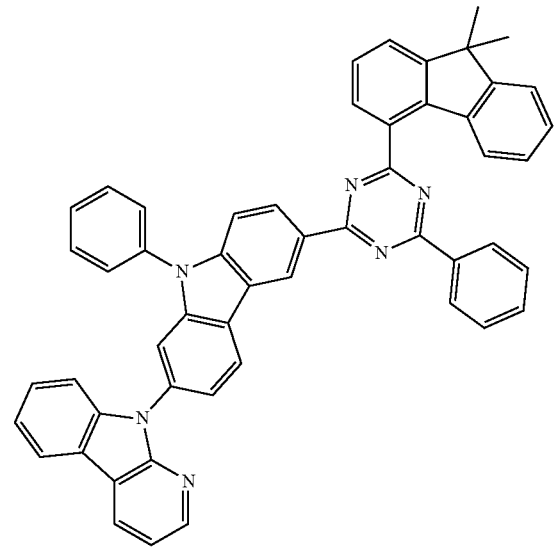
370
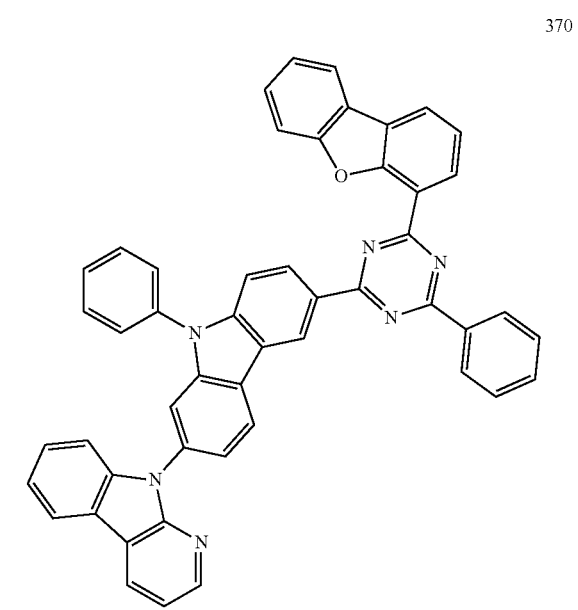

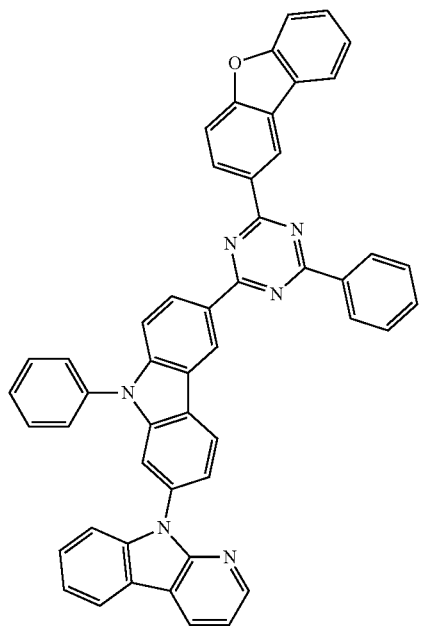
371
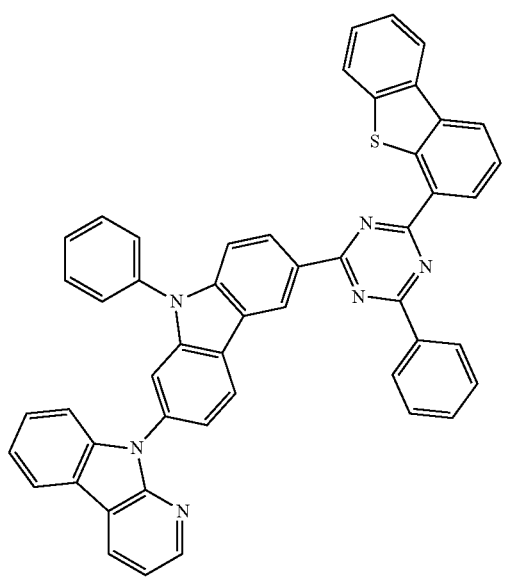
373
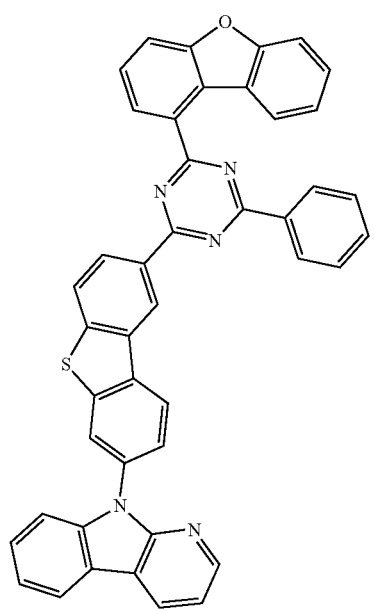
372
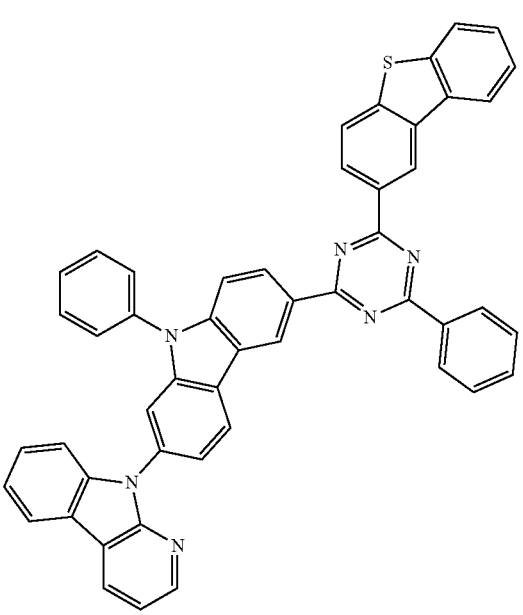
374

375
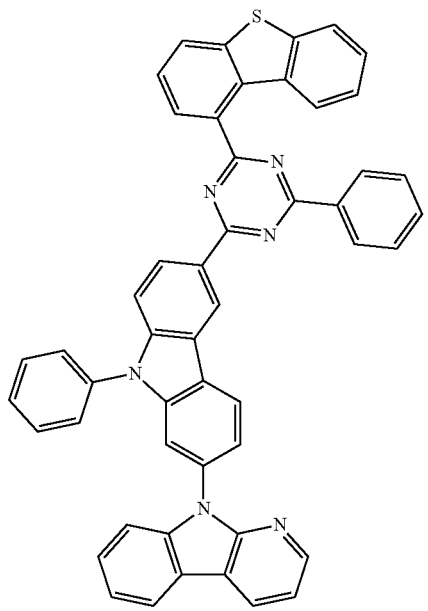
376
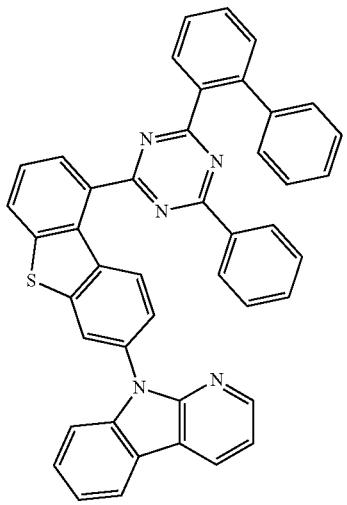
377
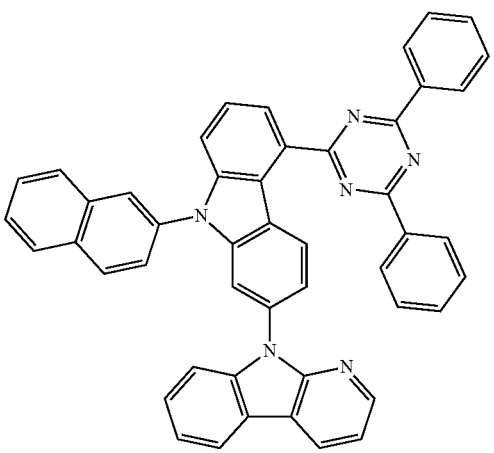
378
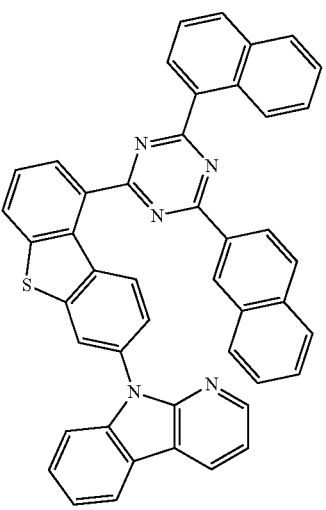
379

179
-continued
380
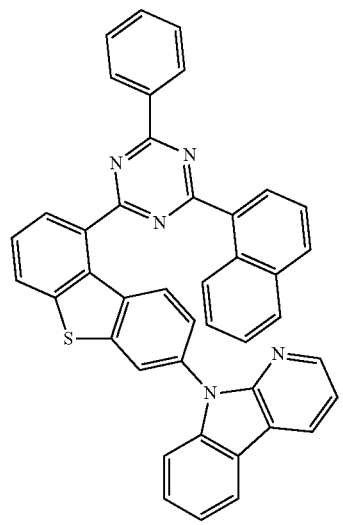
381
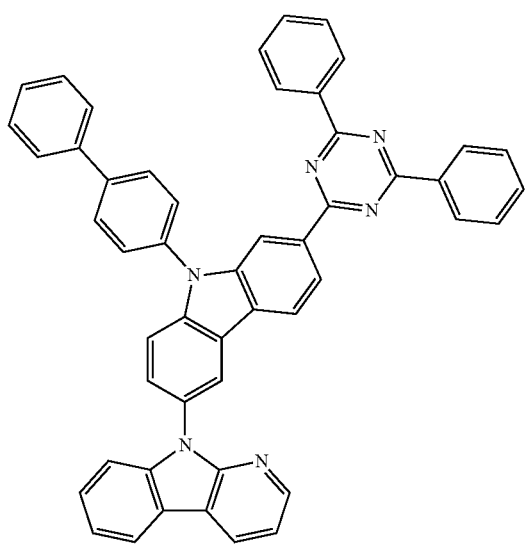
382
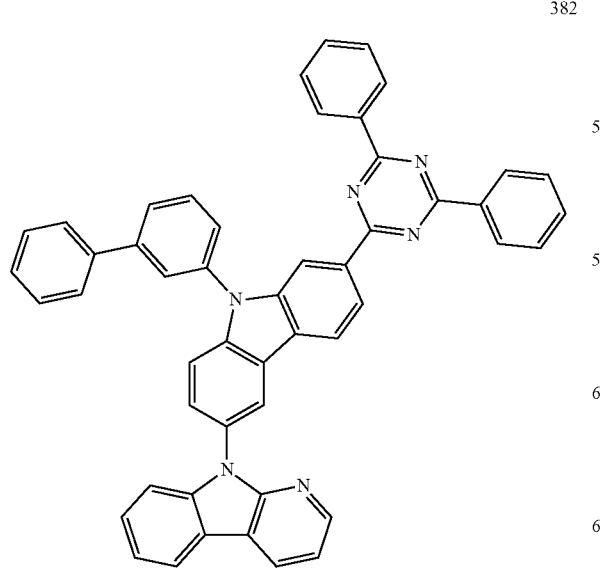
180
-continued
383
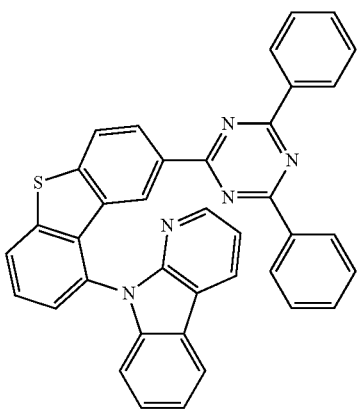
384
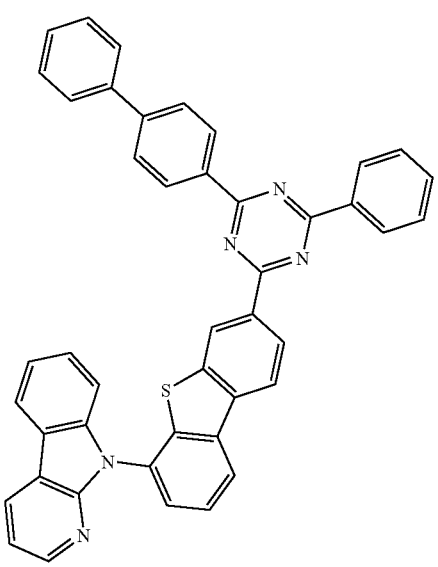
385
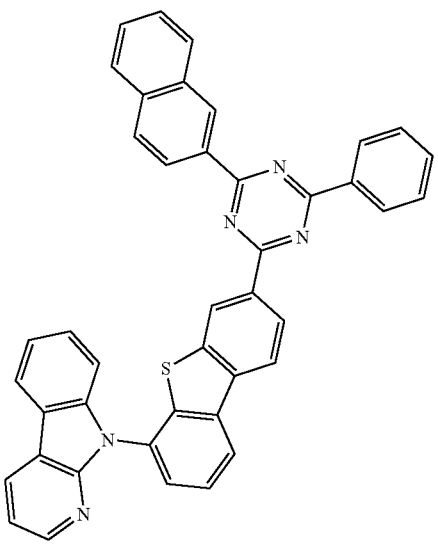

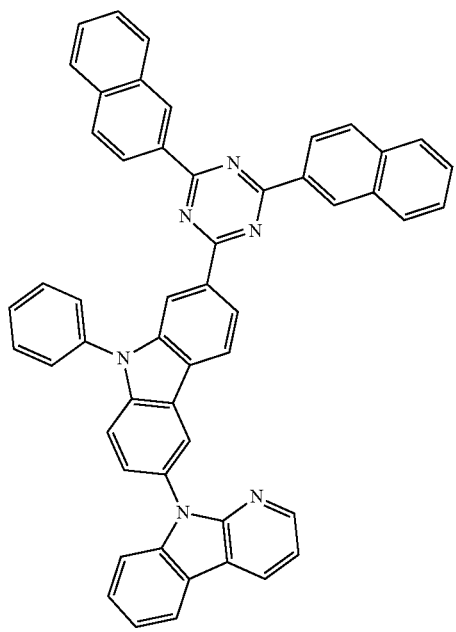
386
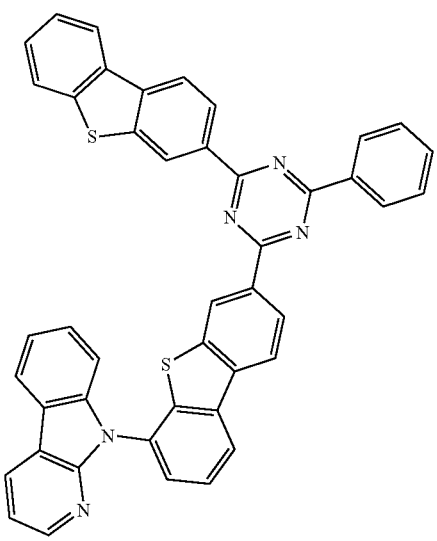
390
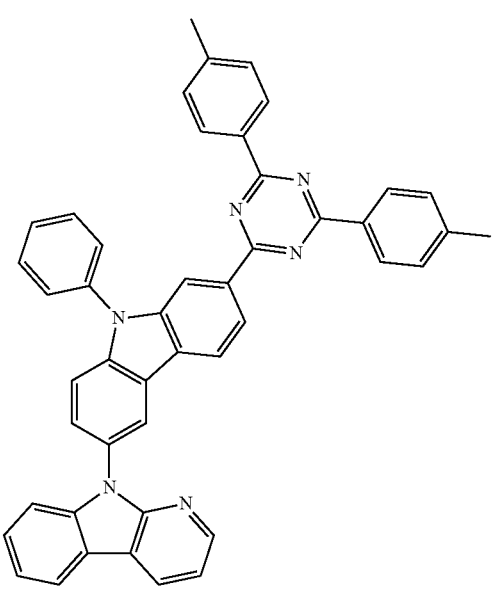
391
389
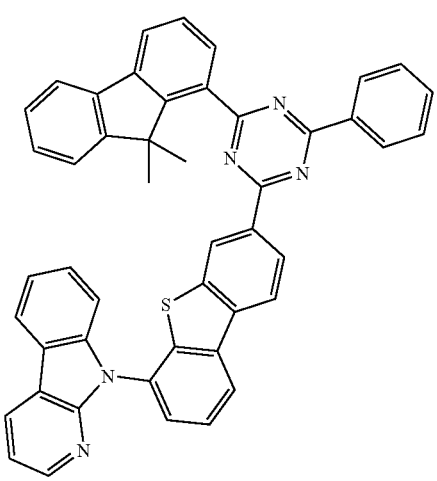
392

| | |
|---|---|
| 393 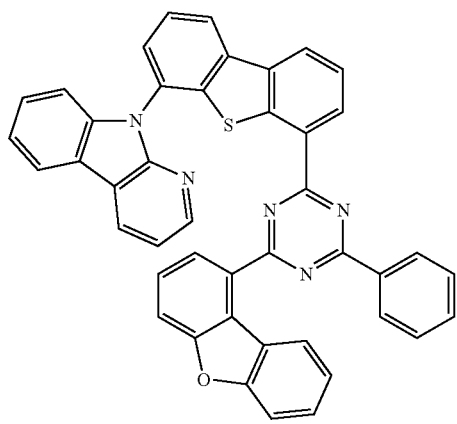 | 396 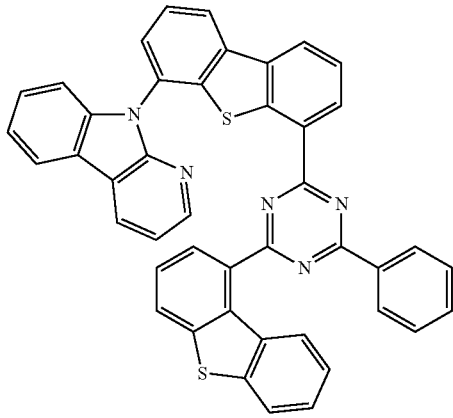 |
| 394 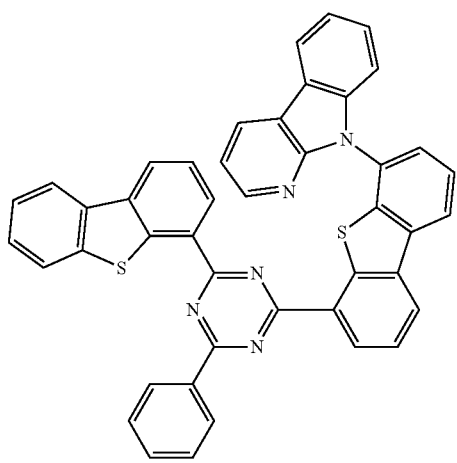 | 397 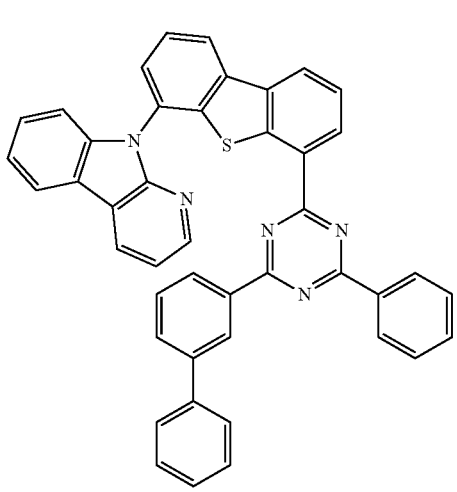 |
| 395 | 398 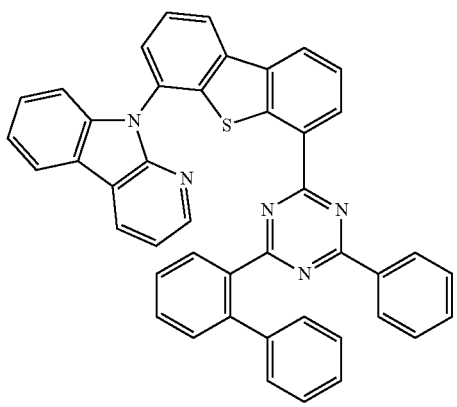 |

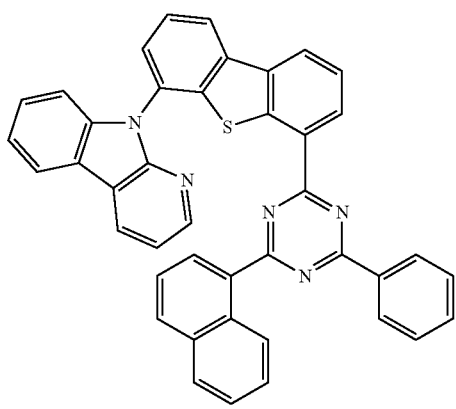

399

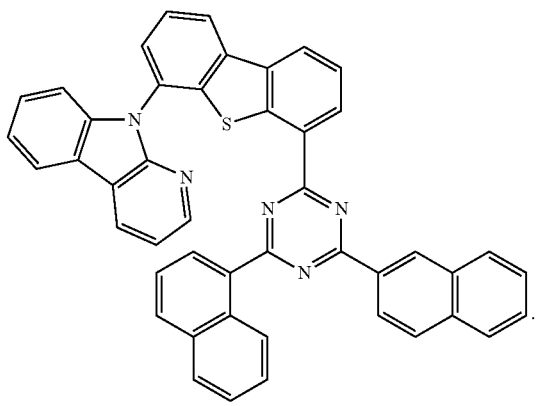

400

The synthetic methods of the heterocyclic compound provided by the discloser are not specially limited, and those skilled in the art can determine a proper synthetic method according to the heterocyclic compounds provided by the disclosure in combination with the preparation methods in the examples. In other words, the examples of the discloser exemplarily provide the preparation methods of the heterocyclic compounds, and the adopted raw materials can be obtained commercially or obtained by the methods well known in the field. All the heterocyclic compounds provided by the disclosure can be obtained by those skilled in the art according to the preparation methods in these exemplary examples, all specific preparation methods for preparing the heterocyclic compounds are no longer described in detail, and those skilled in the art should not be understood as limiting the discloser.

The discloser further provides an organic electroluminescent device. As shown in FIG. 1, the organic electroluminescent device includes an anode 100 and a cathode 200 which are oppositely arranged, and a functional layer arranged between the anode 100 and the cathode 200; the functional layer includes the heterocyclic compound provided by the discloser. The heterocyclic compound provided by the discloser can be used for forming at least one organic thin layer of the functional layer so as to improve the service life characteristic and the efficiency characteristic of the organic electroluminescent device. The organic electroluminescent device may be a blue light device or a green light device.

Optionally, the functional layer includes an organic light-emitting layer 330, and the organic light-emitting layer 330 contains the heterocyclic compound provided by the discloser.

According to one embodiment, as shown in FIG. 1, the organic electroluminescent device includes an anode 100, a hole transporting layer 321, an organic light-emitting layer 330, an electron transporting layer 340 and a cathode 200 which are sequentially stacked. The heterocyclic compound provided by the discloser may be applied to the organic light-emitting layer 330 of the organic electroluminescent device, so that the service life of the organic electroluminescent device is prolonged, and the luminous efficiency of the organic electroluminescent device is improved.

Optionally, the anode 100 includes an anode material, which is preferably a material with a large work function that facilitates hole injection into the functional layer. Specific examples of the anode material include, but are not limited to, metals such as nickel, platinum, vanadium, chromium, copper, zinc and gold, or an alloy thereof; metal oxides such as zinc oxide, indium oxide, indium tin oxide (ITO) and indium zinc oxide (IZO); combinations of metals and oxides, such as ZnO: Al or $SnO_2$:Sb; or a conductive polymer such as poly(3-methylthiophene), poly[3,4-(ethylene-1,2-dioxy)thiophene] (PEDT), polypyrrole and polyaniline. A transparent electrode containing indium tin oxide (ITO) as the anode is preferably included.

Optionally, the hole transporting layer 321 includes one or more hole transporting materials. The hole transporting materials may be selected from carbazole polymers, carbazole-connected triarylamine compounds, or other types of compounds, which are not specially limited in the present discloser.

Optionally, the organic light-emitting layer 330 includes a host material and a guest material, holes injected into the organic light-emitting layer 330 and electrons injected into the organic light-emitting layer 330 may be recombined in the organic light-emitting layer 330 to form excitons, the excitons transfer energy to the host material, then the host material transfers energy to the guest material, so that the guest material can emit light. The host material of the organic light-emitting layer 330 may be composed of the heterocyclic compound of the present discloser. The guest material of the organic light-emitting layer 330 may be a compound having a condensed aryl ring or a derivative thereof, a compound having a heteroaryl ring or a derivative thereof, an aromatic amine derivative, or other materials, which is not specially limited in the discloser.

Optionally, the electron transporting layer 340 is a single-layer structure or a multi-layer structure, and it include one or more electron transporting materials. The electron transporting materials may be selected from, but are not limited to, a benzimidazole derivative, an oxadiazole derivative, a quinoxaline derivative, or other electron transporting materials.

Optionally, the cathode 200 includes a cathode material, which is a material with a small work function that contributes to electron injection into the functional layer. Specific examples of the cathode materials include, but are not limited to, metals such as magnesium, calcium, sodium, potassium, titanium, indium, yttrium, lithium, gadolinium, aluminum, silver, tin and lead, or an alloy thereof; or multilayer materials such as LiF/Al, Liq/Al, LiO$_2$/Al, LiF/Ca, LiF/Al, and BaF$_2$/Ca. A metal electrode containing aluminum as the cathode is preferably included. In one embodiment of the present discloser, the material of the cathode 200 is a magnesium-silver alloy.

Optionally, as shown in FIG. 1, a hole injecting layer 310 is also be arranged between the anode 100 and the hole transporting layer 321, so that the capability of injecting holes into the hole transporting layer 321 is enhanced. The hole injecting layer 310 may be made of a benzidine derivative, a starburst arylamine compound, a phthalocyanine derivative, or other materials, which is not specially limited in the present discloser.

Optionally, as shown in FIG. 1, an electron blocking layer 322 is also be arranged between the hole transporting layer 321 and the organic light-emitting layer 330 so as to block electrons from being transported to the side of the hole transporting layer 321, improve the recombination rate of the electrons and holes in the organic light-emitting layer 330 and protect the hole transporting layer 321 from being impacted by the electrons. The material of the electron blocking layer 322 may be carbazole polymers, carbazole-connected triarylamine compounds, or other feasible structures.

Optionally, as shown in FIG. 1, an electron injecting layer 350 is also be arranged between the cathode 200 and the electron transporting layer 340 so as to enhance the capability of injecting electrons into the electron transporting layer 340. The electron injecting layer 350 may include an inorganic material such as an alkali metal sulfide and an alkali metal halide, or may include a complex of an alkali metal and an organic substance.

Figure 2:
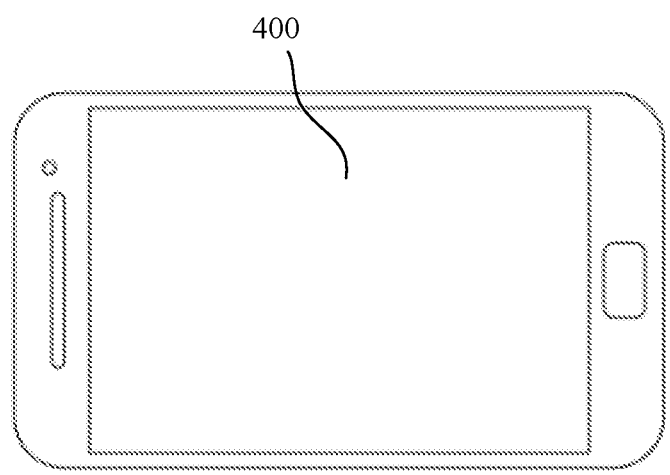
FIG. 2 is a structural schematic diagram of an electronic device in one embodiment of the discloser.

The discloser also provides an electronic device 400, as shown in FIG. 2, the electronic device 400 includes any one of the organic electroluminescent devices described in the above embodiments of the organic electroluminescent device. The electronic device 400 may be a display device, a lighting device, an optical communication device, or other types of electronic devices, and may include, for example, but is not limited to, a computer screen, a mobile phone screen, a television, an electronic paper, an emergency lighting lamp, an optical module and the like. Since the electronic device 400 is provided with any organic electroluminescent device described in the above embodiments of the organic electroluminescent device, the electronic device 400 has the same beneficial effects, which will not be repeated here.

The present disclosure is further described in detail below by examples. However, the following examples are merely illustrative of the disclosure, and are not intended to limit the disclosure.

Synthesis Example 1: Synthesis of Compound 6

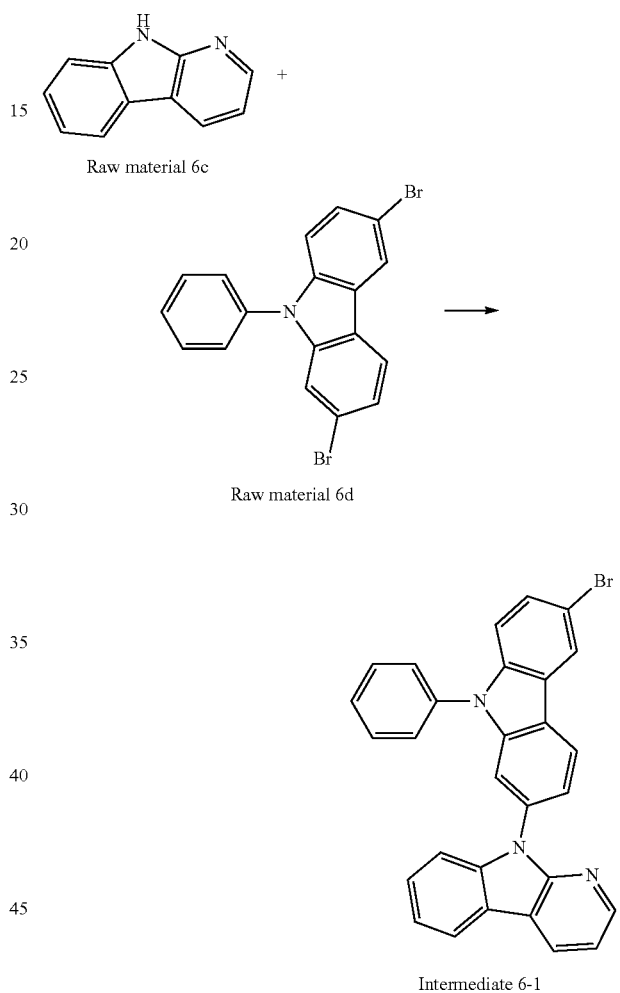

(1) Nitrogen (0.100 L/min) was introduced into a three-necked flask provided with a mechanical stirrer, a thermometer and a condenser tube for replacement for 15 min, and Raw material 6d (50 mmol), Raw material 6c (37.5 mmol), potassium carbonate (100 mmol), 18-crown-6-ether (6 mmol), 1,10-phenanthroline (6 mmol), cuprous iodide (12 mmol) and 125 mL of xylene were sequentially added. Stirring was started, the temperature was raised to 130° C. to 135° C. to react for 7 h, then 125 mL of toluene and 125 mL of water were added into the reaction solution under stirring, liquid separation was performed, and the water phase was extracted once with 125 mL of methylbenzene. Organic phases were mixed, and washed with water twice, dried over 5 g of anhydrous sodium sulfate, filtered, and concentrated (50° C. to 60° C., −0.09 MPa to −0.08 MPa) until no liquid drops flowed out, 30 mL of ethanol was added while stirring, and filtering was performed to obtain Intermediate 6-1 (24 mmol, yield: 64%).

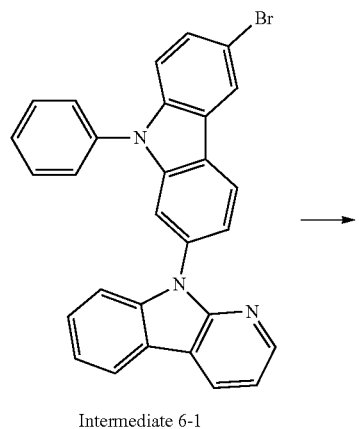

Intermediate 6-1

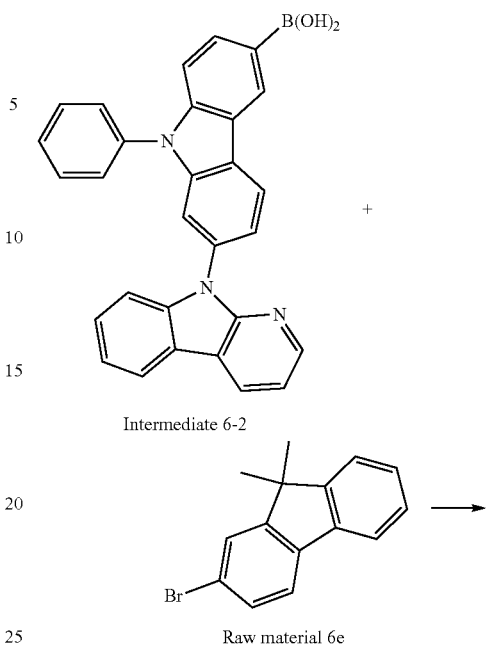

Intermediate 6-2

Raw material 6e

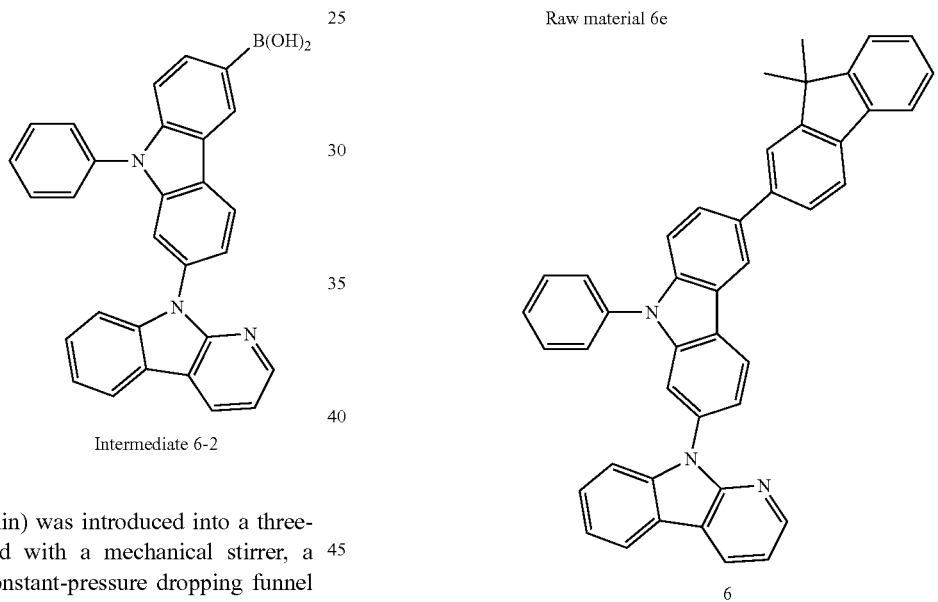

6

(2) Nitrogen (0.100 L/min) was introduced into a three-necked flask provided with a mechanical stirrer, a thermometer and a constant-pressure dropping funnel for replacement for 15 min, Intermediate 6-1 (24 mmol) and 60 mL of tetrahydrofuran were added, stirring was started, cooling was performed with liquid nitrogen to −90° C. to −80° C., 2 mol/L n-hexane solution of n-butyllithium (28 mmol) was dropwise added, the temperature was kept for 1 hour after dropwise adding, tributyl borate (32 mmol) was dropwise added, the temperature was kept for 1 hour after dropwise adding, 150 mL of water, 30.00 mL of petroleum ether and 2.4 mL of concentrated hydrochloric acid were added into the reaction solution, full stirring was performed, liquid separation was performed, and the organic phase was washed with water for 4 times, then filtered to obtain a crude product, pulping was performed with 24.0 mL of toluene for 0.5 h, filtering was performed, and drip washing was performed with toluene to obtain Intermediate 6-2 (15 mmol, yield: 63%).

(3) Nitrogen (0.100 L/min) was introduced into a three-necked reaction flask provided with a mechanical stirrer, a thermometer and a condenser tube for replacement for 15 min, Raw material 6e (15 mmol), Intermediate 6-2 (15 mmol), potassium carbonate (30 mmol), tetrakis(triphenylphosphine)palladium (0.15 mmol), 35 mL of toluene and 15 mL of water were added, stirring was started, heating was performed to 65° C. to 70° C., and the reaction was carried out for 4 h while heat preservation, 35 mL of water was added into the reaction solution while stirring, standing and liquid separation were performed, the water phase was extracted once with 35 mL of toluene, liquid separation was performed, and the organic phases were mixed, then washed twice with 35 mL of water. 5 g of anhydrous sodium sulfate was added into the organic phase for drying, filtering was performed, the organic phase was concentrated (−0.08 MPa to −0.09 MPa, 55°

C. to 65° C.) until no liquid flowed out, 15 mL of petroleum ether was added while stirring, and filtering was performed to obtain the compound 6 (7.49 g, yield: 830%), m/z=602.3 [M+H]$^+$.

Synthesis Examples 2 to 7

According to the method in Synthesis example 1, compounds listed in Table 1 were synthesized respectively, except that Raw material 6d and Raw material 6e were replaced with Raw material Id and Raw material e respectively, and the adopted main raw materials, the structures of the synthesized compounds, the total yield of the compounds in the whole process and the mass spectrum result are shown in Table 1.

TABLE 1
| Synthesis example No. | Compound No. | Raw material Id | Raw material Ie | Compound structure | Yield, % | Mass spectrum (m/z), [M + H]+ |
|---|---|---|---|---|---|---|
| 2 | 10 | 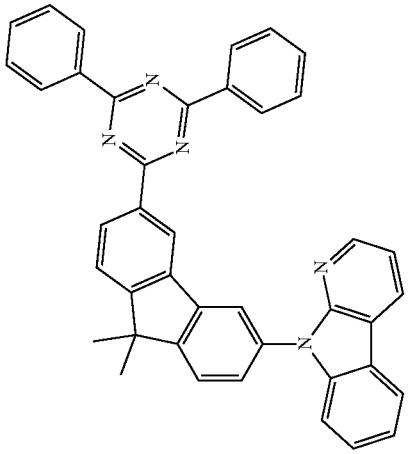 |  | 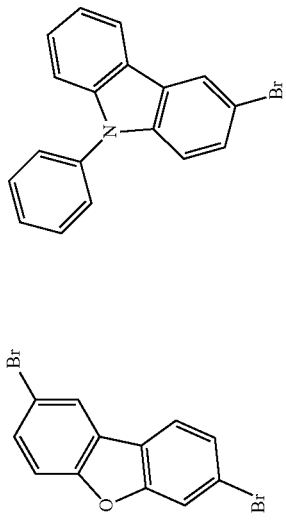 | 33 | 592.5 |
| 3 | 18 | 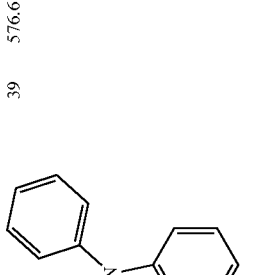 | | 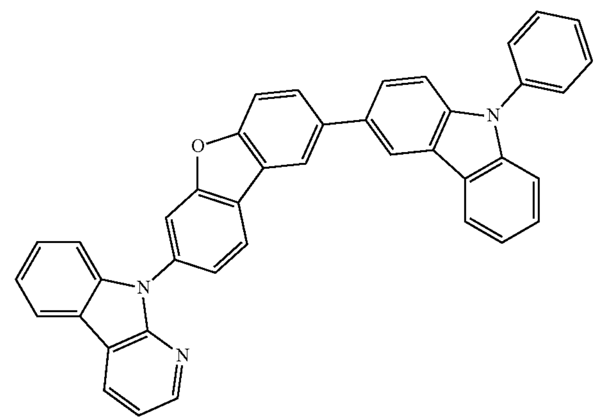 [SMILES: c1ccc(-n2c3ccccc3c3cc(-c4ccc5oc6cc(-n7c8ccccc8c8cccnc87)ccc6c5c4)ccc32)cc1] | 39 | 576.6 |

TABLE 1-continued

| Synthesis example No. | Compound No. | Raw material Id | Raw material Ie | Compound structure | Yield, % | Mass spectrum (m/z), [M + H]+ |
|---|---|---|---|---|---|---|
| 4 | 50 | | | 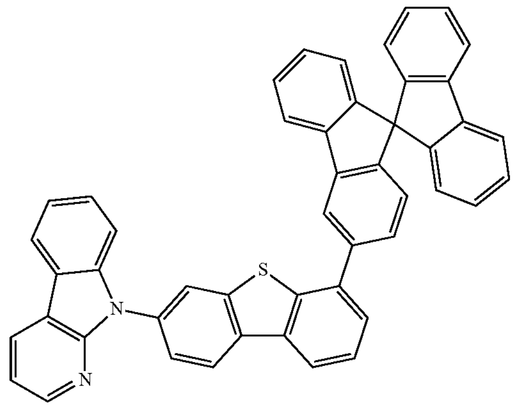 [SMILES: c1ccc2c(c1)-c1ccccc1C21c2ccccc2-c2cc(-c3cccc4c3sc3cc(-n5c6ccccc6c6cccnc65)ccc34)ccc21] | 35 | 665.2 |
| 5 | 66 | | | 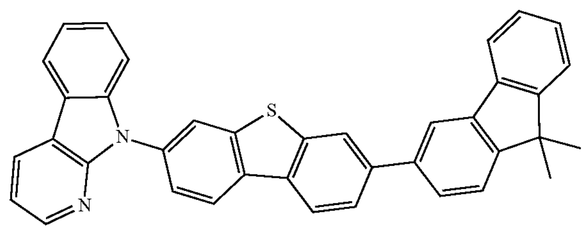 [SMILES: CC1(C)c2ccccc2-c2cc(-c3ccc4c(c3)sc3cc(-n5c6ccccc6c6cccnc65)ccc34)ccc21] | 31 | 543.5 |

TABLE 1-continued

| Synthesis example No. | Compound No. | Raw material Id | Raw material Ie | Compound structure | Yield, % | Mass spectrum (m/z), [M + H]+ |
|---|---|---|---|---|---|---|
| 6 | 77 | | | 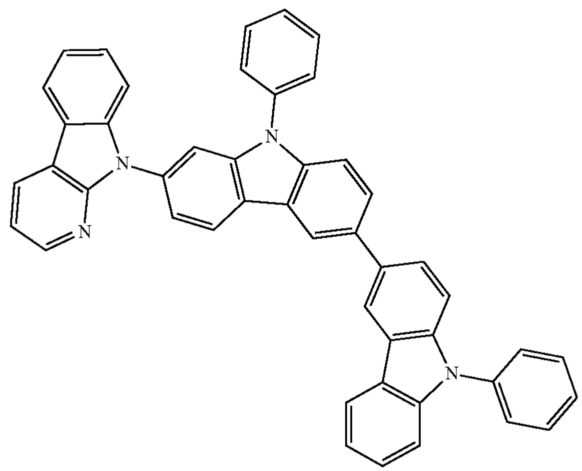 [SMILES: c1ccc(-n2c3ccccc3c3cc(-c4ccc5c(c4)c4ccc(-n6c7ccccc7c7cccnc76)cc4n5-c4ccccc4)ccc32)cc1] | 33 | 651.3 |
| 7 | 81 | | | 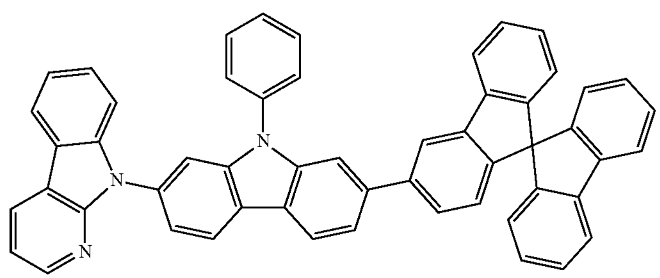 [SMILES: c1ccc(-n2c3cc(-c4ccc5c(c4)-c4ccccc4C54c5ccccc5-c5ccccc54)ccc3c3ccc(-n4c5ccccc5c5cccnc54)cc32)cc1] | 34 | 724.6 |

Synthesis of Intermediate I

1. Synthesis of Intermediate 1

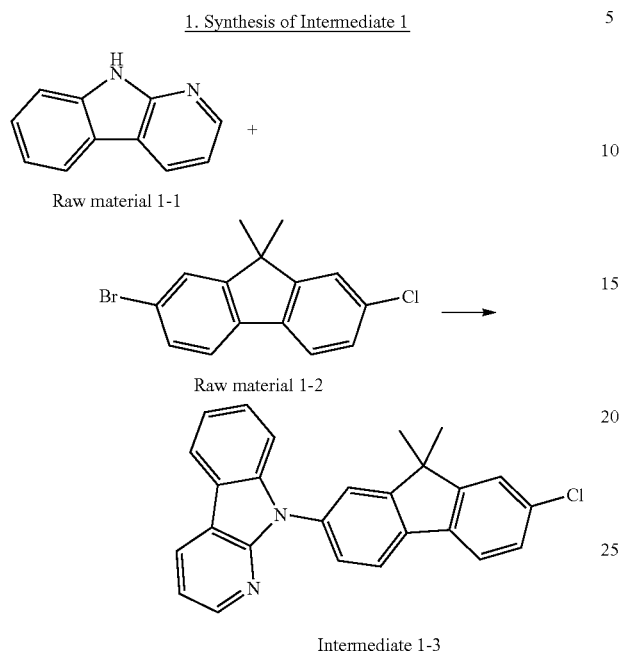

Raw material 1-1

Raw material 1-2

Intermediate 1-3

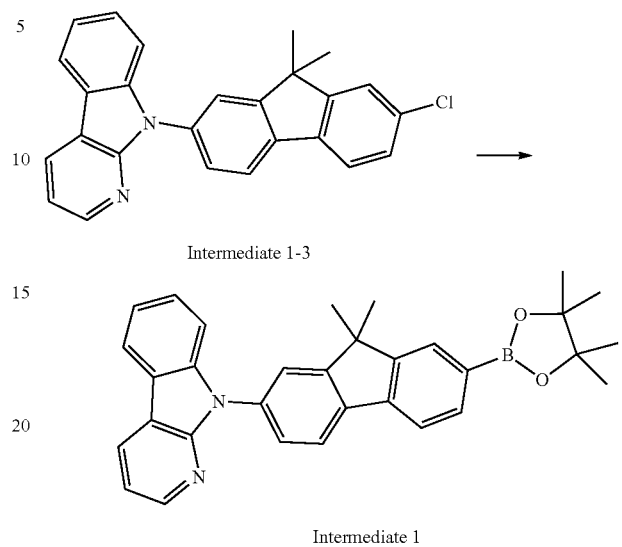

Intermediate 1-3

Intermediate 1

(1) Nitrogen (0.100 L/min) was introduced into a three-necked flask provided with a mechanical stirrer, a thermometer and a condenser tube for replacement for 15 min, and Raw material 1-1 (8.4 g, 50 mmol), Raw material 1-2 (16.8 g, 55 mmol), potassium carbonate (13.8 g, 100 mmol), 18-crown-6-ether (1.3 g, 5 mmol), 1,10-phenanthroline (1.0 g, 5 mmol), cuprous iodide (1.9 g, 10 mmol) and 130 mL of xylene were sequentially added. Stirring was started, the temperature was raised to 130° C. to 135° C. to react for 10 h. 130 mL of toluene and 130 mL of water were added into the reaction solution while stirring, liquid separation was performed, and the water phase was extracted once with 130 mL of toluene. The organic phases were mixed, and then washed with water twice, dried over 5 g of anhydrous sodium sulfate, filtered, and concentrated (50° C. to 60° C., −0.09 MPa to −0.08 MPa) until no liquid drops flowed out, 25 mL of ethanol was added while stirring, and filtering was performed to obtain Intermediate 1-3 (15.8 g, yield: 80%).

(2) Nitrogen (0.100 L/min) was introduced into a three-necked flask provided with a mechanical stirrer and a thermometer for replacement for 15 min, Intermediate 1-3 (15.8 g, 40 mmol), pinacol diborate (12.2 g, 48 mmol), potassium acetate (7.9 g, 80 mmol) and 80 mL of 1,4-dioxane were sequentially added, stirring was started, heating was performed to 60° C. to 65° C., bis(tricyclohexylphosphine)palladium dichloride (0.30 g, 0.4 mmol) was added, heating was continuously performed to 85° C. to 90° C., the temperature was kept for 5 h, then 60 mL of water was added, extraction was performed with 100 mL of dichloromethane, the water phase was extracted with 30 mL of dichloromethane, and the organic phases were mixed, washed with water twice, dried over 2 g of anhydrous sodium sulfate, filtered, and concentrated (40° C. to 45° C., −0.06 MPa to −0.05 MPa) until no liquid flowed out, 20 mL of cyclohexane was added, and filtering was performed to obtain Intermediate 1 (15.1 g, yield: 77.5%).

2. Intermediates shown in Table 2 were synthesized according to the synthesis method of Intermediate 1, except that Raw material I-2 was used to replace Raw material 1-2, and Raw material I-2, the structures of the intermediates and the total yield are shown in Table 2.

TABLE 2

| Intermediate I No. | Raw material 1-1 | Raw material I-2 | Structure of Intermediate I | Total yield, % |
|---|---|---|---|---|
| Intermediate 2 | <img> | <img> | <img> | 58.7 |

TABLE 2-continued

| Intermediate I No. | Raw material I-1 | Raw material I-2 | Structure of Intermediate I | Total yield, % |
|---|---|---|---|---|
| Intermediate 3 | | | | 55.3 |
| Intermediate 4 | | | | 60.5 |
| Intermediate 5 | | | | 62.8 |
| Intermediate 6 | | | | 59.7 |

TABLE 2-continued
| Intermediate I No. | Raw material 1-1 | Raw material I-2 | Structure of Intermediate I | Total yield, % |
|---|---|---|---|---|
| Intermediate 7 | | | | 56.8 |
| Intermediate 8 | | | | 55.9 |
| Intermediate 9 | | | | 58.7 |
Synthesis Example 8: Synthesis of Compound 95
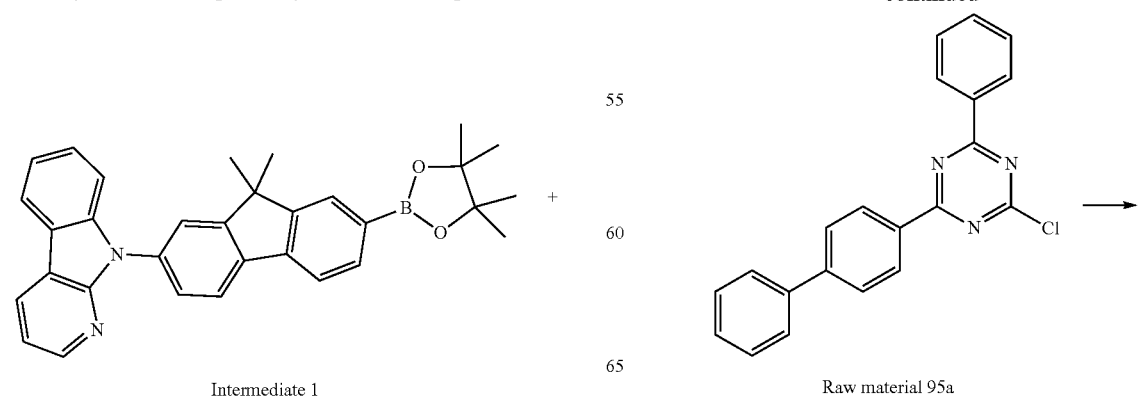
Intermediate 1
Raw material 95a -continued

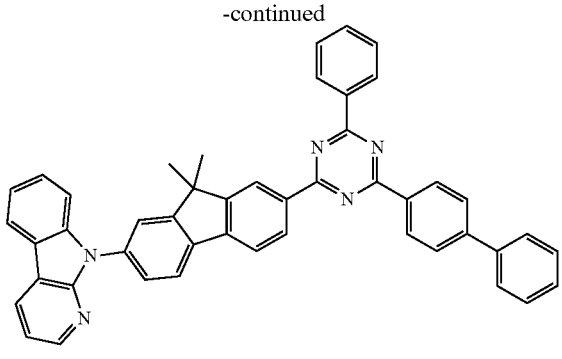

95

Nitrogen (0.100 L/min) was introduced into a three-necked reaction flask provided with a mechanical stirrer, a thermometer and a condenser tube for replacement for 15 min, Intermediate 1 (9.7 g, 20 mmol), Raw material 95a (7.2 g, 21 mmol), potassium carbonate (5.5 g, 40 mmol), tetrakis(triphenylphosphine)palladium (0.23 g, 0.2 mmol), 50 mL of methylbenzene and 20 mL of water were added, stirring was started, heating was performed to 65° C. to 70° C., and the reaction was carried out for 4 h while heat preservation, 50 mL of water was added into the reaction solution while stirring, standing and liquid separation were performed, the water phase was extracted once with 50 mL of toluene, liquid separation was performed, and the organic phases were mixed, washed twice with 50 mL of water. 5 g of anhydrous sodium sulfate was added into the organic phase for drying, filtering was performed, the organic phase was concentrated (−0.08 MPa to −0.09 MPa, 55° C. to 65° C.) until no liquid flowed out, 20 mL of ethanol was added while stirring, and filtering was performed to obtain the compound 95 (12.0 g, yield: 90.0%), m/z=668.3 [M+H]$^+$. NMR of the compound 95: $^1$H-NMR (CDCl$_3$, 400 MHz) δ ppm: 8.71-8.68 (m, 2H), 8.45-8.41 (m, 3H), 8.21-8.17 (m, 2H), 8.06-8.02 (m, 3H), 7.93 (s, 1H), 7.81-7.77 (m, 3H), 7.70 (s, 1H), 7.62-7.56 (m, 6H), 7.50-7.48 (m, 1H), 7.43-7.40 (m, 1H), 7.30-7.26 (dd, 2H), 7.19-7.15 (m, 2H), 2.54 (s, 6H).

Synthesis Examples 9-30

Compounds shown in Table 3 were synthesized by referring to the synthesis method in synthesis example 8, except that the intermediate I was used to replace the intermediate 1, a raw material Ia was used to replace the raw material 95, and the adopted main raw materials, the yield of the compounds and a mass spectrum result are shown in Table 3.

TABLE 3

| Synthesis example No. | Compound No. | Raw material Ia | Intermediate I | Compound structure | Yield, % | Mass spectrum (m/z), [M + H]+ |
|---|---|---|---|---|---|---|
| 9 | 31 | | | 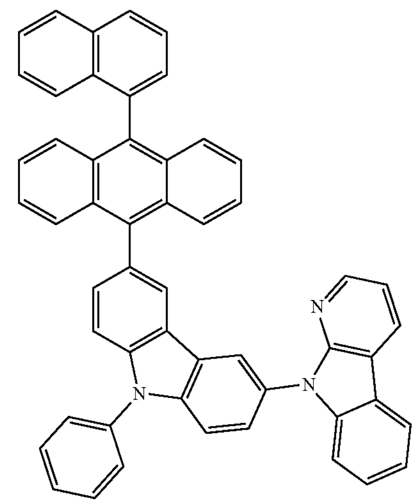 [SMILES: c1ccc(-n2c3ccc(-c4c5ccccc5c(-c5cccc6ccccc56)c5ccccc45)cc3c3cc(-n4c5ccccc5c5cccnc54)ccc32)cc1] | 88.5 | 712.3 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 10 | 34 | 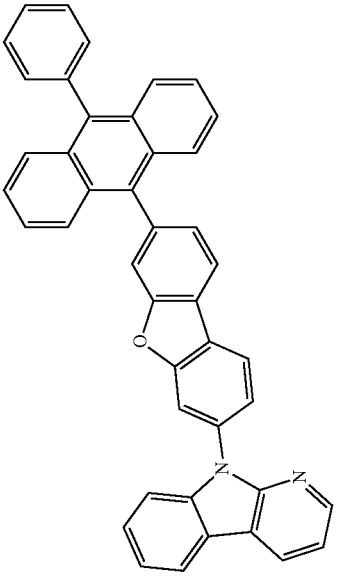 | 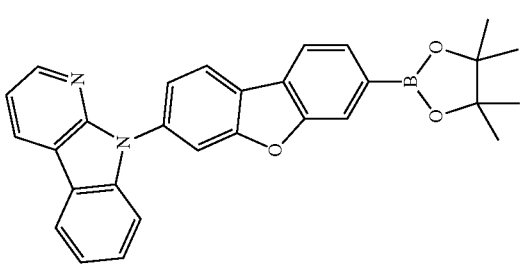 | 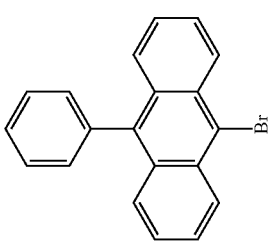 | 91.5 | 587.3 |

TABLE 3-continued

| Synthesis example No. | Compound No. | Raw material Ia | Intermediate I | Compound structure | Yield, % | Mass spectrum (m/z), [M + H]+ |
|---|---|---|---|---|---|---|
| 11 | 98 | | | 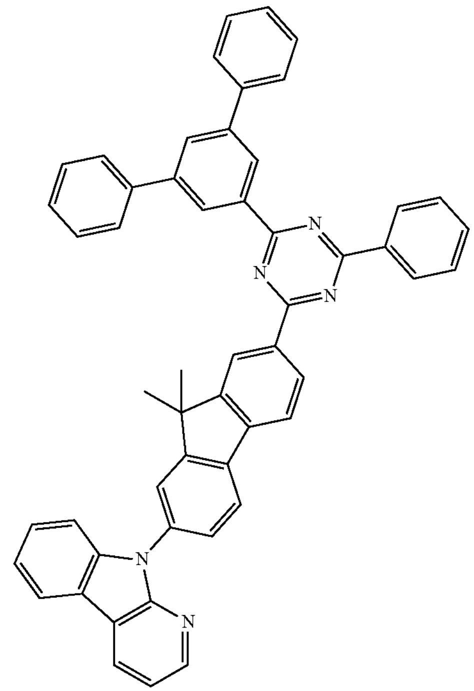 [SMILES: CC1(C)c2cc(-c3nc(-c4ccccc4)nc(-c4cc(-c5ccccc5)cc(-c5ccccc5)c4)n3)ccc2-c2ccc(-n3c4ccccc4c4cccnc43)cc21] | 82.4 | 744.3 |

TABLE 3-continued

| Synthesis example No. | Compound No. | Raw material Ia | Intermediate I | Compound structure | Yield, % | Mass spectrum (m/z), [M + H]+ |
|---|---|---|---|---|---|---|
| 12 | 103 | | | 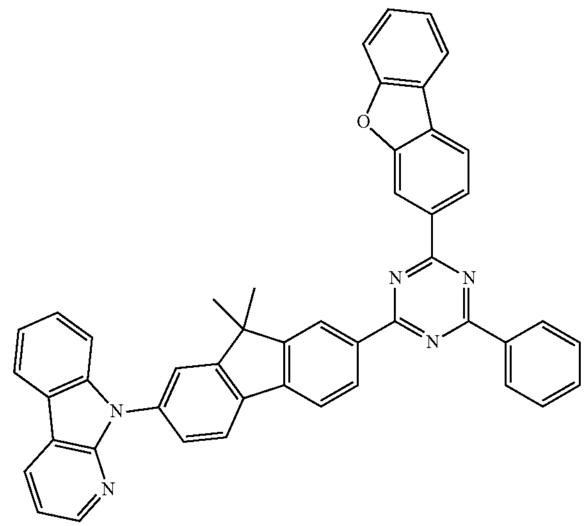 [SMILES: CC1(C)c2cc(-c3nc(-c4ccccc4)nc(-c4ccc5c(c4)oc4ccccc45)n3)ccc2-c2ccc(-n3c4ccccc4c4cccnc43)cc21] | 81.1 | 682.4 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 13 | 110 | 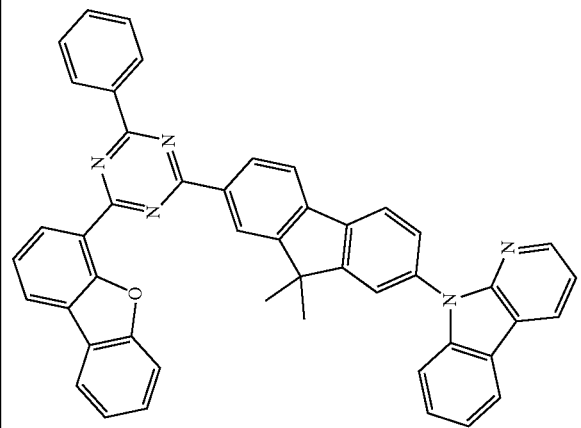 | 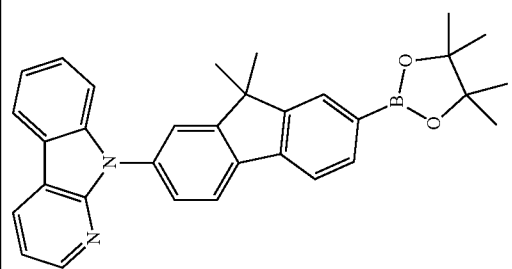 | 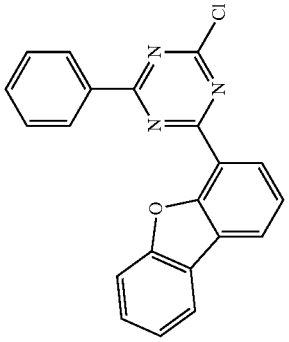 | 84.5 | 682.7 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 14 | 118 | 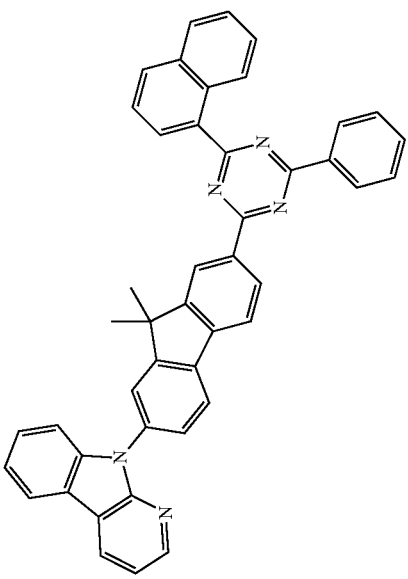 | 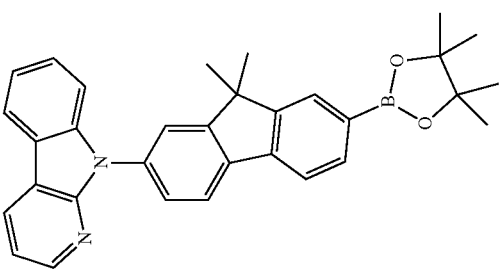 | 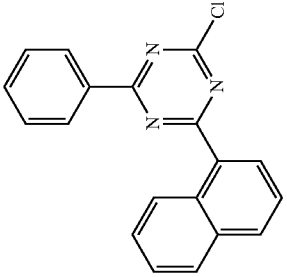 | 85.7 | 642.6 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 15 | 131 | 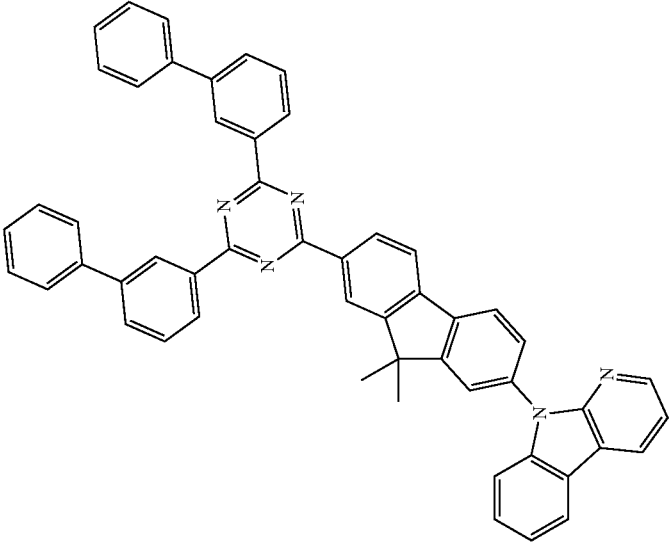 | 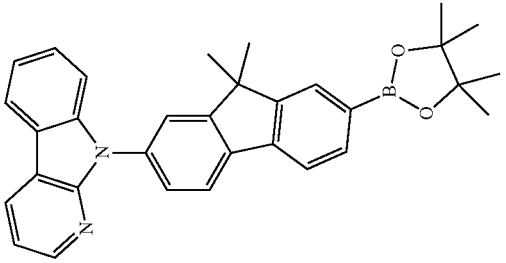 | 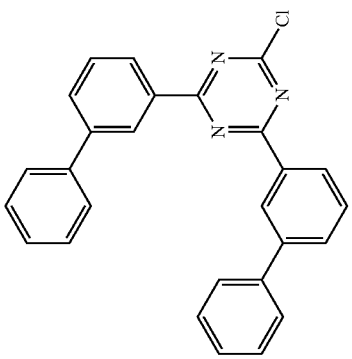 | 86.2 | 744.5 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 16 | 187 | 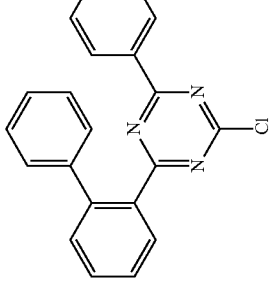 | 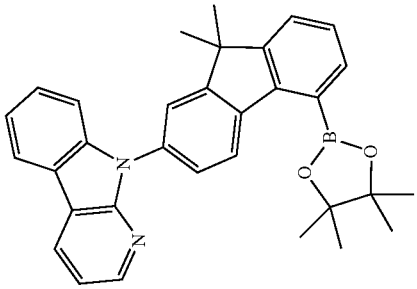 | 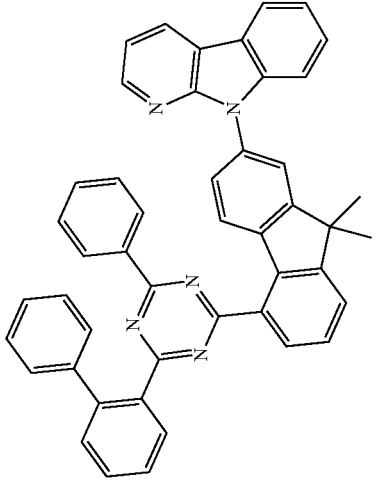 | 87.4 | 668.3 |
| 17 | 209 | 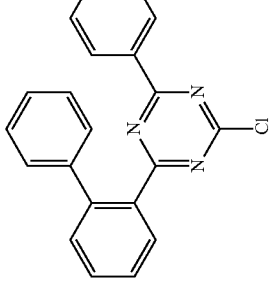 | 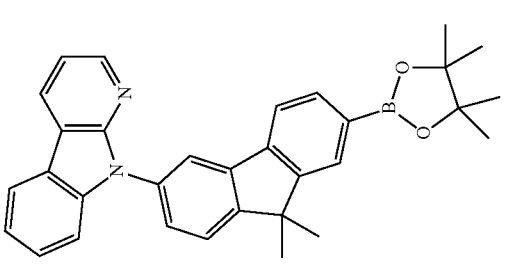 | 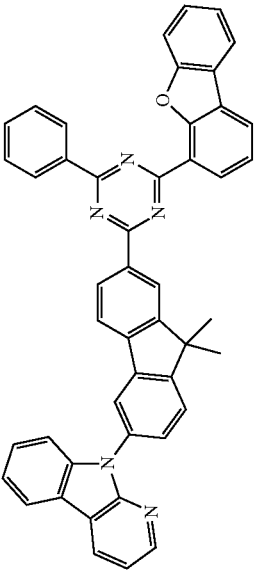 | 82.9 | 682.3 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 18 | 222 | 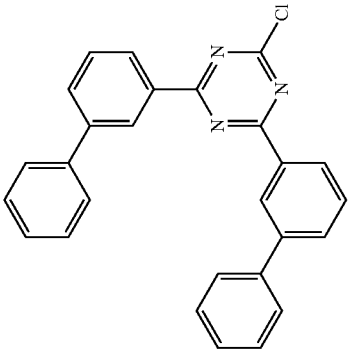 | 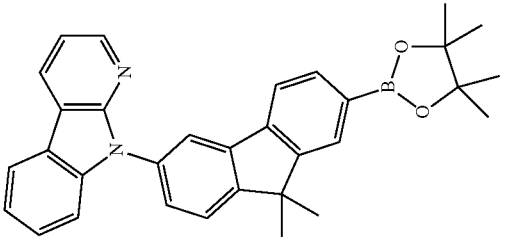 | 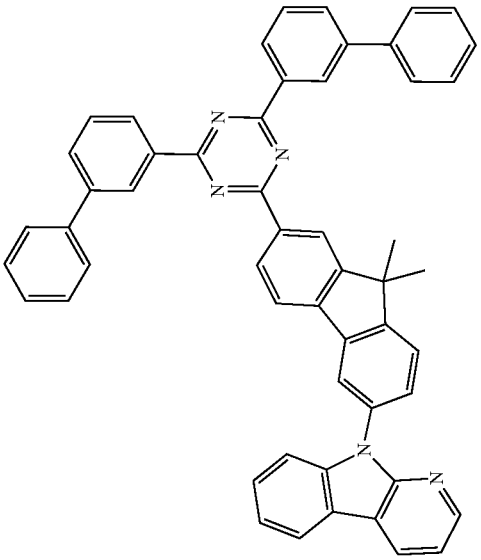 | 88.6 | 744.5 |
| 19 | 229 | 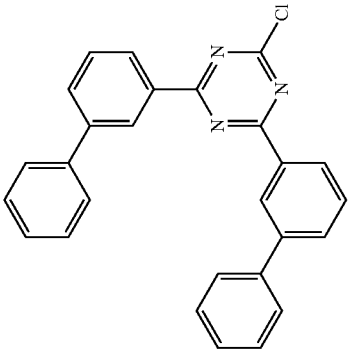 | 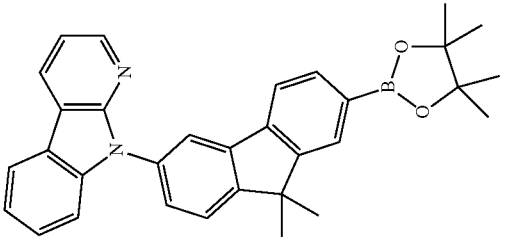 | 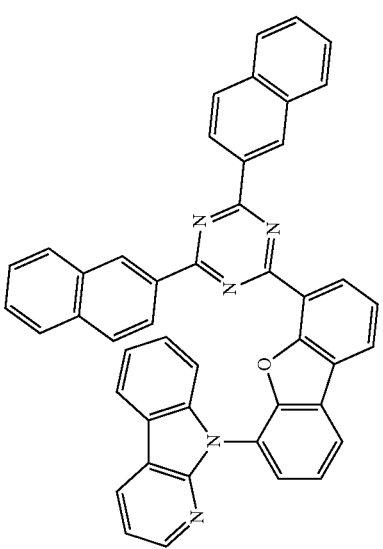 | 89.5 | 666.2 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 20 | 230 | 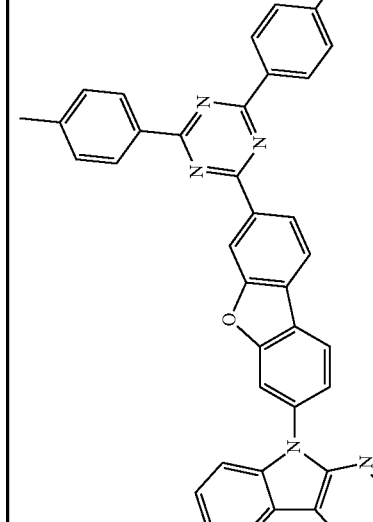 | 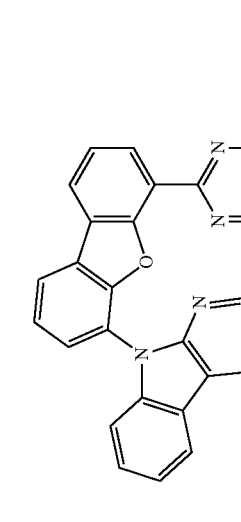 | 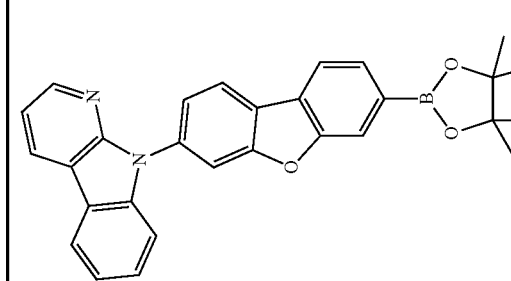 | 84.6 | 594.2 |
| 21 | 243 | 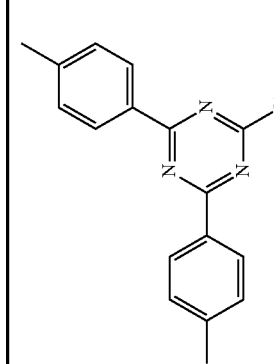 | 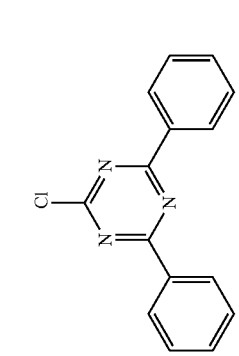 | 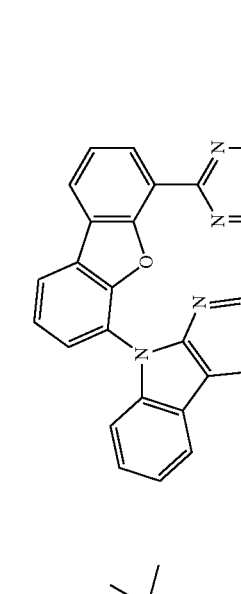 | 85.6 | 566.3 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 22 | 253 | 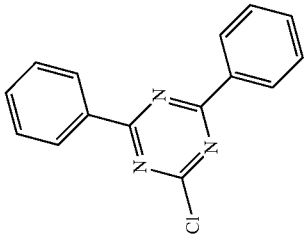 | 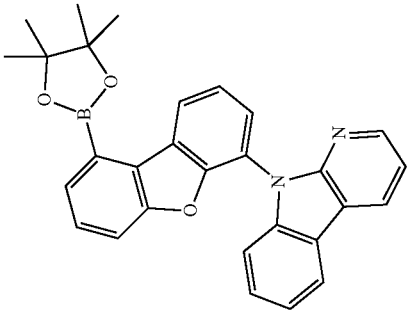 | 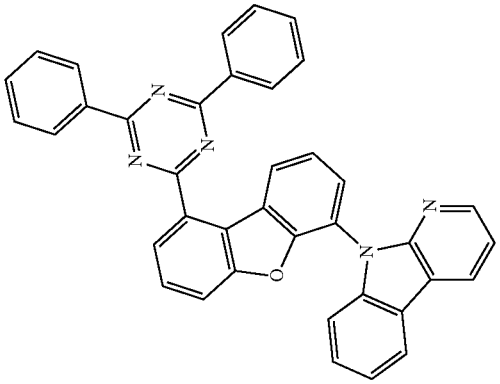 | 83.8 | 566.2 |
| 23 | 306 | 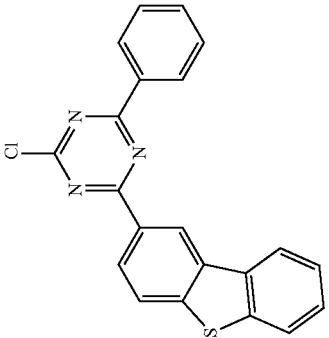 | 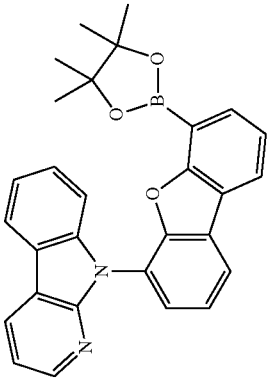 | 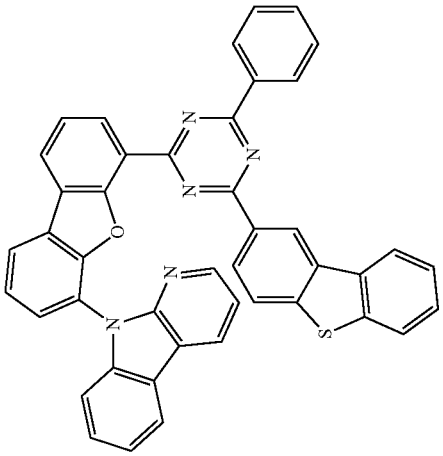 | 83.4 | 672.4 |

TABLE 3-continued

| Synthesis example No. | Compound No. | Raw material Ia | Intermediate I | Compound structure | Yield, % | Mass spectrum (m/z), [M + H]+ |
|---|---|---|---|---|---|---|
| 24 | 321 | | | 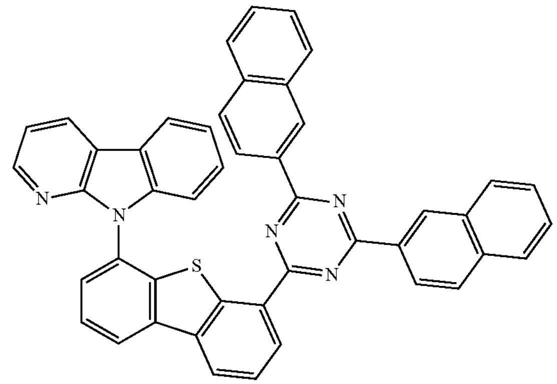 [SMILES: c1ccc2cc(-c3nc(-c4ccc5ccccc5c4)nc(-c4cccc5c4sc4c(-n6c7ccccc7c7cccnc76)cccc45)n3)ccc2c1] | 80.9 | 682.2 |
| 25 | 359 | | | 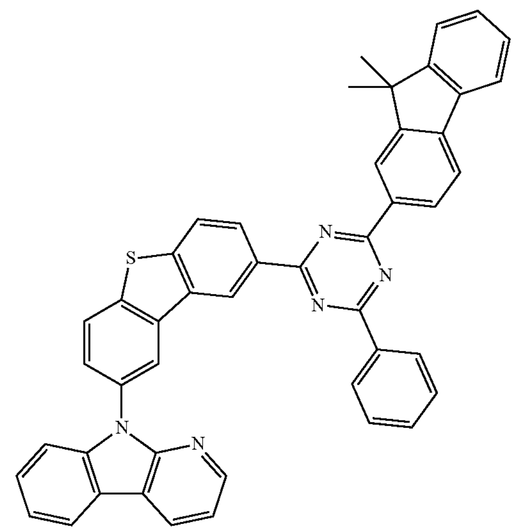 [SMILES: CC1(C)c2ccccc2-c2ccc(-c3nc(-c4ccccc4)nc(-c4ccc5sc6ccc(-n7c8ccccc8c8cccnc87)cc6c5c4)n3)cc21] | 81.6 | 698.5 |

TABLE 3-continued
| Synthesis example No. | Compound No. | Raw material Ia | Intermediate I | Compound structure | Yield, % | Mass spectrum (m/z) [M + H]+ |
|---|---|---|---|---|---|---|
| 26 | 360 | 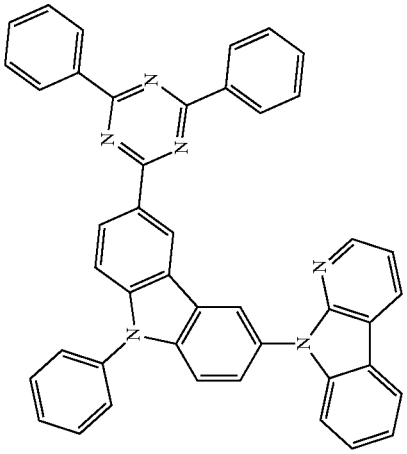 | 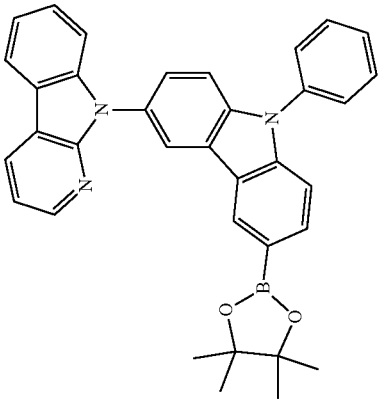 | 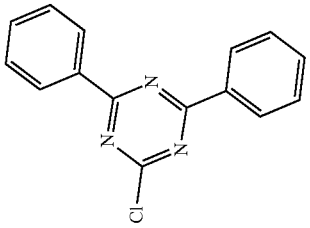 | 88.4 | 641.3 |

TABLE 3-continued
| Synthesis example No. | Compound No. | Raw material Ia | Intermediate I | Compound structure | Yield, % | Mass spectrum (m/z), [M + H]+ |
|---|---|---|---|---|---|---|
| 27 | 361 | | | 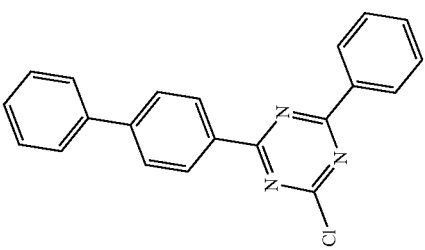 | 85.7 | 717.2 |

TABLE 3-continued

| Synthesis example No. | Compound No. | Raw material Ia | Intermediate I | Compound structure | Yield, % | Mass spectrum (m/z), [M + H]+ |
|---|---|---|---|---|---|---|
| 28 | 362 | | | 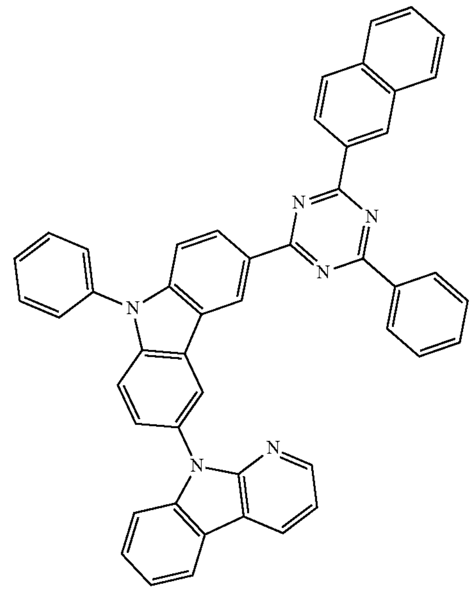 [SMILES: c1ccc(-c2nc(-c3ccc4ccccc4c3)nc(-c3ccc4c(c3)c3cc(-n5c6ccccc6c6cccnc65)ccc3n4-c3ccccc3)n2)cc1] | 87.6 | 691.1 |
| 29 | 393 | | | 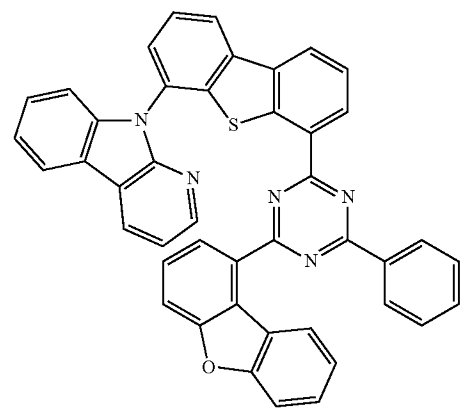 [SMILES: c1ccc(-c2nc(-c3cccc4c3sc3c(-n5c6ccccc6c6cccnc65)cccc34)nc(-c3cccc4oc5ccccc5c34)n2)cc1] | 85.4 | 672.3 |

TABLE 3-continued

| Synthesis example No. | Compound No. | Raw material Ia | Intermediate I | Compound structure | Yield, % | Mass spectrum (m/z), [M + H]+ |
|---|---|---|---|---|---|---|
| 30 | 394 | | | 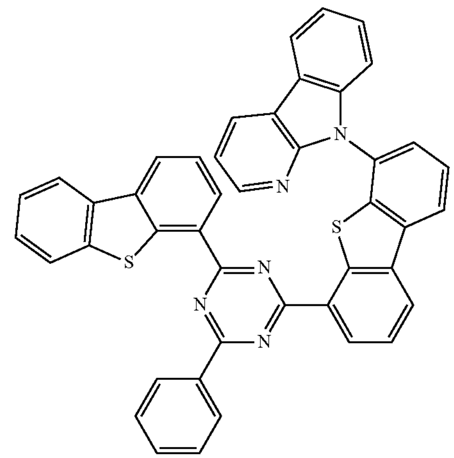 [SMILES: c1ccc(-c2nc(-c3cccc4c3sc3ccccc34)nc(-c3cccc4c3sc3c(-n5c6ccccc6c6cccnc65)cccc34)n2)cc1] | 86.6 | 688.5 |
| 31 | 395 | | | 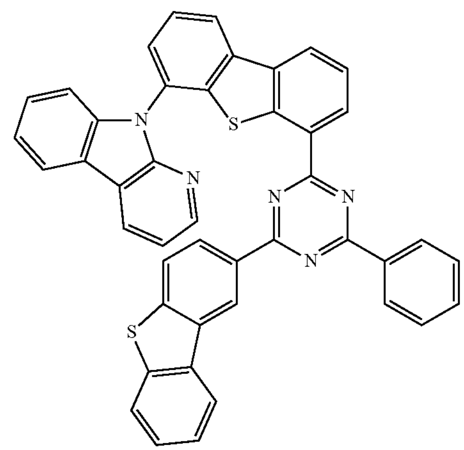 | 86.9 | 688.3 |

NMR of the compound 229: ¹H-NMR (CDCl₃, 400 MHz) δ ppm: 9.12 (s, 1H), 9.07 (s, 1H), 8.59-8.56 (m, 2H), 8.53-8.50 (m, 2H), 8.45-8.43 (d, 1H), 8.27-8.24 (m, 2H), 8.18-8.15 (m, 3H), 8.11-8.06 (m, 5H), 7.69-7.65 (m, 4H), 7.62-7.59 (m, 2H), 7.38-7.34 (m, 2H), 7.25-7.21 (m, 2H).

Synthesis of Intermediate II

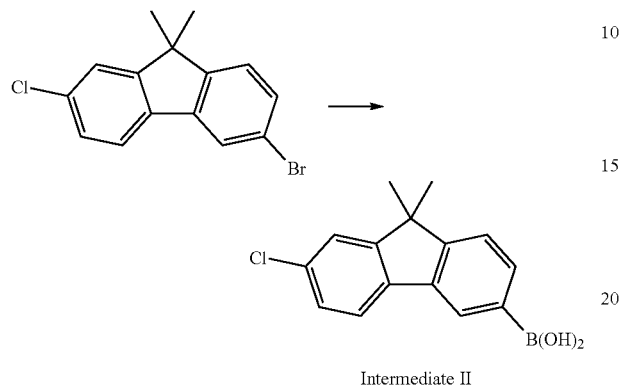

Intermediate II

Nitrogen (0.100 L/min) was introduced into a three-necked flask provided with a mechanical stirrer, a thermometer and a constant-pressure dropping funnel for replacement for 15 min, 6-bromo-2-chloro-9,9-dimethyl-9H-fluorene (15.3 g, 50 mmol) and 100 mL of tetrahydrofuran were added, stirring was started, cooling was performed with liquid nitrogen to −90° C. to −80° C., 2 mol/L n-hexane solution of n-butyllithium (60 mmol) was dropwise added, the temperature was kept for 1 hour after dropwise adding, tributyl borate (15.0 g, 65.2 mmol) was dropwise added, the temperature was kept for 1 hour after dropwise adding, 200 mL of water, 40 mL of petroleum ether and 3 mL of concentrated hydrochloric acid were added into the reaction solution, full stirring was performed, liquid separation was performed, the organic phase was washed with water for 4 times, and filtered to obtain a crude product, pulping was performed with 50.0 mL of toluene for 0.5 h, and filtering was performed to obtain Intermediate II (9.7 g, yield: 71%).

Synthesis Example 32: Synthesis of Compound 168

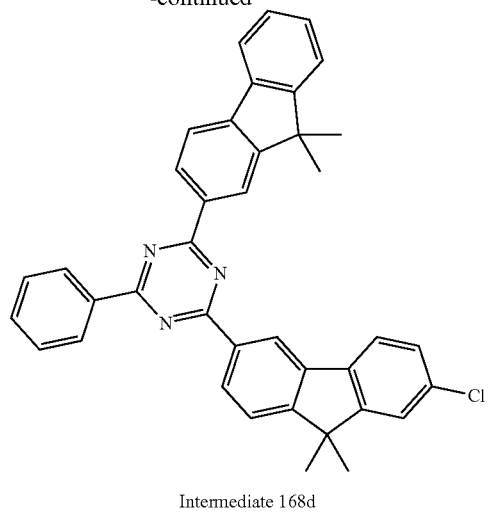

Intermediate 168d (1) Nitrogen (0.100 L/min) was introduced into a three-necked reaction flask provided with a mechanical stirrer, a thermometer and a condenser tube for replacement for 15 min, Intermediate II (8.2 g, 30 mmol), Raw material 168c (11.5 g, 30 mmol), potassium carbonate (8.3 g, 60 mmol), tetrakis(triphenylphosphine)palladium (0.35 g, 0.3 mmol), 60 mL of toluene and 20 mL of water were added, stirring was started, heating was performed to 65° C. to 70° C., and the reaction was carried out for 5 h while heat preservation, 50 mL of water was added into the reaction solution while stirring, standing and liquid separation were performed, the water phase was extracted once with 50 mL of toluene, liquid separation was performed, the organic phases were mixed and washed twice with 50 mL of water. 5 g of anhydrous sodium sulfate was added into the organic phase for drying, filtering was performed, the organic phase was concentrated (−0.08 MPa to −0.0 MPa, 55° C. to 65° C.) until no liquid flowed out, 20 mL of cyclohexane was added while stirring, and filtering was performed to obtain Intermediate 168d (13.8 g, yield: 80.0%).

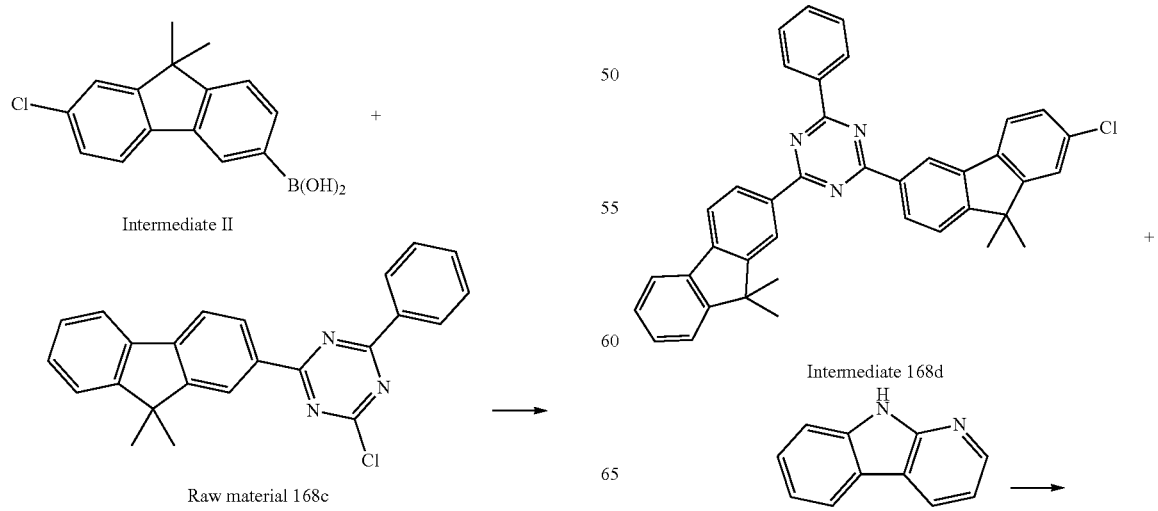

-continued

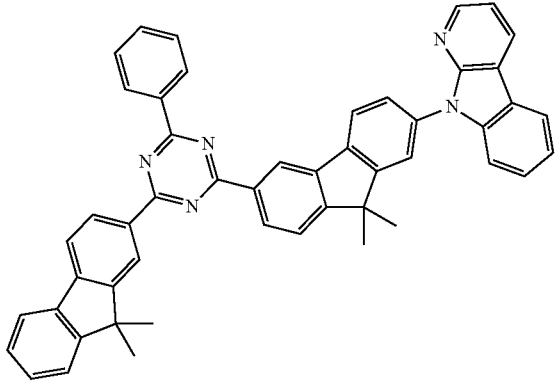

168

(2) Nitrogen (0.100 L/min) was introduced into a three-necked flask provided with a mechanical stirrer, a thermometer and a condenser tube for replacement for 15 min, Intermediate 168d (11.5 g, 20 mmol), 9H-pyrido[2,3-B]indole (3.7 g, 22 mmol), potassium carbonate (5.5 g, 40 mmol), 18-crown-6-ether (0.5 g, 2 mmol), 1,10-phenanthroline (0.4 g, 2 mmol), cuprous iodide (0.8 g, 4 mmol) and 60 mL of xylene were sequentially added, stirring was started, the temperature was raised to 130° C. to 135° C. to react for 15 h. 80 mL of toluene and 80 mL of water were added into the reaction solution while stirring, liquid separation was performed, and the water phase was extracted once with 50 mL of toluene, the organic phases were mixed and washed with water twice, dried over 5 g of anhydrous sodium sulfate, filtered, and concentrated (50° C. to 60° C., −0.09 MPa to −0.08 MPa) until no liquid drops flowed out, 15 mL of ethanol was added while stirring, and filtering was performed to obtain the compound 168 (8.5 g, yield: 60%), m/z=708.3 [M+H]$^+$.

Synthesis Examples 33 to 34

The compound 178 and the compound 171 were respectively synthesized by referring to the method in Synthesis example 32, except that Raw material 168c was replaced by Raw material Ic, and Raw material Ic, the total yield of the compounds and the mass spectrum result are shown in Table 4.

TABLE 4

| Synthesis example No. | Compound No. | Raw material Ic | Compound structure | Total yield, % | Mass spectrum (m/z), [M + H]+ |
|---|---|---|---|---|---|
| 33 | 178 | | 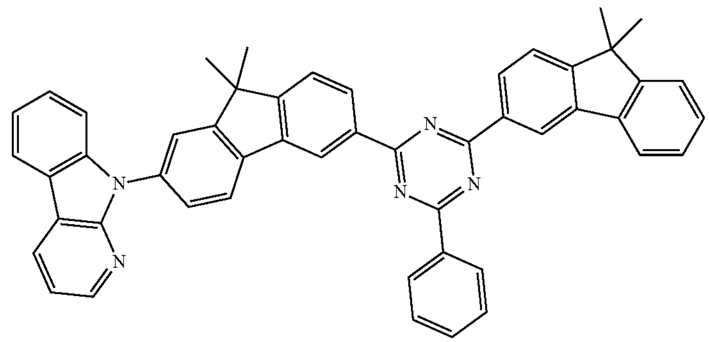 [SMILES: CC1(C)c2ccccc2-c2cc(-c3nc(-c4ccccc4)nc(-c4ccc5c(c4)-c4ccc(-n6c7ccccc7c7cccnc76)cc4C5(C)C)n3)ccc21] | 42.9 | 708.3 |
| 34 | 171 | | 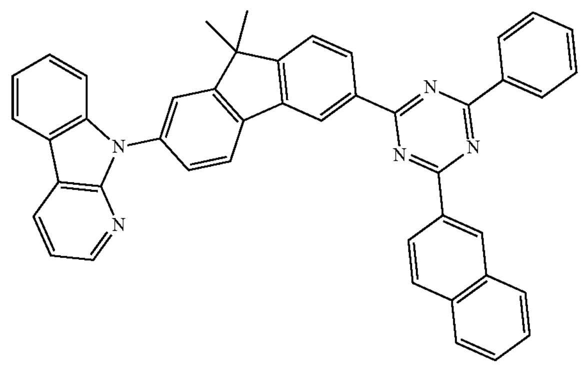 [SMILES: CC1(C)c2ccc(-c3nc(-c4ccccc4)nc(-c4ccc5ccccc5c4)n3)cc2-c2ccc(-n3c4ccccc4c4cccnc43)cc21] | 46.1 | 642.3 |

245

Manufacturing of an organic electroluminescent device

Example 1

The manufacturing method of the organic electroluminescent device includes the following steps:
(1) firstly, a glass bottom plate with an indium tin oxide (ITO) electrode of 1500 Å was ultrasonically cleaned by using distilled water and methanol sequentially, and dried;
(2) then cleaning was performed for 5 min by using oxygen plasma, and the cleaned anode base plate was loaded into vacuum deposition equipment;
(3) compound 2T-NATA (CAS: 185690-41-9) was vacuum deposited on the ITO electrode to form a hole injecting layer with a thickness of 500 Å, then NPB (CAS: 123847-85-8) was vacuum deposited on the hole injecting layer to form a hole transporting layer with a thickness of 800 Å, and TQTPA (CAS: 1142945-07-0) was evaporated on the hole transporting layer to form an electron blocking layer with a thickness of 200 Å. Then, the compound 6 serving as a light-emitting host material and a dopant BNP3FL (CAS: 669016-17-5) serving as a guest material were co-deposited on the electron blocking layer at a film thickness ratio of 100:3 to form an organic light-emitting layer with a thickness of 300 Å;
(4) TPBi was vacuum deposited on the light-emitting layer to form a hole blocking layer with a thickness of 200 Å; and
(5) DBimiBphen and LiQ was mixed at a weight ratio of 1:1, and the mixture was vacuum deposited on the hole blocking layer to form an electron transporting layer with a thickness of 300 Å. Then LiQ was evaporated on the electron transporting layer to form an electron injecting layer with a thickness of 15 Å, then magnesium (Mg) and silver (Ag) were mixed at an evaporation rate of 1:9, and the mixture was vacuum-evaporated on the electron injecting layer to form a cathode with a thickness of 120 Å.

Finally, CP-1 was evaporated on the cathode to form a covering layer (CPL) with a thickness of 650 Å, thereby completing the manufacturing of the organic light-emitting device. The structures of TPBi, DBimiBphen, LiQ and CP-1 are as follows:

246

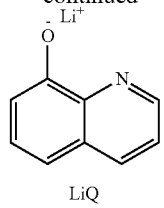

LiQ

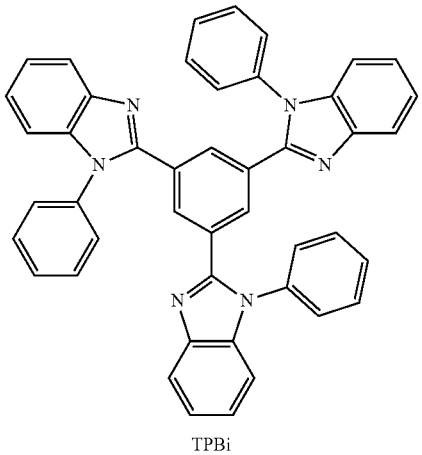

TPBi

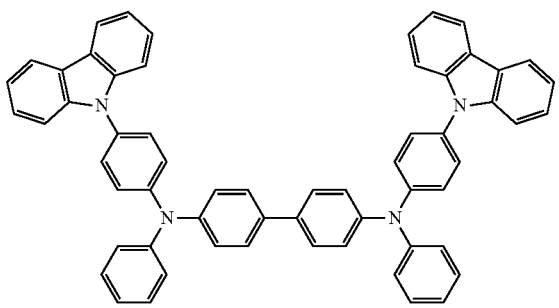

CP-1

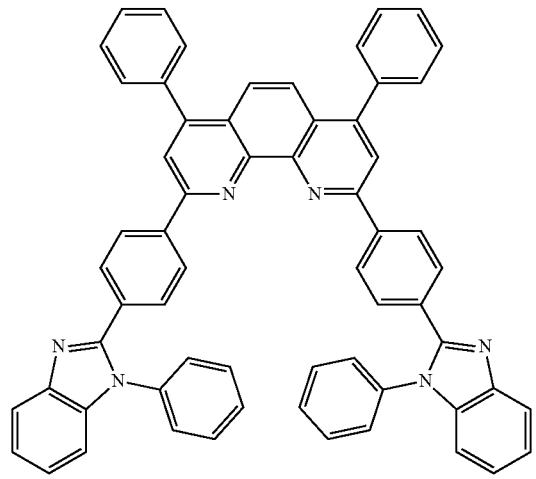

DBimiBphen

Examples 2 to 9

The organic electroluminescent device was manufactured by adopting the same method as in Example 1, except that in Examples 2 to 9, the compounds shown in Table 5 were used to replace the compound 6 to serve as host material to manufacture the organic electroluminescent device.

Comparative Examples 1 to 4

In comparative examples 1 to 4, the organic electroluminescent device was manufactured by using the same method as in Example 1, except that DMFL-CBP, a compound A, a compound B, and a compound C were used respectively as a host material of the organic light-emitting layer to replace the compound 6. The structural formulas of DMFL-CBP, the compound A, the compound B and the compound C are as follows:

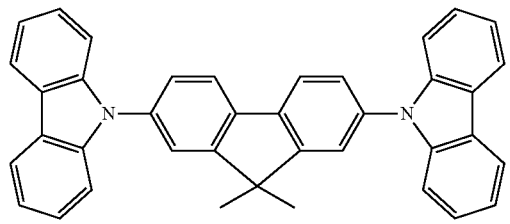

DMFL-CBP

A

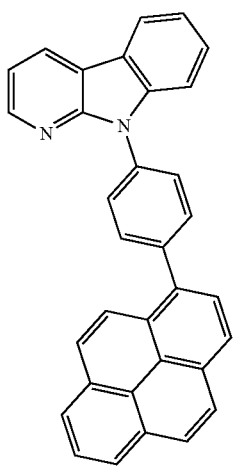

B

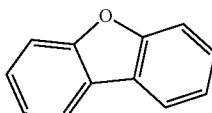

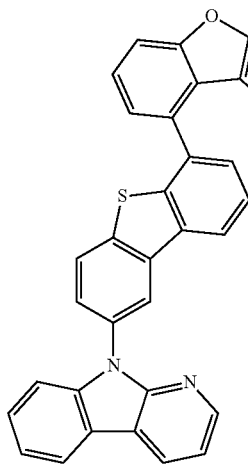

C

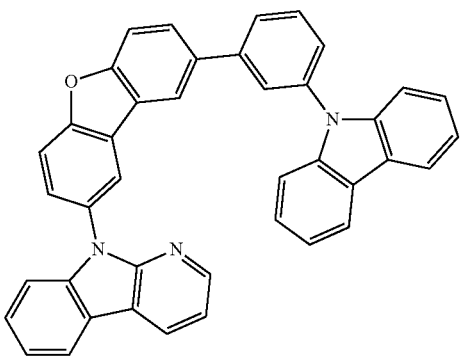

The T95 service life of the prepared organic electroluminescent devices was tested under the condition of 15 mA/cm², and data such as the voltage, the efficiency and the chromaticity coordinate of the prepared organic electroluminescent device were tested under a constant current density of 10 mA/cm², and the result is shown in Table 5.

TABLE 5

| No. | Host material | Operating voltage (V) | Current efficiency (Cd/A) | External quantum efficiency (EQE) | Chromaticity coordinate (CIEy) | Service life T95 (h) |
|---|---|---|---|---|---|---|
| Example 1 | Compound 6 | 3.9 | 6.8 | 12.6 | 0.054 | 258 |
| Example 2 | Compound 10 | 4.0 | 6.6 | 12.8 | 0.051 | 256 |
| Example 3 | Compound 18 | 3.9 | 6.1 | 11.6 | 0.053 | 213 |
| Example 4 | Compound 31 | 3.9 | 6.4 | 12.3 | 0.051 | 234 |
| Example 5 | Compound 34 | 3.9 | 6.2 | 11.9 | 0.050 | 238 |
| Example 6 | Compound 50 | 3.8 | 6.7 | 12.4 | 0.051 | 215 |
| Example 7 | Compound 66 | 3.9 | 6.3 | 12.1 | 0.054 | 209 |
| Example 8 | Compound 77 | 3.9 | 6.6 | 11.6 | 0.053 | 249 |
| Example 9 | Compound 81 | 3.9 | 6.7 | 13.0 | 0.051 | 218 |
| Comparative example 1 | DMFL-CBP | 4.2 | 5.3 | 10.6 | 0.052 | 168 |
| Comparative example 2 | Compound A | 4.1 | 5.0 | 10.2 | 0.050 | 159 |
| Comparative example 3 | Compound B | 3.9 | 5.8 | 10.8 | 0.052 | 198 |
| Comparative example 4 | Compound C | 3.9 | 5.9 | 11.0 | 0.051 | 184 |

It can be seen from Table 5 that the current efficiency of the organic electroluminescent devices prepared in examples 1 to 9 is at least improved by 3.4% compared with that of the organic electroluminescent devices prepared in comparative examples 1 to 4, and the external quantum efficiency is at least improved by 5.5% compared with that in comparative examples. The T95 service life in examples 1 to 9 is at least 5.6% longer than the T95 service life in comparative examples 1 to 4. In addition, the devices in examples 1 to 9 also have relatively low driving voltage.

Example 10

An ITO substrate (manufactured by Corning) with an ITO thickness of 1500 Å was cut into a size of 40 mm (length)× 40 mm (width)×0.7 mm (thickness) to be prepared into an experimental substrate with a cathode, an anode and an insulating layer pattern by adopting a photoetching process, and surface treatment was performed by utilizing ultraviolet ozone and $O_2$:$N_2$ plasma so as to increase the work function of the anode (the experimental substrate) and remove scum.

m-MTDATA was vacuum-evaporated on the experiment substrate (the anode) to form a hole injecting layer with a thickness of 100 Å, and NPB was evaporated on the hole injecting layer to form a hole transporting layer with a thickness of 1000 Å.

EB-1 was evaporated on the hole transporting layer to form an electron blocking layer with a thickness of 400 Å.

The compound 95 as a host material was evaporated on the hole blocking layer and doped with Ir(ppy)$_3$, which served as a guest material, at a film thickness ratio of 100:3 to from an organic light-emitting layer with a thickness of 330 Å.

ET-1 and LiQ were mixed at a weight ratio of 1:1, and the mixture was evaporated to form an electron transporting layer with a thickness of 280 Å, LiQ was evaporated on the electron transporting layer to form an electron injecting layer with a thickness of 13 Å, then magnesium (Mg) and silver (Ag) were mixed at an evaporation rate of 1:9, and the mixture was vacuum-evaporated on the electron injecting layer to form a cathode with a thickness of 105 Å.

In addition, CP-1 with a thickness of 700 Å was evaporated on the cathode to form an organic capping layer (CPL), thereby completing manufacturing of the organic light-emitting device. The structures of the above main materials used for preparing the device are as follows:

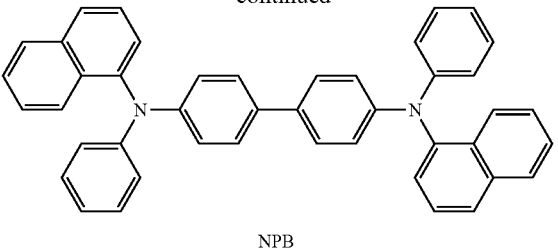

NPB

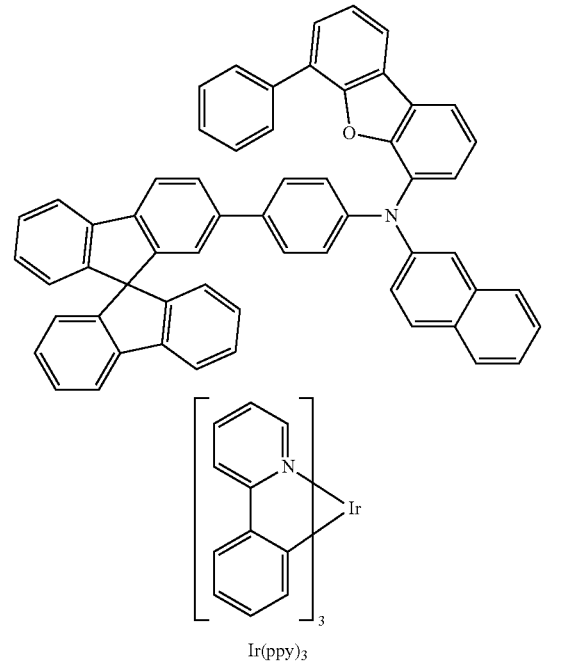

EB-1

Ir(ppy)$_3$

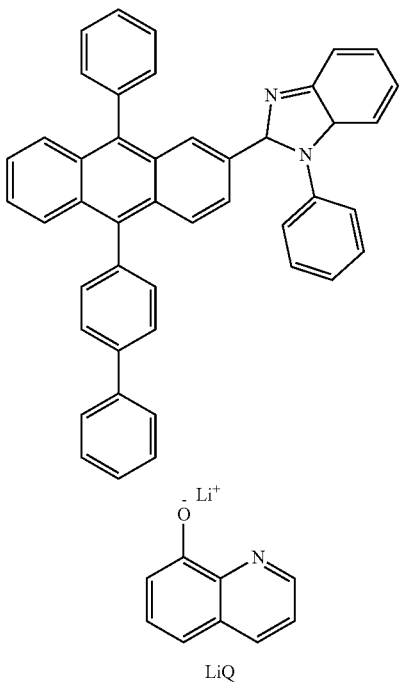

ET-1

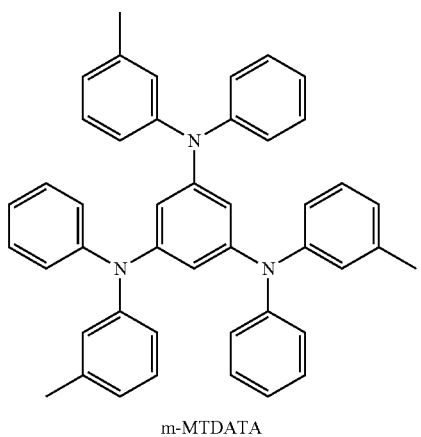

m-MTDATA

LiQ

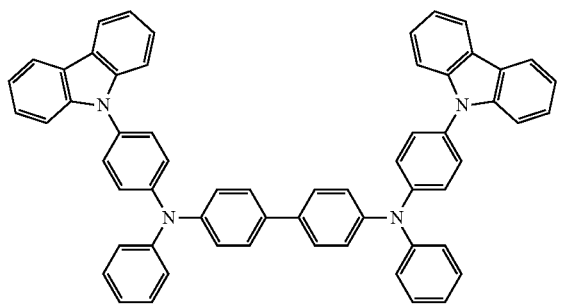

CP-1

Examples 11 to 34

In addition to using compounds shown in Table 6 as a light-emitting host when the organic light-emitting layer was formed, the organic electroluminescent device was manufactured by the same method as in Example 10.

Comparative Examples 5 to 6

In the comparative examples 5 to 6, a compound D and a compound E were respectively used to replace the compound 95, the organic electroluminescent device was manufactured by adopting the same method as in Example 10, and the structural formulas of the compound D and the compound E are as follows:

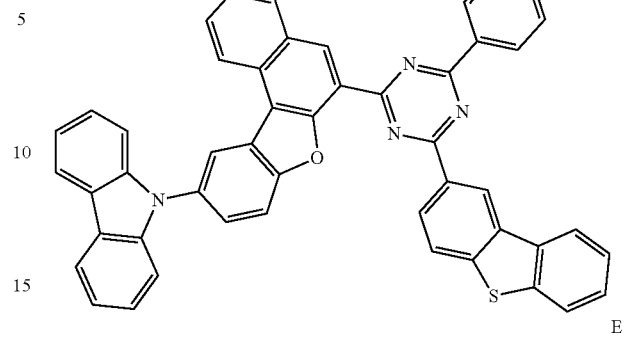

D

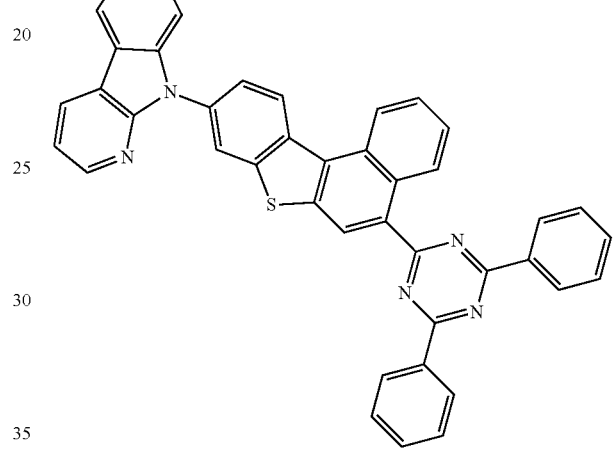

E

The T95 service life of the prepared organic electroluminescent device was tested under the condition of 15 mA/cm$^2$, and the driving voltage, the efficiency and the chromaticity coordinate of the prepared organic electroluminescent device were tested under the constant current density of 10 mA/cm$^2$, and the result is shown in Table 6.

TABLE 6

| No. | Light-emitting host material | Operating voltage (V) | Current efficiency Cd/A | Chromaticity coordinate CIEx, CIEy | External quantum efficiency EQE % | T95 service life (h) |
| --- | --- | --- | --- | --- | --- | --- |
| Example 10 | Compound 95 | 3.85 | 81.23 | 0.263, 0.700 | 21.60 | 556 |
| Example 11 | Compound 98 | 3.76 | 80.57 | 0.261, 0.702 | 20.90 | 534 |
| Example 12 | Compound 103 | 3.88 | 81.23 | 0.262, 0.701 | 21.57 | 565 |
| Example 13 | Compound 110 | 3.90 | 79.34 | 0.259, 0.700 | 20.09 | 534 |
| Example 14 | Compound 118 | 3.74 | 78.68 | 0.260, 0.704 | 19.94 | 526 |
| Example 15 | Compound 131 | 3.83 | 77.14 | 0.261, 0.701 | 18.12 | 527 |
| Example 16 | Compound 168 | 3.79 | 81.26 | 0.261, 0.701 | 21.71 | 573 |
| Example 17 | Compound 171 | 3.79 | 80.24 | 0.261, 0.701 | 20.74 | 521 |
| Example 18 | Compound 178 | 3.81 | 78.56 | 0.260, 0.703 | 19.86 | 524 |
| Example 19 | Compound 187 | 3.81 | 81.45 | 0.258, 0.700 | 21.67 | 507 |
| Example 20 | Compound 209 | 3.74 | 80.45 | 0.262, 0.703 | 20.83 | 557 |
| Example 21 | Compound 222 | 3.85 | 81.83 | 0.262, 0.702 | 21.89 | 576 |

TABLE 6-continued

| No. | Light-emitting host material | Operating voltage (V) | Current efficiency Cd/A | Chromaticity coordinate CIEx, CIEy | External quantum efficiency EQE % | T95 service life (h) |
|---|---|---|---|---|---|---|
| Example 22 | Compound 229 | 3.82 | 79.56 | 0.259, 0.699 | 20.16 | 557 |
| Example 23 | Compound 230 | 3.84 | 80.58 | 0.259, 0.702 | 20.91 | 541 |
| Example 24 | Compound 243 | 3.80 | 80.21 | 0.258, 0.701 | 20.84 | 586 |
| Example 25 | Compound 253 | 3.78 | 78.68 | 0.260, 0698 | 20.51 | 537 |
| Example 26 | Compound 306 | 3.71 | 79.41 | 0.262, 0.701 | 20.11 | 581 |
| Example 27 | Compound 321 | 3.92 | 70.24 | 0.261, 0.697 | 18.08 | 462 |
| Example 28 | Compound 359 | 3.96 | 68.24 | 0.259, 0.700 | 17.81 | 443 |
| Example 29 | Compound 360 | 3.90 | 67.54 | 0.258, 0.697 | 17.79 | 433 |
| Example 30 | Compound 361 | 3.96 | 69.21 | 0.260, 0.703 | 18.00 | 485 |
| Example 31 | Compound 362 | 3.94 | 66.24 | 0.263, 0.697 | 17.55 | 471 |
| Example 32 | Compound 393 | 3.92 | 68.35 | 0.262, 0.701 | 17.84 | 468 |
| Example 33 | Compound 394 | 3.91 | 68.54 | 0.264, 0.702 | 17.89 | 456 |
| Example 34 | Compound 395 | 3.94 | 66.48 | 0.259, 0.700 | 17.60 | 450 |
| Comparative example 5 | Compound D | 4.00 | 57.23 | 0.264, 0.702 | 15.57 | 357 |
| Comparative example 6 | Compound E | 4.13 | 55.21 | 0.262, 0.701 | 14.25 | 335 |

In combination with a result shown in Table 6, it can be seen that comparing with that of the comparative examples 5 to 6, the current efficiency of the organic electroluminescent devices prepared in examples 10 to 34 is at least improved by 15.7%, the external quantum efficiency is at least improved by 12.7%, and the T95 service life is at least improved by 21.3%.

Therefore, compared with the devices in the comparative examples, the organic electroluminescent devices prepared in examples 1 to 34 have higher luminous efficiency and higher external quantum efficiency, the service life characteristic of the device is also obviously improved, and meanwhile, the organic electroluminescent device also has lower driving voltage.

Therefore, the heterocyclic compound provided by the discloser can be applied to the organic electroluminescent device, especially can be used as the host material of the organic light-emitting layer, and can effectively improve the luminous efficiency and the external quantum efficiency of the organic electroluminescent device; meanwhile, the service life of the organic electroluminescent device is prolonged, so that the comprehensive performance of the device is improved.

It should be understood that the present discloser does not limit its discloser to the detailed structure and arrangement of the components proposed in the description. The present discloser can have other embodiments, and can be implemented and executed in a variety of ways. The above deformation forms and modification forms fall within the scope of the discloser. It should be understood that the discloser, which is applied and defined herein, extends to all alternative combinations of two or more individual features mentioned or apparent herein and/or in the accompanying drawings. All these different combinations constitute several alternative aspects of the discloser. The embodiments described in the description describe the best way known to implement the present discloser and will enable those skilled in the art to utilize the present discloser.

What is claimed is:

1. A heterocyclic compound, having a structure as shown in Formula 1-1:

Formula 1-1

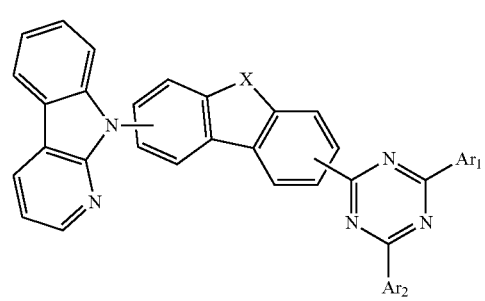

wherein X is selected from $C(R_1R_2)$, $N(R_3)$, O or S; and $R_1$, $R_2$ and $R_3$ are each independently selected from an alkyl with 1 to 4 carbon atoms, or an aryl with 6 to 12 carbon atoms; and $Ar_1$ and $Ar_2$ are the same or different, and are each independently selected from a substituted or unsubstituted aryl with 6 to 18 carbon atoms, or a substituted or unsubstituted heteroaryl with 6 to 15 carbon atoms, the heteroatom of the heteroaryl is O or S; and the substituents in $Ar_1$ and $Ar_2$ are each independently selected from fluorine, deuterium, cyano, phenyl, an alkyl with 1 to 4 carbon atoms, cyclopentyl, or cyclohexyl.

2. The heterocyclic compound according to claim 1, wherein

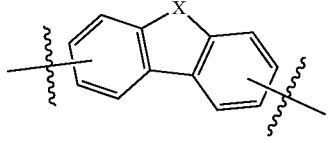

is selected from the following groups:

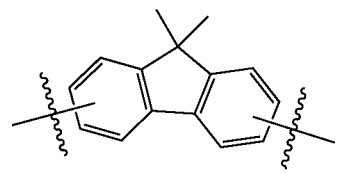

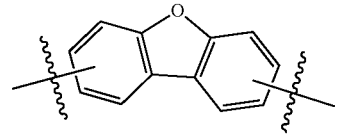

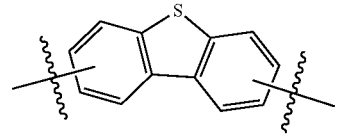

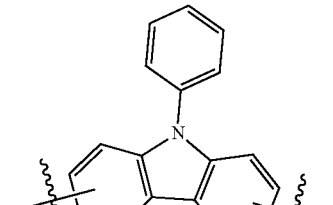

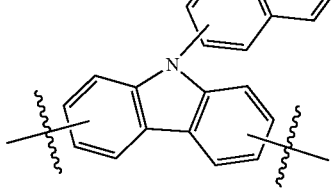

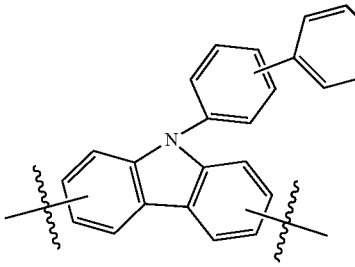

3. The heterocyclic compound according to claim 1, wherein $Ar_1$ and $Ar_2$ are the same or different, and are each independently selected from a substituted or unsubstituted group W, wherein the unsubstituted group W is selected from the following groups:

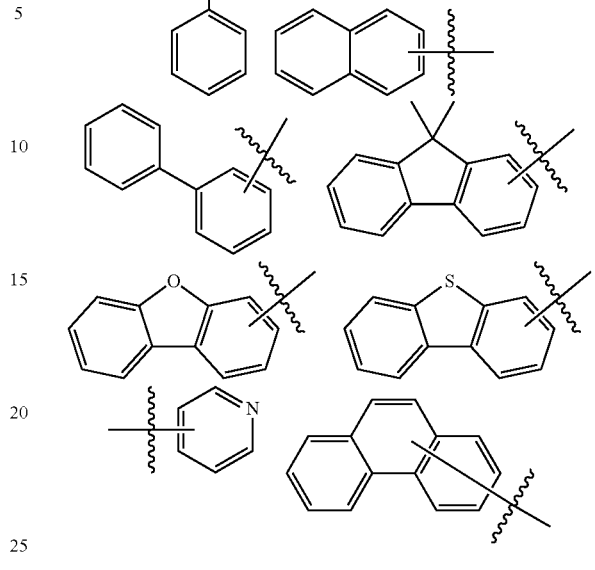

wherein the substituted group W has one or two or more substituents, and the substituents are each independently selected from deuterium, fluorine, cyano, methyl, tert-butyl, phenyl, cyclopentyl, or cyclohexyl.

4. The heterocyclic compound according to claim 1, wherein $Ar_1$ and $Ar_2$ are each independently selected from the following groups:

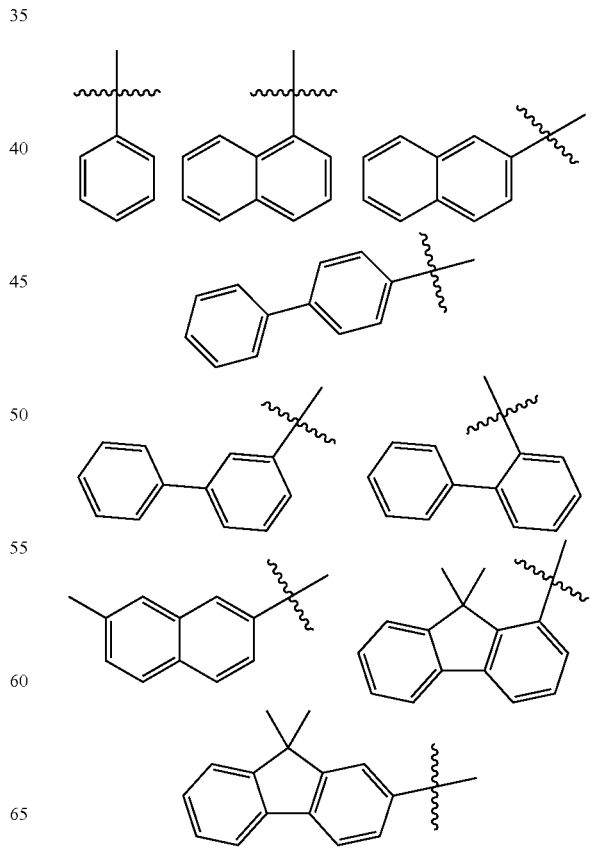

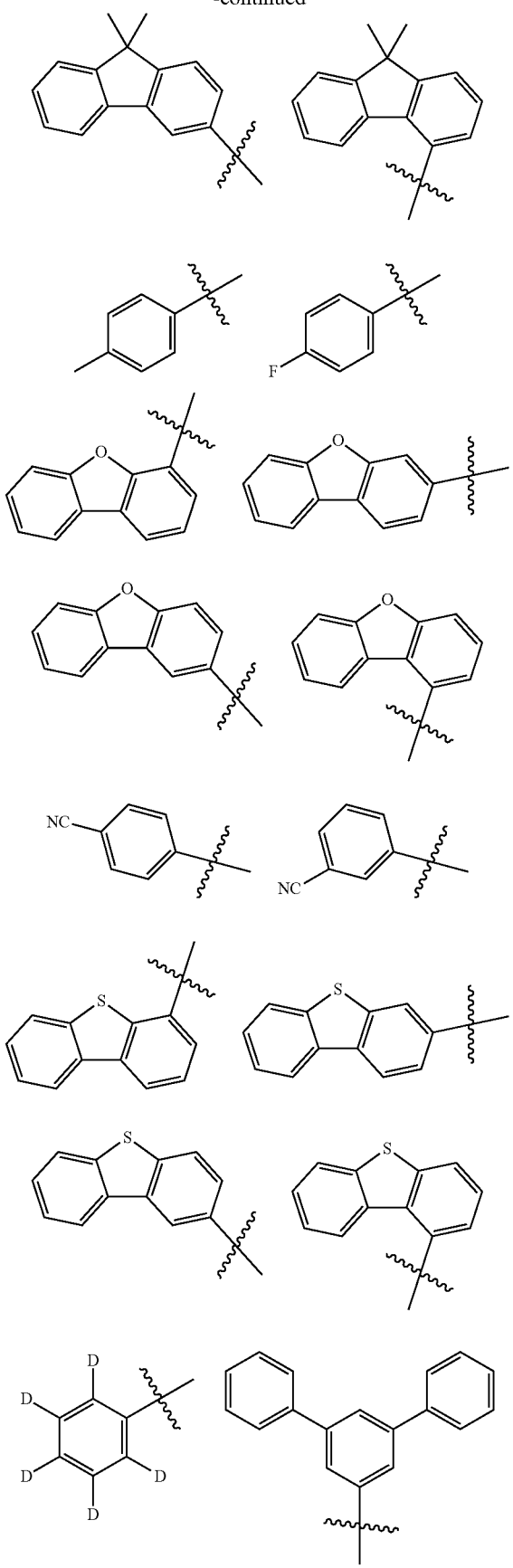

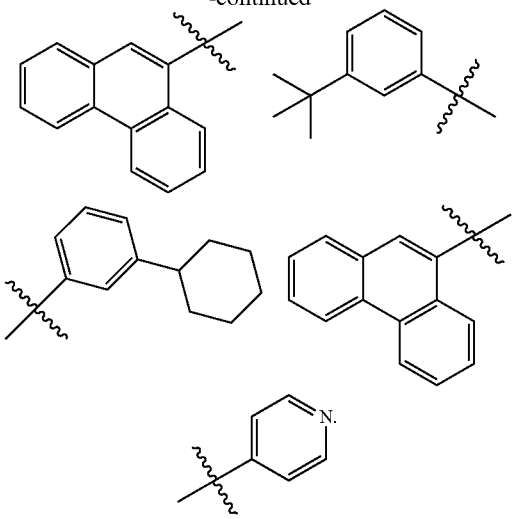

5. The heterocyclic compound according to claim 1, wherein the total number of carbon atoms of $Ar_1$ and $Ar_2$ is 12 to 30.

6. The heterocyclic compound according to claim 1, wherein the heterocyclic compound has a structure as shown in Formula 1:

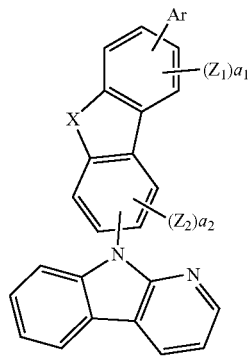

Formula 1 wherein X is selected from $C(R_1R_2)$, $N(R_3)$, O or S;
$R_1$, $R_2$ and $R_3$ are each independently selected from an alkyl with 1 to 4 carbon atoms, or an aryl with 6 to 12 carbon atoms;
$a_1$ and $a_2$ are 3;
$Z_1$ and $Z_2$ are selected from hydrogen; and
Ar is selected from the following groups:

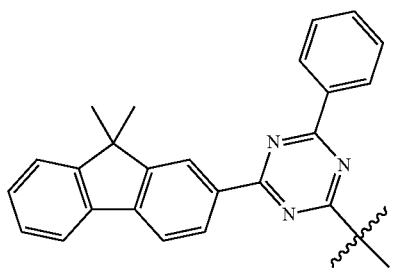

-continued

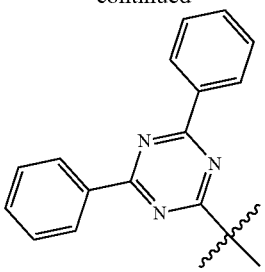

7. The heterocyclic compound according to claim 6, wherein

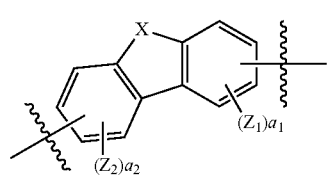

is an unsubstituted group Q, wherein the unsubstituted group Q is selected from the following groups:

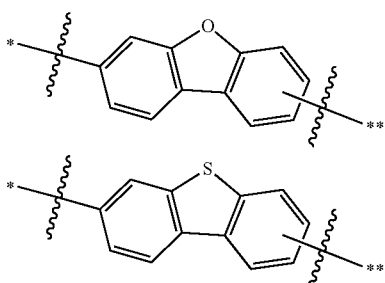

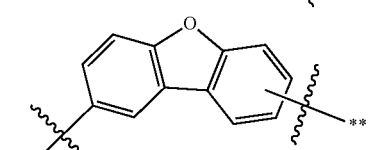

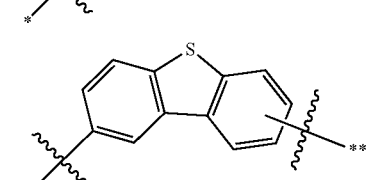

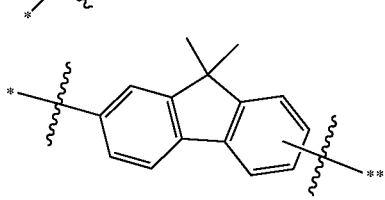

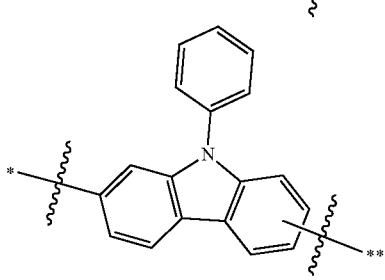

-continued

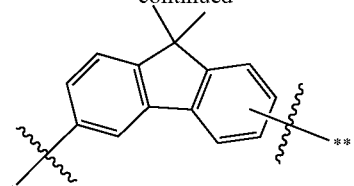

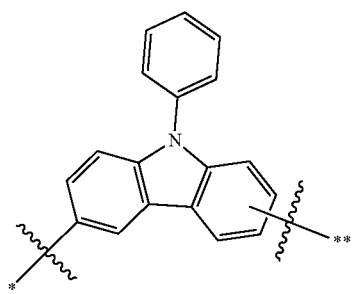

where * represents a connecting point of the unsubstituted group Q to

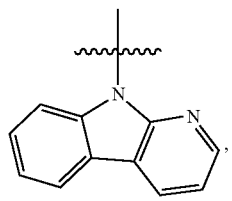 [SMILES: *n1c2ccccc2c2cccnc21]

and ** represents a connecting point of the unsubstituted group Q to Ar.

8. The heterocyclic compound according to claim 1, wherein the heterocyclic compound is selected from the following compounds:

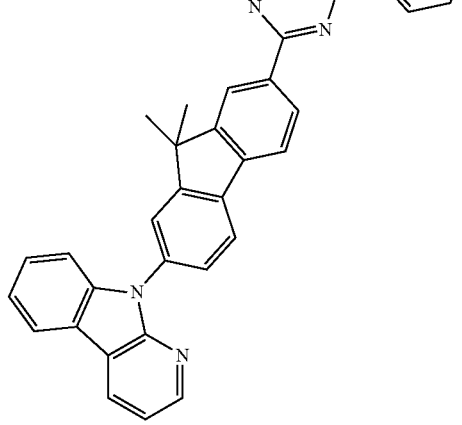

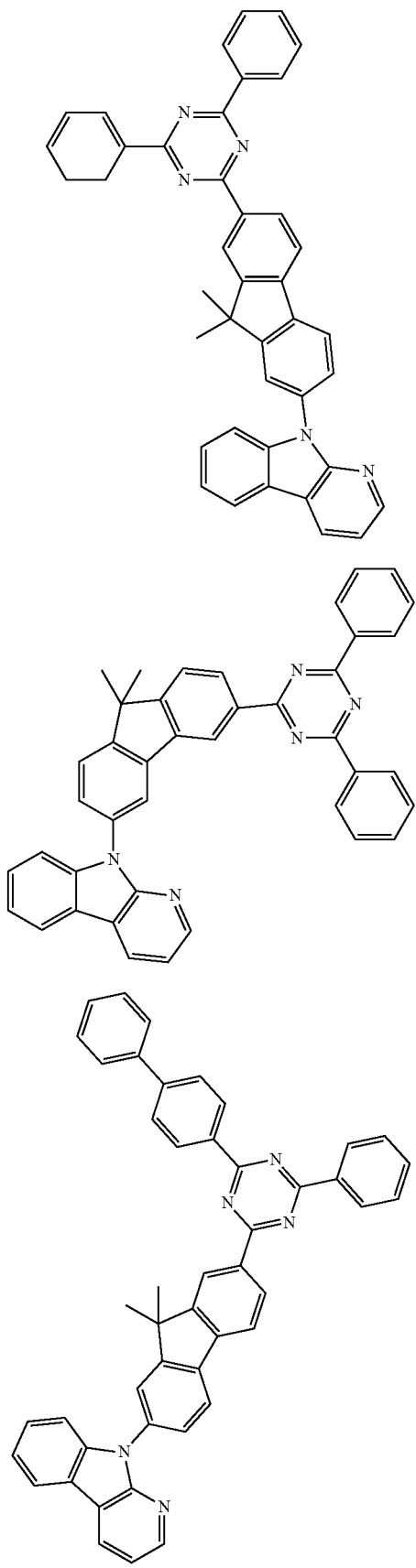
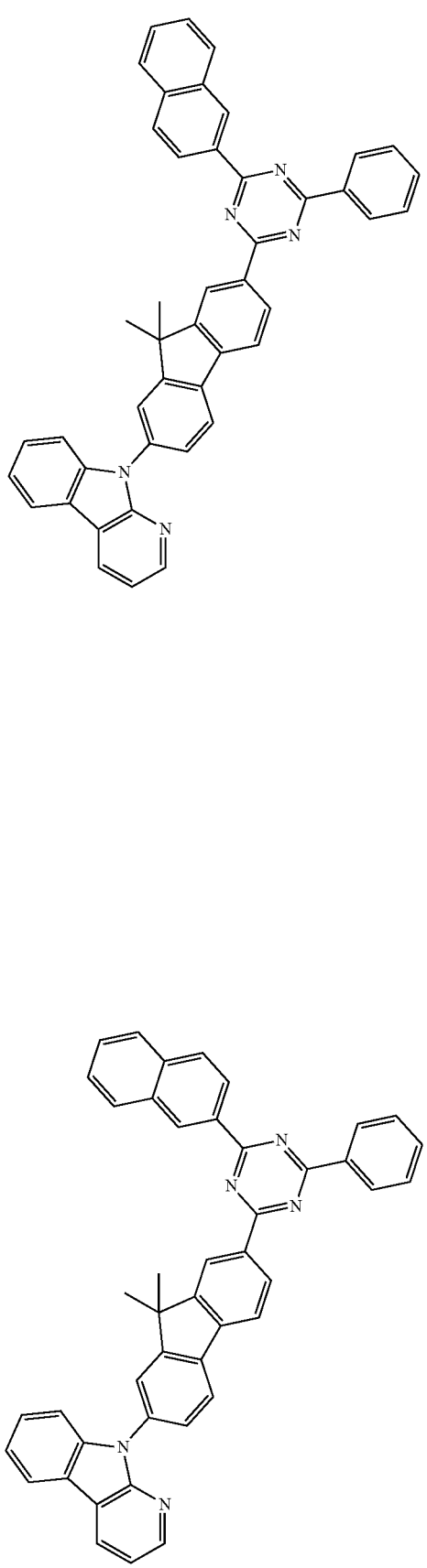

98
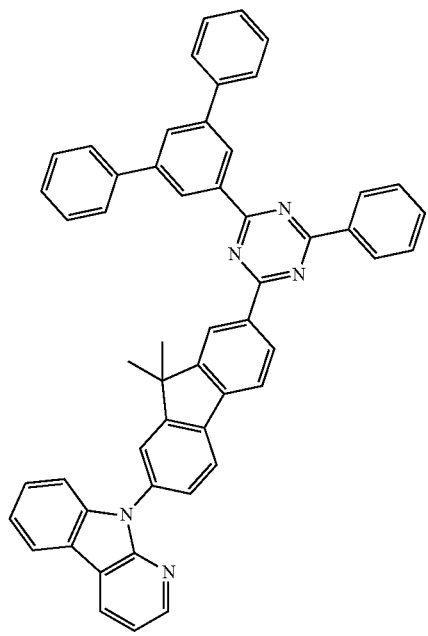
100
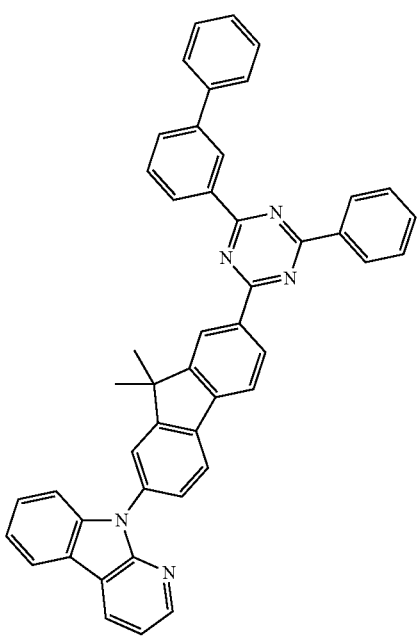
99
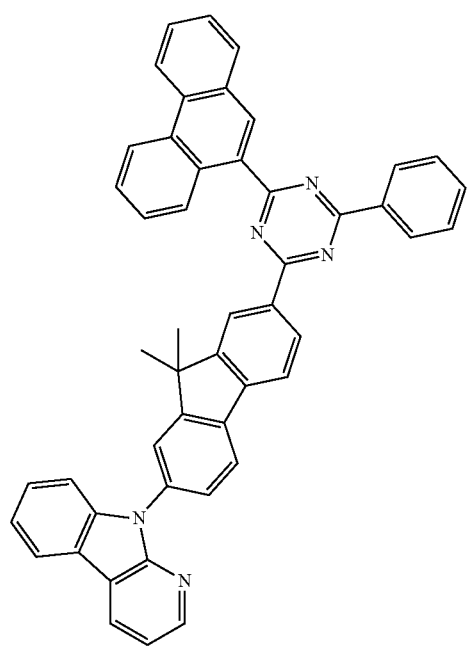
101
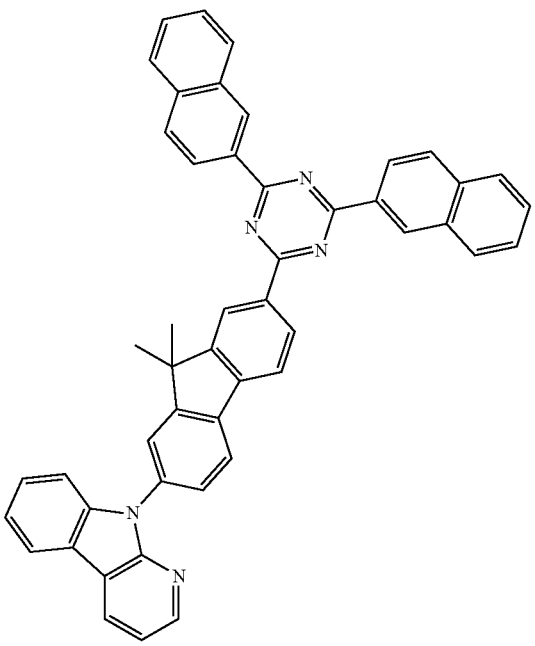

102
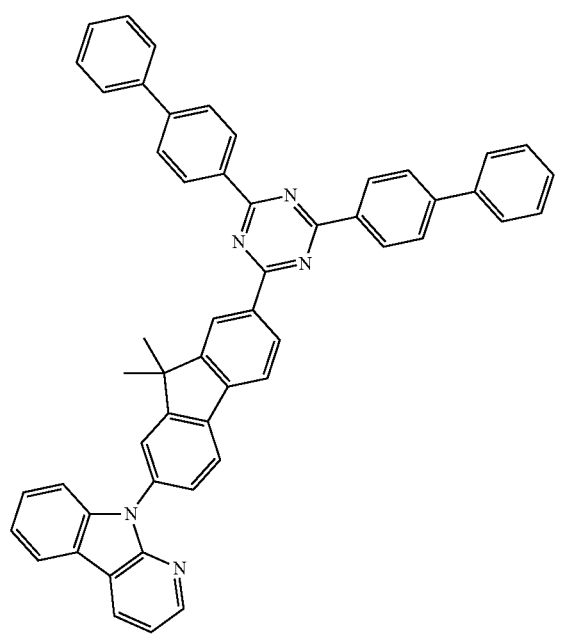
104
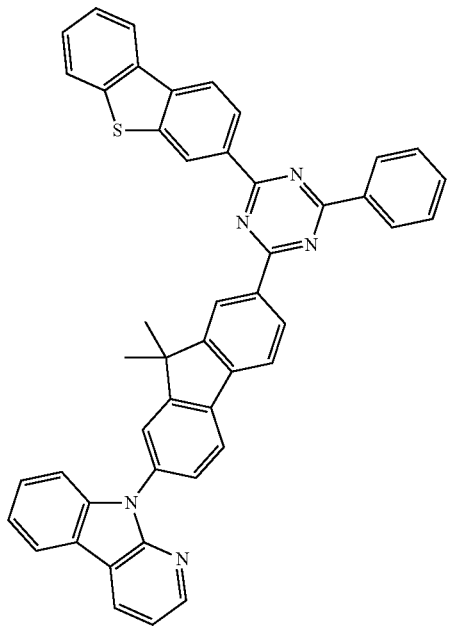
103
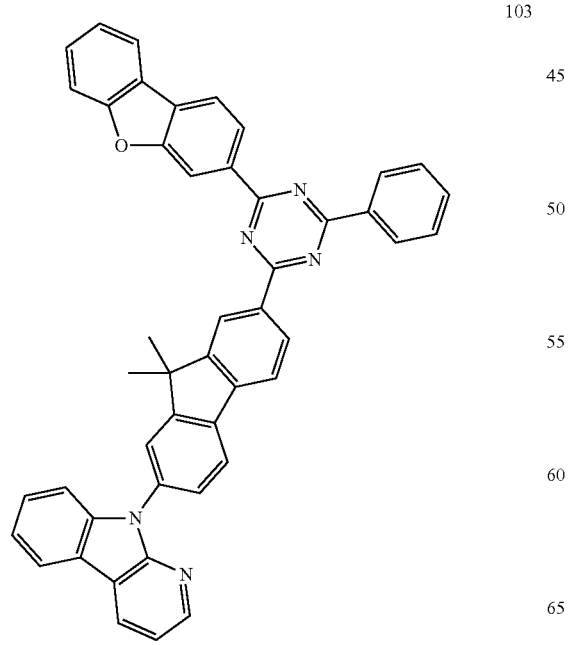
105
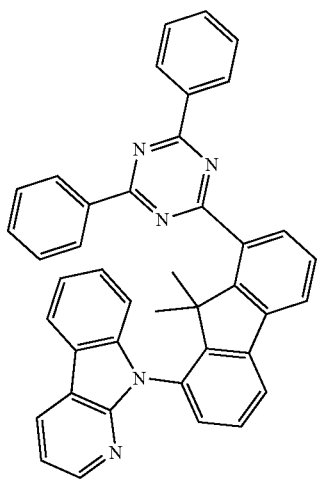

267
-continued
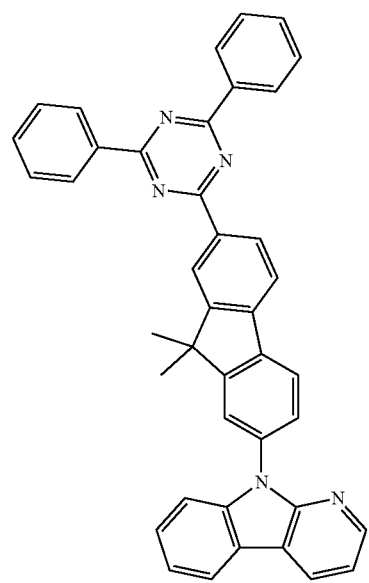
106
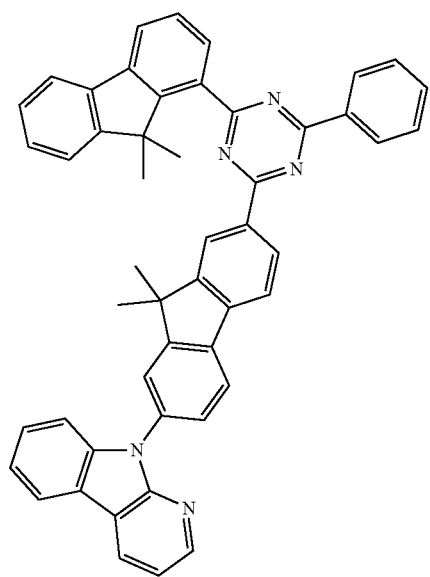
107
268
-continued
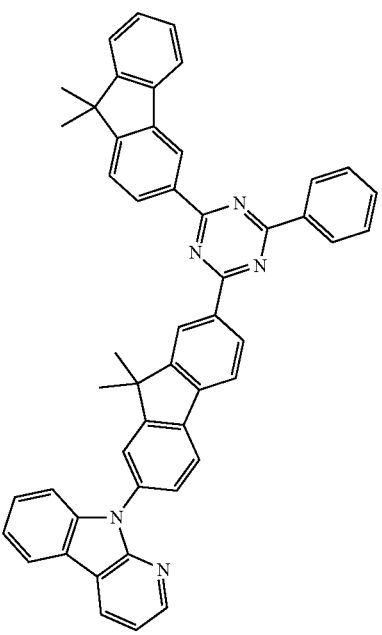
108
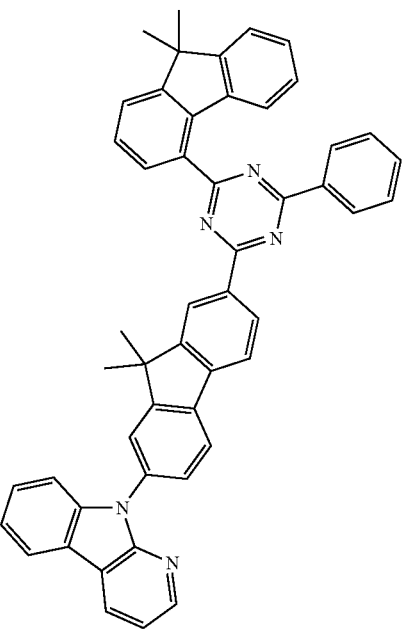
109

269
-continued
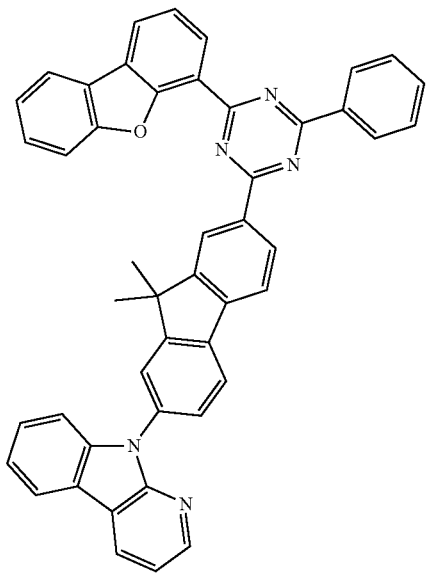
110
270
-continued
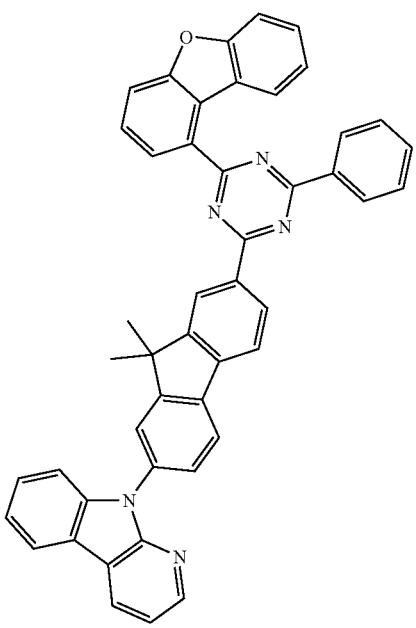
112
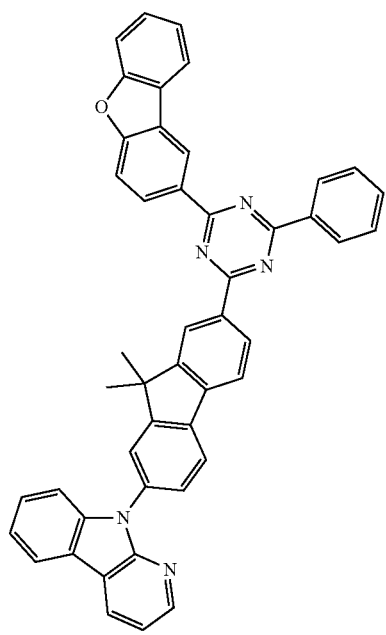
111
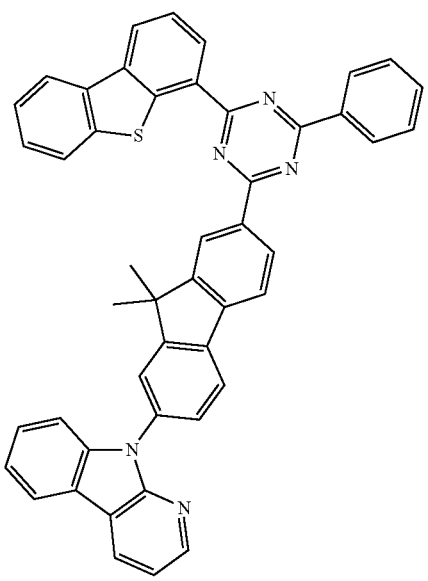
113

271
-continued
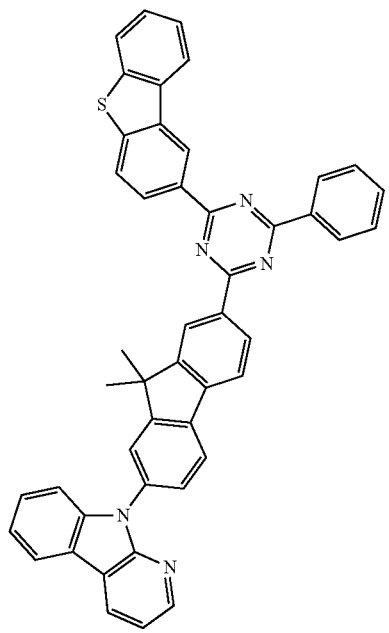
114
272
-continued
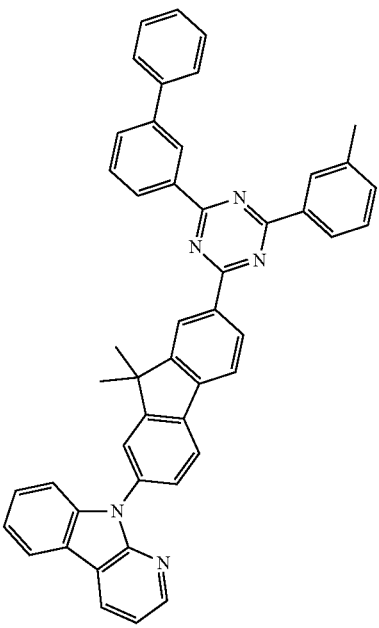
116
115
117

273
-continued
118
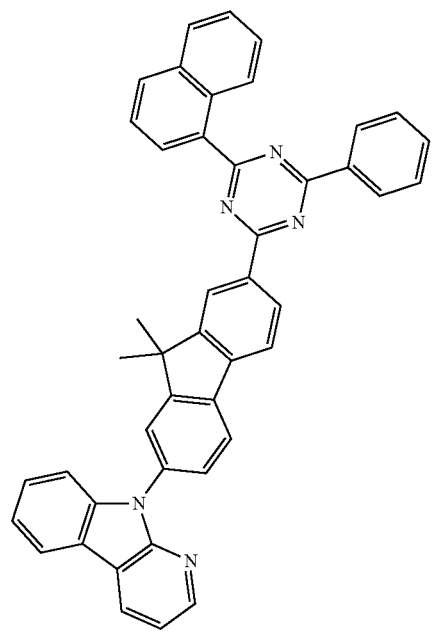
119
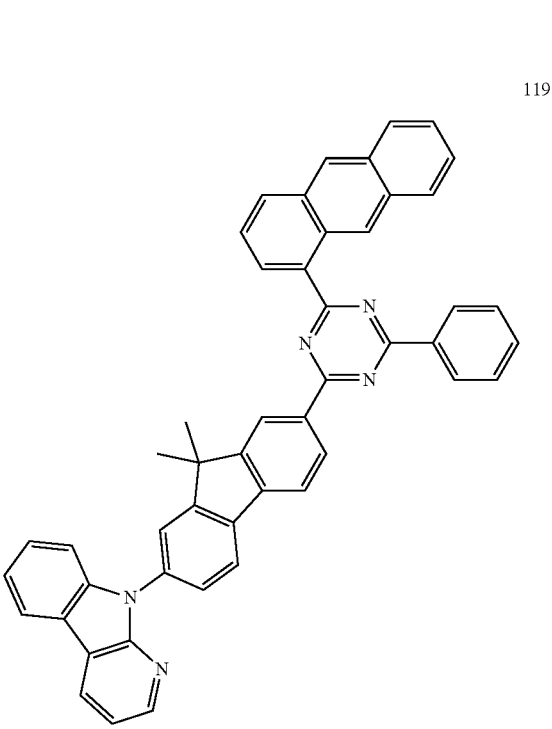
274
-continued
120
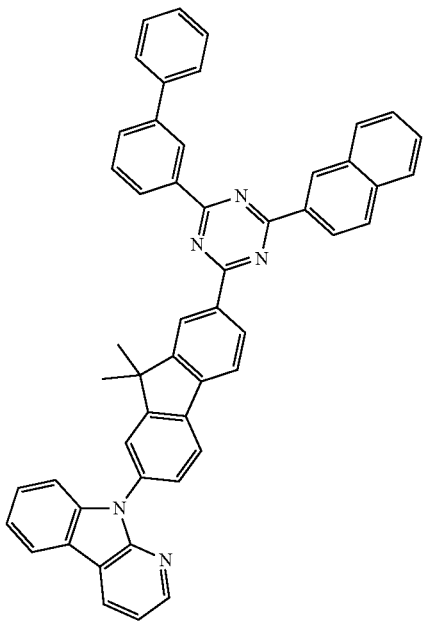
121
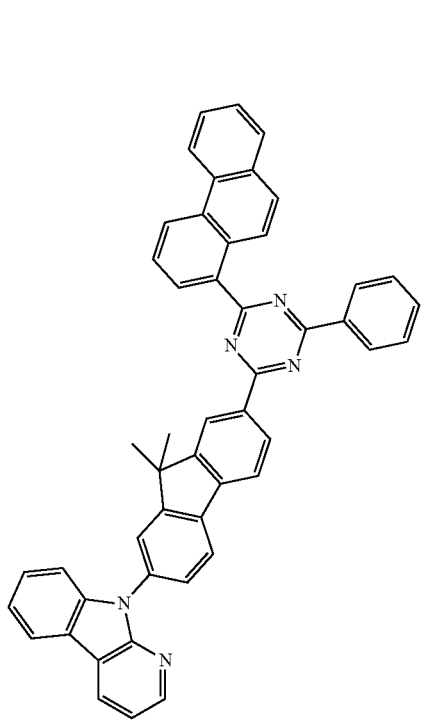

122
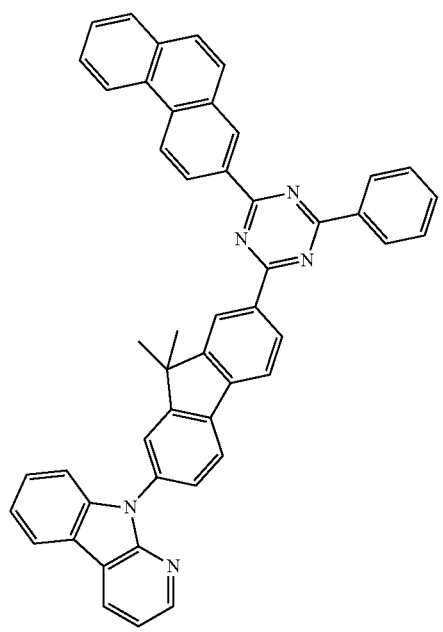
124
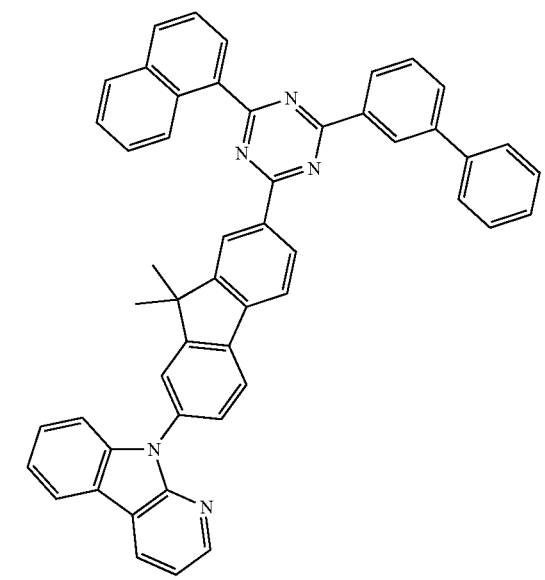
125
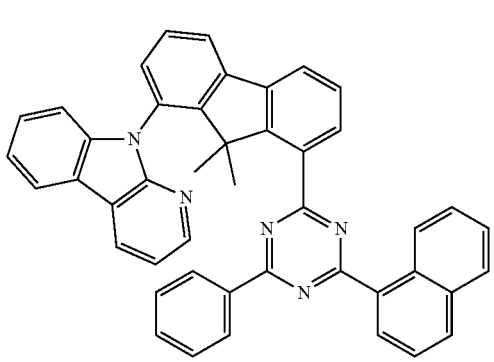
123
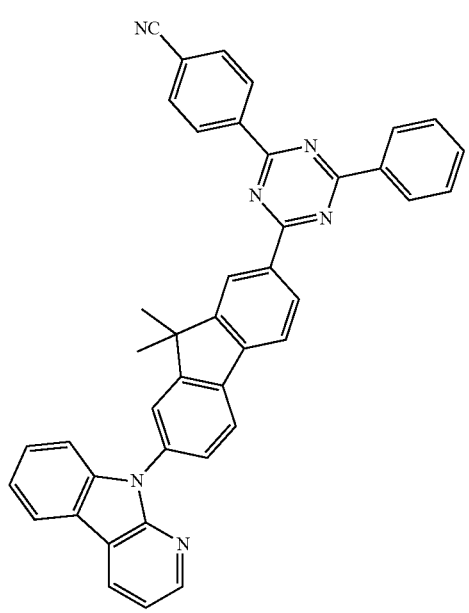
126
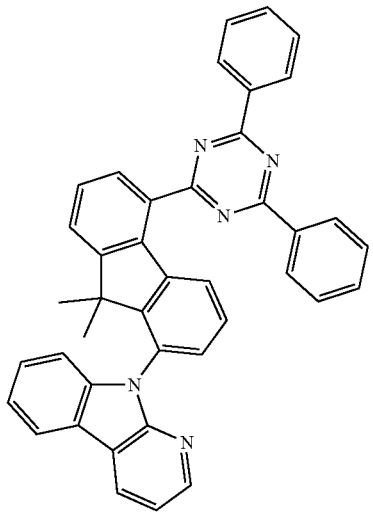

127
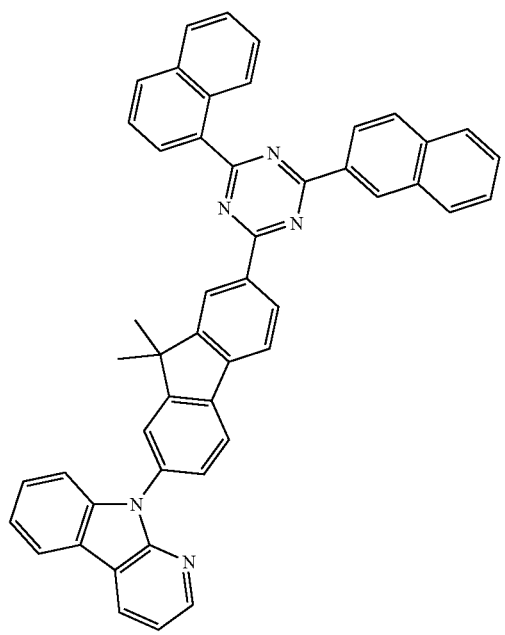
129
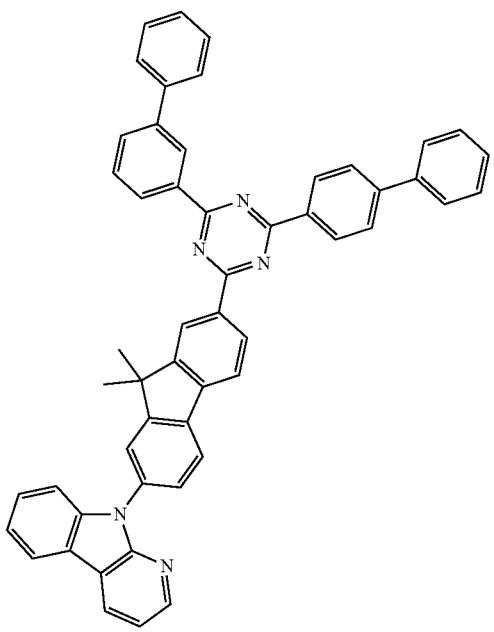
128
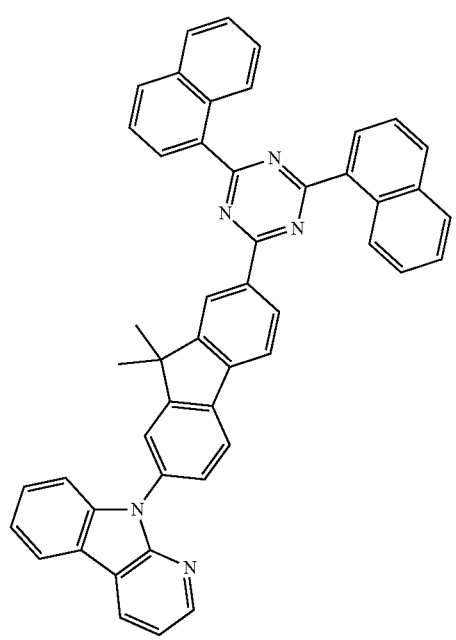
130
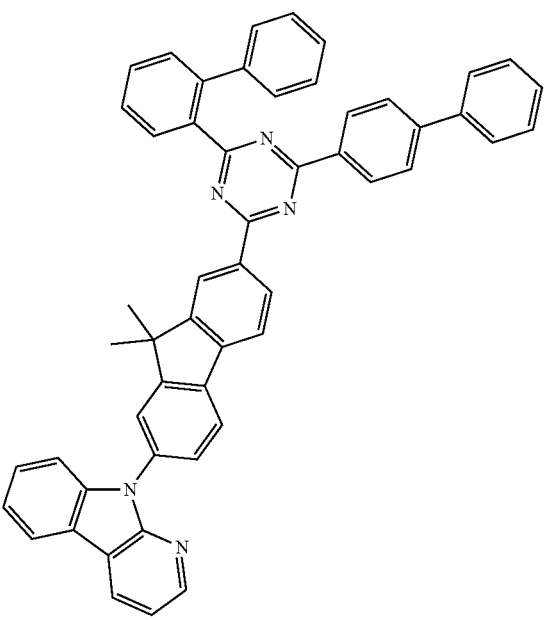

279
-continued
131
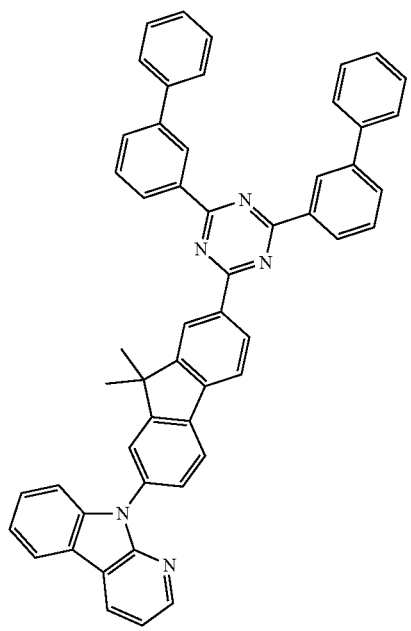
132
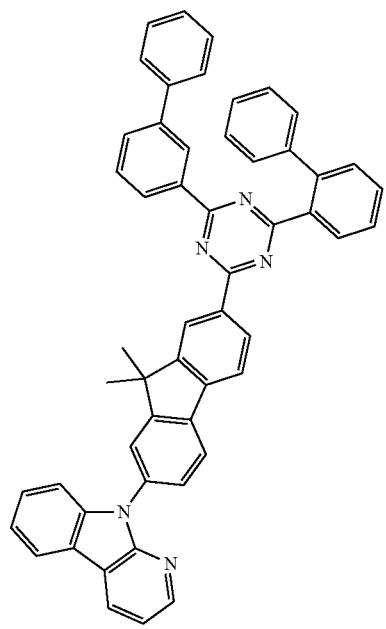
280
-continued
133
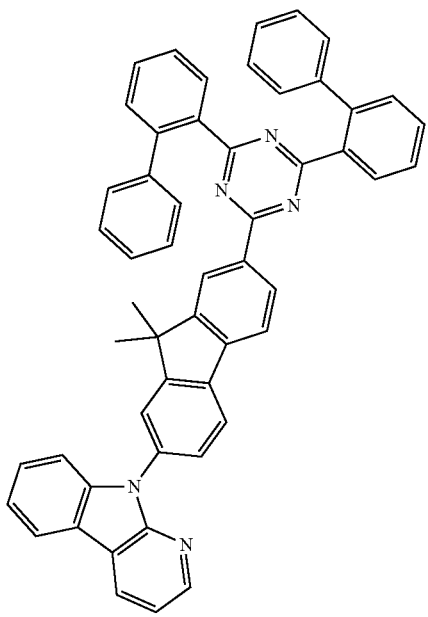
134
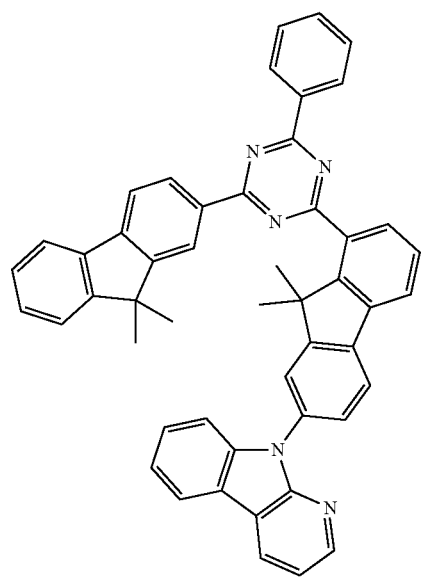

281
-continued
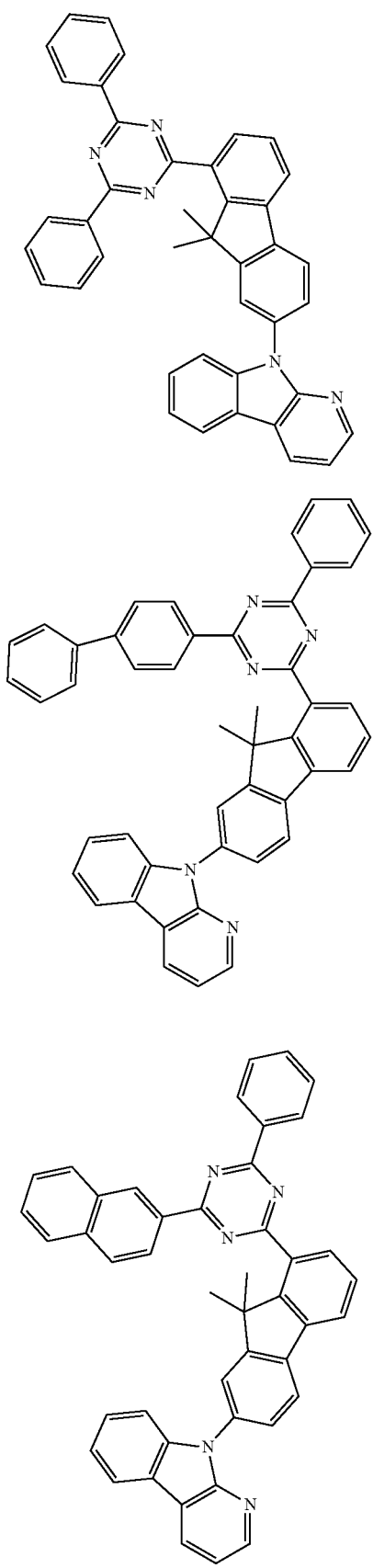
135
136
137
282
-continued
138
139

-continued
140
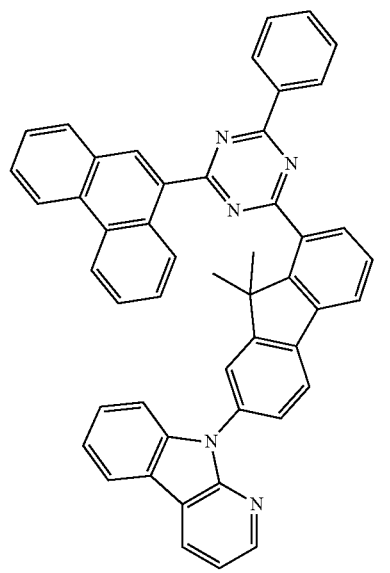
141
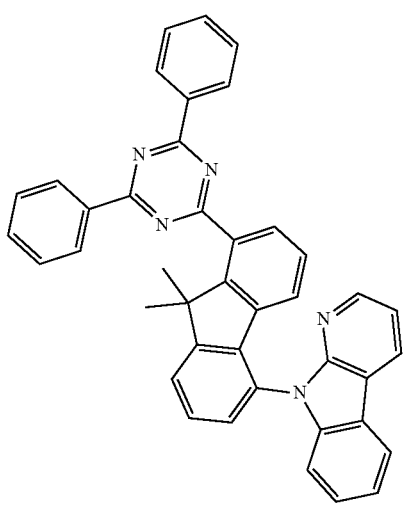
-continued
143
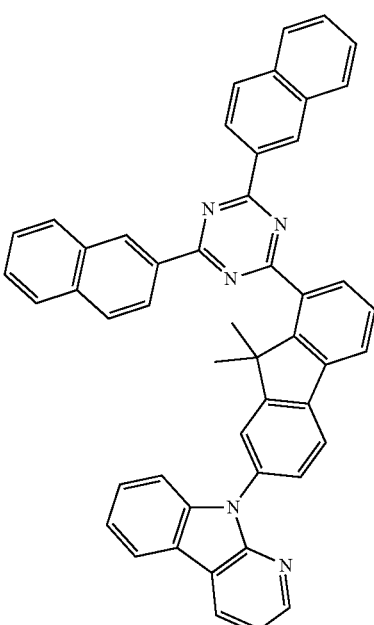
144
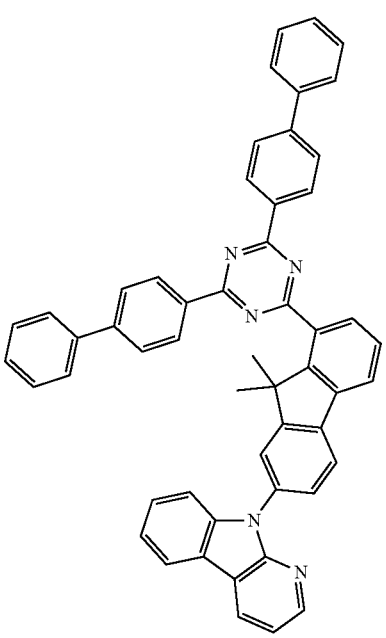
142

145
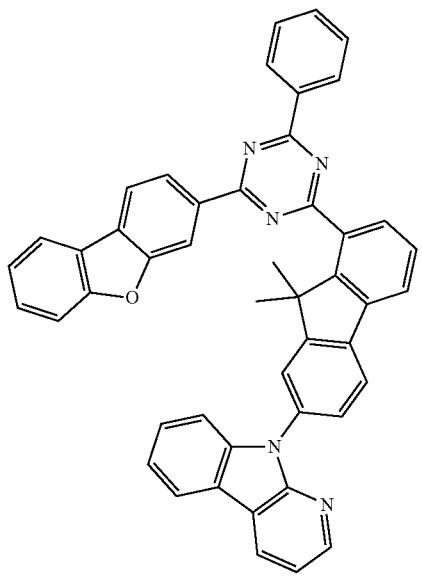
146
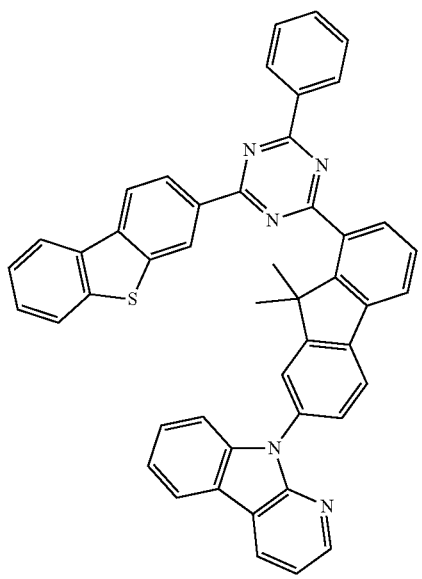
147
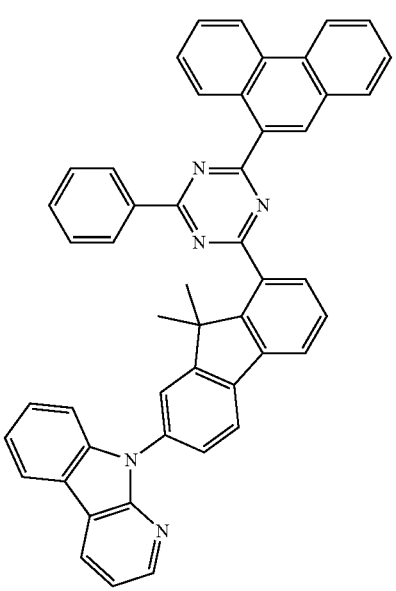
148
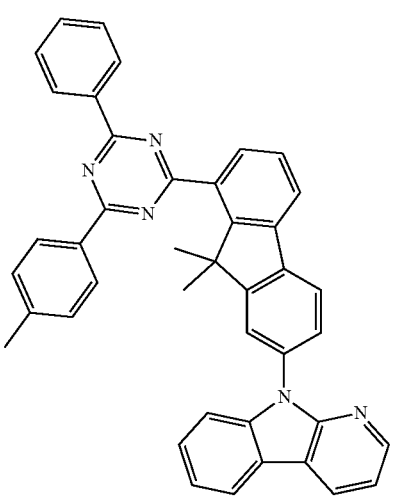
149
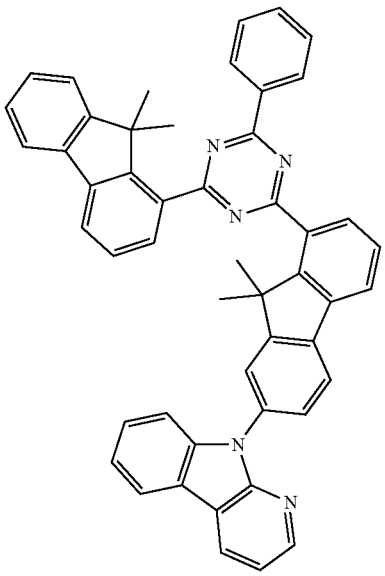

150
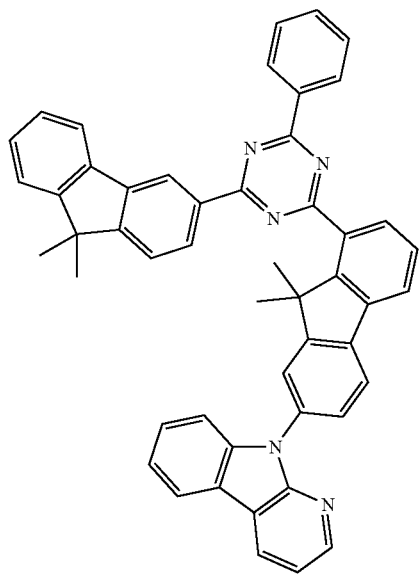
151
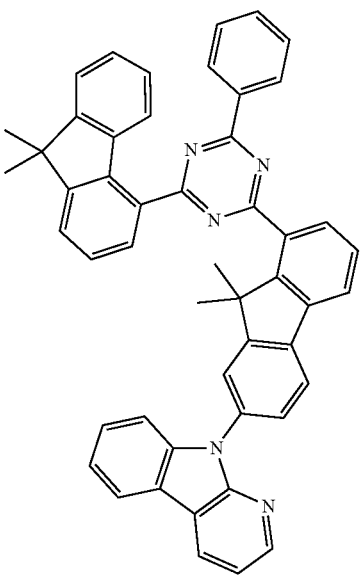
152
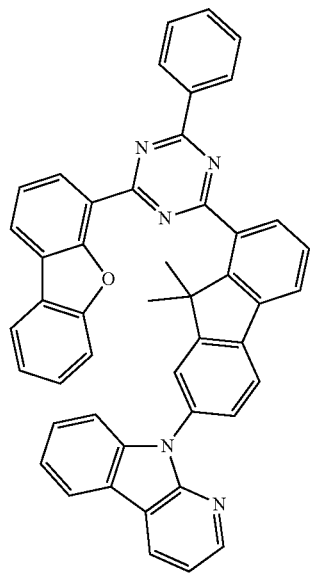
153
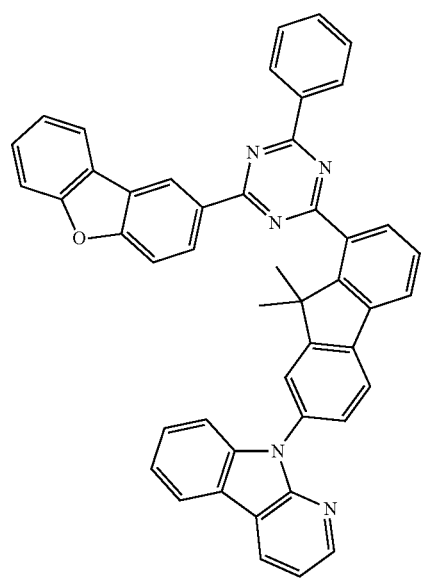

154
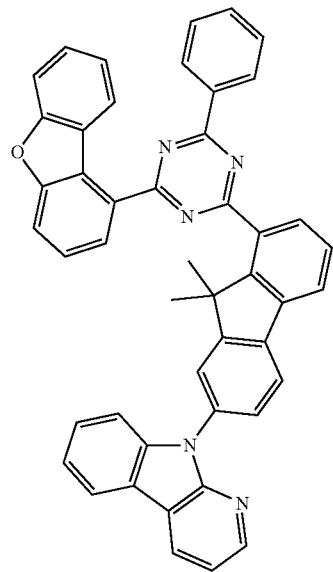
156
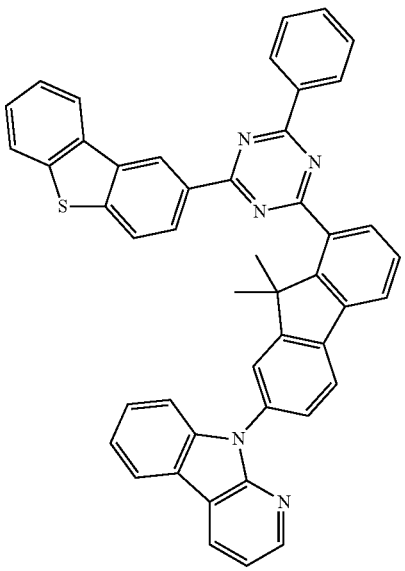
155
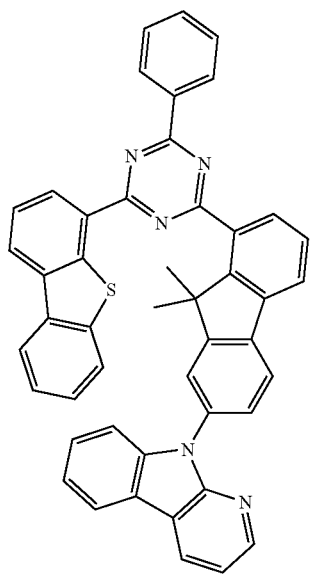
157
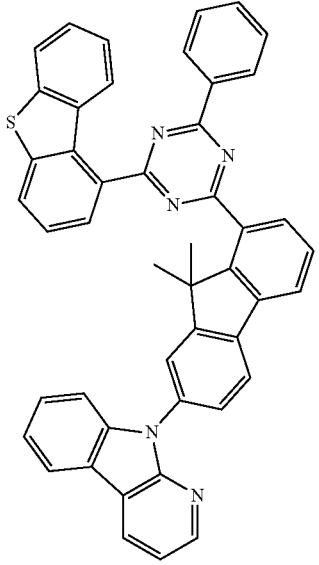

291
-continued
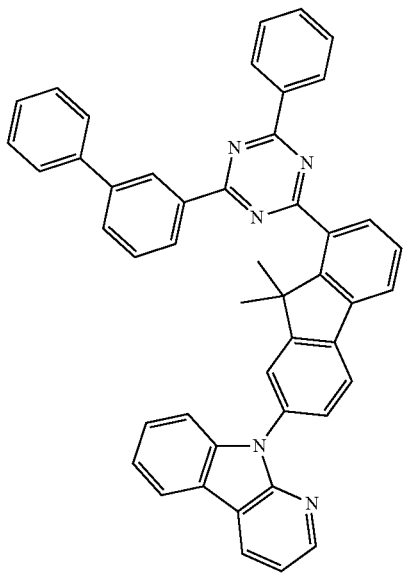
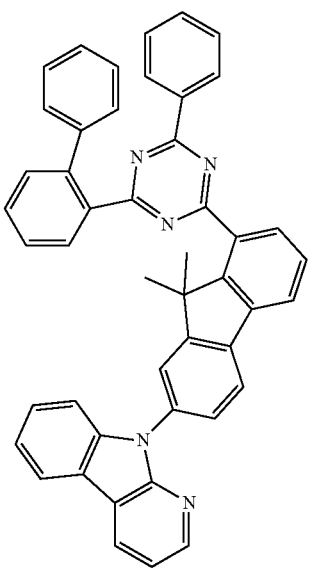
292
-continued
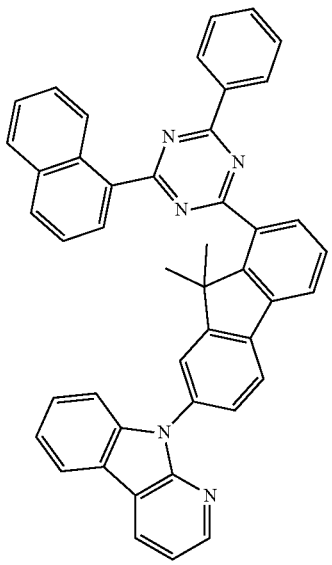
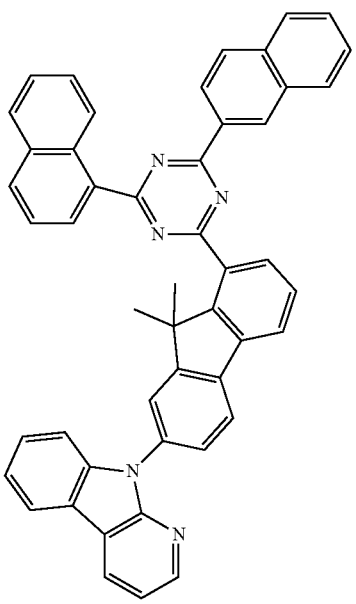

293
-continued
162
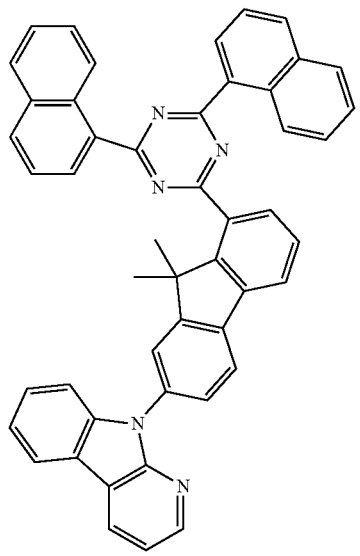
163
294
-continued
164
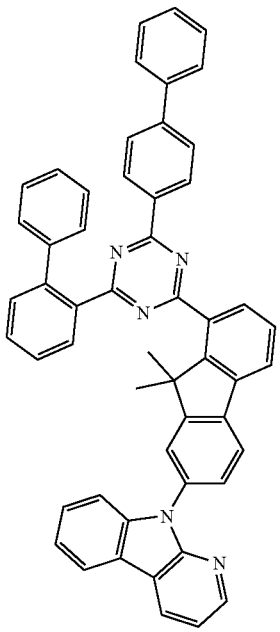
165
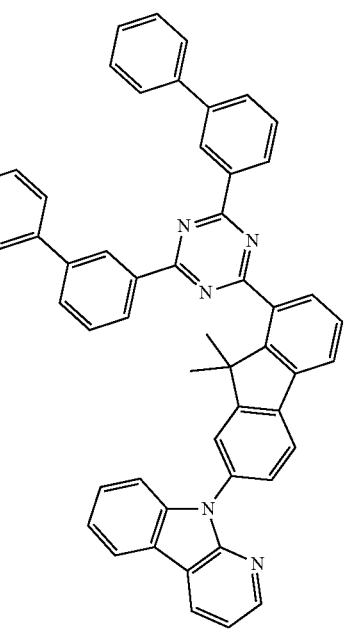

-continued
166
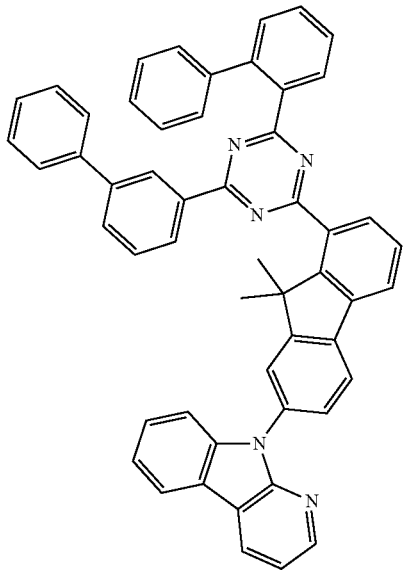
167
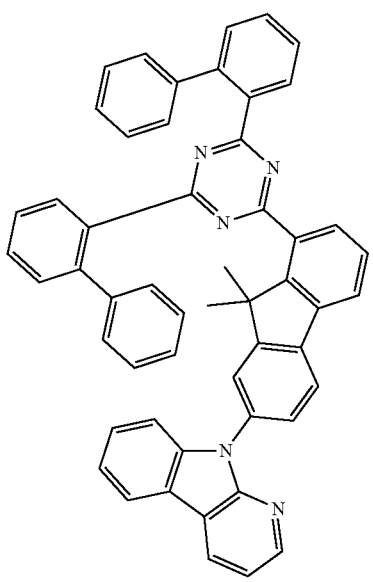
-continued
168
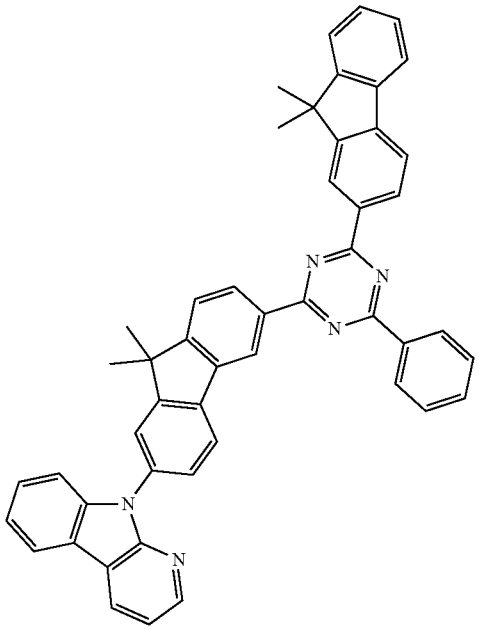
169
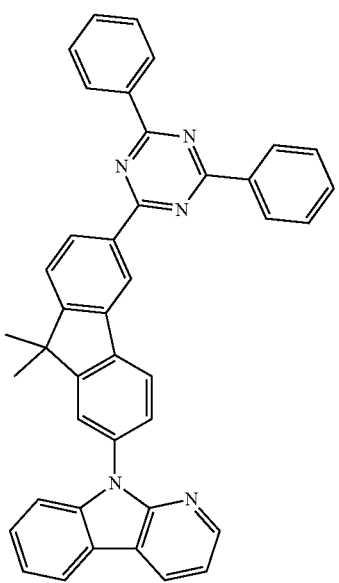

297
-continued
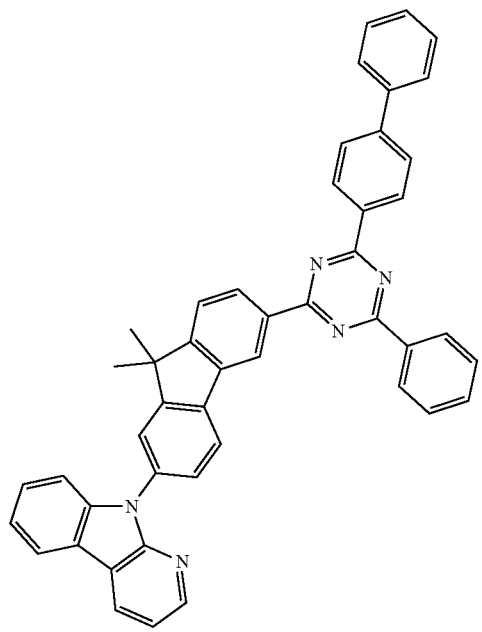
170
171
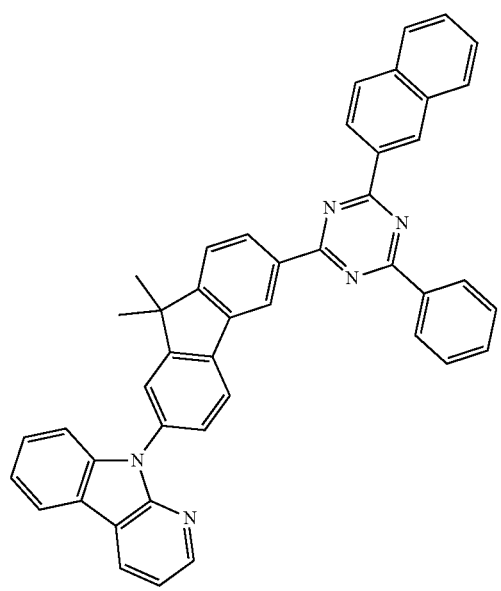
298
-continued
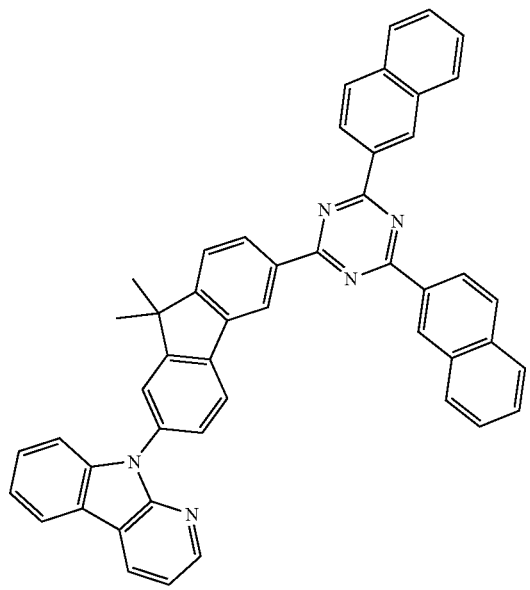
172
173
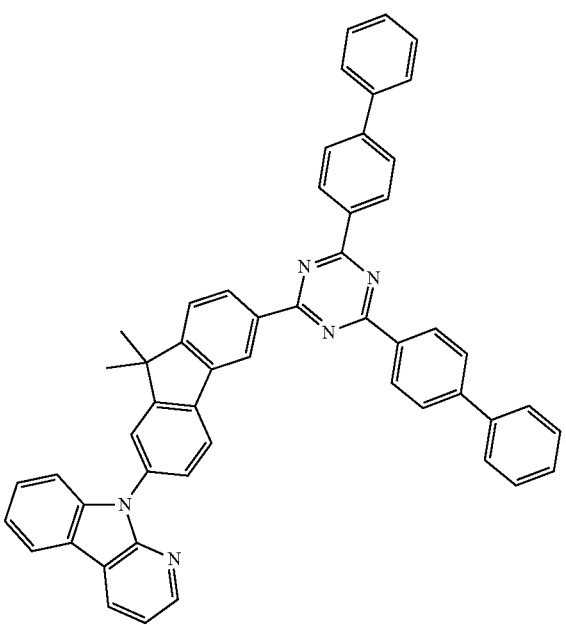

174
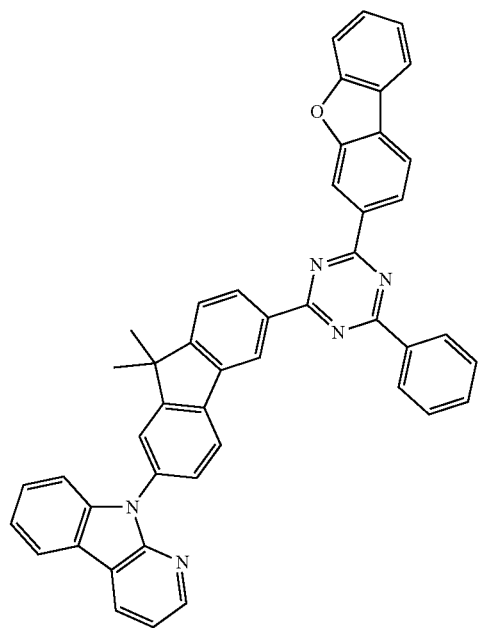
175
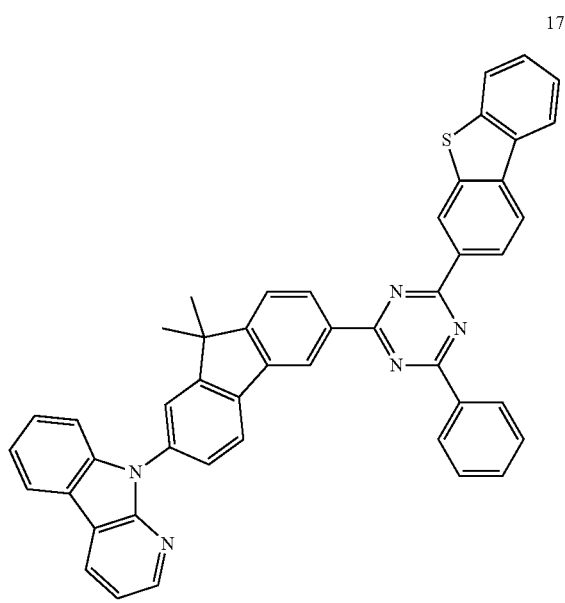
176
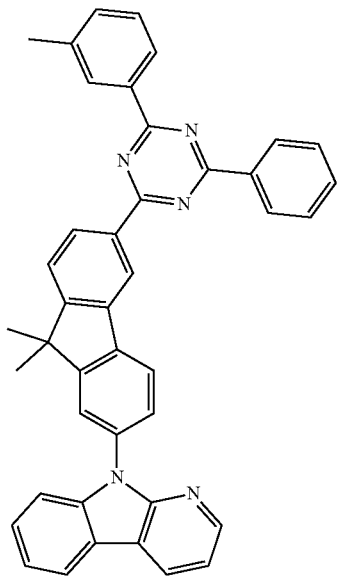
177
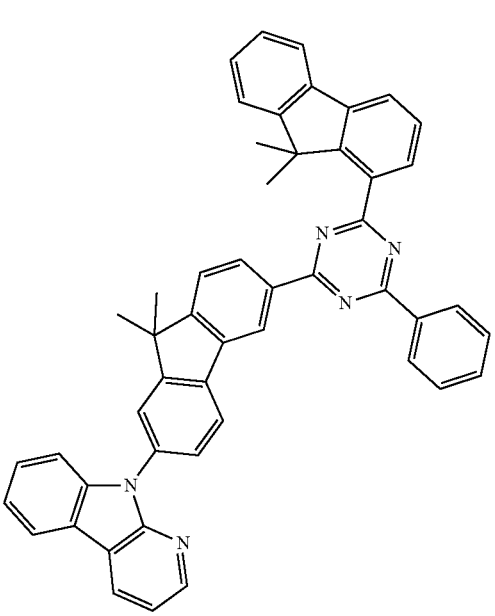

301
-continued
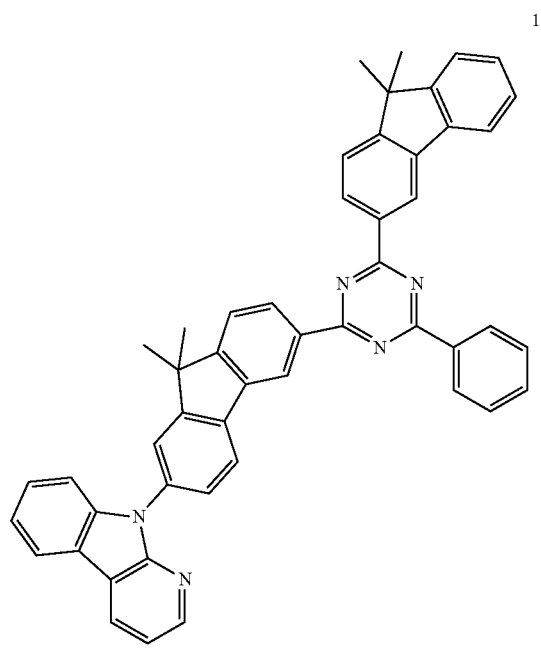
178
302
-continued
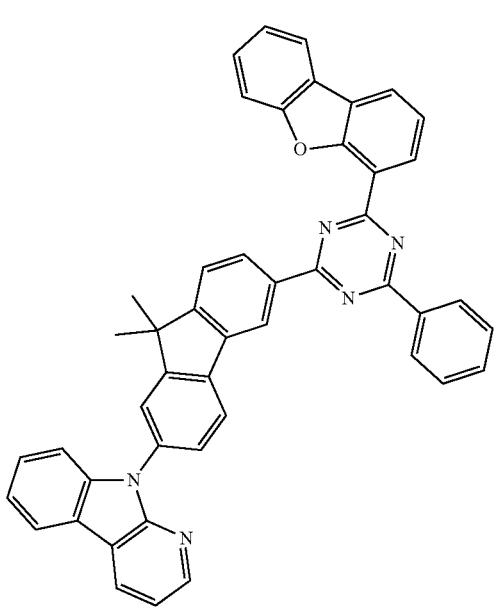
180
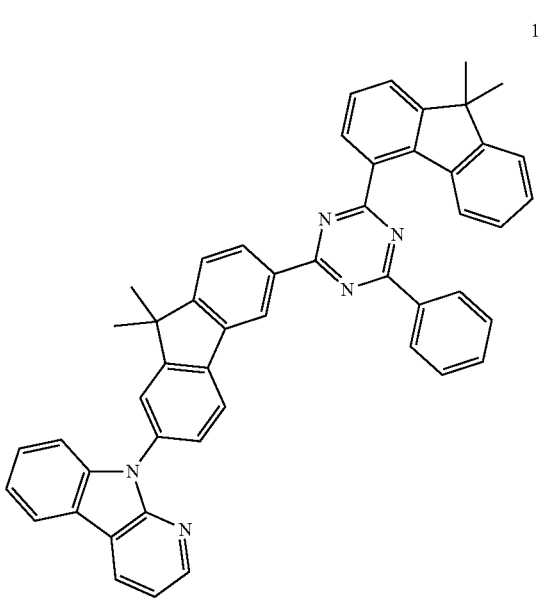
179
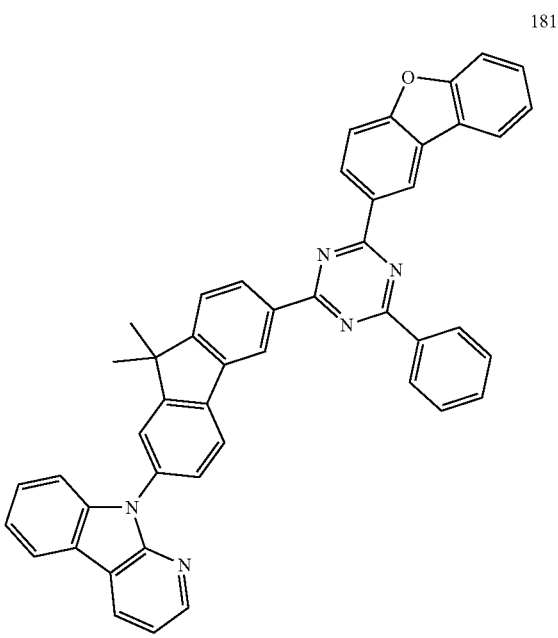
181

303
-continued
182
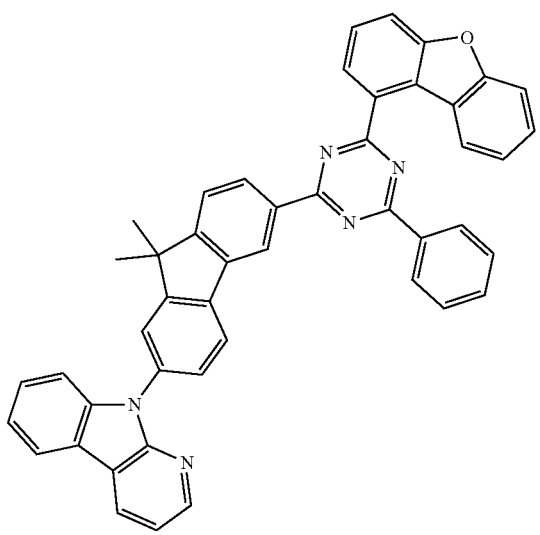
183
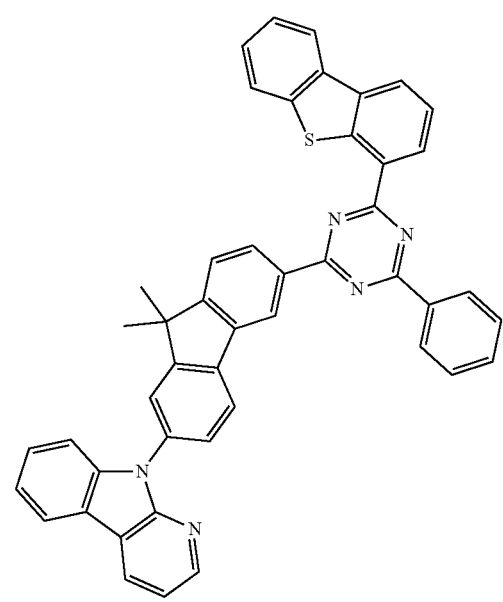
304
-continued
184
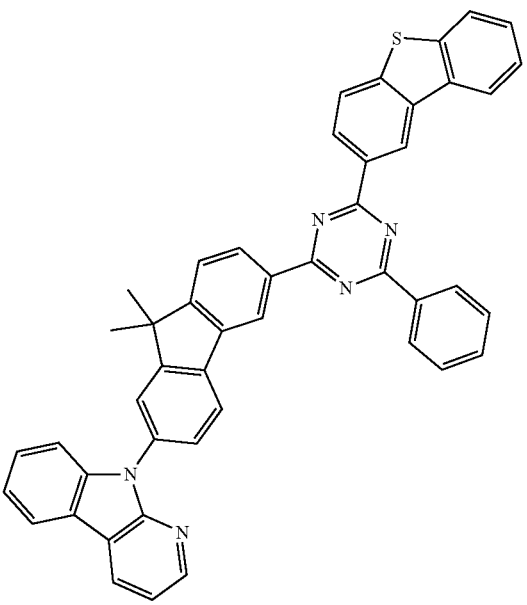
185
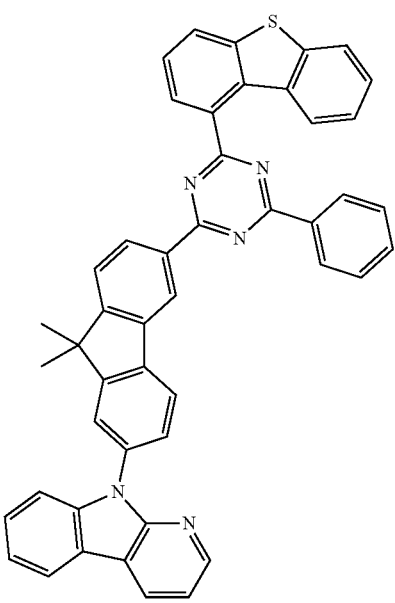

186
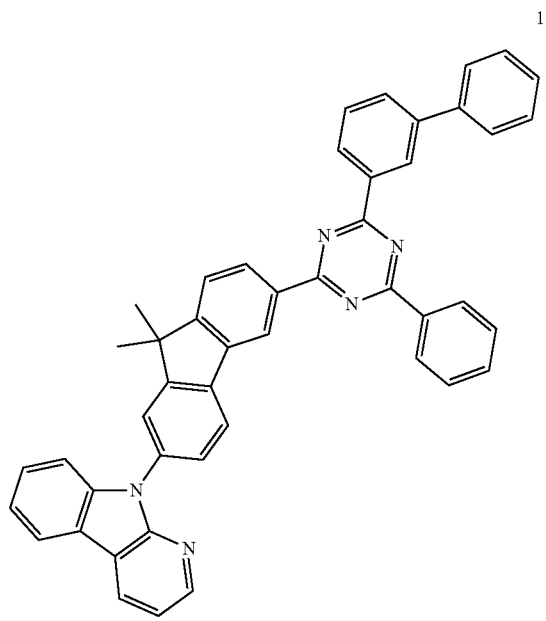
187
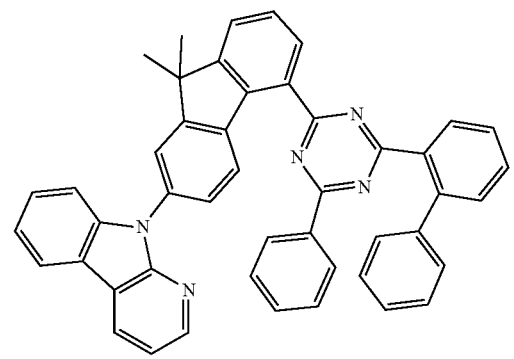
188
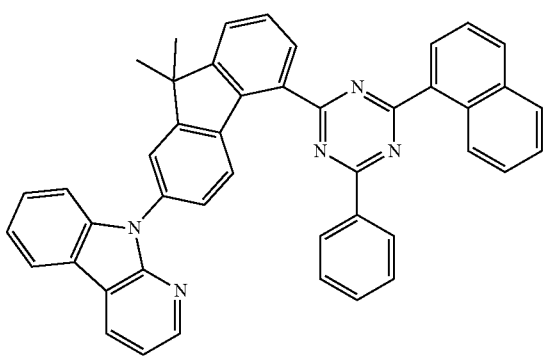
189
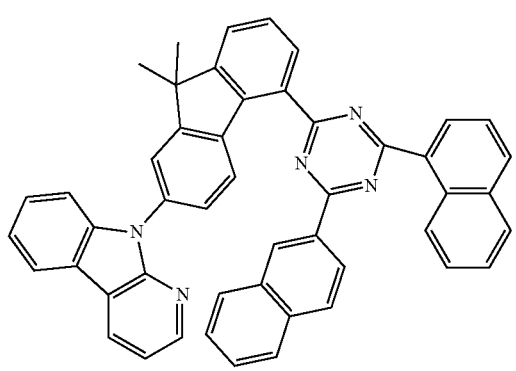
190
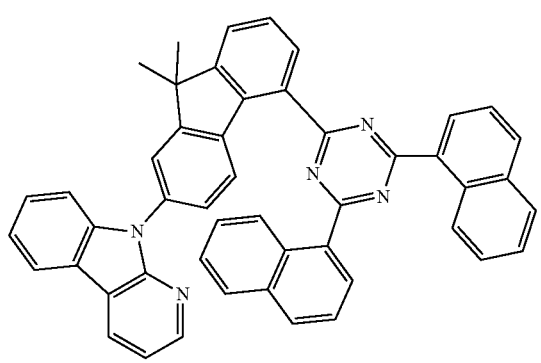
191
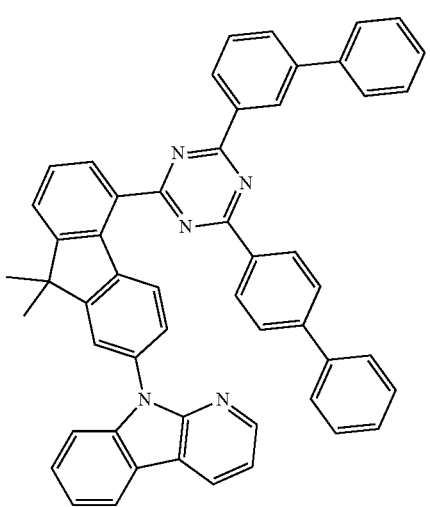

307
-continued
192
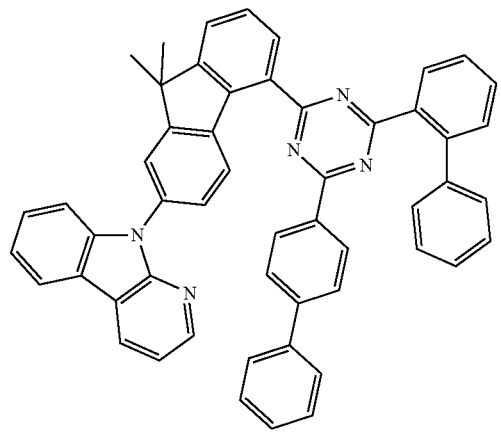
193
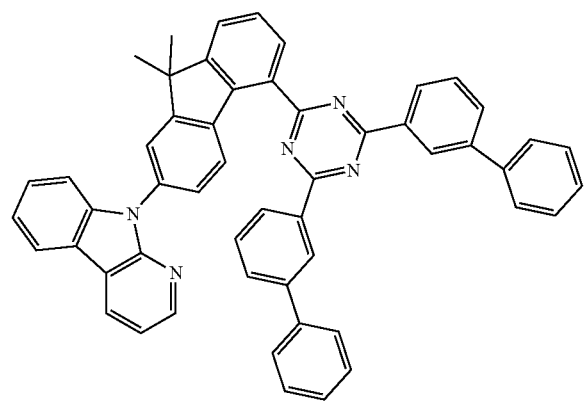
194
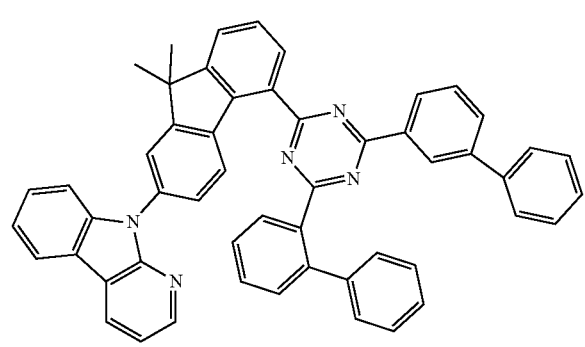
308
-continued
195
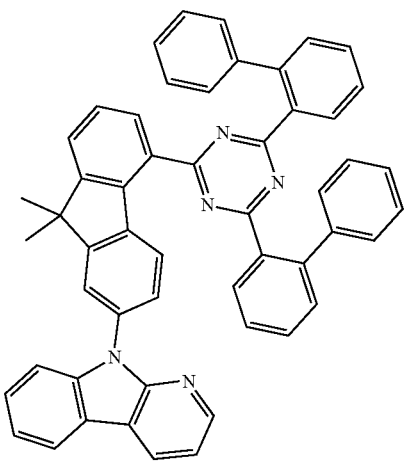
196
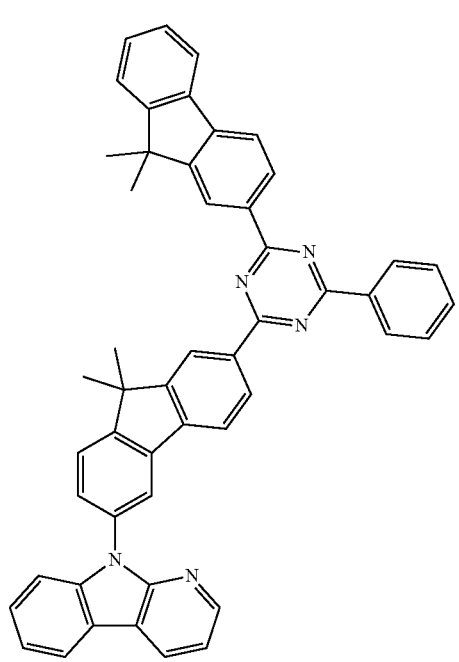
197
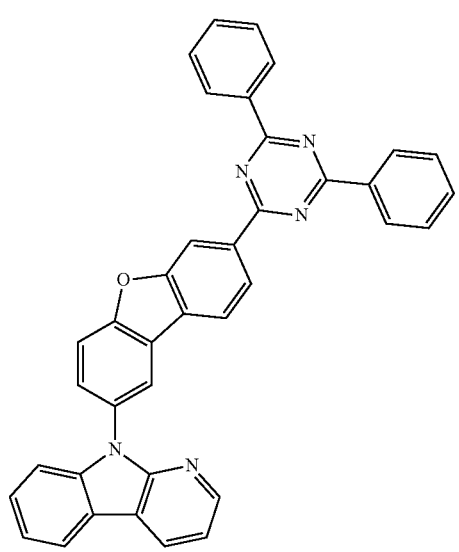

-continued
198
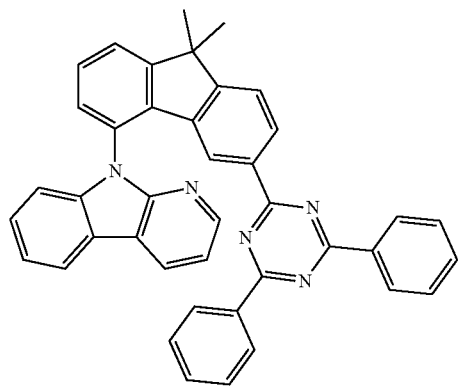
199
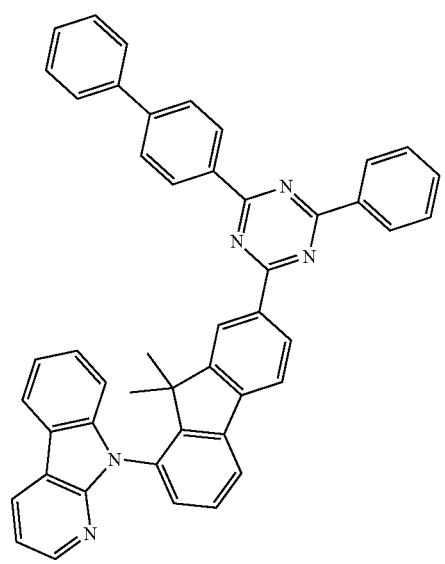
200
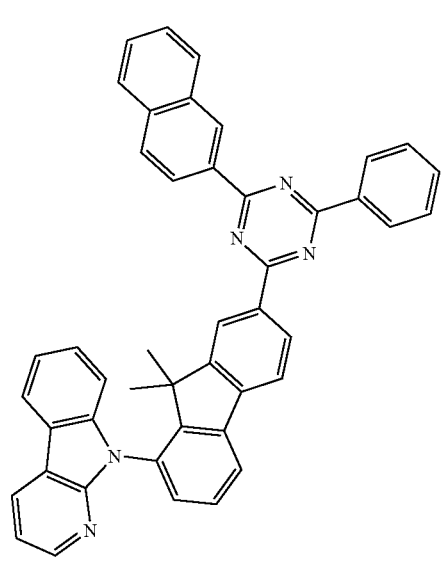
-continued
201
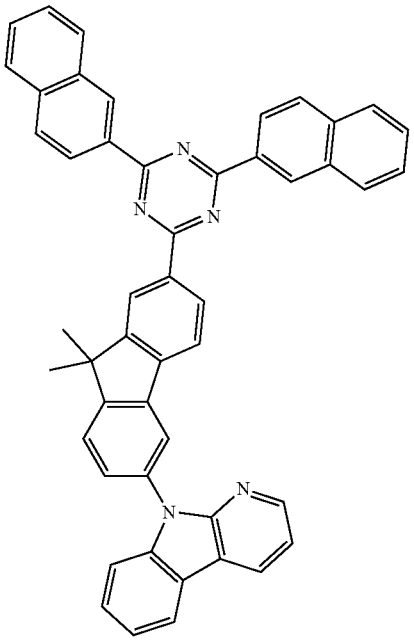
202
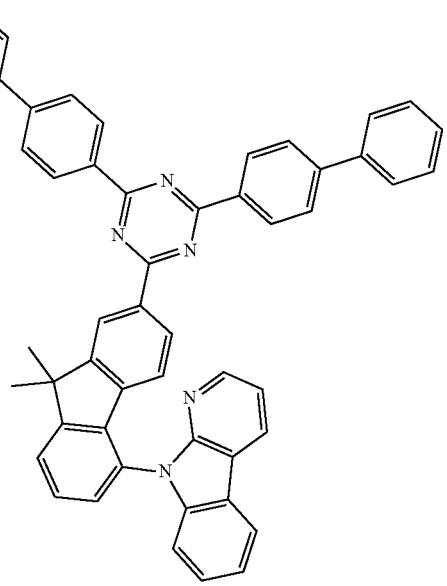

311
-continued
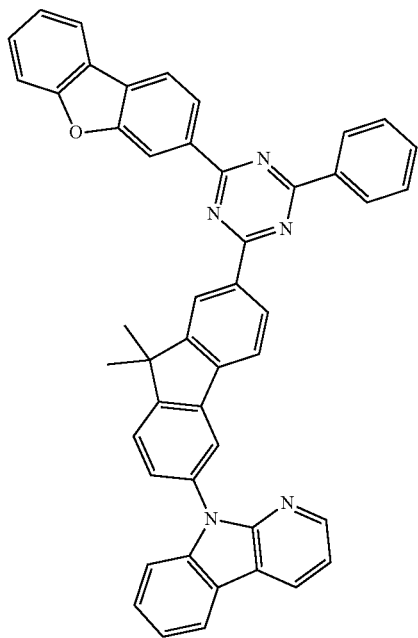
203
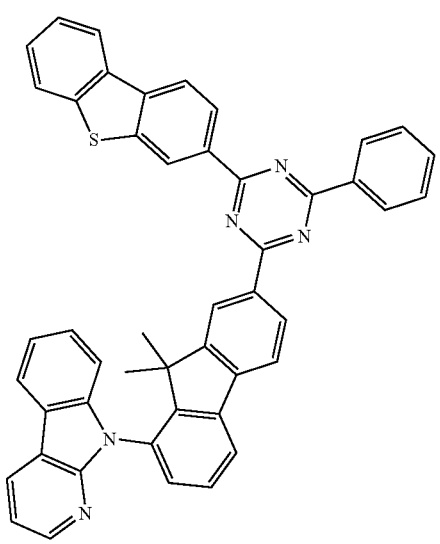
204
312
-continued
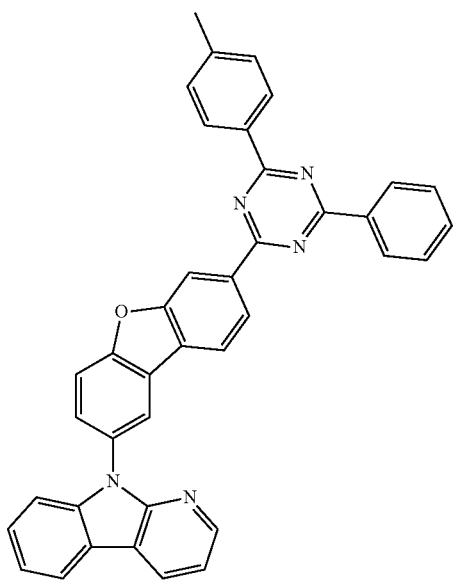
205
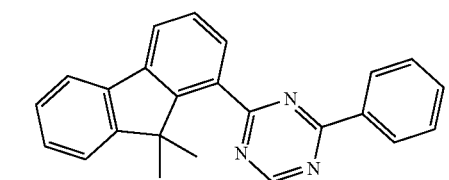
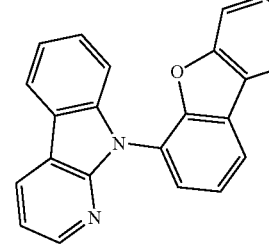
206
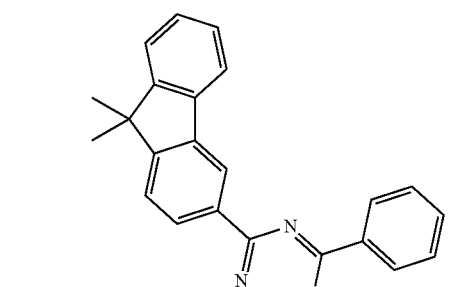
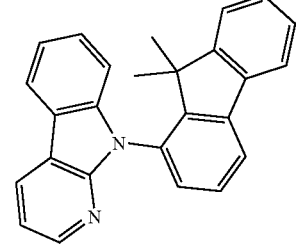
207

208
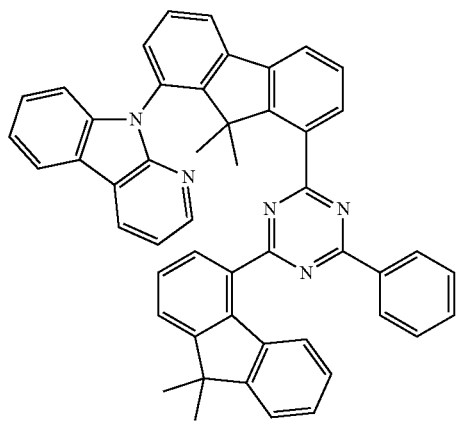
209
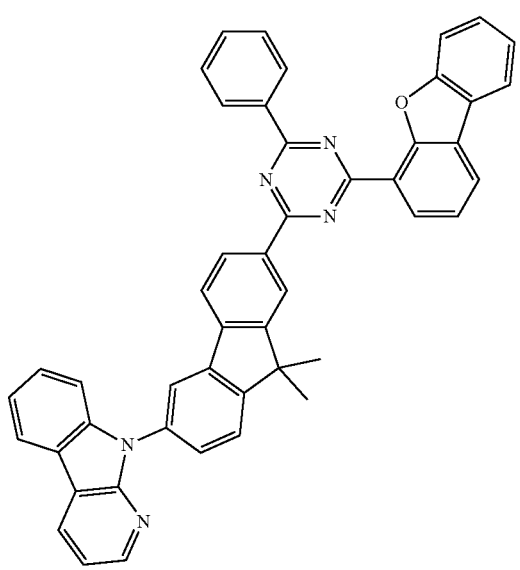
210
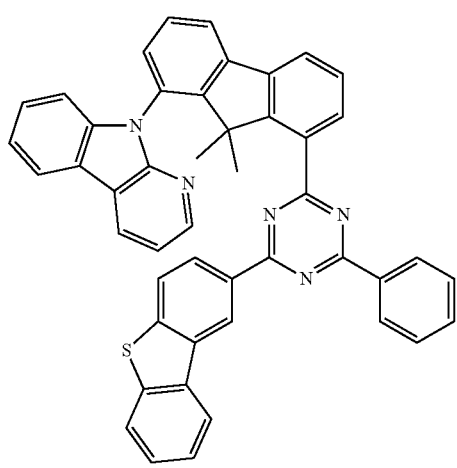
211
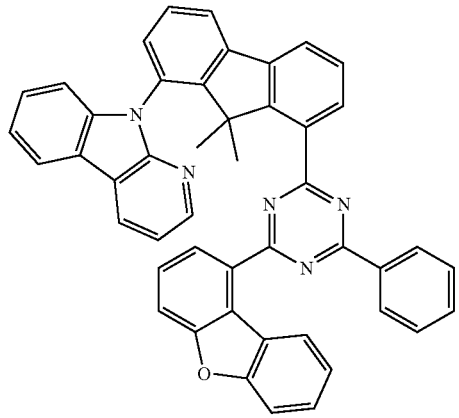
212
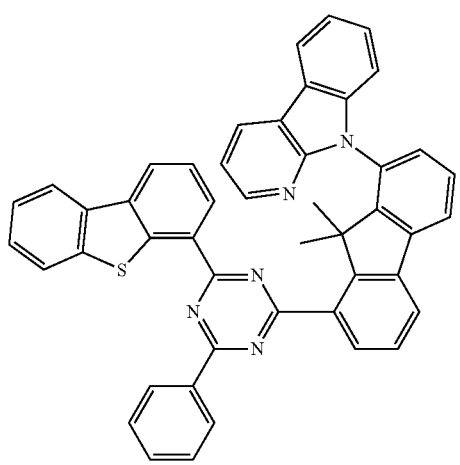
213
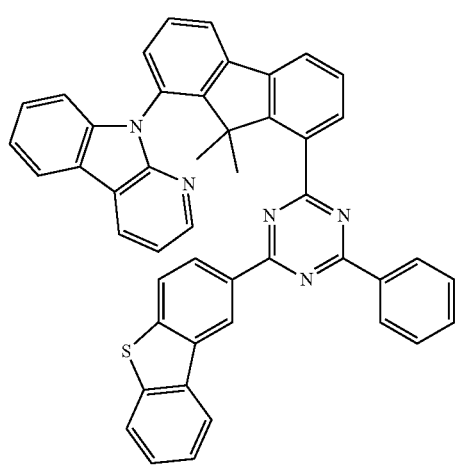

-continued
214
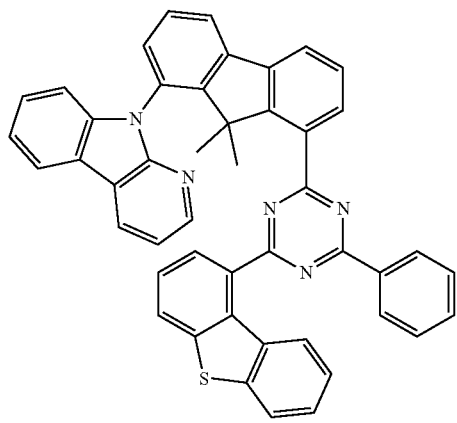
215
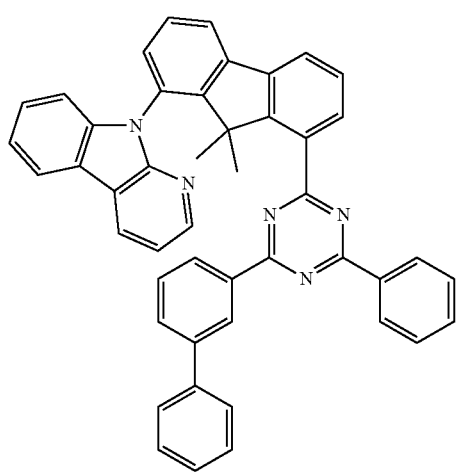
216
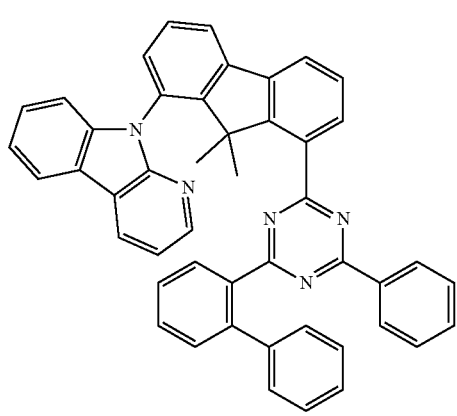
-continued
217
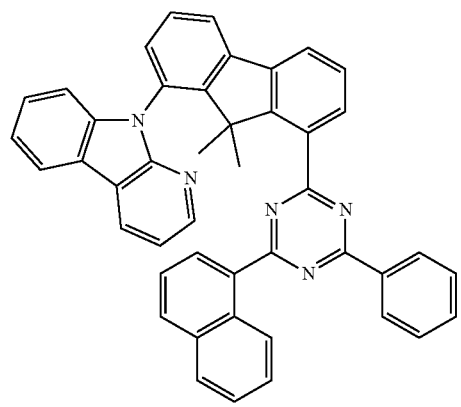
218
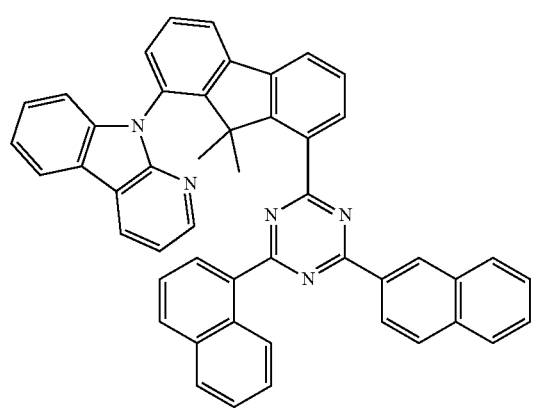
219
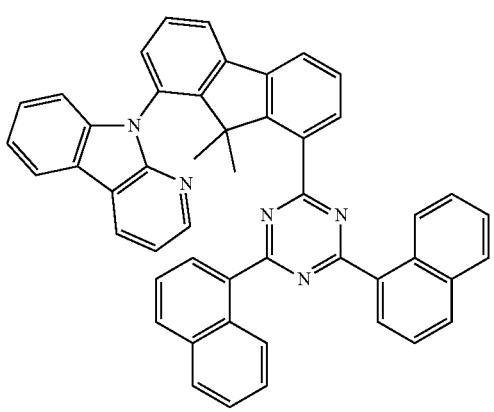

-continued
220
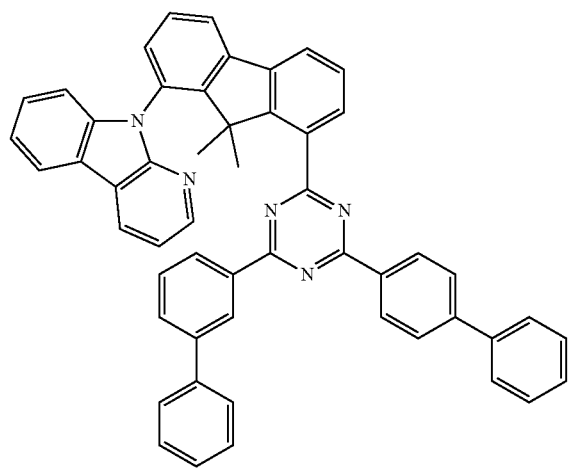
221
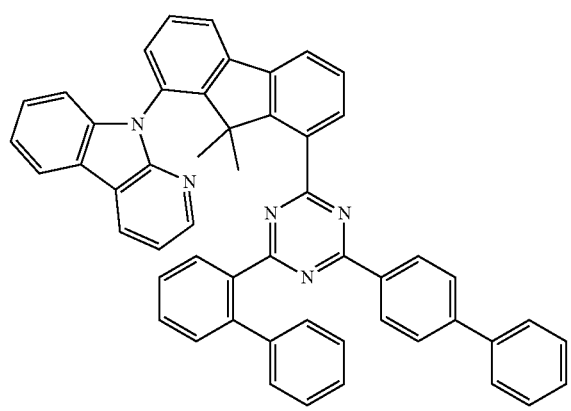
222
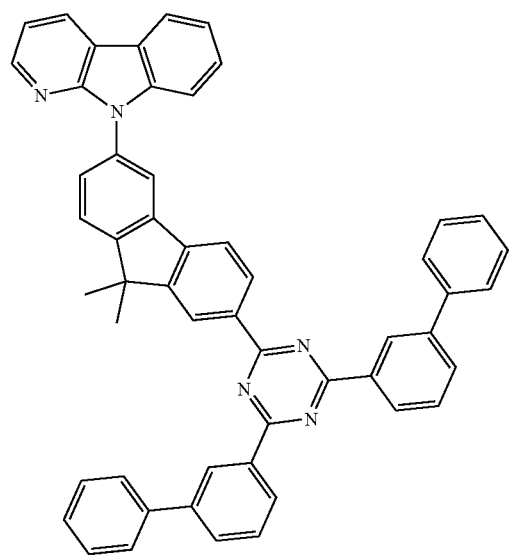
-continued
223
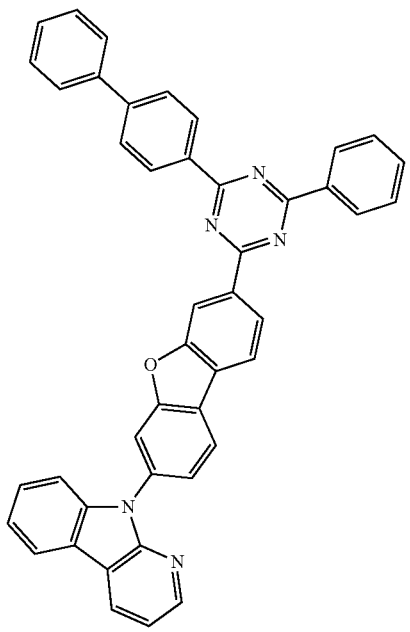
224
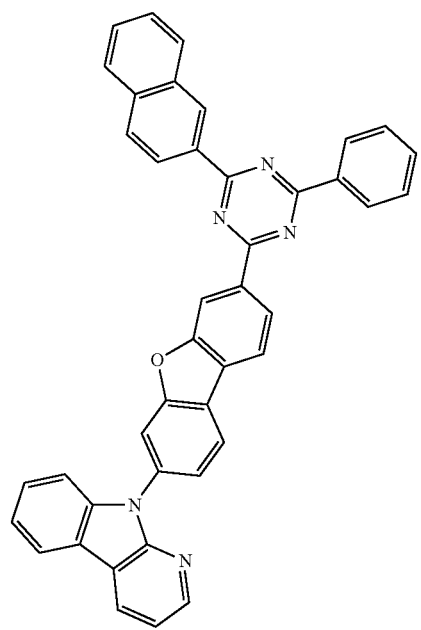

319
-continued
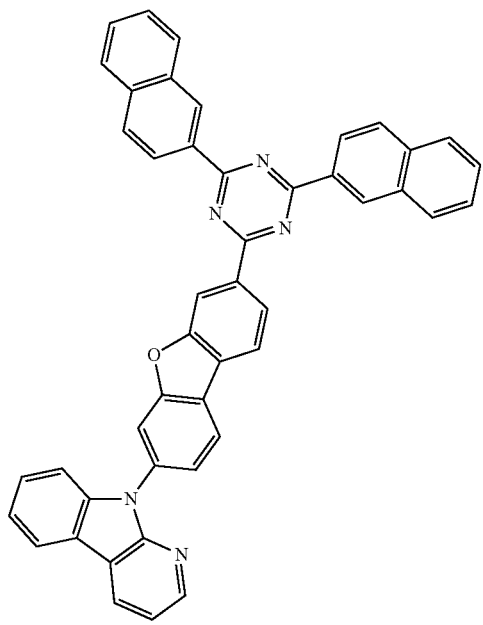
225
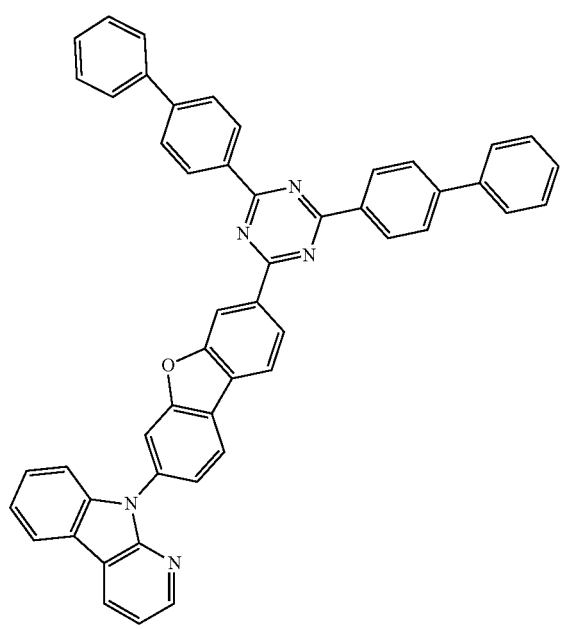
226
320
-continued
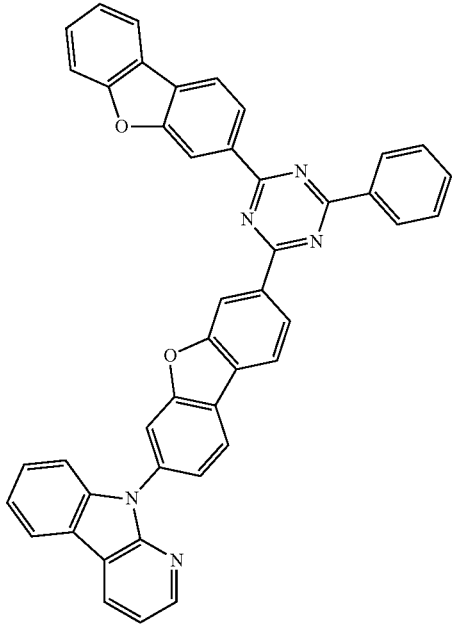
227
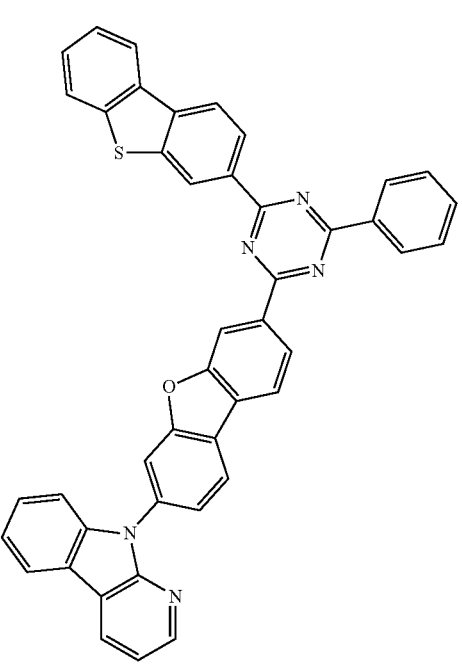
228

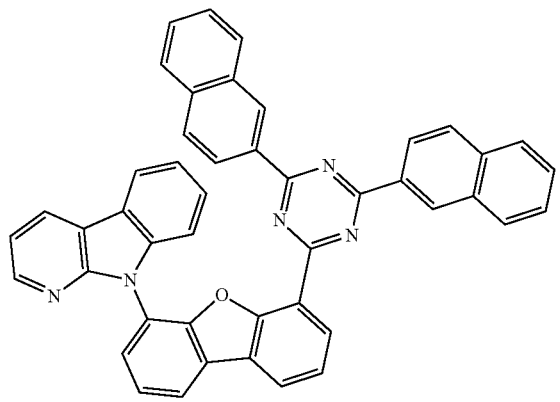
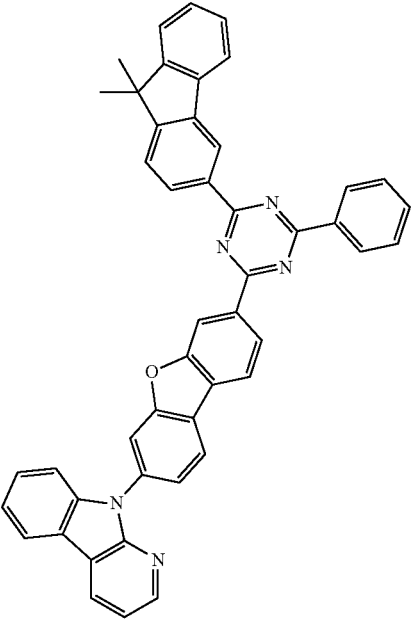
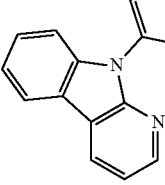

234
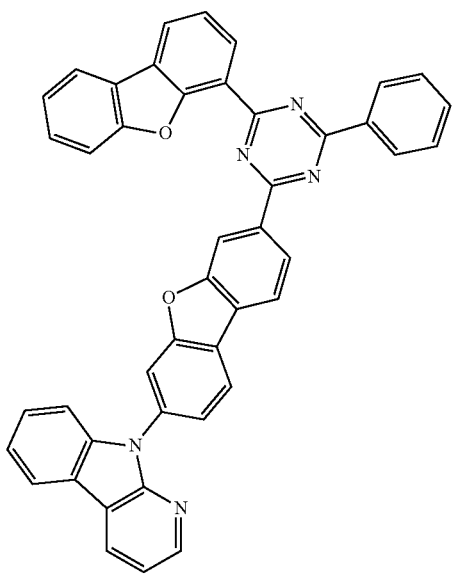
236
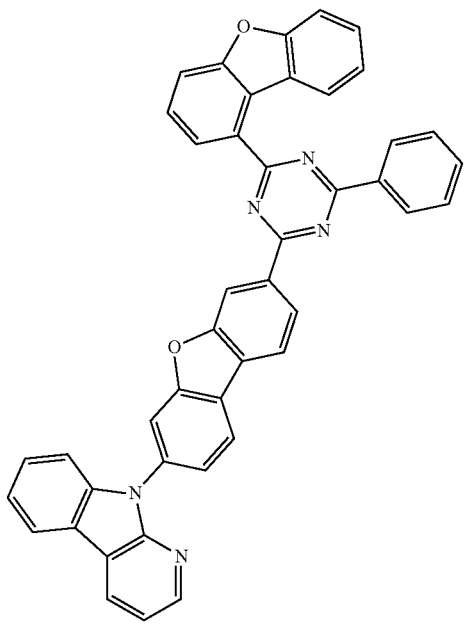
235
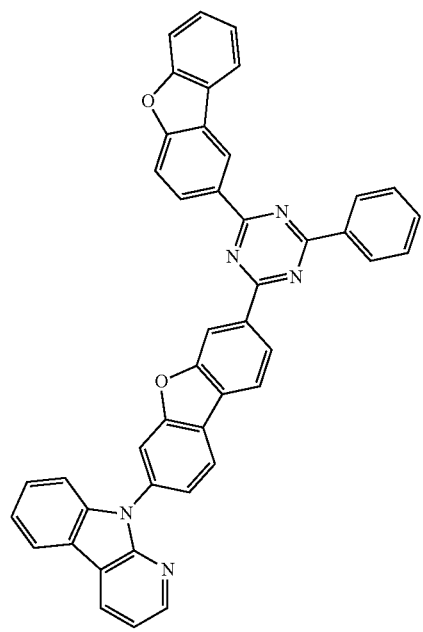
237
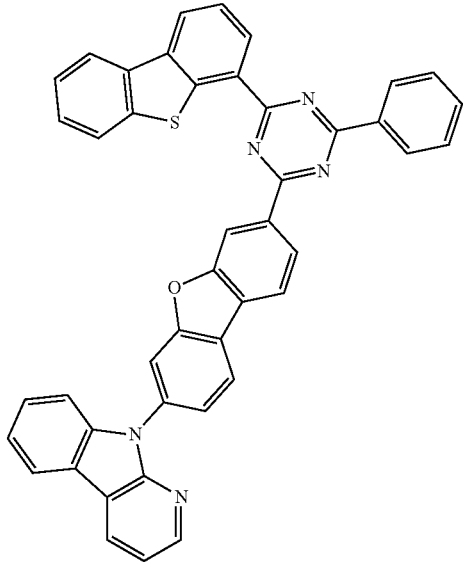

325
-continued
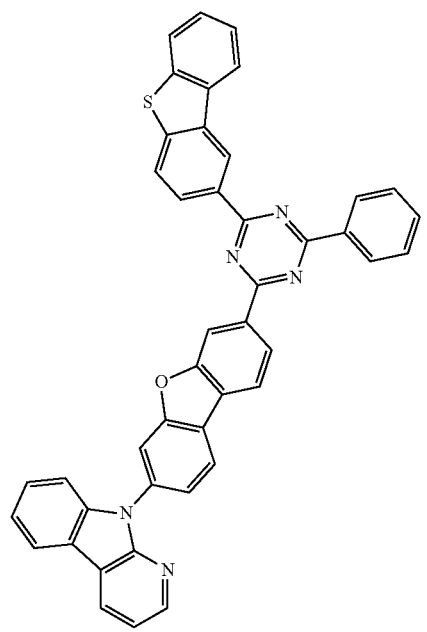
238
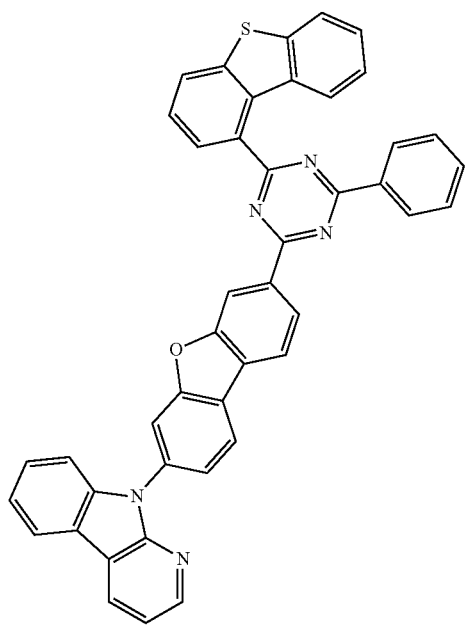
239
326
-continued
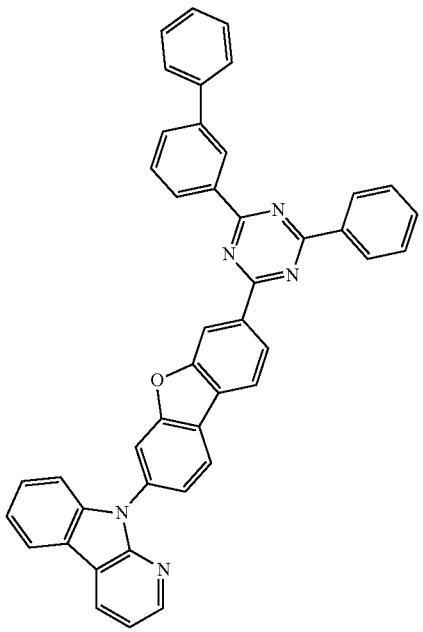
240
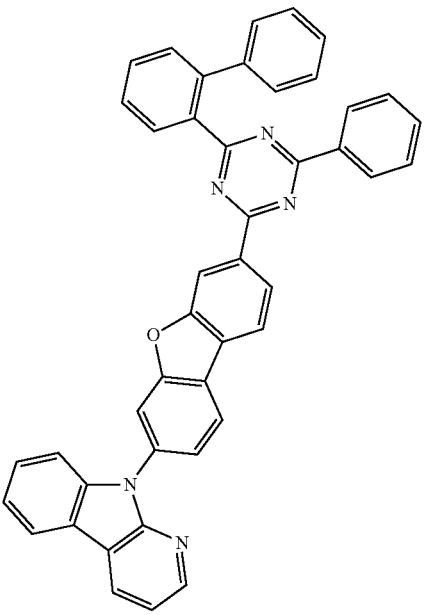
241

242
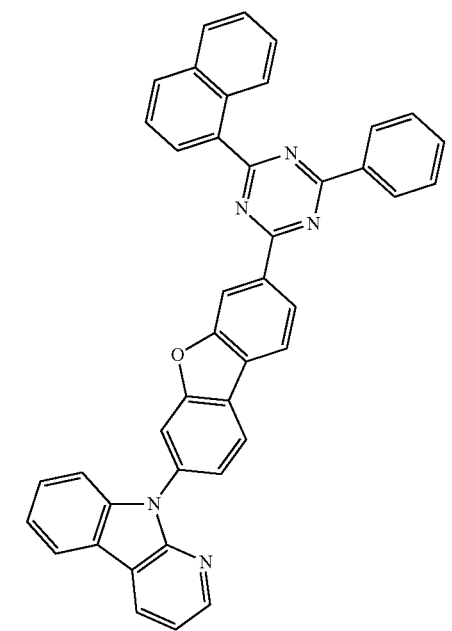
243
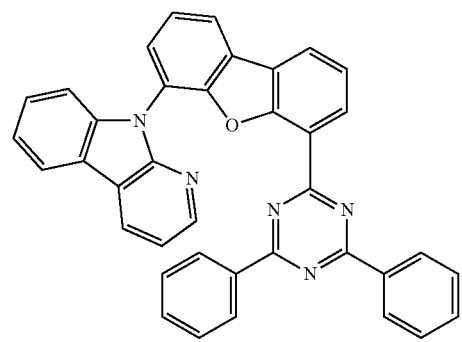
244
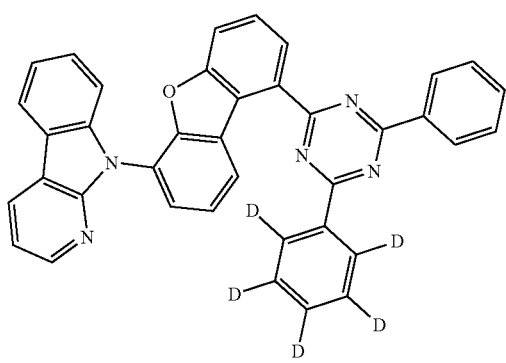
245
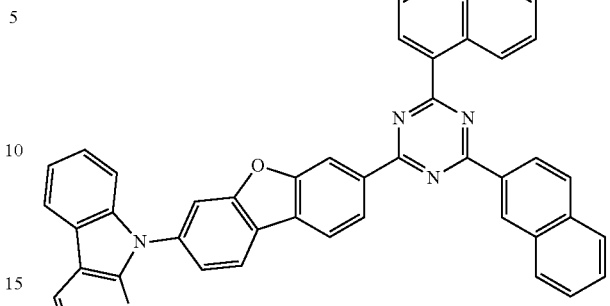
246
247
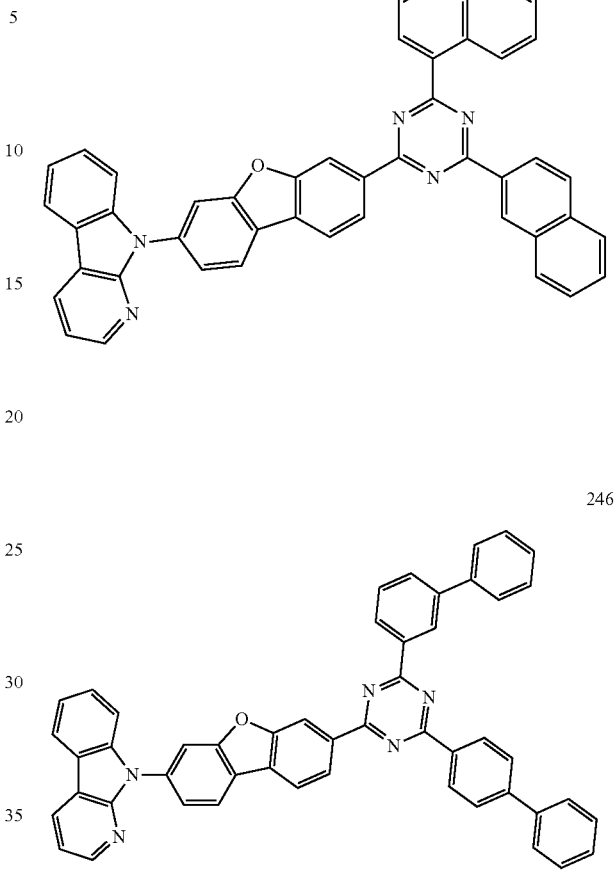

248
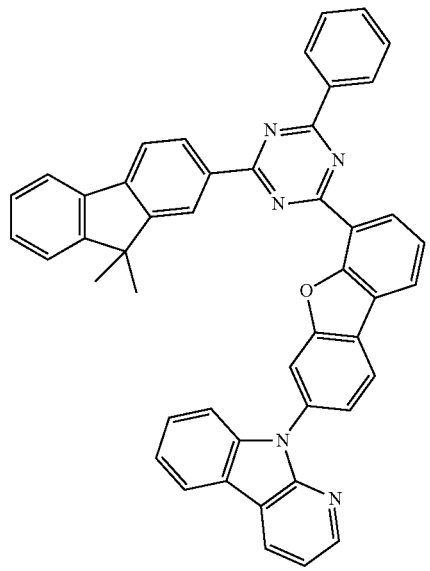
249
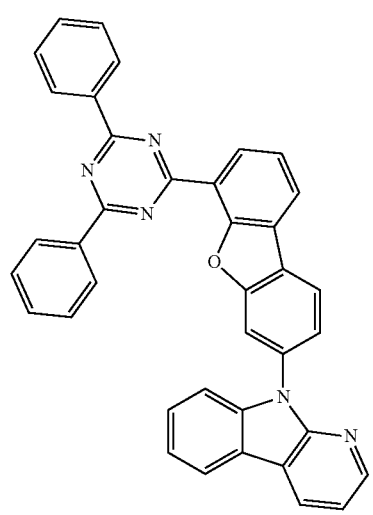
250
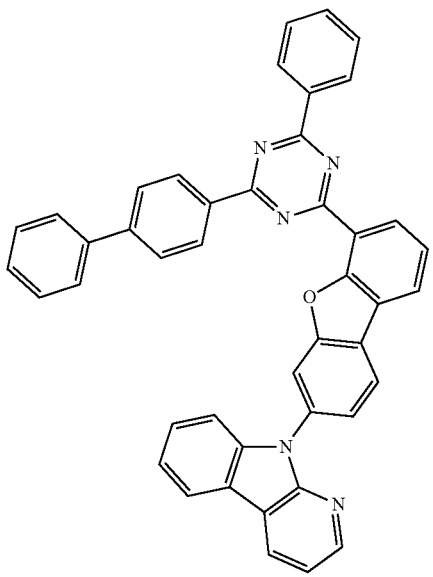
251
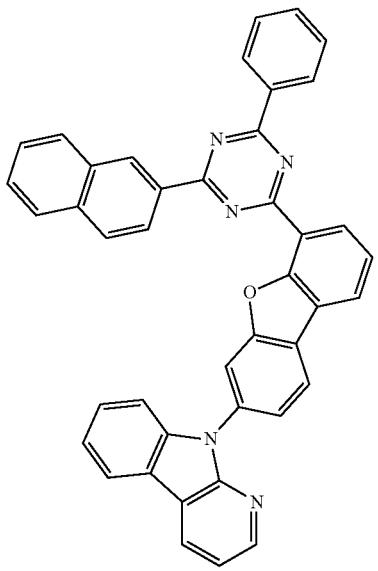
252
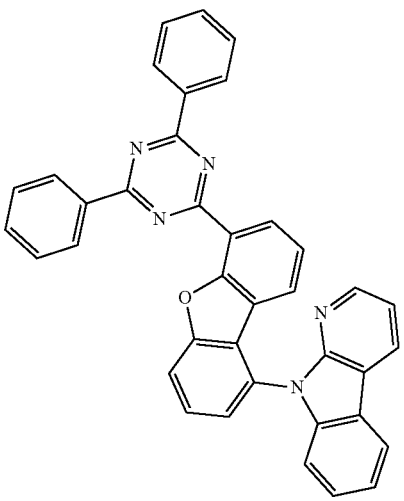
253
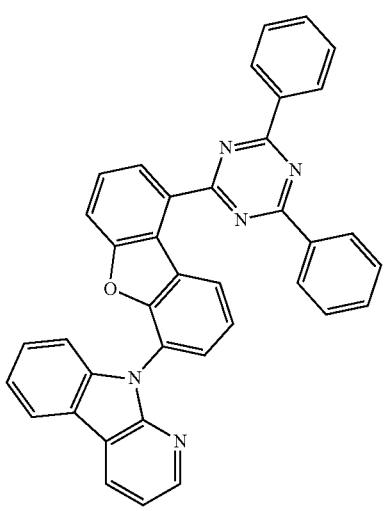

331
-continued
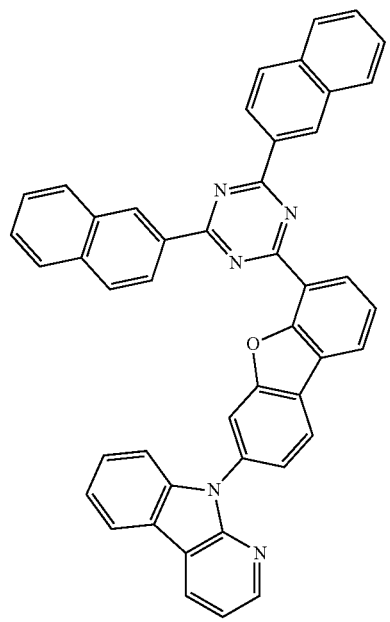
254
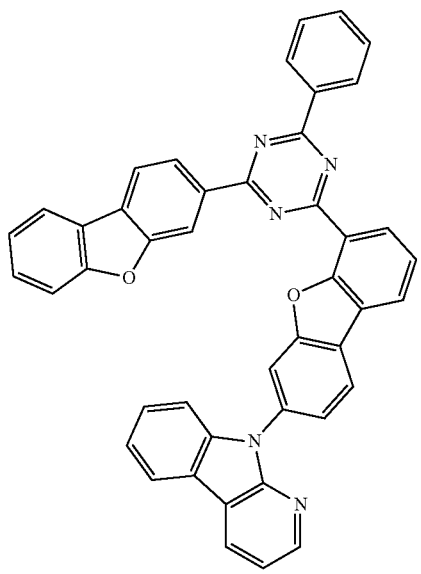
255
332
-continued
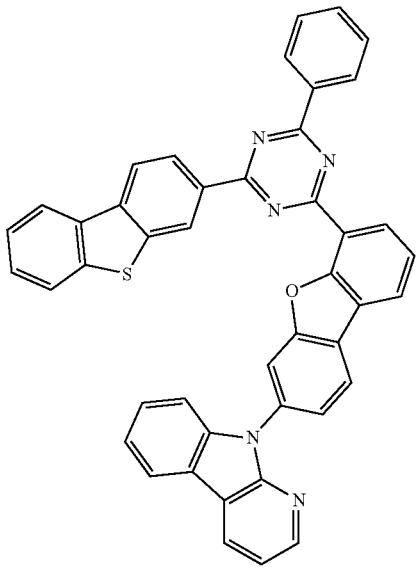
256
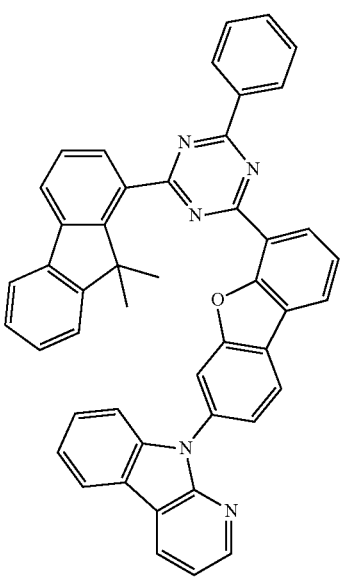
257

258
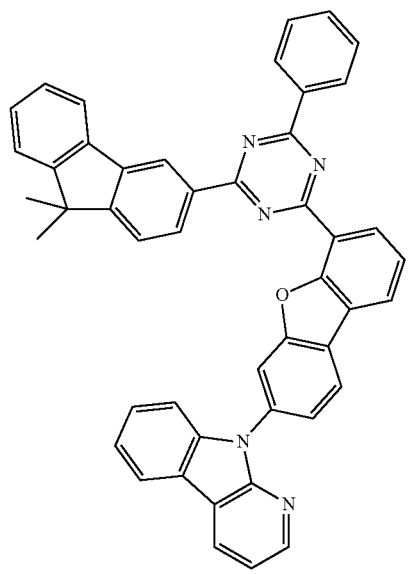
259
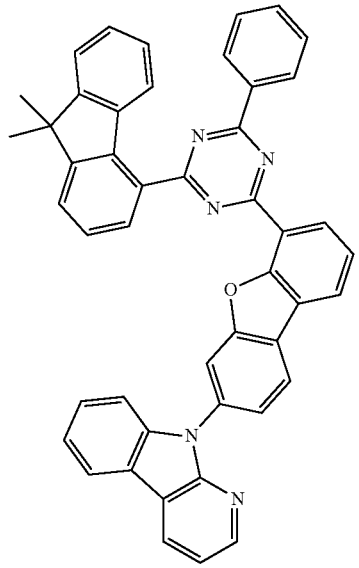
260
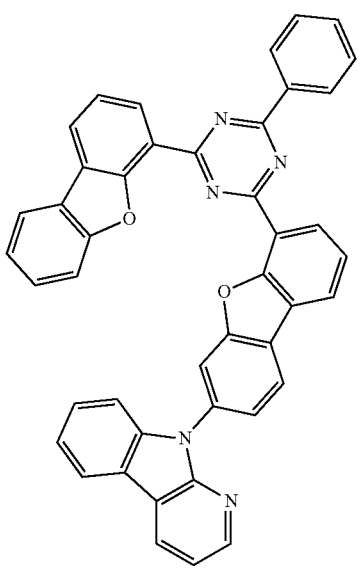
261
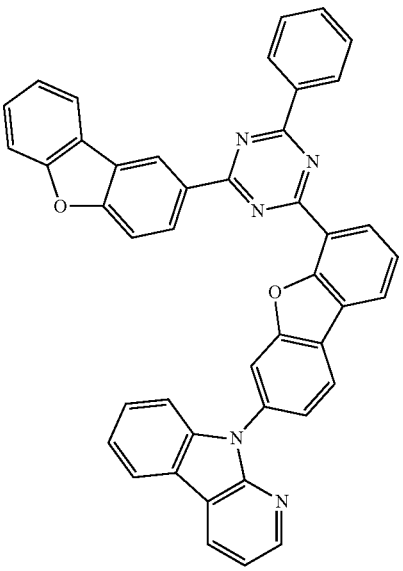

262
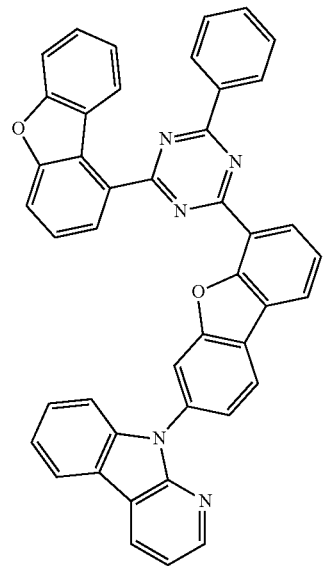
263
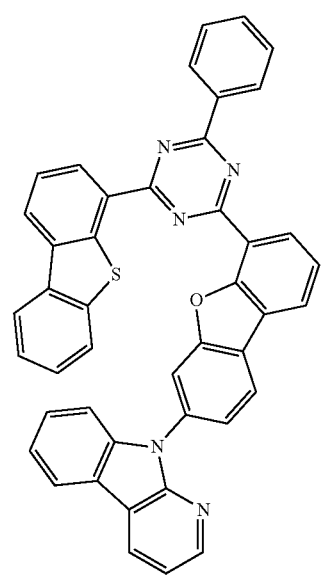
264
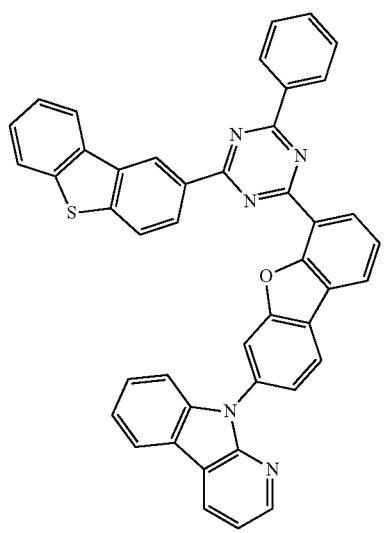
265
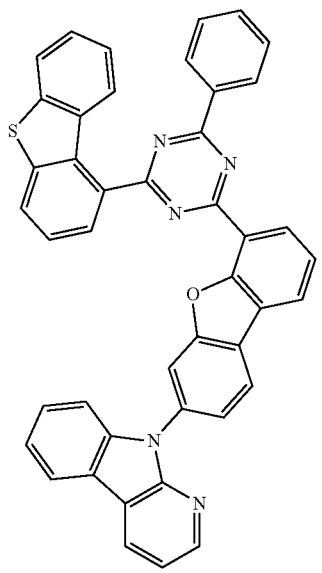
266
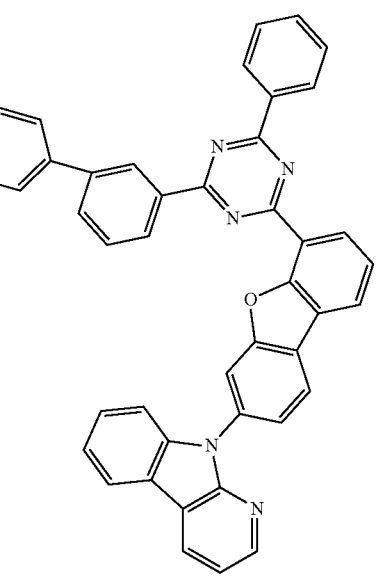

337
-continued
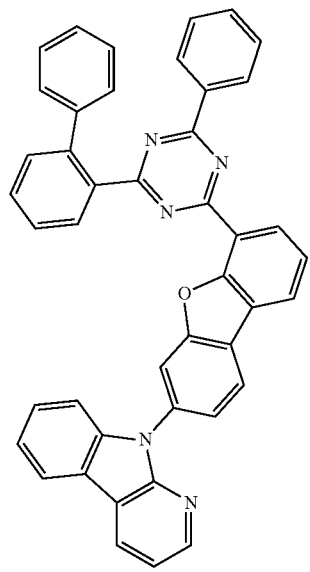
267
268
338
-continued
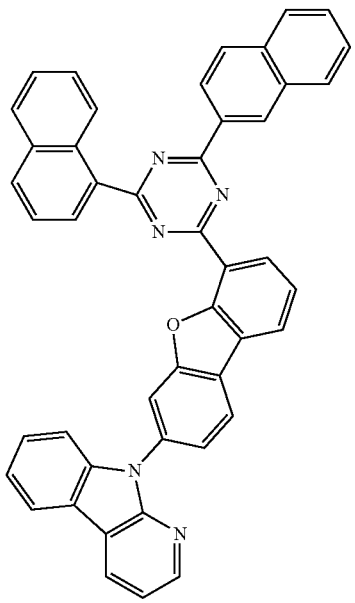
269
270

271
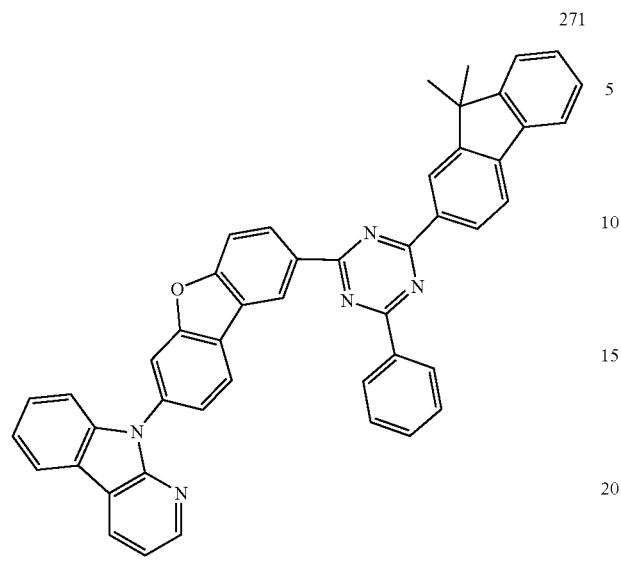
273
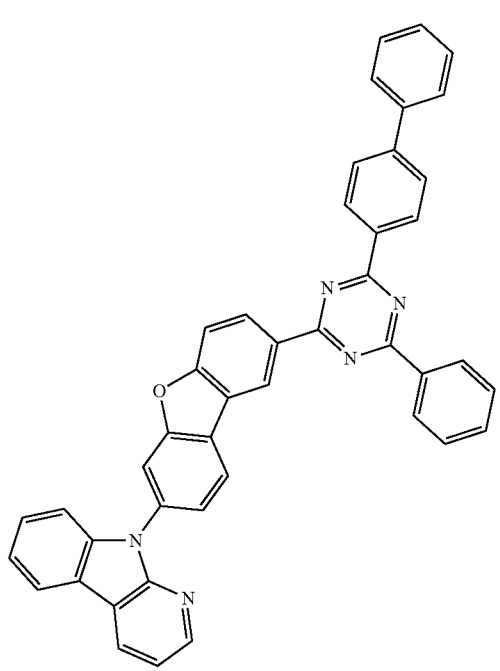
272
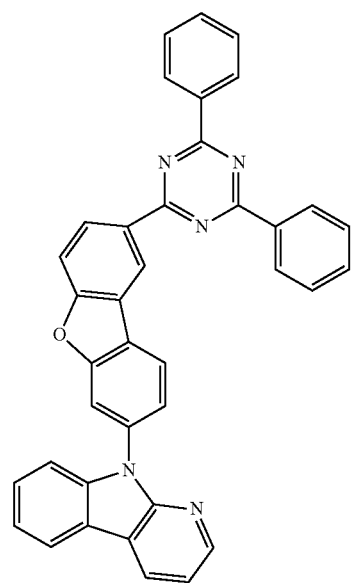
274

275
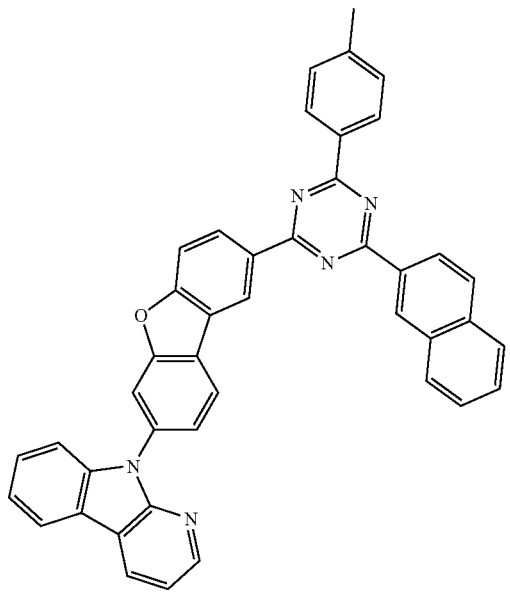
276
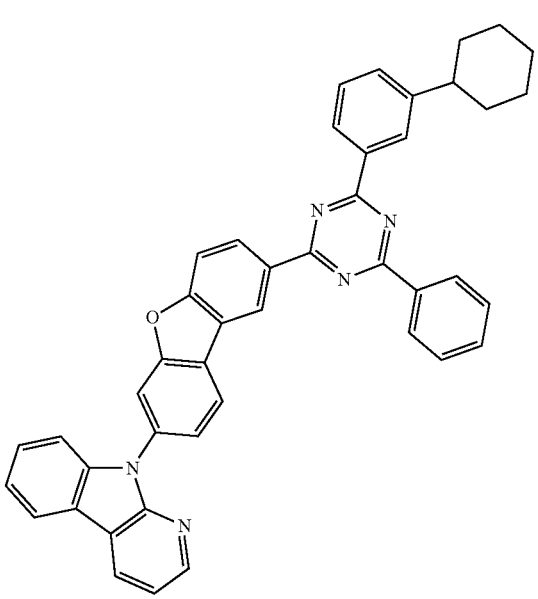
277
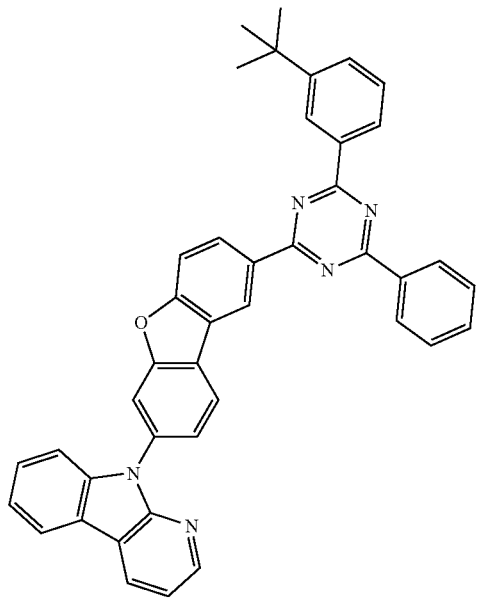
278
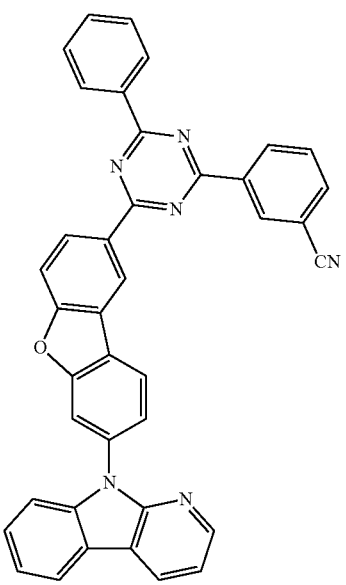

-continued
279
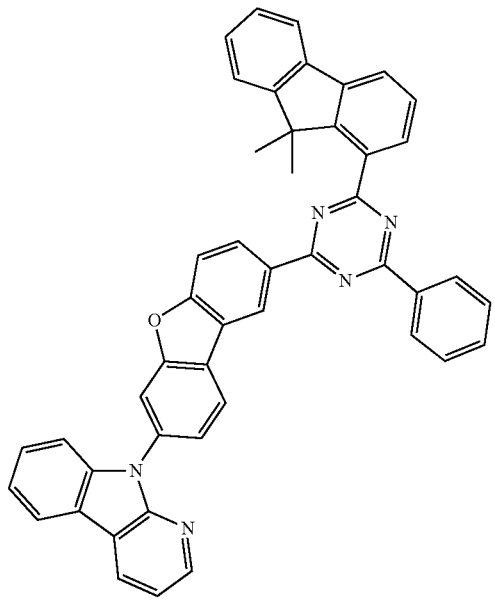
-continued
281
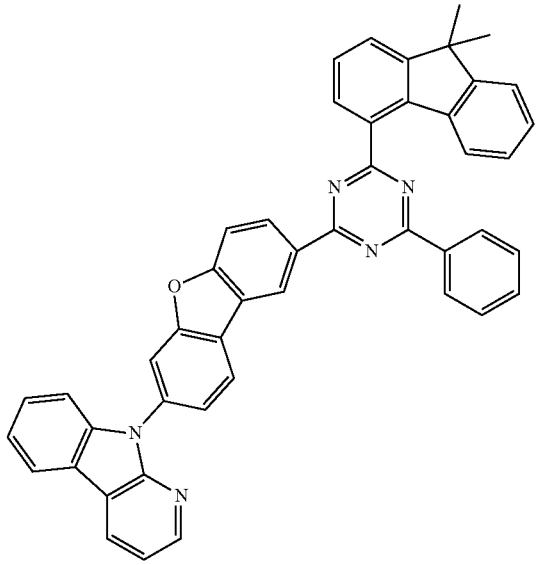
280
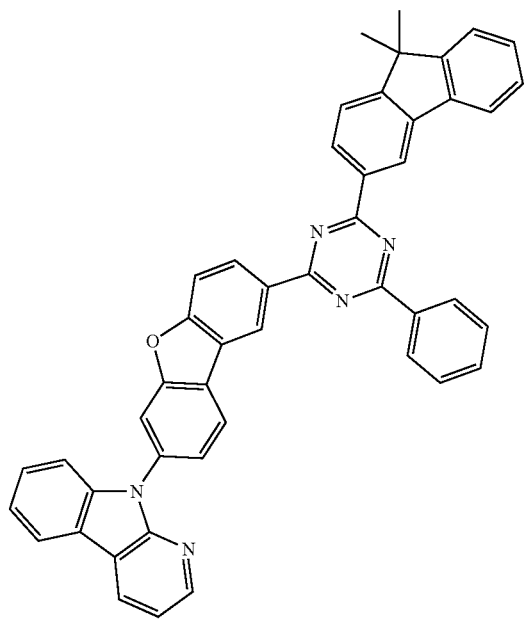
282
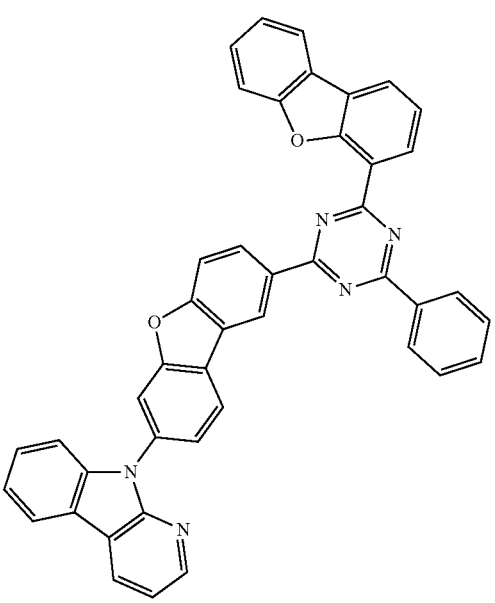

283
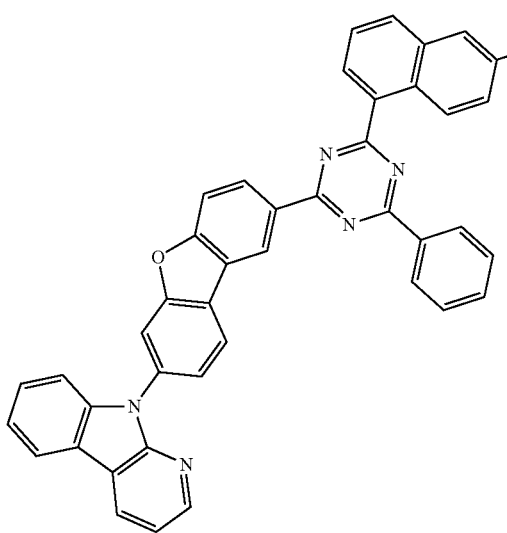
284
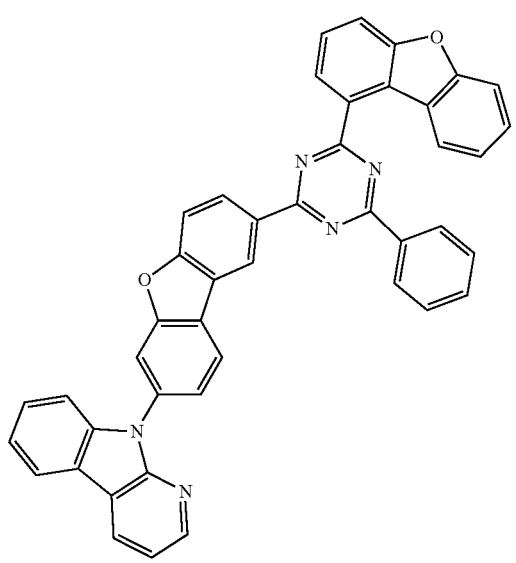
285
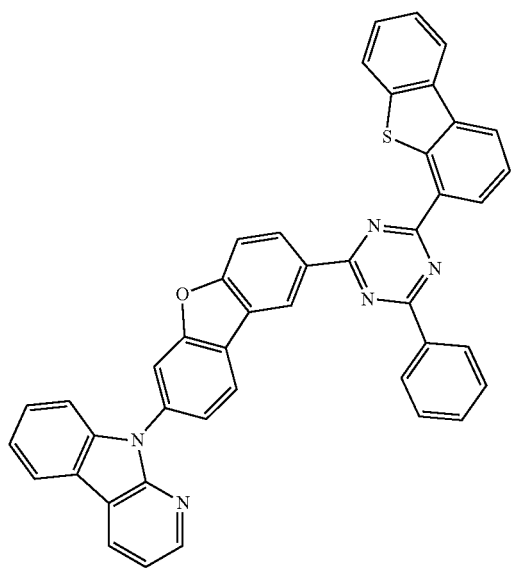
286
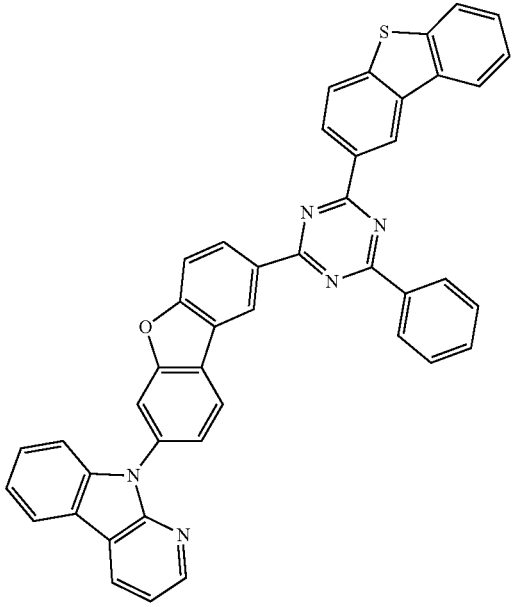
287
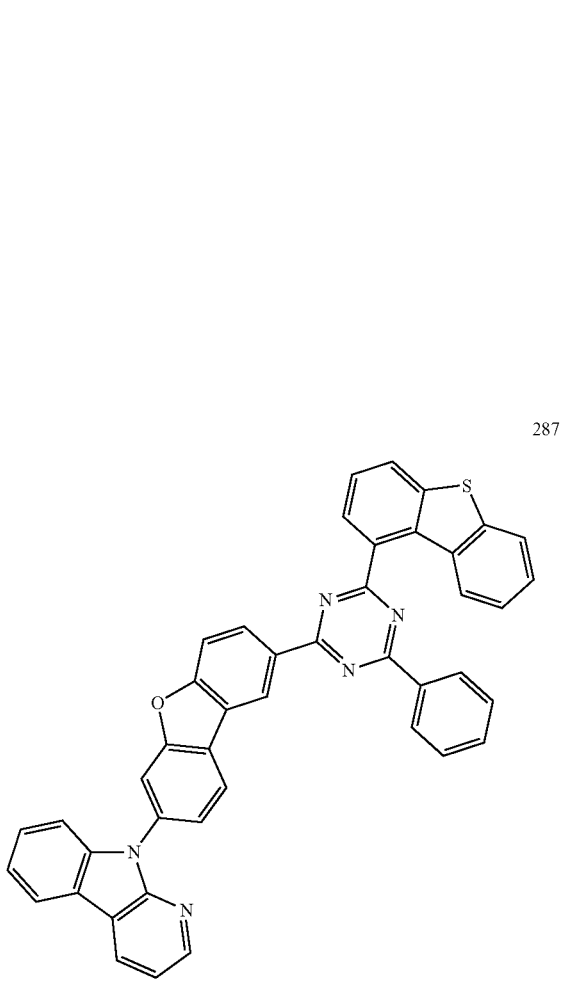

288
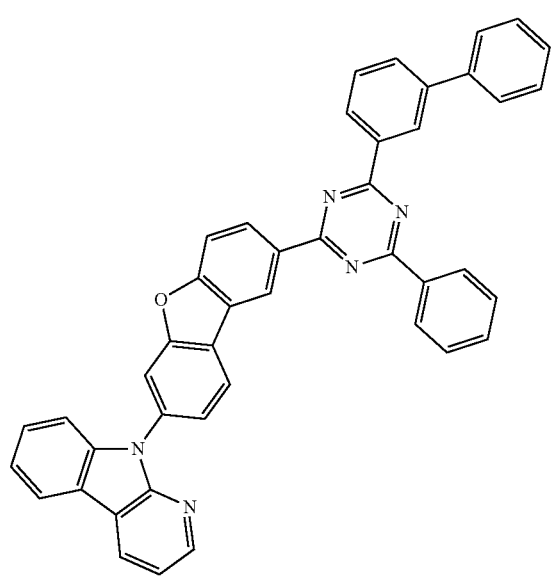
289
291
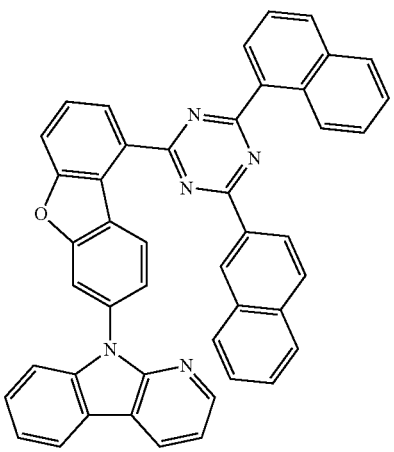
292
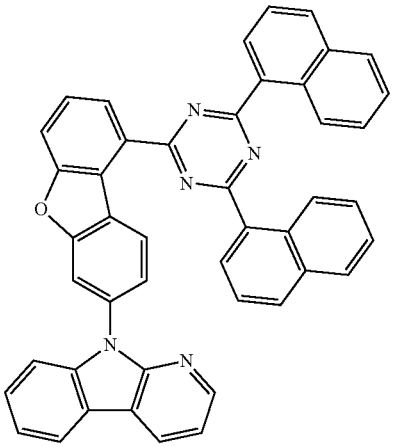
290
293
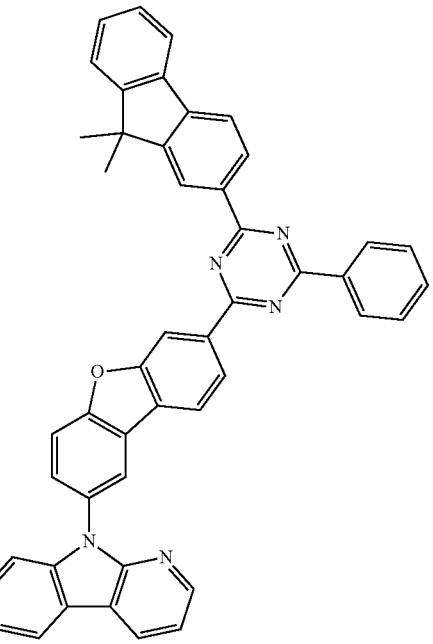

294
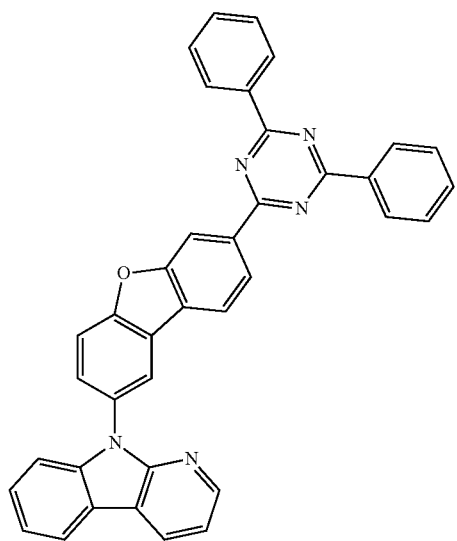
295
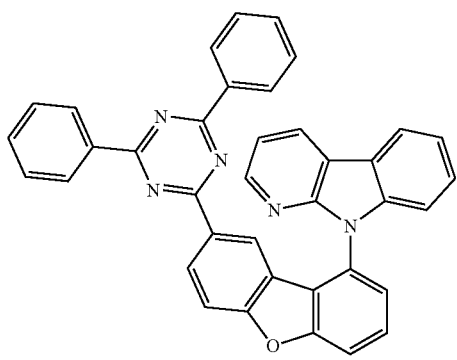
296
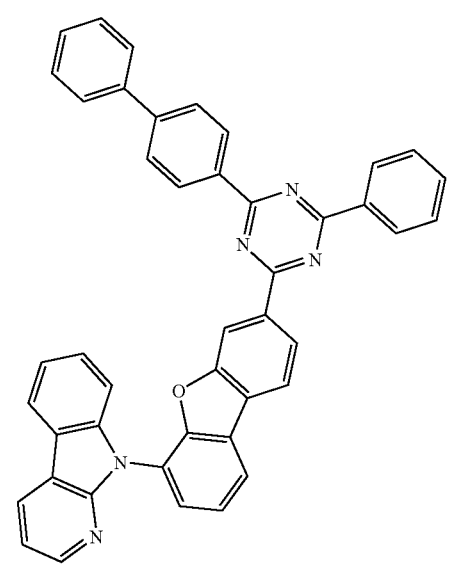
297
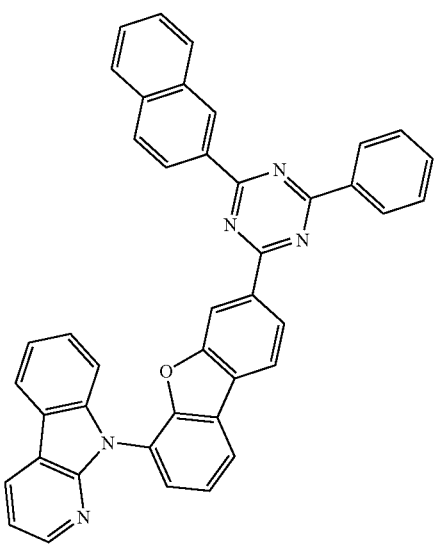
298
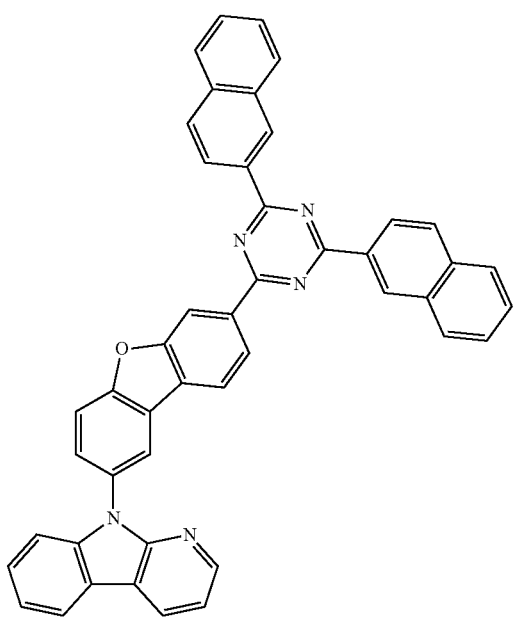

299
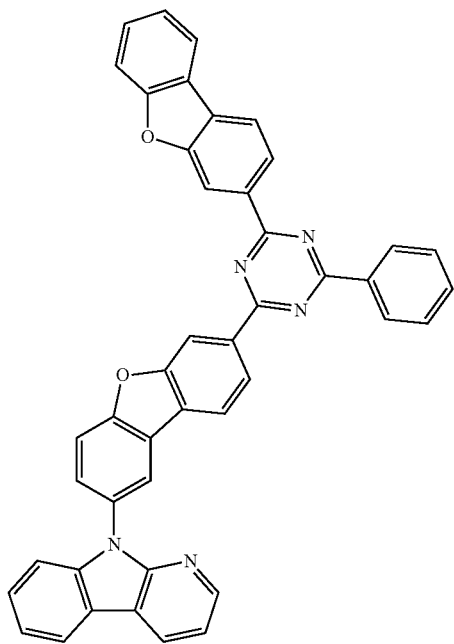
300
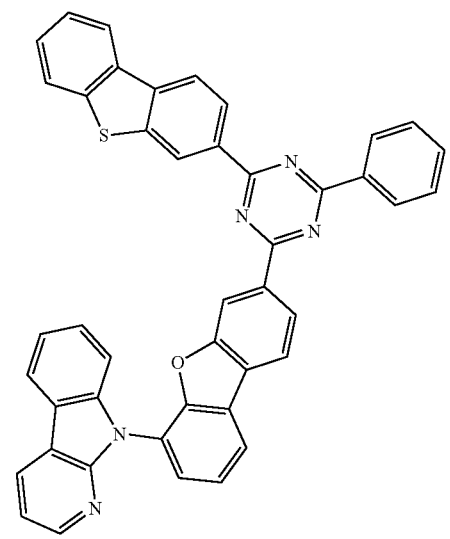
301
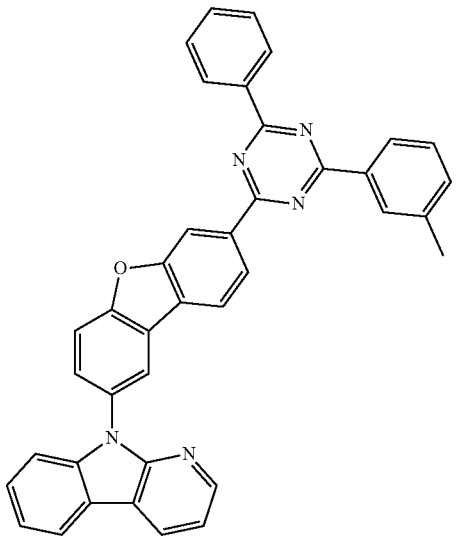
302
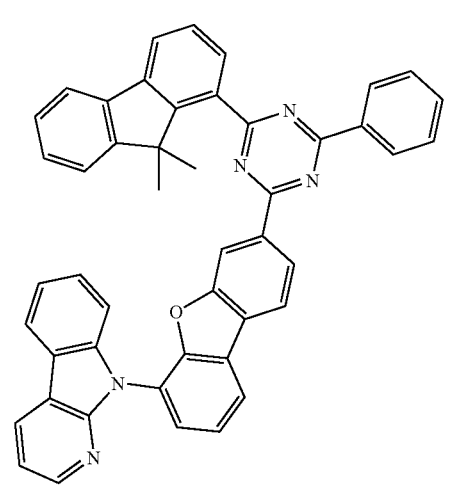
303
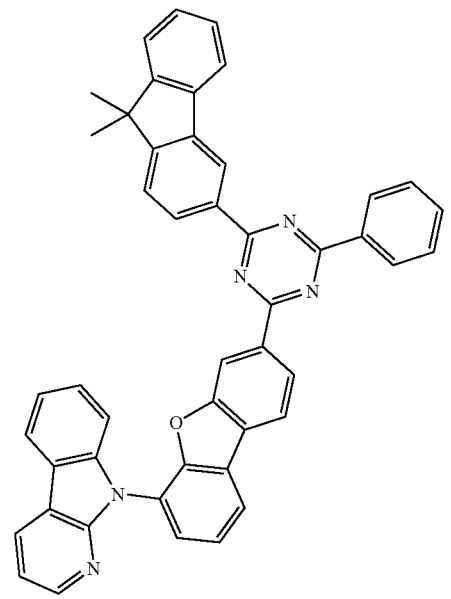

353
-continued
304
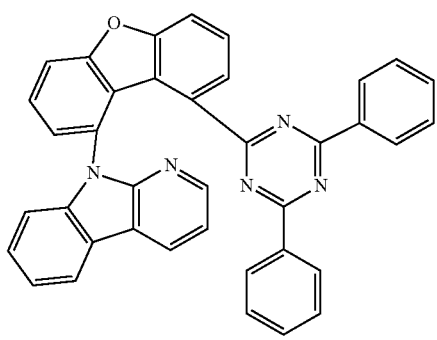
305
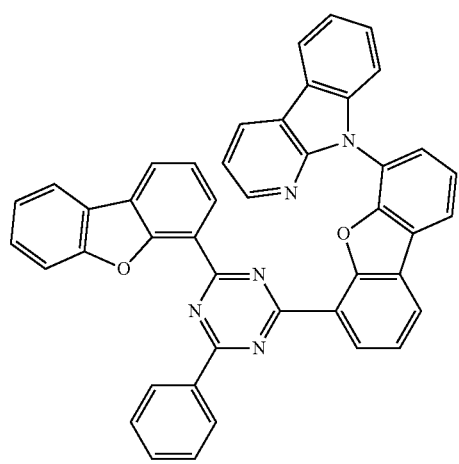
306
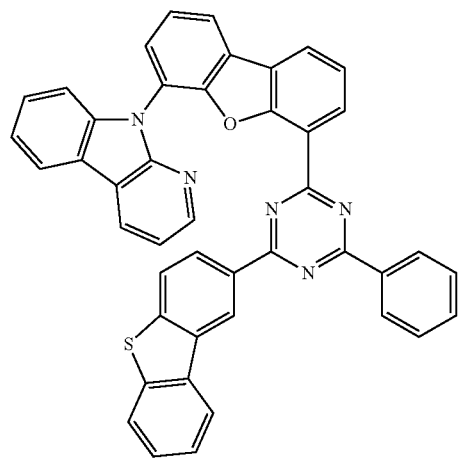
354
-continued
307
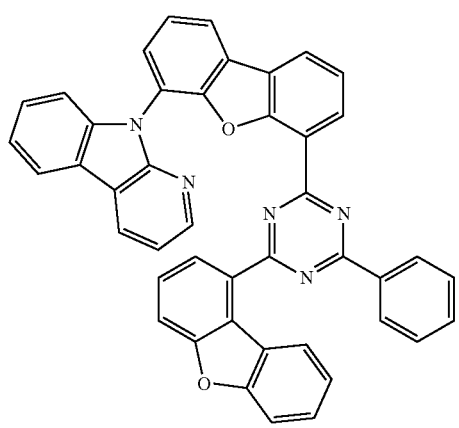
308
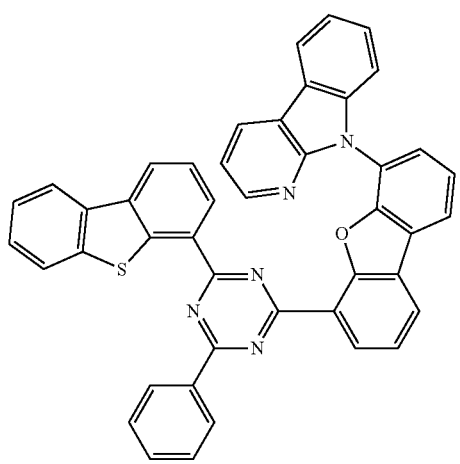
309
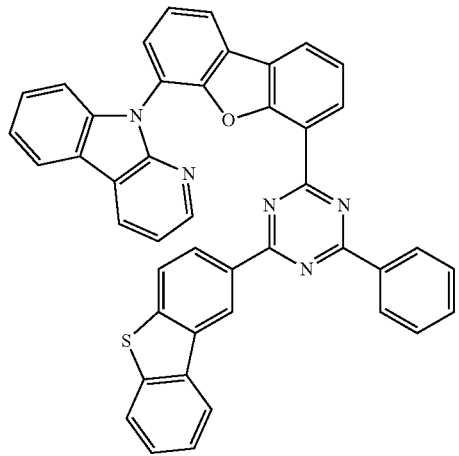

355
-continued
356
-continued
310
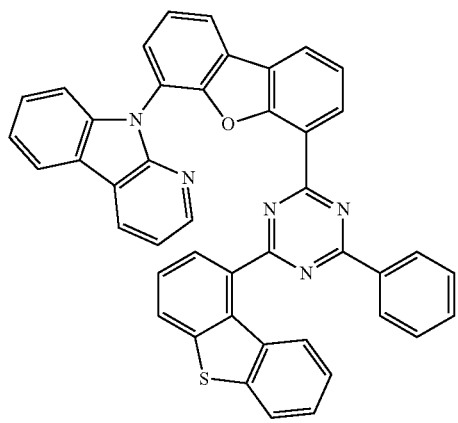
311
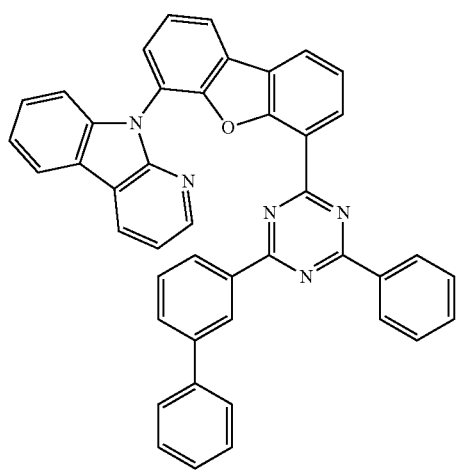
312
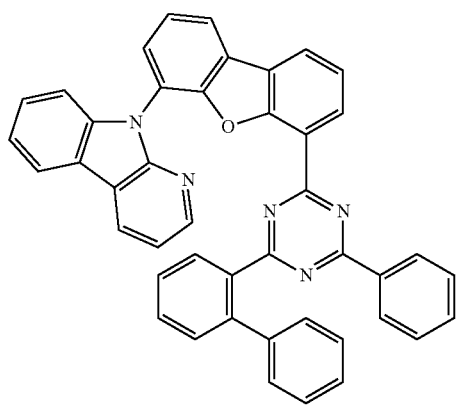
313
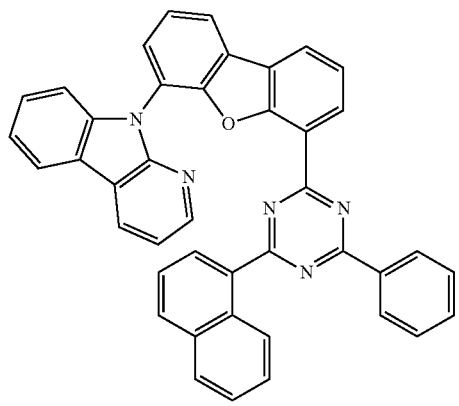
314
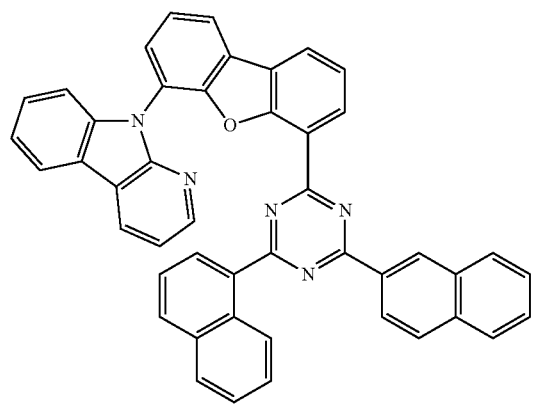
315
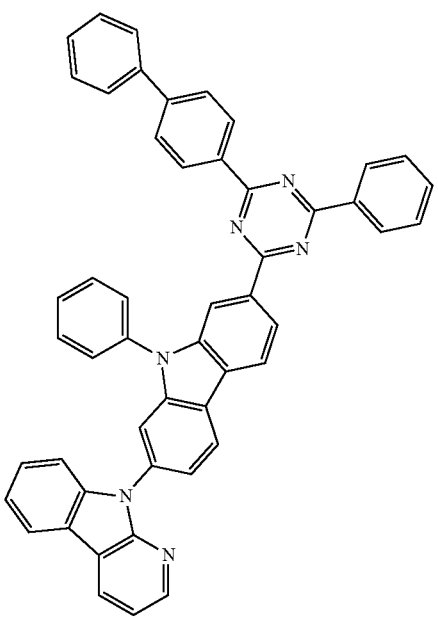

357
-continued
316
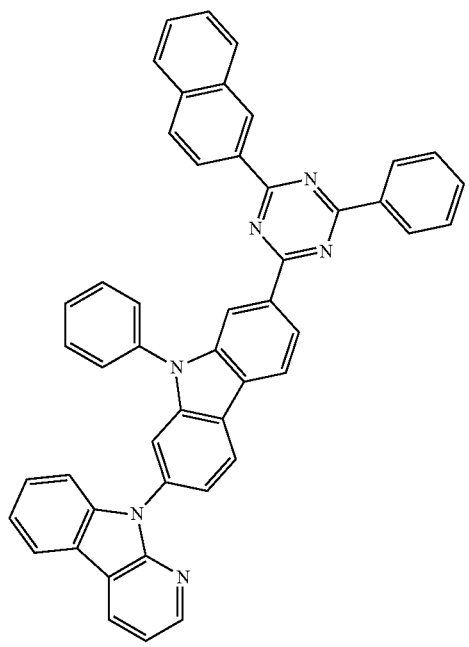
317
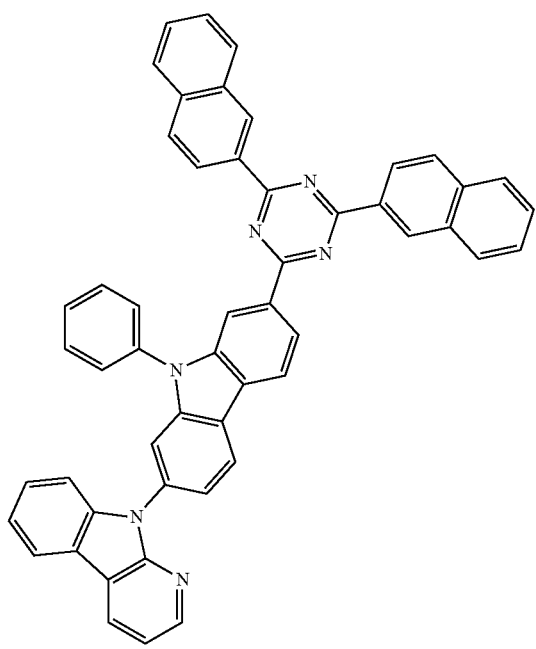
358
-continued
318
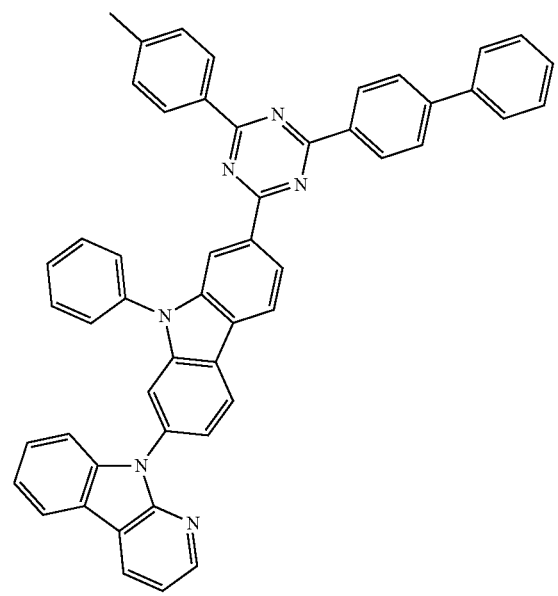
319
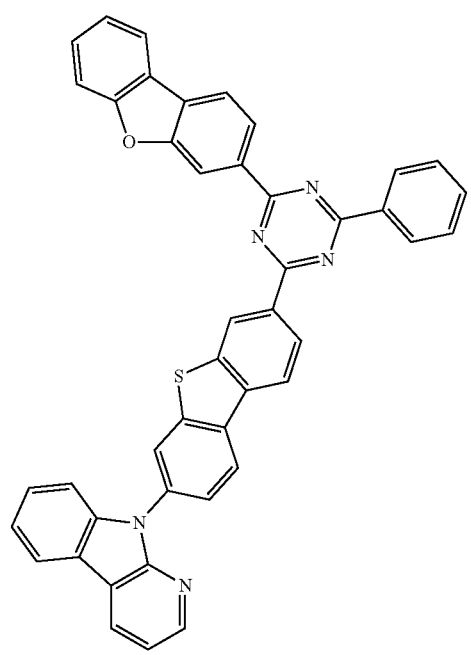

359
-continued
320
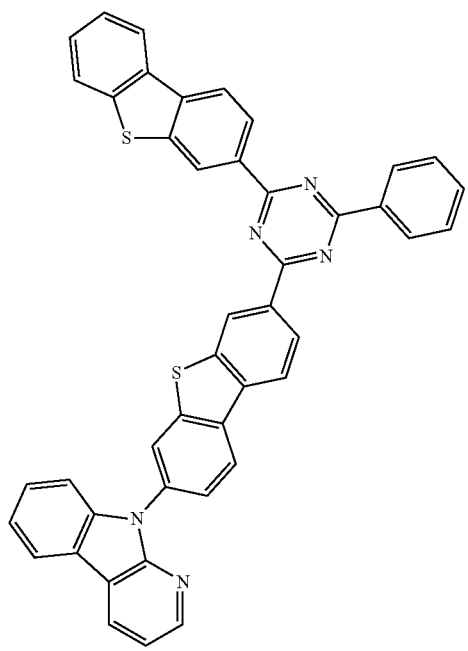
321
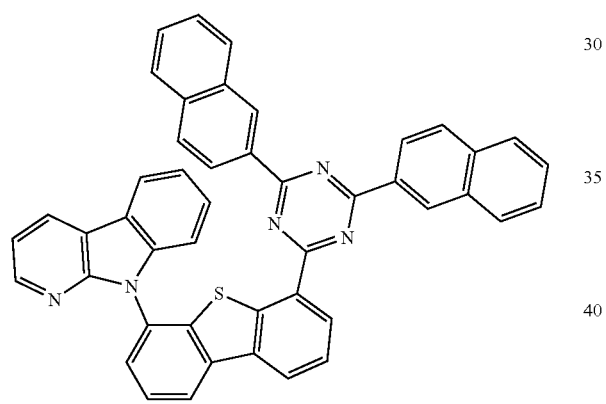
322
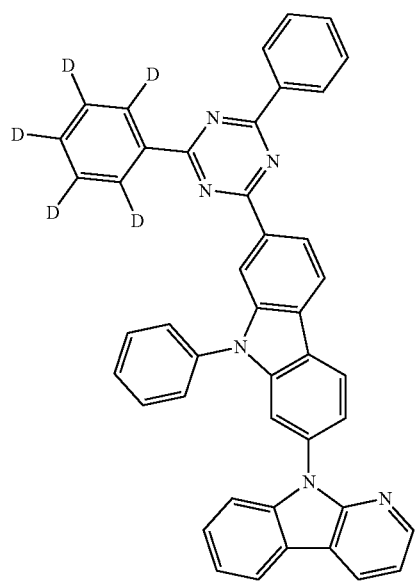
360
-continued
323
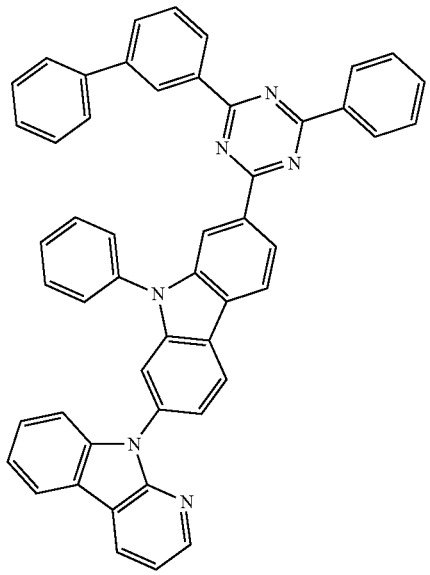
324
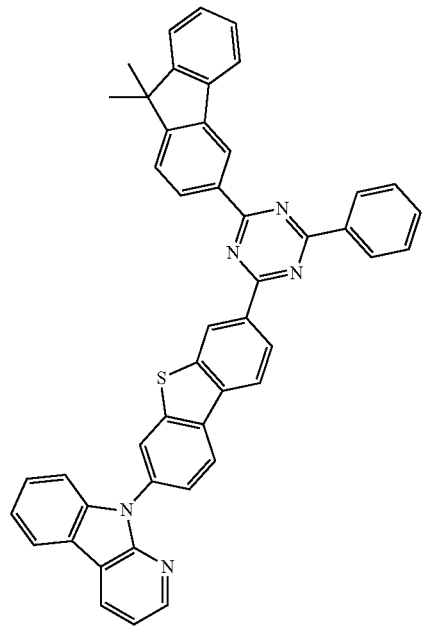

361
-continued
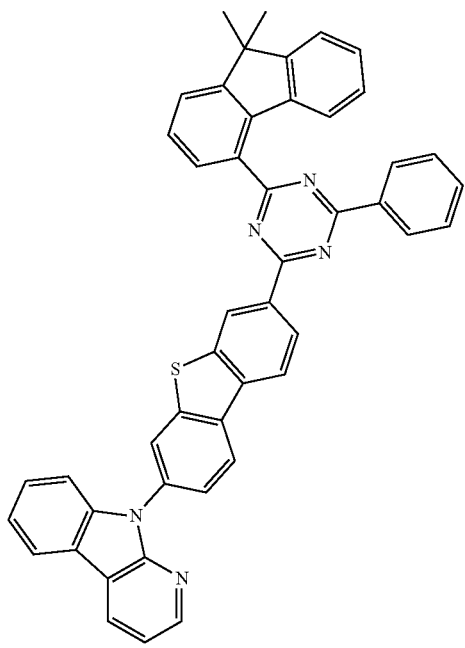
325
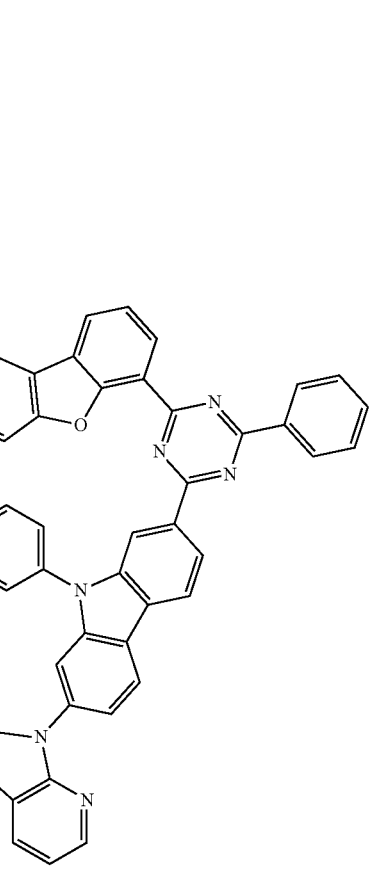
326
362
-continued
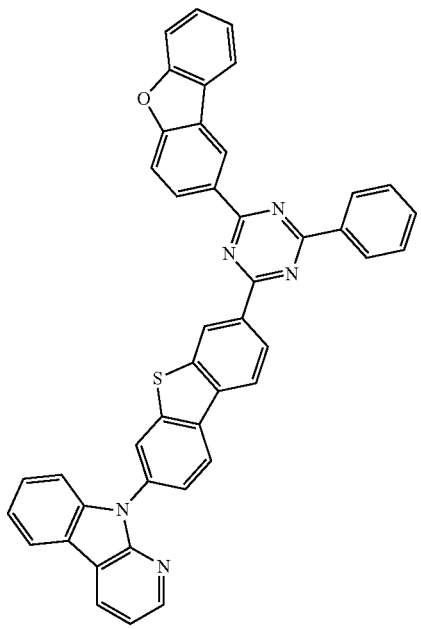
327
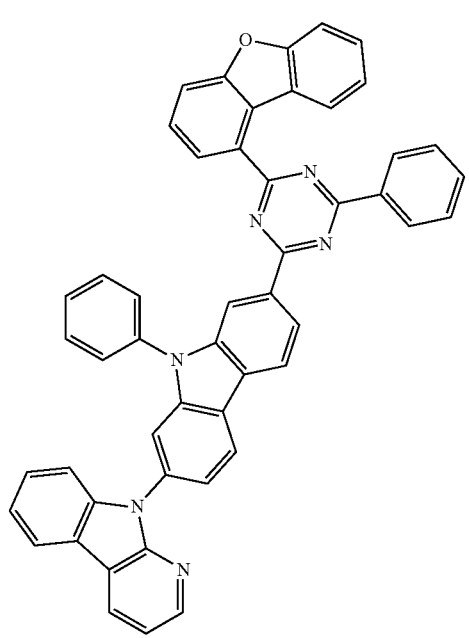
328

329
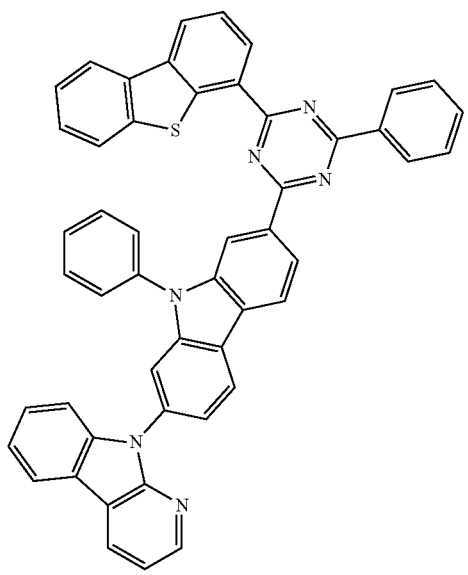
330
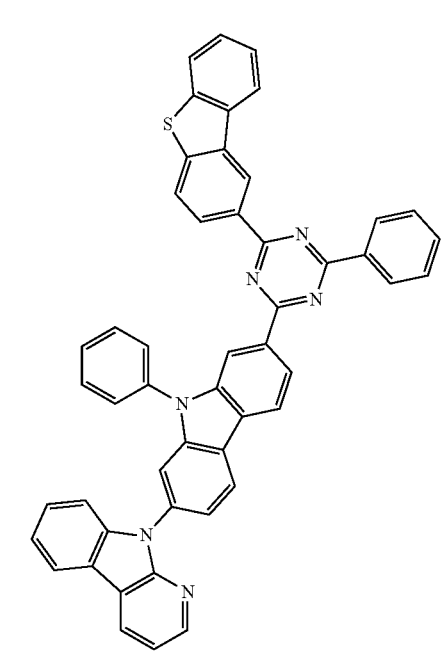
331
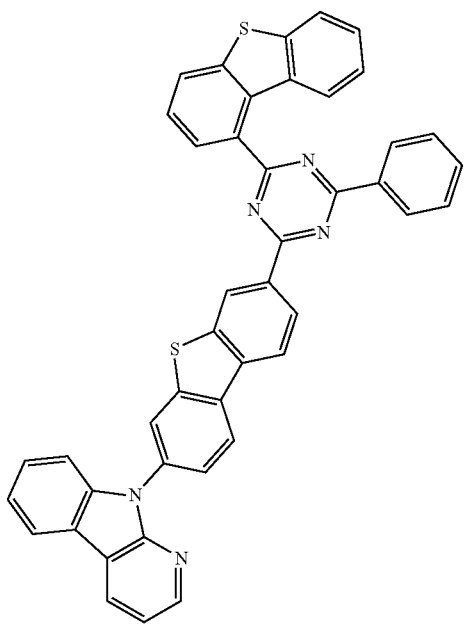
332
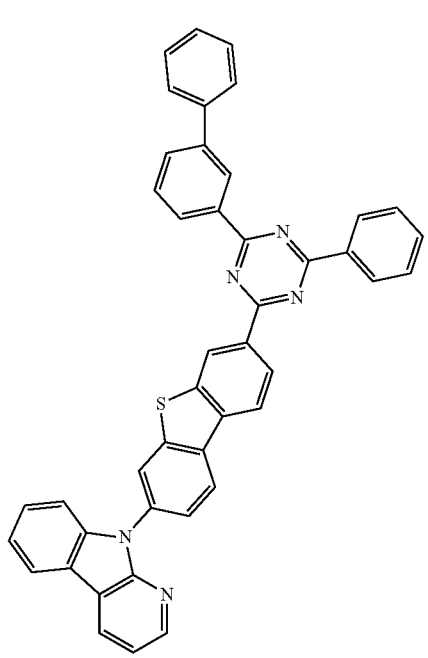

333
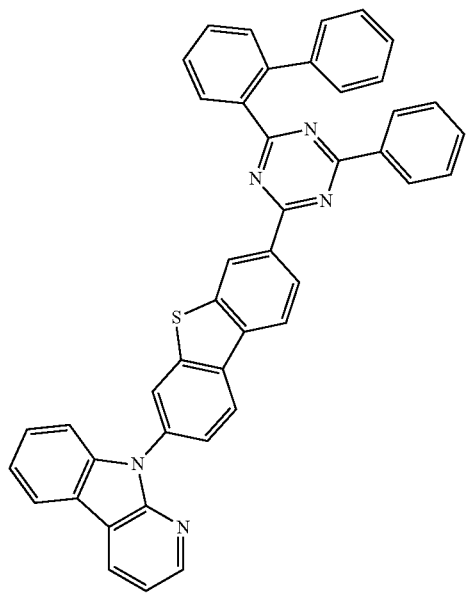
335
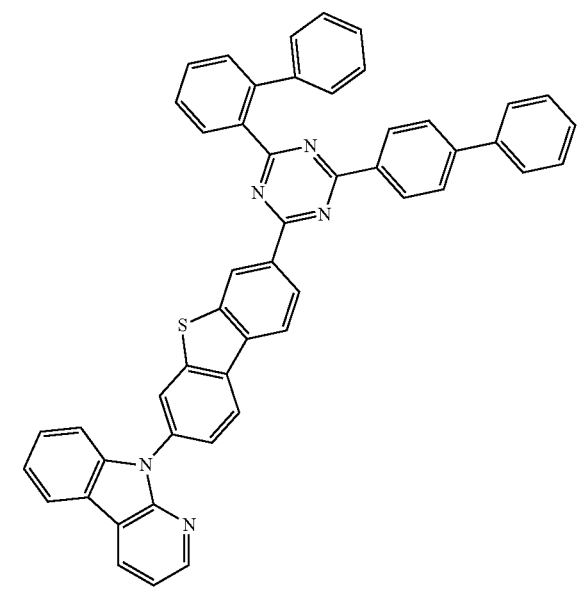
336
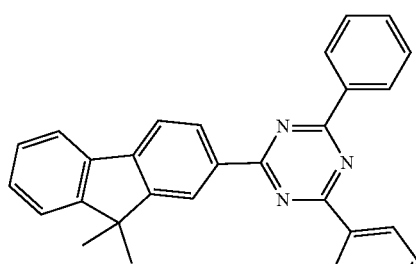
334
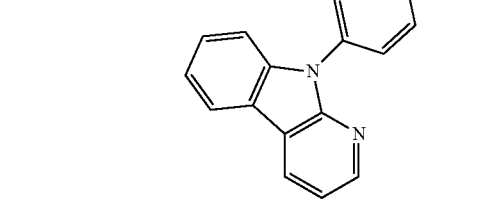
337
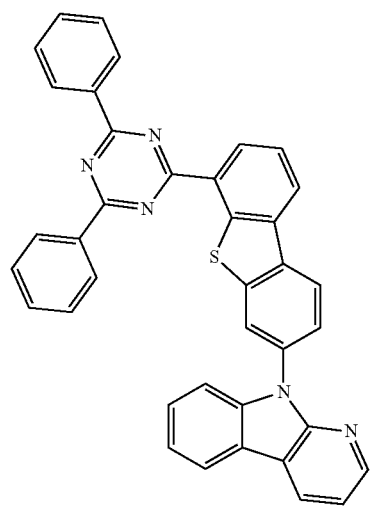

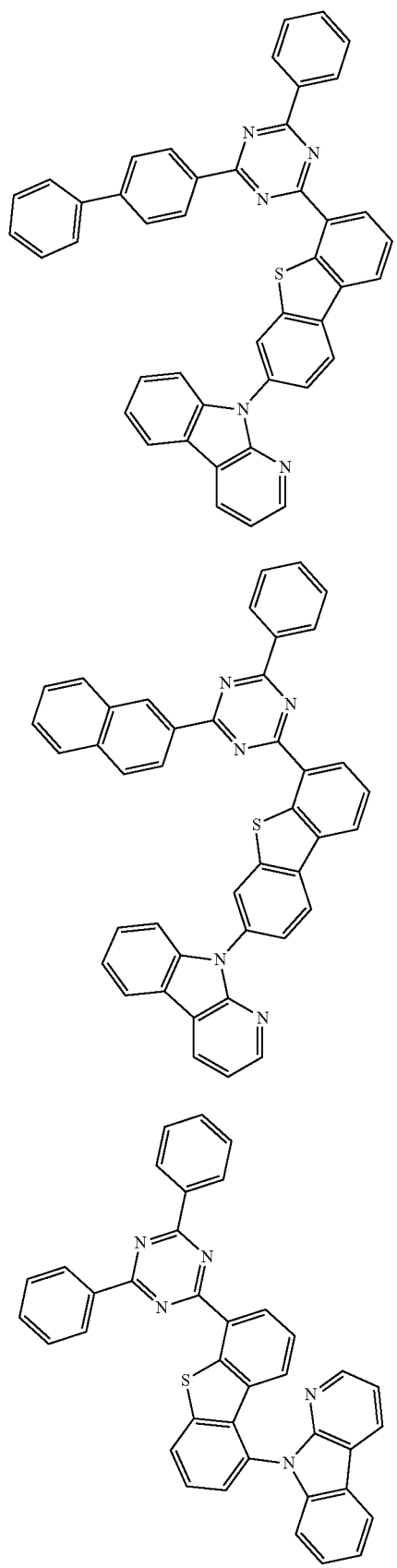

343
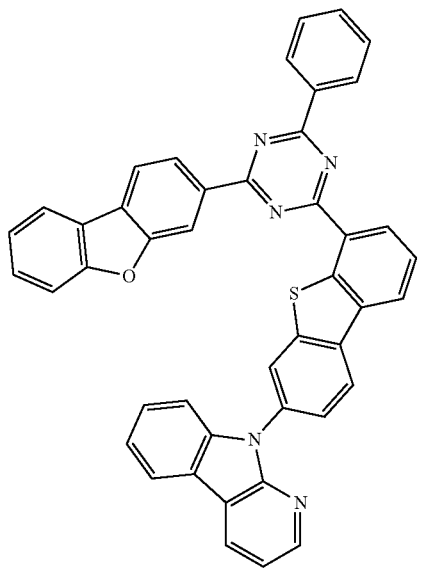
344
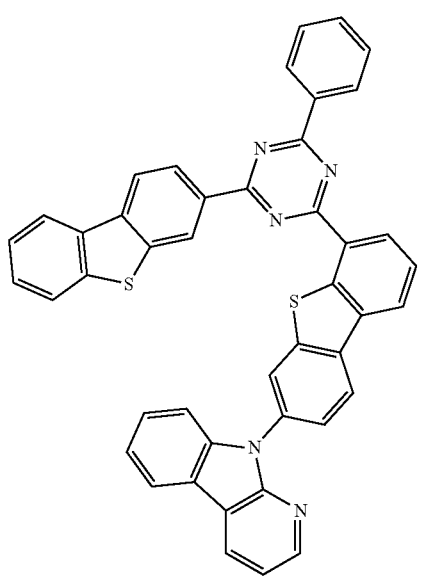
345
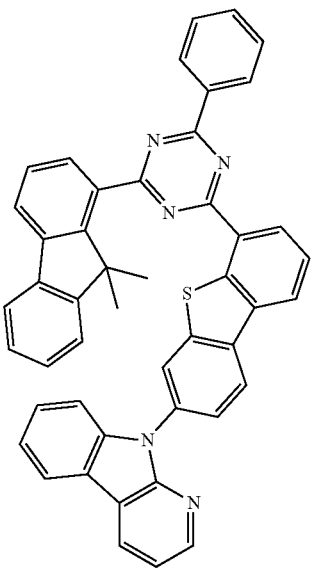
346
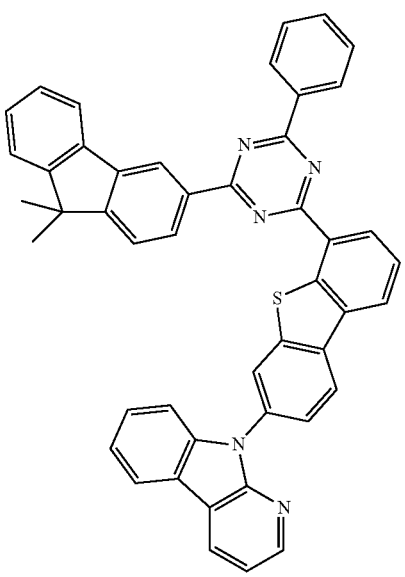

371
-continued
347
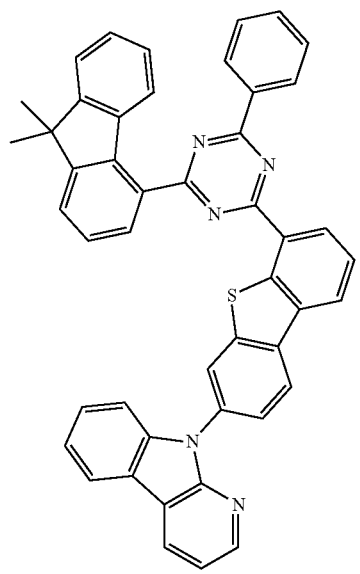
348
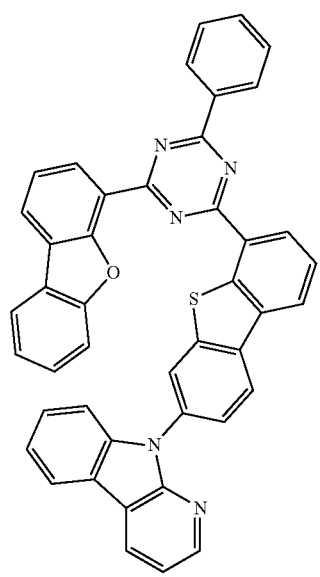
372
-continued
349
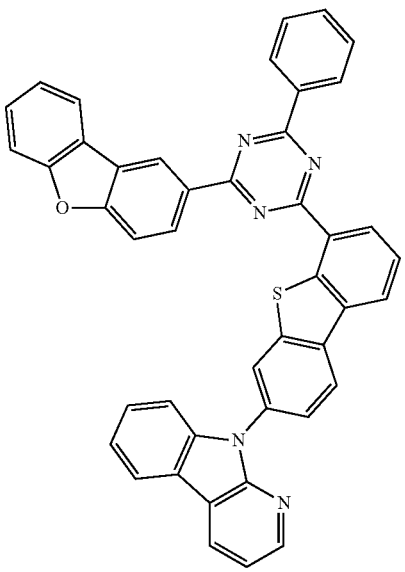
350
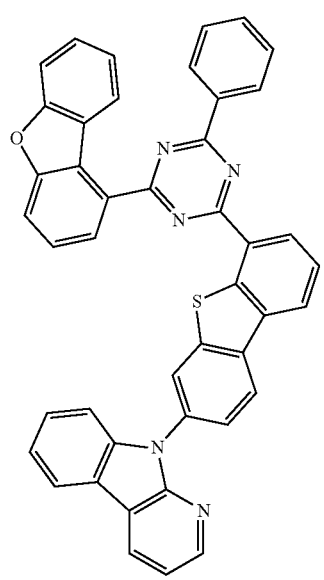

351
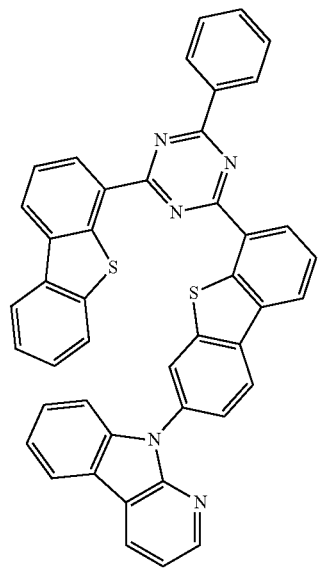
352
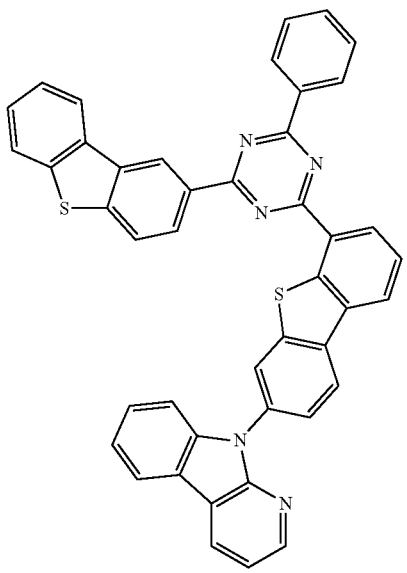
353
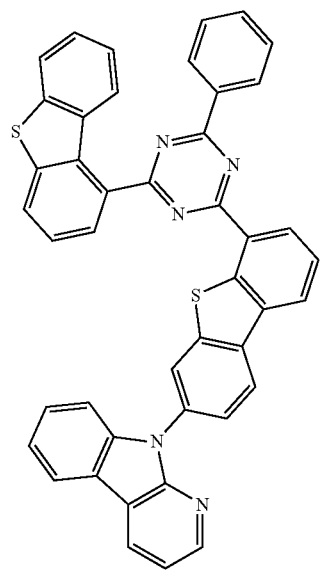
354
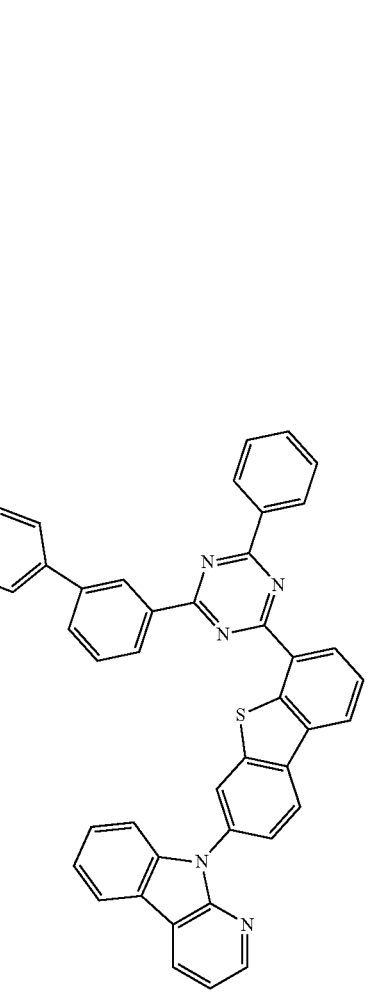

355
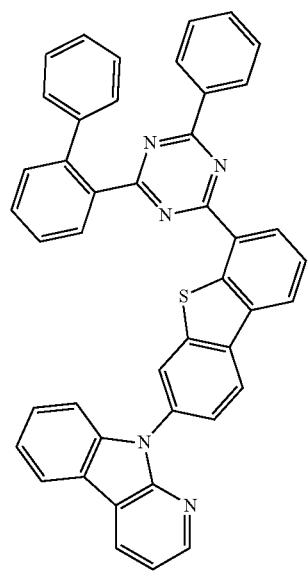
356
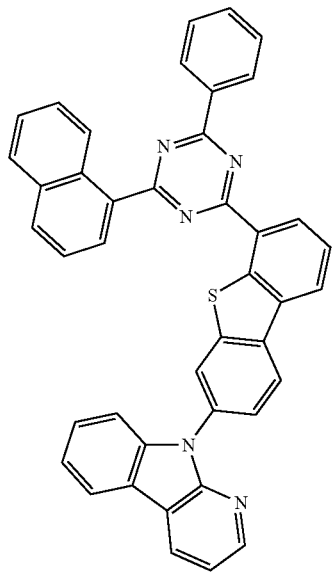
357
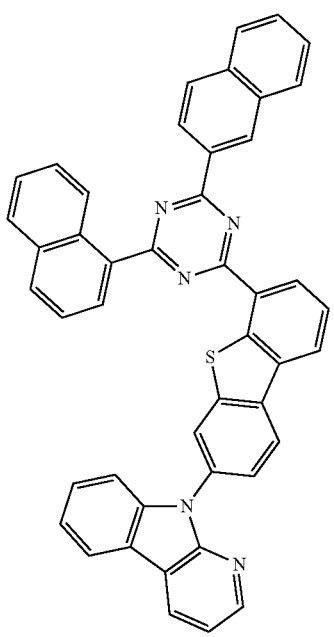
358
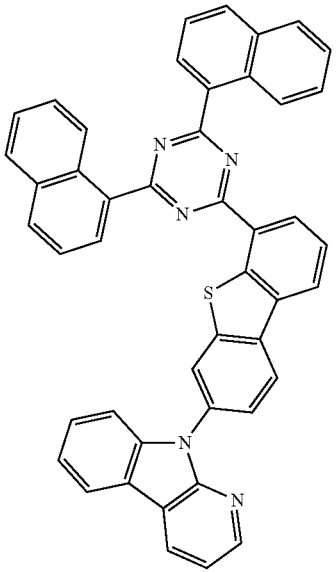

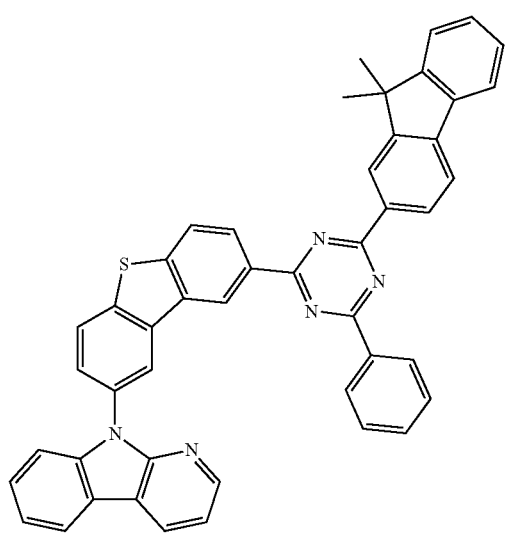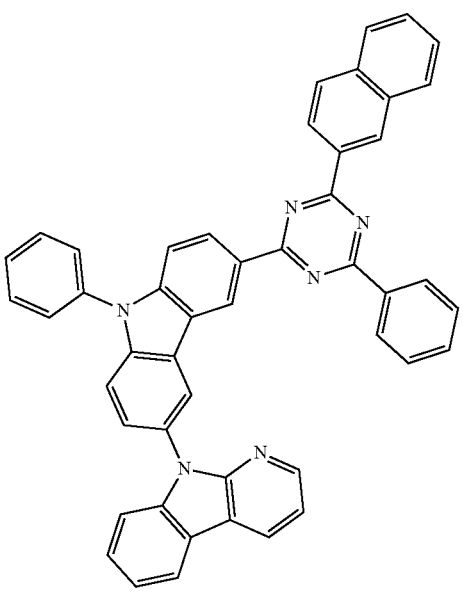

379
-continued
364
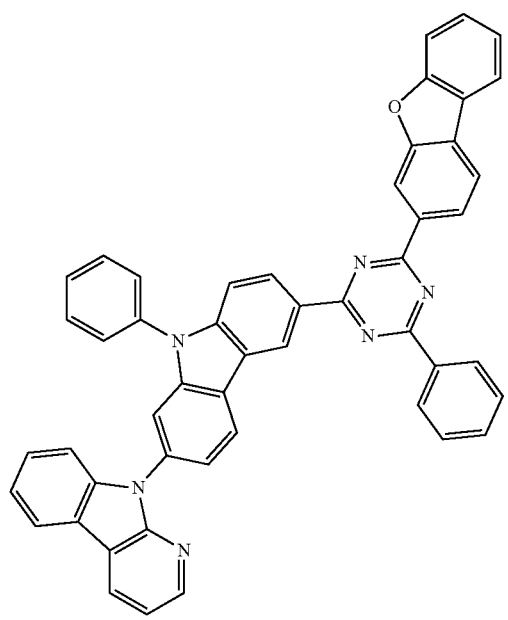
365
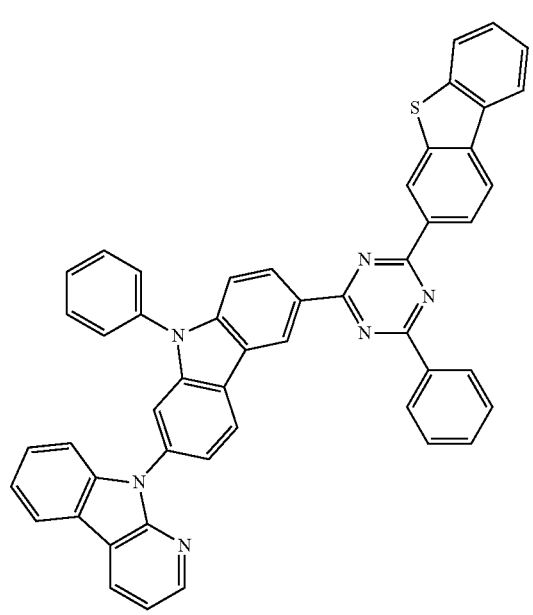
380
-continued
366
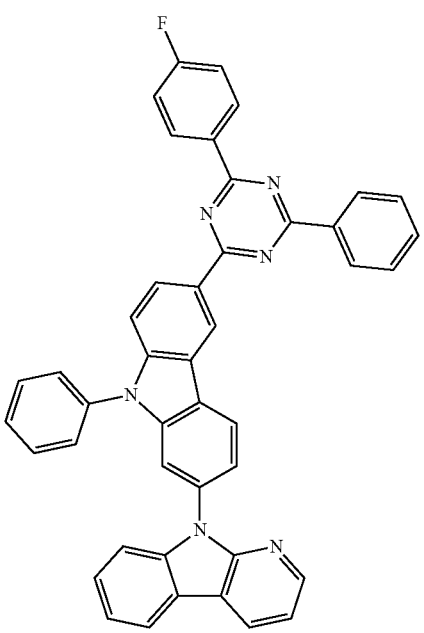
367
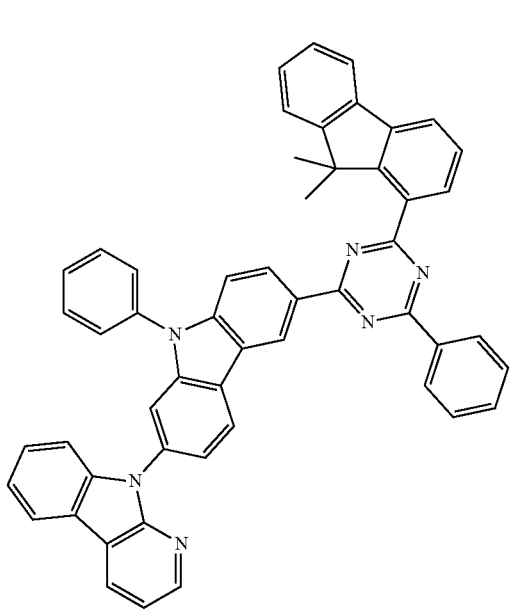

381
-continued
368
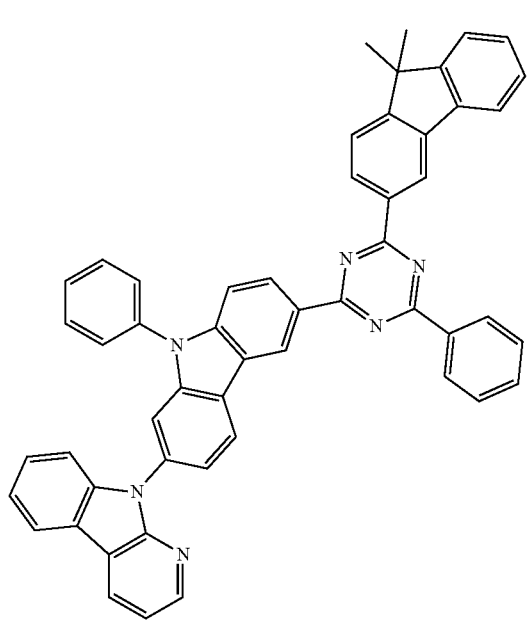
369
382
-continued
370
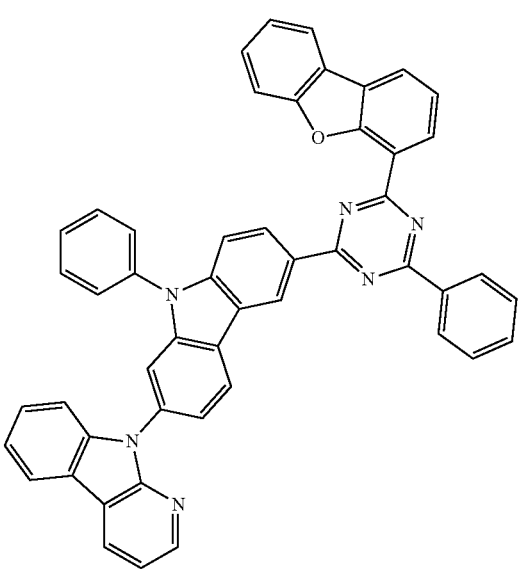
371

383
-continued
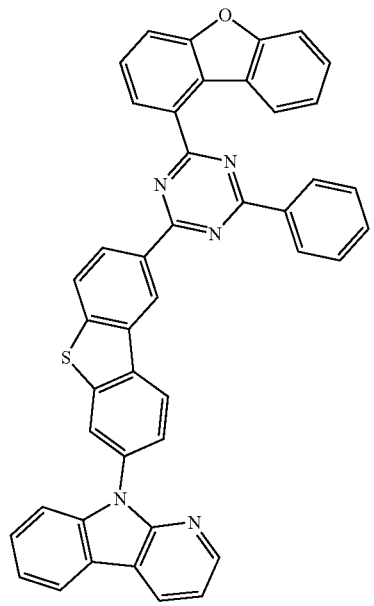
372
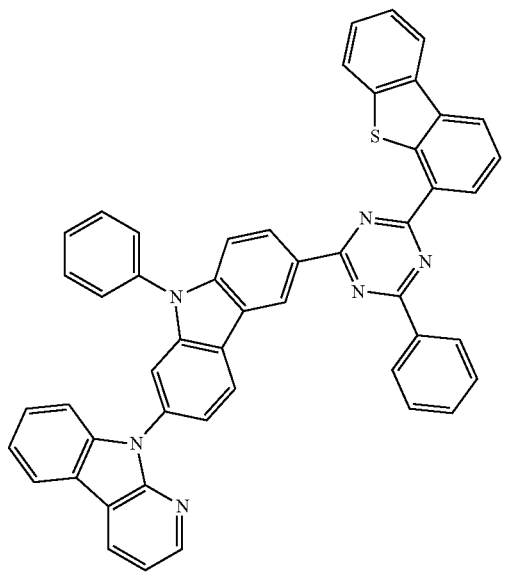
373
384
-continued
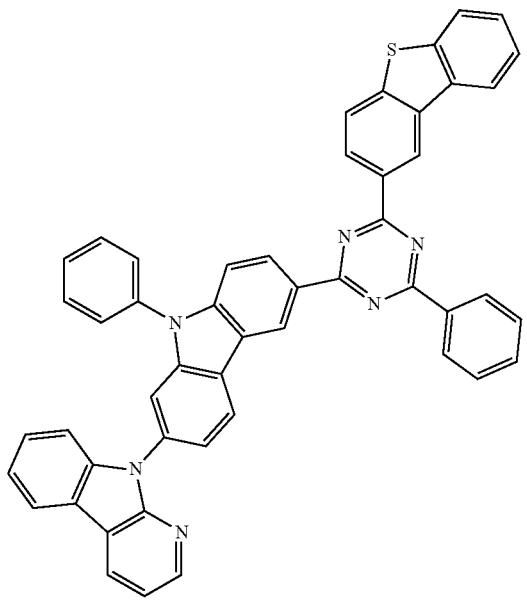
374
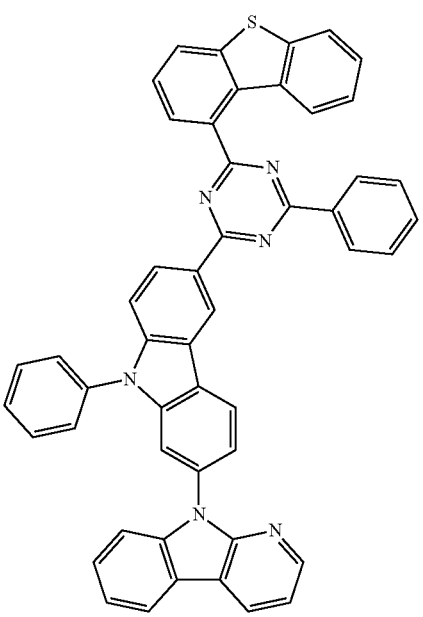
375

385
-continued
376
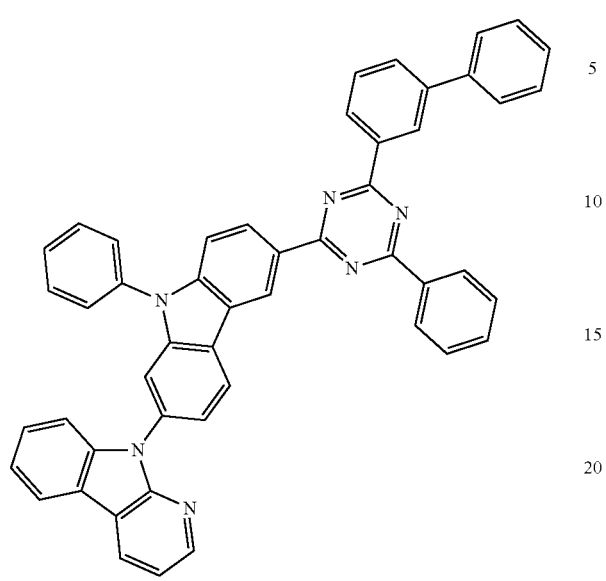
377
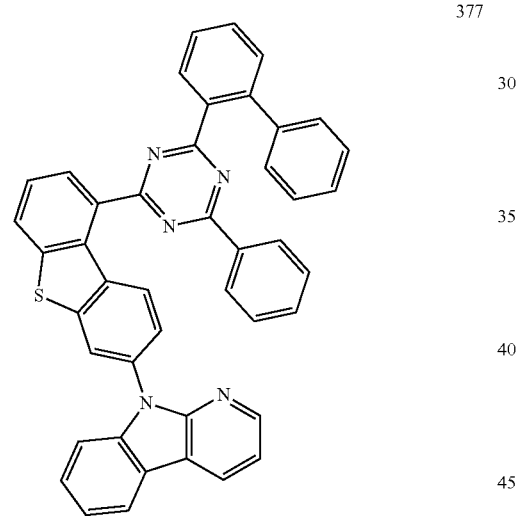
378
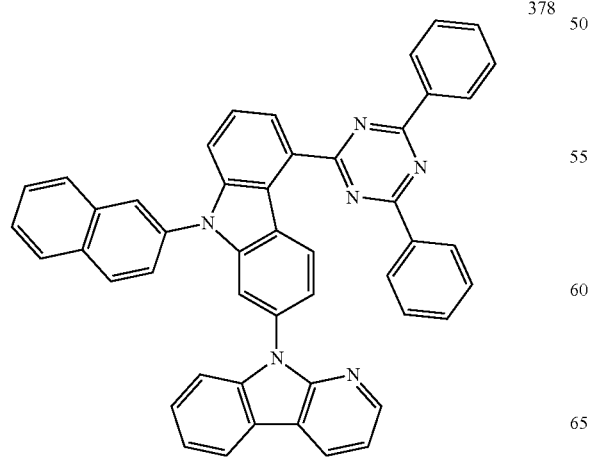
386
-continued
379
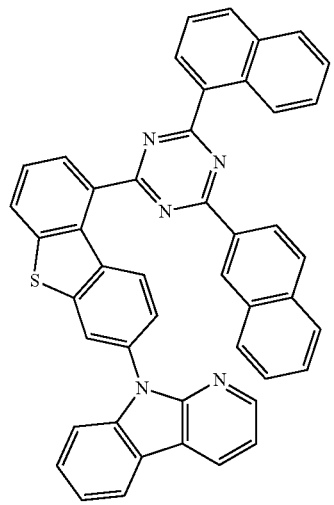
380
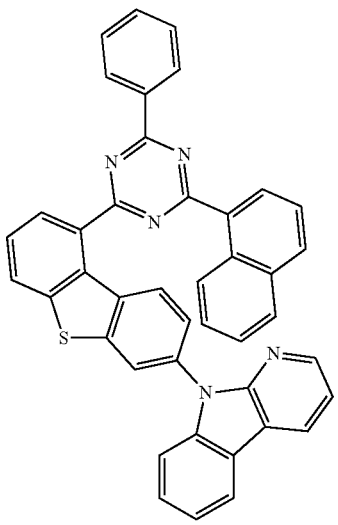
381
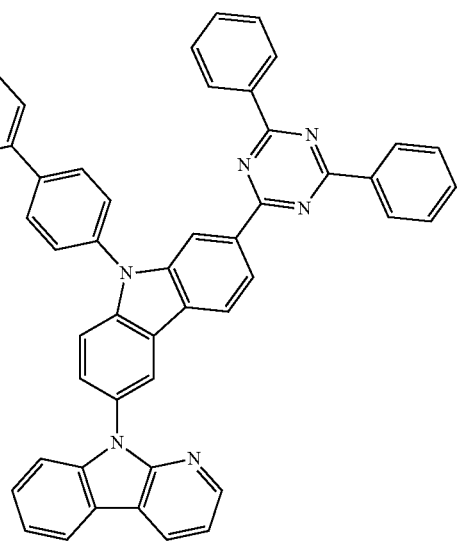

387
-continued
382
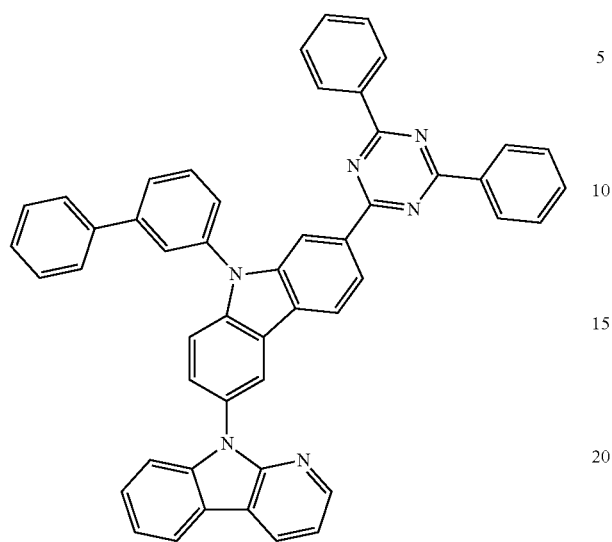
383
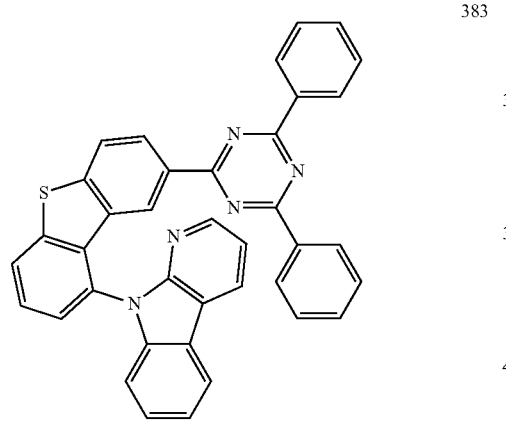
384
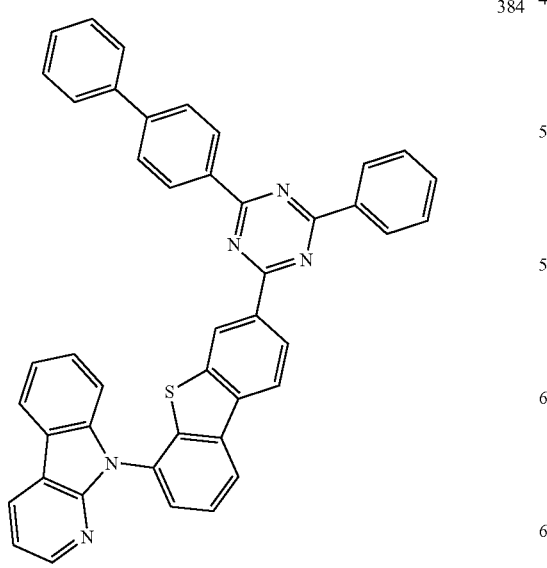
388
-continued
385
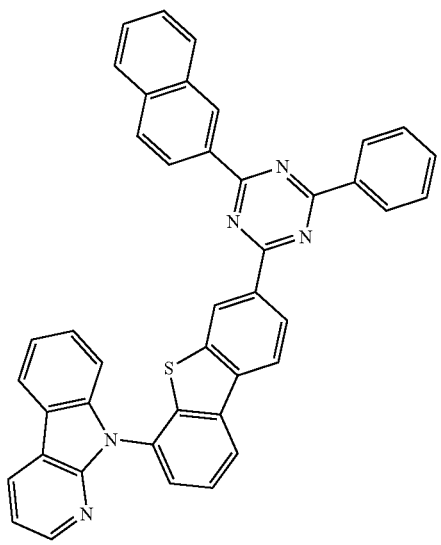
386
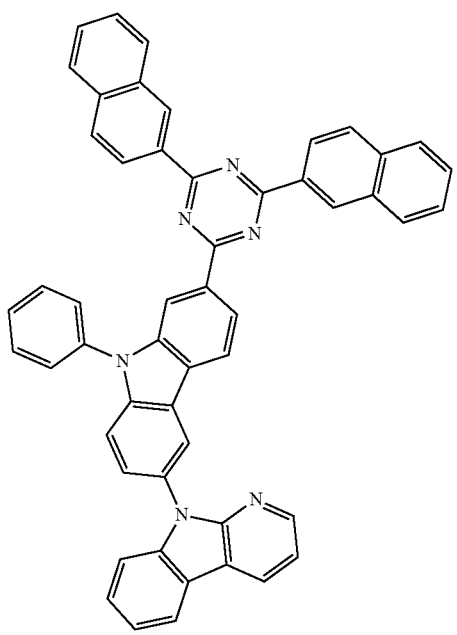

389
-continued
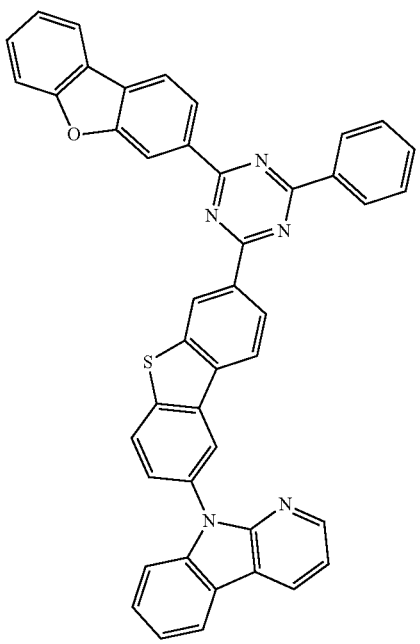
390
-continued
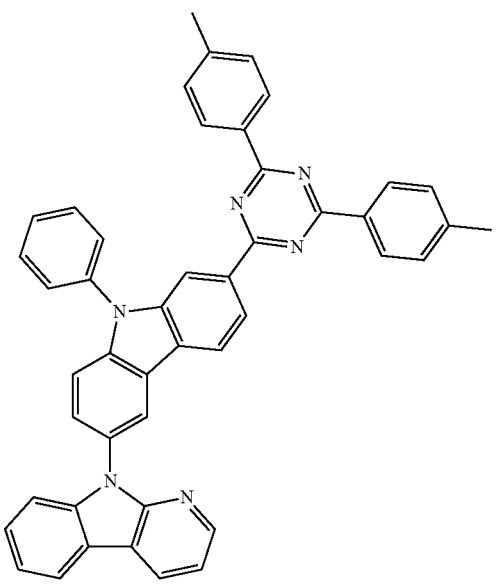
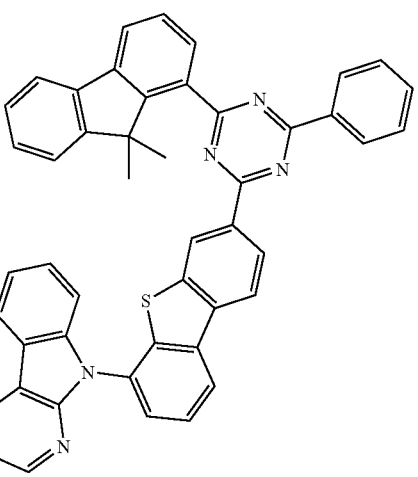
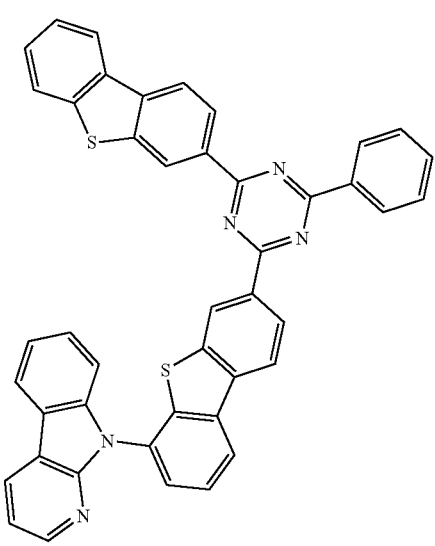
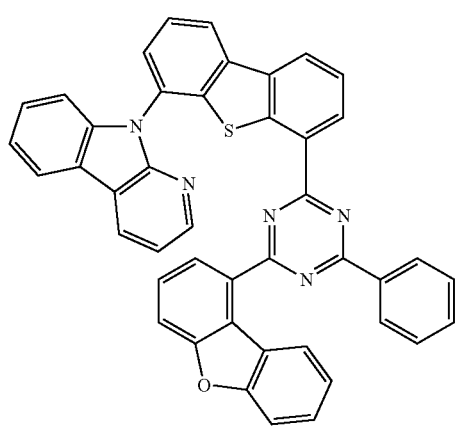

-continued
394
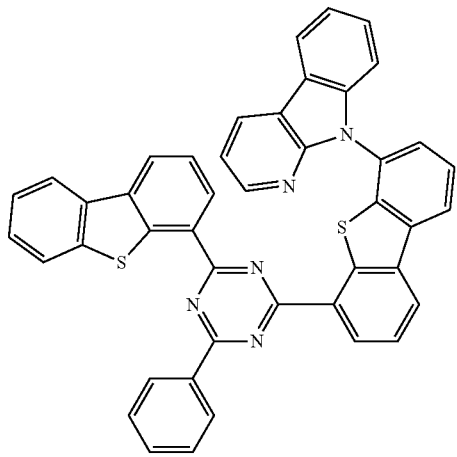
395
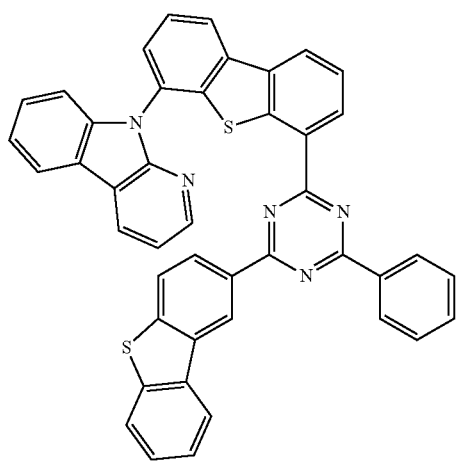
396
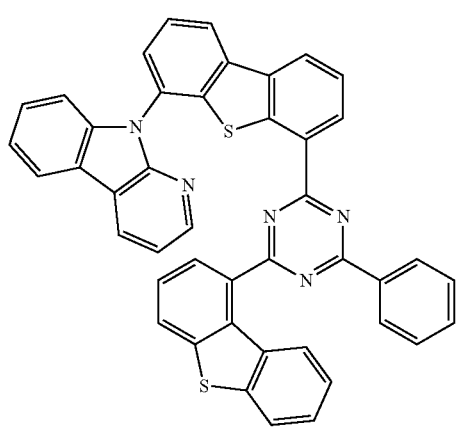
-continued
397
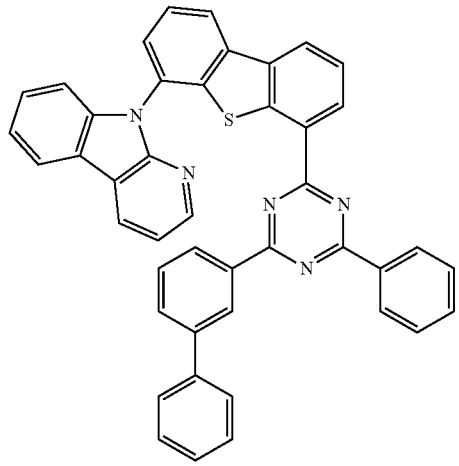
398
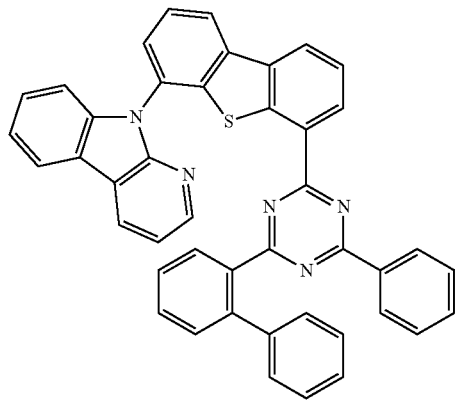
399
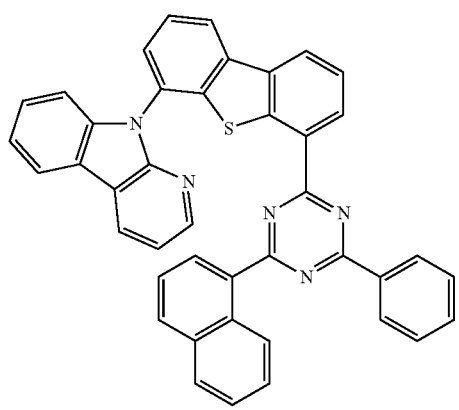

-continued

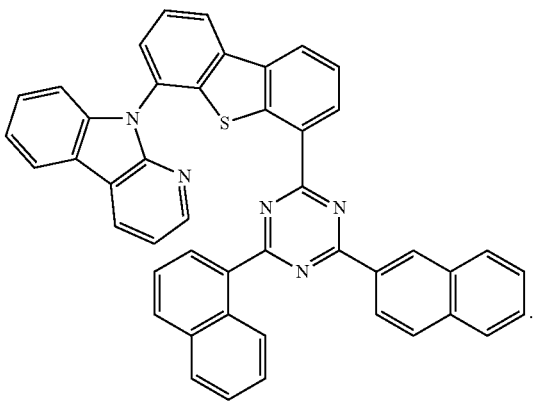

400

9. An organic electroluminescent device, comprising an anode and a cathode which are oppositely arranged, and a functional layer arranged between the anode and the cathode; wherein the functional layer comprises the heterocyclic compound according to claim 1.

10. The organic electroluminescent device according to claim 9, wherein the functional layer comprises an organic light-emitting layer, and the organic light-emitting layer comprises the heterocyclic compound.

11. An electronic device, comprising the organic electroluminescent device according to claim 9.

12. The organic electroluminescent device according to claim 10, wherein the organic light-emitting layer comprises a host material and a guest material, and the host material is the heterocyclic compound.

* * * * *